United States Patent
Strome et al.

(10) Patent No.: US 9,512,210 B2
(45) Date of Patent: *Dec. 6, 2016

(54) IMMUNOGLOBULIN CONSTANT REGION FC RECEPTOR BINDING AGENTS

(71) Applicants: UNIVERSITY OF MARYLAND, BALTIMORE, Baltimore, MD (US); GLIKNIK INC., Baltimore, MD (US)

(72) Inventors: Scott E. Strome, Reisterstown, MD (US); Dan H. Schulze, Towson, MD (US); David S. Block, Ruxton, MD (US); Henrik Olsen, Baltimore, MD (US)

(73) Assignees: GLIKNIK INC., Baltimore, MD (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/221,148

(22) Filed: Mar. 20, 2014

(65) Prior Publication Data

US 2015/0056185 A1    Feb. 26, 2015

Related U.S. Application Data

(63) Continuation of application No. 12/602,609, filed as application No. PCT/US2008/065428 on May 30, 2008, now Pat. No. 8,680,237.

(60) Provisional application No. 61/015,547, filed on Dec. 20, 2007, provisional application No. 61/015,127, filed on Dec. 19, 2007, provisional application No. 60/941,644, filed on Jun. 1, 2007.

(51) Int. Cl.
*C07K 16/06* (2006.01)
*C07K 16/00* (2006.01)
*C07K 19/00* (2006.01)
*A61P 43/00* (2006.01)
*C07K 16/18* (2006.01)
*C07K 16/32* (2006.01)
*C07K 16/28* (2006.01)
*A61K 39/00* (2006.01)

(52) U.S. Cl.
CPC .............. *C07K 16/18* (2013.01); *C07K 16/00* (2013.01); *C07K 16/065* (2013.01); *C07K 16/28* (2013.01); *C07K 16/32* (2013.01); *A61K 2039/505* (2013.01); *C07K 2317/50* (2013.01); *C07K 2317/52* (2013.01); *C07K 2317/526* (2013.01); *C07K 2317/53* (2013.01); *C07K 2317/55* (2013.01); *C07K 2319/00* (2013.01)

(58) Field of Classification Search
CPC . C07K 16/00; C07K 2317/50; C07K 2317/52; C07K 2317/53; C07K 2317/55; C07K 2317/526; C07K 2319/00; C07K 16/32; C07K 16/18; C07K 16/28; C06K 16/65
See application file for complete search history.

(56) References Cited

U.S. PATENT DOCUMENTS

| | | | |
|---|---|---|---|
| 5,681,566 A | 10/1997 | Stevenson | |
| 5,877,396 A | 3/1999 | Ravetch et al. | |
| 6,004,781 A | 12/1999 | Seed | |
| 6,660,266 B1 | 12/2003 | Mosser et al. | |
| 7,511,121 B2 | 3/2009 | Arnason et al. | |
| 7,524,487 B2 | 4/2009 | Mosser et al. | |
| 7,666,622 B2 | 2/2010 | Sharma et al. | |
| 8,680,237 B2 * | 3/2014 | Strome | C07K 16/00 530/350 |
| 2002/0115157 A1 | 8/2002 | Davis et al. | |
| 2003/0216546 A1 | 11/2003 | Tykocinski et al. | |
| 2004/0062763 A1 | 4/2004 | Mosser et al. | |
| 2004/0110226 A1 | 6/2004 | Lazar et al. | |
| 2004/0147731 A1 | 7/2004 | Parkos | |
| 2004/0151725 A1 | 8/2004 | Gray et al. | |
| 2005/0033029 A1 | 2/2005 | Lu | |
| 2005/0249723 A1 | 11/2005 | Lazar | |
| 2006/0275254 A1 | 12/2006 | Kim et al. | |
| 2007/0269369 A1 | 11/2007 | Gegg et al. | |
| 2008/0260738 A1 | 10/2008 | Moore et al. | |
| 2009/0117133 A1 | 5/2009 | Arnason et al. | |
| 2009/0136485 A1 | 5/2009 | Chu et al. | |
| 2009/0217401 A1 | 8/2009 | Korman et al. | |
| 2009/0252729 A1 | 10/2009 | Farrington et al. | |
| 2009/0304696 A1 | 12/2009 | Lawson et al. | |

(Continued)

FOREIGN PATENT DOCUMENTS

EP    0439540 B1    6/1995
EP    2006305 A9    7/2009

(Continued)

OTHER PUBLICATIONS

Shields, et al., Journal of Biol Chem 276(6): 6591-6504, 2001.*
Van Noort et al., International Review of Cytology 178: 127-205, 1998.*
Goldenberg et al., P & T 37(3): 175-184, Mar. 2012.*
"Synthetic peptides with high biochemical activity," downloaded on Sep. 7, 2012 from http://www.genosphere-biotech.com/Long-Active-Peptides.html, 1 page.
Abaza et al., "Effect of amino acid substitutions outside an antigenic site on protein binding to monoclonal antibodies of predetermined specificity obtained by peptide immunization: demonstration with region 94-100 (antigenic site 3) of myoglobin," Journal of Protein Chemistry, 11(5):433-444 (1992).

(Continued)

*Primary Examiner* — Phuong Huynh
(74) *Attorney, Agent, or Firm* — Cooley LLP

(57) ABSTRACT

IVIG replacement compounds are derived from recombinant and/or biochemical creation of immunologically active biomimetic(s). These replacement compounds are then screened in vitro to assess each replacements compound's efficiency at modulating immune function. Particular replacement compounds are selected for further in vivo validation and dosage/administration optimization. Finally, the replacement compounds are used to treat a wide range of diseases, including inflammatory and autoimmune diseases.

12 Claims, 49 Drawing Sheets

(56) References Cited

U.S. PATENT DOCUMENTS

| | | |
|---|---|---|
| 2009/0304715 A1 | 12/2009 | Masuho et al. |
| 2010/0048877 A1 | 2/2010 | Ruker et al. |
| 2010/0093979 A1 | 4/2010 | Lazar |
| 2010/0143353 A1 | 6/2010 | Mosser et al. |
| 2010/0227805 A1 | 9/2010 | Karin et al. |
| 2010/0239633 A1 | 9/2010 | Strome et al. |
| 2011/0243966 A1 | 10/2011 | Farrington et al. |
| 2011/0305697 A1 | 12/2011 | Walczak |
| 2012/0283417 A1 | 11/2012 | Mosser et al. |
| 2012/0309941 A1 | 12/2012 | Strome et al. |
| 2013/0156765 A1 | 6/2013 | Block et al. |
| 2014/0072582 A1 | 3/2014 | Block et al. |
| 2014/0105913 A1 | 4/2014 | Strome et al. |
| 2014/0335075 A1 | 11/2014 | Strome et al. |
| 2014/0370012 A1 | 12/2014 | Block et al. |

FOREIGN PATENT DOCUMENTS

| | | |
|---|---|---|
| WO | WO 90/04413 A1 | 5/1990 |
| WO | WO 94/15640 A1 | 7/1994 |
| WO | WO 00/09560 A2 | 2/2000 |
| WO | WO 02/072608 A2 | 9/2002 |
| WO | WO 03/105898 A1 | 12/2003 |
| WO | WO 2005/000895 A2 | 1/2005 |
| WO | WO 2005/007809 A2 | 1/2005 |
| WO | WO 2005/077981 A2 | 8/2005 |
| WO | WO 2005/089503 A2 | 9/2005 |
| WO | WO 2006/008739 A2 | 1/2006 |
| WO | WO 2006/061650 A2 | 6/2006 |
| WO | WO 2007/100083 A1 | 9/2007 |
| WO | WO 2008/138131 A1 | 11/2008 |
| WO | WO 2008/151088 A2 | 12/2008 |
| WO | WO 2010/065578 A2 | 6/2010 |
| WO | WO 2011/060242 A2 | 5/2011 |
| WO | WO 2012/001647 A2 | 1/2012 |
| WO | WO 2012/016073 A2 | 2/2012 |

OTHER PUBLICATIONS

Alegre and Fallarino (2006) "Mechanisms of CTLA-4-Ig in tolerane induction," Curr. Pharmaceutical Design, 12(2):149-160.

Anderson, C. A. et al., "Cutting Edge: Biasing immune responses by directing antigen to macrophage Fcγ receptors," J. Immunology, 168:3697-3701 (2002).

Aubin, et al. (2010) "Indirect inhibition of in vivo and in vitro T-cell responses by intravenous immunoglobulins due to impaired antigen presentation," Blood, 115(9):1727-1734.

Augener, et al. (1985) "Are aggregates of IgG the effective part of high-dose immunoglobulin therapy in adult idtiopathic thrombocytopenic purpura (ITP)?" Blut, 50:249-252.

Barrionuevo, et al. (2003) "Immune complex-FcγR interaction modulates monocyte/macrophage molecules involved in inflammation and immune response," Clin. Exp. Immunol. 133(2):200-207.

Bazin, et al. (2004) "Tetramolecular immune complexes are more efficient than IVIg to prevent antibody-dependent in vitro and in vivo and in in vivo phagocytosis of blood cells," British J. Haematol. 127(1):90-96.

Campbell, A. M., "Monoclonal Antibody Technology," In Laboratory Techniques in Biochemistry and Molecular Biology, vol. 13, Elsevier Science Publishers, pp. 1-32 (1984).

Caron et al., "Engineered Humanized Dimeric Forms of IgG are More Effective Antibodies," J. Exp. Med. 176:1191-1195 (1992).

Chappel et al., "Identification of the Fcγ receptor class I binding site in human IgG through the use of recombinant IgGl/IgG2 hybrid and point-mutated antibodies," Proc. Natl. Acad. Sci. USA 88:9036-9040 (1991).

Chougnet et al., "Molecular analysis of decreased interleukin-12 production in person infected with human immunodeficiency virus," J. Infectious Diseases, 174:46-53 (1996).

Cohen, P., "Systemic Autoimmunity," In Fundamental Immunology, 4th edition, Philadelphia, Lippencot-Raven Publishers, pp. 1067-1088 (1999).

Colman et al., "Effects of amino acid sequence changes on antibody-antigen interactions," Research in Immunology, 145(1):33-36 (1994).

Constantine, M. M. et al., "Intravenous immunoglobulin utilization in the Canadian Atlantic provinces: a report of the Atlantic Collaborative Intravenous Immune Globulin utilization working group," Transfusion, 47:2072-2080 (2007).

Davidson et al, "T helper celll-type CD4+ T cells, but not B cells, mediate colitis in interleukin 10-deficient mice," J. Exp. Med., 184:241-251 (1996).

Davis, A.C., et al., "Intermolecular disulfide bonding in IgM: effects of replacing cysteine residues in the μ heavy chain," EMBO J. 8(9):2519-2526 (1989).

Debre, et al. (1993) "Infusion of Fcγ fragments for treatment of children with acute immune thrombocytopenic purpura," Lancet, 342:945-49.

Deo, Y. M. et al., "Clinical significance of lgG Fc receptors and FcγR-directed immunotherapies," Immunology Today, 18(3):127-135 (1997).

Dinarello, C. A., "Proinflammatory and anti-inflammatory cytokines as mediators in the pathogenesis of septic shock," Chest, 112:321S-329S (1997).

European examination report mailed May 18, 2011 in co-pending European application No. 08769936.9, 7 pages.

European Search Report, EP appl. No. 13169230.3, 15 pages (Oct. 25, 2013).

Flanagan et al., "Soluble Fc Fusion Proteins for Biomedical Research," Meth. Mol. Biol. 378:33-52 (2007).

Gavin, A. L. et al., "Cutting Edge: Identification of the Mouse lgG3 Receptor: Implications for Antibody Effector Function at the Interface Between Innate and Adaptive Immunity," J. lmmunol., 160(1):20-23 (1998).

Gerber, J. S. et al., "Reversing Lipopolysaccharide Toxicity by Ligating the Macrophage Fcγ Receptors," J. Immunology, 166:6861-6868 (2001).

Gliknik website. www.gliknik.com/research/stradomer.php, 2012.

Greenwood et al. (1994) "Engineering multiple domains forms of the therapeutic antibody Campath-1H: Effect on complement Lysis," Ther. Immunol 1(5):247-255.

Hart et al., "Comparison of the suppressive effects of interleukin-10 and interleukin-4 on synovial fluid macrophages and blood monocytes from patients with inflammatory arthritis," Immunology, 84:536-542 (1995).

Huang, et al. (2005) "In vitro study of combination of rhOPG-Fc and alendronate on inhibition osteoclast," Zhonghua Wai Ke Za Zhi 43(12):812-816. (Abstract Only, Article in Chinese).

International Preliminary Report on Patentability, mailed Jan. 29, 2013 in co-pending related International application No. PCT/US2011/045768.

International Search Report and Written Opinion for International Application No. PCT/US2011/045768, 15 pages, mailed Mar. 8, 2012.

International Search Report for PCT/US2008/065428, 5 pages, mailed Feb. 10, 2009.

International Search Report for PCT/US2013/023404, 4 pages, mailed Apr. 15, 2013.

International Search Report for PCT/US2013/055800, 7 pages, mailed Mar. 4, 2014.

Jain et al., "Fully recombinant IgG2a Fc multimers (stradomers) effectively treat collagen-induced arthritis and prevent idiopathic thrombocytopenic purpura in mice," Arthritis Res. Ther. 14(4):R192, 12 pages (2012).

Jefferis, R. et al., "Interaction sites on human lgG-Fc for FcγR: current models," Immunol. Lett., 82(1-2):57-65 (2002).

Kacskovics et al., "Fc receptors in livestock species," Vet. Immunol. Immunopathol. 102:351-362 (2004).

Landschulz et al., "The Leucine Zipper: A Hypothetical Structure Common to a New Class of DNA Binding Proteins," Science 240:1759-1764 (1988).

Lee, J. K. "Determination of the Molecular Size Distribution of Immunoglobulin G (1gG) In Intravenous IgG-Albumin Formulations by High-Performance Liquid Chromatography," Journal of Chromatography, 444:141-152 (1988).

(56) References Cited

OTHER PUBLICATIONS

Lemieux and Bazin (2006) "Autoantibody-Induced Formation of Immune Complexes in Normal Human Serum," Curr. Pharm Design, 12:173-179.
Levinson, D. R., "Intravenous Immune Globulin: medicare payment and availability," Report to DHHS, OEI-03-05-00404 (2007).
Liew, "TH1 and TH2 cells: a historical perspective," Nature Reviews, Immunology, 2:55-60 (2002).
Lucas et al., "ERK activation following macrophage FcγR ligation leads to chromatin modifications at the IL-10 locus," Journal of Immunology, 175:469-477 (2005).
Lund et al., "Multiple Interactions of IgG with Its Core Oligosaccharide Can Modulate Recognition by Complement and Human Fcγ Receptor I and Influence the Synthesis of Its Oligosaccharide Chains," J. Immunol. 157:4963-4969 (1996).
Monoclonal antibody 13-1 heavy chain-mouse, GenBank Accession # PC4436 (Date: Feb. 4, 1998).
Mosser et al., "Interleukin-10: new perspectives on an old cytokine," Immunological Reviews, 226(1):205-218 (2008).
Mosser, D. M., "The Many Faces of Macrophage Activation," J. Leukocyte Biology, 73:209-212 (2003).
Nagashima, et al. (2008) "Tandemly repeated Fc domain augments binding avidities of antibodies for Fcγ receptors, resulting in enhanced antibody-dependent cellular cytotoxicity," Mol. Immunol. 45:2752-2763.
Nagashima et al., "Fc Taryotaika ni yoru Kokassei Kotai," Proc. 126th Ann. Meet. Pharm. Soc. Japan 126:107 (abstract No. P28[S]am-551) (2006).
Ngo et al., "Computational complexity, protein structure prediction, and the levinthal paradox," in the Protein Folding Problem and Tertiary Structure Prediction, Boston: Birkhauser, pp. 433 and 492-495 (1994).
Nimmerjahn and Ravetech (2010) "Antibody-mediated modulation of immune responses," Immunological Rev. 236:265-275.
Office Action for U.S. Appl. No. 12/602,609, mailed Jan. 24, 2013.
Office Action for U.S. Appl. No. 12/602,609, mailed Aug. 29, 2012.
Ong, et al. (2005) "How to accelerate the endothelialization of stents," Archives de maladies du coeur et des vaisseaux, 98(2):123-126.
Partial European Search Report, EP appl. No. 13169230.3, 8 pages (Jul. 31, 2013).
Ratcliffe et al., "Measurement of the binding activity of defined IgG aggregates to macrophage Fc receptors," Immunology Letters, 7(2):73-76 (1983).
Reff and Heard, "A review of modifications to recombinant antibodies: attempt to increase efficacy in oncology applications," Crit. Rev. Oncol./Hematol. 40:25-35 (2001).
Reeth et al., "Positive selection vectors to generate fused genes for the expression of his-tagged proteins," BioTechniques, 25:898-904 (1998).
Salfeld, "Isotype selection in antibody engineering," Nat. Biotechnol. 25:1369-1372 (2007).
Schuurman et al., "The inter-heavy chain disulfide bonds of IgG4 are in equilibrium with intra-chain disulfide bonds," Mol. Immunol. 38:1-8 (2001).
Shields et al., "High Resolution Mapping of the Binding Site on Human IgG1 for FcγRI, FCγRII, FCγRIII, and FcRn and Design of IgG1 Variants with Improved Binding to the FcγR*," J. Biol. Chem. 276:6591-6604 (2001).
Siragam, et al. (2006) "Intravenous immunoglobulin ameliorates ITP via activating Fcγ receptors on dendritic cells," Nature Med. 12(6):668-692.
Smith and Morrison (1994) "Recombinant polymeric IgG: an approach to engineering more potent antibodies" Biotechnol. 12:683-688.
Smith et al., "Addition of a μ-tailpiece to IgG results in polymeric antibodies with enhanced effector functions including complement-mediated cytolysis by IgG4," J. Immunol 154:2226-2236 (1995).
Song, et al. (2002) "Monoclonal IgG can ameliorate immune thrombocytopenia in a murine model of ITP: an alternative to IVIG," Blood, 101(9):3708-3713.
Stevenson, G. T. et al., "Engineered antibody for treating lymphoma," Recent Res. Canc. Res. 159:104-112 (2002).
Sundaram et al., "Lipopolysaccharide-induced suppression of erythrocyte binding and phagocytosis via FcγRI, FcγRII, FcγRIII, and CR3 receptors in murine macrophages," J. Leukocyte Biology, 54:81-88 (1993).
Supplemental European Search Report for EP 08769936.9, mailed May 26, 2010.
Supplementary European Search Report, EP appl. 11813204.2, 6 pages (Jul. 3, 2015).
Sutterwala, F. et al., "Reversal of Proinflammatory Responses by Ligating the macrophage Fcγ Receptor Type I," Journal of Experimental Medicine, 188(1):217-222 (1998).
Sutterwala, F. et al., "Selective Suppression of Interleukin-12 Induction After Macrophage Receptor Litigation," J. Exp. Med., 185:1977-1985 (1985).
Tankersley, D. L., "Dimer Formation in immunoglobulin Preparations and Speculations on the Mechanism of Action of Intravenous Immune Globulin in Autoimmune Diseases," Immunological Reviews, 39:159-172 (1994).
Teeling, et al. (2001) "Therapeutic efficacy of intravenous immunoglobulin preparations depends on the immunoglobulin G dimers: studies in experimental immune thrombocytopenia," Blood, 98(4):1095-1099.
Tha-In, et al. (2008) "Modulation of the cellular immune system by intravenous immunoglobulin," Trends Immunol. 29(12): 608-615.
Thiruppathi et al., "Recombinant IgG2a Fc (M045) multimers effectively suppress experimental autoimmune myasthenia gravis," J. Autoimmunity 52(2):64-73 (2014).
Tremblay, T. et al., "Picogram doses of lipopolysaccharide exacerbate antibody-mediated thrombocytopenia and reduce the therapeutic efficacy of intravenous immunoglobulins in mice," British Journal of Hematology, 139:297-302 (2007).
Vialtel, P. et al., "Nucleation-controlled Polymerization of human Monoclonal Immunoglobulin G Cryoglobulins," The Journal of Biological Chemistry; 257(7): 3811-3818 (1982).
Wright, J. K. et al., "Dimeric, Trimeric and Tetrameric Complexes of Immunoglobulin G Fix Complement," Biochem. J., 187:775-780 (1980).
Written Opinion of the International Searching Authority, PCT appl. No. PCT/US2013/023404, 16 pages, mailed Apr. 15, 2013.
Written Opinion of the International Searching Authority, PCT appl. No. PCT/US2013/0055800, 22 pages, mailed Mar. 4, 2014.
Zang, C., "Annual founders week deemed a 'huge success,'" VOICE University of Maryland, pp. 1-5, http://umvoice.com/2011/12/annual-founders-week-deemed-a-huge-success/, visited website Dec. 10, 2012.
Zhang et al., "Alteration in the IL-2 signal peptide affects secretion of proteins in vitro and in vivo," Journal Gene Medicine, 7:354-365 (2005).
Zhang et al., "Dynamic and transient remodeling of the macrophages IL-10 promoter during transcription," Journal of Immunology, 177:1282-1288 (2006).
Supplementary European Search Report, EP appl. 13741129.4, 5 pages (Nov. 4, 2015).

* cited by examiner

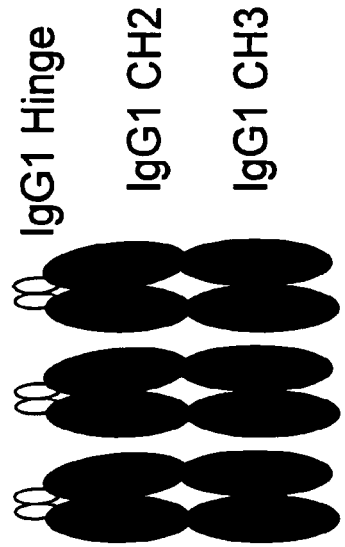

FIGURE 2B

Multiple dimerized IgG1 Fc fragment sticking together through "sticky" protein-protein interactions
- Sometimes referred to in the literature as Fc fragment multimers IgG1 Hinge
IgG1 CH2
IgG1 CH3

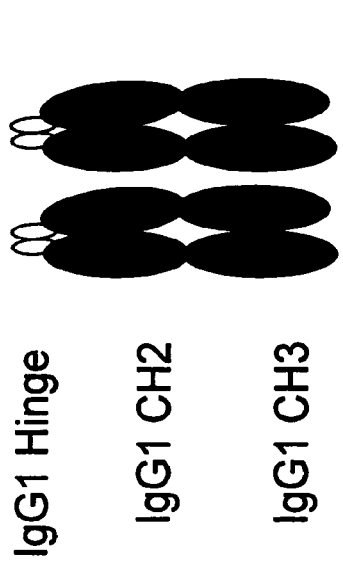

FIGURE 2A

Two dimerized IgG1 Fc fragment sticking together through "sticky" protein-protein interactions
- Sometimes referred to in the literature as Fc fragment dimers IgG1 Hinge
IgG1 CH2
IgG1 CH3

IgG1 Fc - IgG3 Fc- IgE Fc 3-stradomer monomer 2 (IgG1 Fc) stradomer monomer

IgG1 Fc - IgG3 Fc - IgE Fc serial stradomer auto-dimerized 2 (IgG1 Fc) serial stradomer auto-dimerized IgG1 (hinge - CH2) - IgG3 (hinge - CH2) - IgE (hinge - CH2) serial stradomer auto-dimerized IgG1 Hinge
IgG1 CH2
IgG3 Hinge
IgG3 CH2
IgE Hinge
IgE CH2

IgG1 Fc - IgG1 (hinge - CH2) serial stradomer auto-dimerized

IgG1 Hinge
IgG1 CH2
IgG1 CH3
IgG1 Hinge
IgG1 CH2

IgG3 Fc – IgG1 Fc serial stradomer

IgG3 Hinge
IgG3 CH2
IgG3 CH3
IgG1 Hinge
IgG1 CH2
IgG1 CH3

IgE (hinge) - IgG1 Fc - IgG1 (hinge – CH2) – IgE (CH3) serial stradomer

IgE Hinge
IgG1 Hinge
IgG1 CH2
IgG1 CH3
IgG1 Hinge
IgG1 CH2
IgE CH3

5 [2{IgG1 (hinge-CH2)- IgG3 CH3} – IgM CH4] – J core stradomer

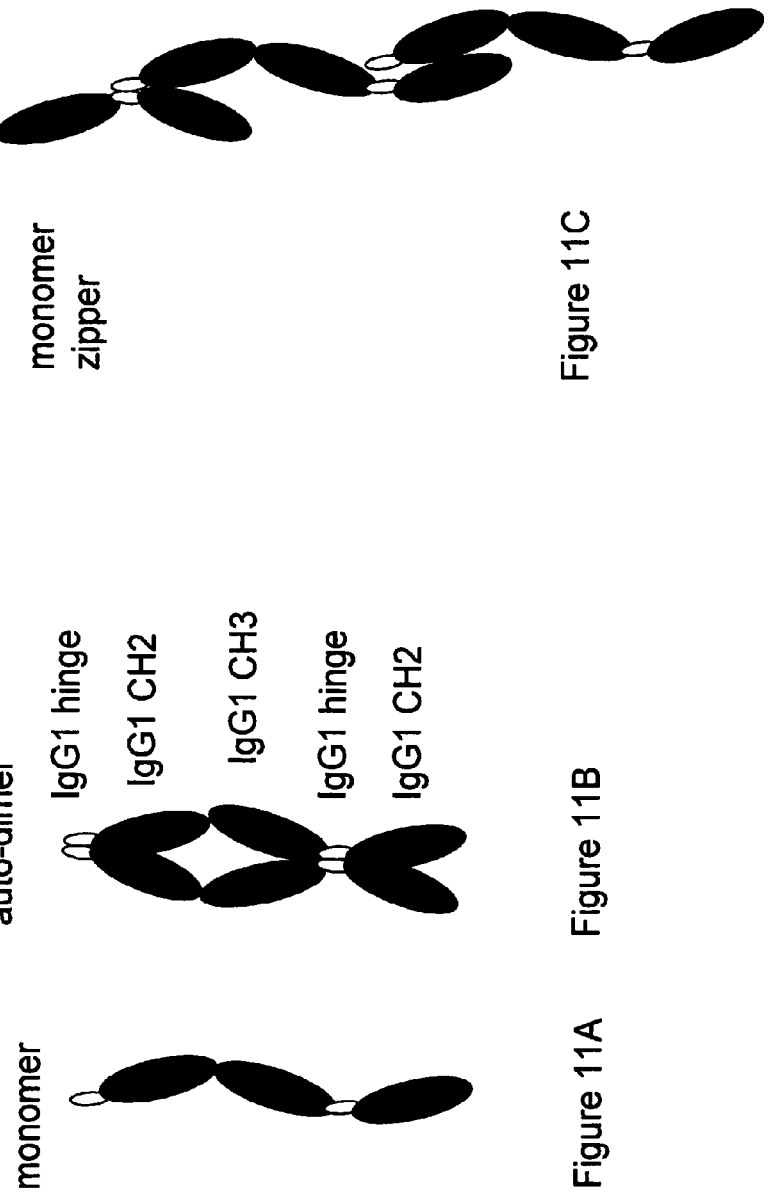

IgG3 Fc – IgG1 Fc stradomer monomer

IgG3 Hinge
IgG3 CH2
IgG3 CH3
IgG1 Hinge
IgG1 CH2
IgG1 CH3

IgG3 Fc – IgG1 Fc – IgG1 Fc – IgG3 Fc branched stradomer dimer

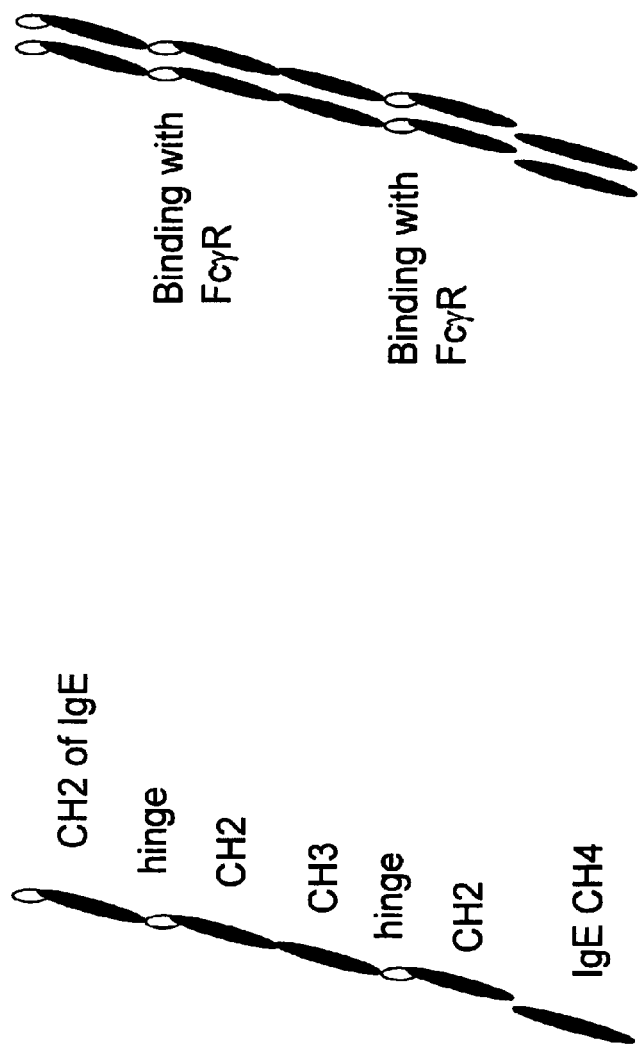

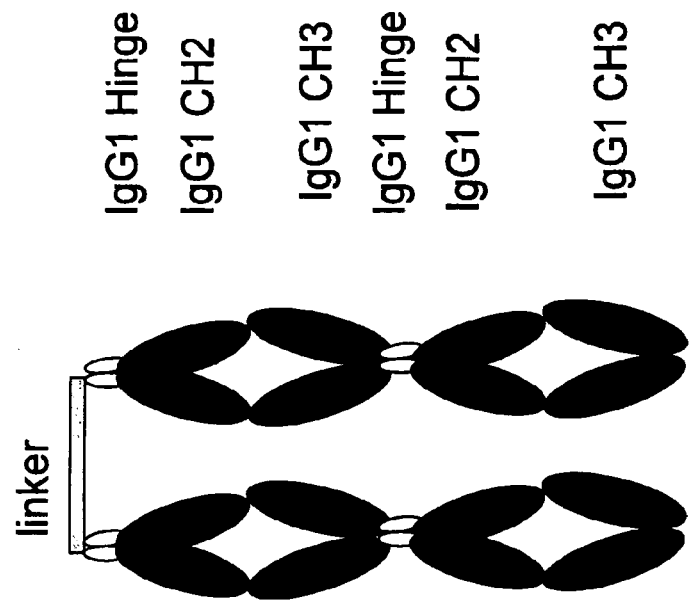
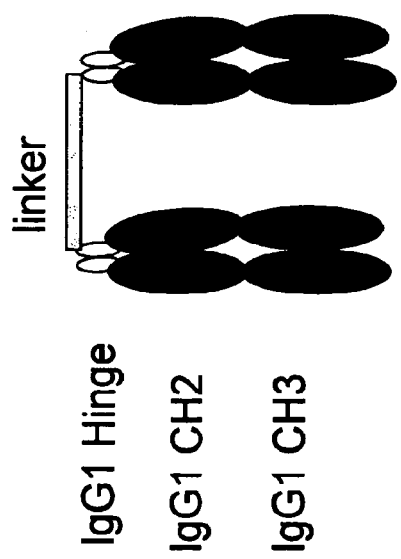
FIGURE 14A
FIGURE 14B

FIG. 15A

IgG1 Fc fragment SEQ ID NO: 1 and 2

```
  1 S   E   P   K   S   C   D   K   T   H   T   C   P   P   C   P   A   P   E   L
  1 AGTGAGCCCAAATCTTGTGACAAAACTCACACATGCCCACCGTGCCCAGCACCTGAACTC

21 L   G   G   P   S   V   F   L   F   P   P   K   P   K   D   T   L   M   I   S
 61 CTGGGGGGACCGTCAGTCTTCCTCTTCCCCCCAAAACCCAAGGACACCCTCATGATCTCC

41 R   T   P   E   V   T   C   V   V   V   D   V   S   H   E   D   P   E   V   K
121 CGGACCCCTGAGGTCACATGCGTGGTGGTGGACGTGAGCCACGAAGACCCTGAGGTCAAG

61 F   N   W   Y   V   D   G   V   E   V   H   N   A   K   T   K   P   R   E   E
181 TTCAACTGGTACGTGGACGGCGTGGAGGTGCATAATGCCAAGACAAAGCCGCGGGAGGAG

81 Q   Y   N   S   T   Y   R   V   V   S   V   L   T   V   L   H   Q   D   W   L
241 CAGTACAACAGCACGTACCGGGTGGTCAGCGTCCTCACCGTCCTGCACCAGGACTGGCTG

101 N   G   K   E   Y   K   C   K   V   S   N   K   A   L   P   A   P   I   E   K
301 AATGGCAAGGAGTACAAGTGCAAGGTCTCCAACAAAGCCCTCCCAGCCCCCATCGAGAAA

121 T   I   S   K   A   K   G   Q   P   R   E   P   Q   V   Y   T   L   P   P   S
361 ACCATCTCCAAAGCCAAAGGGCAGCCCCGAGAACCACAGGTGTACACCCTGCCCCCATCC

141 R   D   E   L   T   K   N   Q   V   S   L   T   C   L   V   K   G   F   Y   P
421 CGGGATGAGCTGACCAAGAACCAGGTCAGCCTGACCTGCCTGGTCAAAGGCTTCTATCCC

161 S   D   I   A   V   E   W   E   S   N   G   Q   P   E   N   N   Y   K   T   T
481 AGCGACATCGCCGTGGAGTGGGAGAGCAATGGGCAGCCGGAGAACAACTACAAGACCACG

181 P   P   V   L   D   S   D   G   S   F   F   L   Y   S   K   L   T   V   D   K
541 CCTCCCGTGCTGGACTCCGACGGCTCCTTCTTCCTCTACAGCAAGCTCACCGTGGACAAG

201 S   R   W   Q   Q   G   N   V   F   S   C   S   V   M   H   E   A   L   H   N
601 AGCAGGTGGCAGCAGGGGAACGTCTTCTCATGCTCCGTGATGCATGAGGCTCTGCACAAC

221 H   Y   T   Q   K   S   L   S   L   S   P   G   K
661 CACTACACGCAGAAGAGCCTCTCCCTGTCTCCGGGTAAA
```

FIG. 15B

IgG2 Fc fragment SEQ ID NO: 3 and 4

```
  1 E   R   K   C   C   V   E   C   P   P   C   P   A   P   P   V   A   G   P   S
  1 GAGCGCAAATGTTGTGTCGAGTGCCCACCGTGCCCAGCACCACCTGTGGCAGGACCGTCA

21 V   F   L   F   P   P   K   P   K   D   T   L   M   I   S   R   T   P   E   V
 61 GTCTTCCTCTTCCCCCCAAAACCCAAGGACACCCTCATGATCTCCCGGACCCCTGAGGTC

41 T   C   V   V   V   D   V   S   H   E   D   P   E   V   Q   F   N   W   Y   V
121 ACGTGCGTGGTGGTGGACGTGAGCCACGAAGACCCCGAGGTCCAGTTCAACTGGTACGTG

61 D   G   V   E   V   H   N   A   K   T   K   P   R   E   E   Q   F   N   S   T
181 GACGGCGTGGAGGTGCATAATGCCAAGACAAAGCCACGGGAGGAGCAGTTCAACAGCACG

81 F   R   V   V   S   V   L   T   V   V   H   Q   D   W   L   N   G   K   E   Y
241 TTCCGTGTGGTCAGCGTCCTCACCGTTGTGCACCAGGACTGGCTGAACGGCAAGGAGTAC

101 K   C   K   V   S   N   K   G   L   P   A   P   I   E   K   T   I   S   K   T
301 AAGTGCAAGGTCTCCAACAAAGGCCTCCCAGCCCCCATCGAGAAAACCATCTCCAAAACC

121 K   G   Q   P   R   E   P   Q   V   Y   T   L   P   P   S   R   E   E   M   T
361 AAAGGGCAGCCCCGAGAACCACAGGTGTACACCCTGCCCCCATCCCGGGAGGAGATGACC

141 K   N   Q   V   S   L   T   C   L   V   K   G   F   Y   P   S   D   I   A   V
421 AAGAACCAGGTCAGCCTGACCTGCCTGGTCAAAGGCTTCTACCCCAGCGACATCGCCGTG

161 E   W   E   S   N   G   Q   P   E   N   N   Y   K   T   T   P   P   M   L   D
481 GAGTGGGAGAGCAATGGGCAGCCGGAGAACAACTACAAGACCACACCTCCCATGCTGGAC

181 S   D   G   S   F   F   L   Y   S   K   L   T   V   D   K   S   R   W   Q   Q
541 TCCGACGGCTCCTTCTTCCTCTACAGCAAGCTCACCGTGGACAAGAGCAGGTGGCAGCAG

201 G   N   V   F   S   C   S   V   M   H   E   A   L   H   N   H   Y   T   Q   K
601 GGGAACGTCTTCTCATGCTCCGTGATGCATGAGGCTCTGCACAACCACTACACGCAGAAG

221 S   L   S   L   S   P   G   K
661 AGCCTCTCCCTGTCTCCGGGTAAA
```

FIG. 15C

IgG3 Fc fragment SEQ ID NO: 5 and 6

```
  1 E   L   K   T   P   L   G   D   T   T   H   T   C   P   R   C   P   E   P   K
  1 GAGCTCAAAACCCCACTTGGTGACACAACTCACACATGCCCACGGTGCCCAGAGCCCAAA

21 S   C   D   T   P   P   P   C   P   R   C   P   E   P   K   S   C   D   T   P
 61 TCTTGTGACACACCTCCCCCGTGCCCACGGTGCCCAGAGCCCAAATCTTGTGACACACCT

41 P   P   C   P   R   C   P   E   P   K   S   C   D   T   P   P   P   C   P   R
121 CCCCCATGCCCACGGTGCCCAGAGCCCAAATCTTGTGACACACCTCCCCCATGCCCACGG

61 C   P   A   P   E   L   L   G   G   P   S   V   F   L   F   P   P   K   P   K
181 TGCCCAGCACCTGAACTCCTGGGAGGACCGTCAGTCTTCCTCTTCCCCCCAAAACCCAAG

81 D   T   L   M   I   S   R   T   P   E   V   T   C   V   V   V   D   V   S   H
241 GATACCCTTATGATTTCCCGGACCCCTGAGGTCACGTGCGTGGTGGTGGACGTGAGCCAC

101 E   D   P   E   V   Q   F   K   W   Y   V   D   G   V   E   V   H   N   A   K
301 GAAGACCCCGAGGTCCAGTTCAAGTGGTACGTGGACGGCGTGGAGGTGCATAATGCCAAG

121 T   K   P   R   E   E   Q   F   N   S   T   F   R   V   V   S   V   L   T   V
361 ACAAAGCCGCGGGAGGAGCAGTTCAACAGCACGTTCCGTGTGGTCAGCGTCCTCACCGTC

141 L   H   Q   D   W   L   N   G   K   E   Y   K   C   K   V   S   N   K   A   L
421 CTGCACCAGGACTGGCTGAACGGCAAGGAGTACAAGTGCAAGGTCTCCAACAAAGCCCTC

161 P   A   P   I   E   K   T   I   S   K   T   K   G   Q   P   R   E   P   Q   V
481 CCAGCCCCCATCGAGAAAACCATCTCCAAAACCAAAGGACAGCCCCGAGAACCACAGGTG

181 Y   T   L   P   P   S   R   E   E   M   T   K   N   Q   V   S   L   T   C   L
541 TACACCCTGCCCCCATCCCGGGAGGAGATGACCAAGAACCAGGTCAGCCTGACCTGCCTG

201 V   K   G   F   Y   P   S   D   I   A   V   E   W   E   S   S   G   Q   P   E
601 GTCAAAGGCTTCTACCCCAGCGACATCGCCGTGGAGTGGGAGAGCAGCGGGCAGCCGGAG

221 N   N   Y   N   T   T   P   P   M   L   D   S   D   G   S   F   F   L   Y   S
661 AACAACTACAACACCACGCCTCCCATGCTGGACTCCGACGGCTCCTTCTTCCTCTACAGC

241 K   L   T   V   D   K   S   R   W   Q   Q   G   N   I   F   S   C   S   V   M
721 AAGCTCACCGTGGACAAGAGCAGGTGGCAGCAGGGGAACATCTTCTCATGCTCCGTGATG

261 H   E   A   L   H   N   R   F   T   Q   K   S   L   S   L   S   P   G   K
781 CATGAGGCTCTGCACAACCGCTTCACGCAGAAGAGCCTCTCCCTGTCTCCGGGTAAA
```

FIG. 15D

IgG4 Fc fragment SEQ ID NO: 7 and 8

```
  1 E   S   K   Y   G   P   P   C   P   S   C   P   A   P   E   F   L   G   G   P
  1 GAGTCCAAATATGGTCCCCCGTGCCCATCATGCCCAGCACCTGAGTTCCTGGGGGGACCA

21 S   V   F   L   F   P   P   K   P   K   D   T   L   M   I   S   R   T   P   E
 61 TCAGTCTTCCTGTTCCCCCCAAAACCCAAGGACACTCTCATGATCTCCCGGACCCCTGAG

41 V   T   C   V   V   V   D   V   S   Q   E   D   P   E   V   Q   F   N   W   Y
121 GTCACGTGCGTGGTGGTGGACGTGAGCCAGGAAGACCCCGAGGTCCAGTTCAACTGGTAC

61 V   D   G   V   E   V   H   N   A   K   T   K   P   R   E   E   Q   F   N   S
181 GTGGATGGCGTGGAGGTGCATAATGCCAAGACAAAGCCGCGGGAGGAGCAGTTCAACAGC

81 T   Y   R   V   V   S   V   L   T   V   V   H   Q   D   W   L   N   G   K   E
241 ACGTACCGTGTGGTCAGCGTCCTCACCGTCGTGCACCAGGACTGGCTGAACGGCAAGGAG

101 Y   K   C   K   V   S   N   K   G   L   P   S   S   I   E   K   T   I   S   K
301 TACAAGTGCAAGGTCTCCAACAAAGGCCTCCCGTCCTCCATCGAGAAAACCATCTCCAAA

121 A   K   G   Q   P   R   E   P   Q   V   Y   T   L   P   P   S   Q   E   E   M
361 GCCAAAGGGCAGCCCCGAGAGCCACAGGTGTACACCCTGCCCCCATCCCAGGAGGAGATG

141 T   K   N   Q   V   S   L   T   C   L   V   K   G   F   Y   P   S   D   I   A
421 ACCAAGAACCAGGTCAGCCTGACCTGCCTGGTCAAAGGCTTCTACCCCAGCGACATCGCC

161 V   E   W   E   S   N   G   Q   P   E   N   N   Y   K   T   T   P   P   V   L
481 GTGGAGTGGGAGAGCAATGGGCAGCCGGAGAACAACTACAAGACCACGCCTCCCGTGCTG

181 D   S   D   G   S   F   F   L   Y   S   R   L   T   V   D   K   S   R   W   Q
541 GACTCCGACGGCTCCTTCTTCCTCTACAGCAGGCTAACCGTGGACAAGAGCAGGTGGCAG

201 E   G   N   V   F   S   C   S   V   M   H   E   A   L   H   N   H   Y   T   Q
601 GAGGGGAATGTCTTCTCATGCTCCGTGATGCATGAGGCTCTGCACAACCACTACACGCAG

221 K   S   L   S   L   S   L   G   K
661 AAGAGCCTCTCCCTGTCTCTGGGTAAA
```

FIG. 16

IgK/IgG1 Fc fragment/IgG1 Fc fragment - SEQ ID NO:17 and 18

```
                                                    M   E   T   D   T   L
  1 GTCAGTTAAGCTTGGTACCGAGCTCGGATCCAGTACCCTTCACCATGGAGACAGACACAC
            HindIII          BamHI
                 KpnI 21   L   L   W   V   L   L   L   W   V   P   G   S   T   G   D   A   A   D   I   Q
 61 TCCTGCTATGGGTACTGCTGCTCTGGGTTCCAGGTTCCACTGGTGACGCGGCAGATATCC
                                                              EcoRV 41   H   S   G   R   S   S   E   P   K   S   C   D   K   T   H   T   C   P   P
121 AGCACAGTGGCGGCCGCTCGAGTGAGCCCAAATCTTGTGACAAAACTCACACATGCCCAC
              NotI   XhoI 61   C   P   A   P   E   L   L   G   G   P   S   V   F   L   F   P   P   K   P   K
181 CGTGCCCAGCACCTGAACTCCTGGGGGGACCGTCAGTCTTCCTCTTCCCCCCAAAACCCA 81   D   T   L   M   I   S   R   T   P   E   V   T   C   V   V   V   D   V   S   H
241 AGGACACCCTCATGATCTCCCGGACCCCTGAGGTCACATGCGTGGTGGTGGACGTGAGCC 101   E   D   P   E   V   K   F   N   W   Y   V   D   G   V   E   V   H   N   A   K
301 ACGAAGACCCTGAGGTCAAGTTCAACTGGTACGTGGACGGCGTGGAGGTGCATAATGCCA 121   T   K   P   R   E   E   Q   Y   N   S*  T   Y   R   V   V   S   V   L   T   V
361 AGACAAAGCCGCGGGAGGAGCAGTACAACAGCACGTACCGGGTGGTCAGCGTCCTCACCG 141   L   H   Q   D   W   L   N   G   K   E   Y   K   C   K   V   S   N   K   A   L
421 TCCTGCACCAGGACTGGCTGAATGGCAAGGAGTACAAGTGCAAGGTCTCCAACAAAGCCC 161   P   A   P   I   E   K*  T   I   S   K   A   K   G   Q   P   R   E   P   Q   V
481 TCCCAGCCCCCATCGAGAAAACCATCTCCAAAGCCAAAGGGCAGCCCCGAGAACCACAGG 181   Y   T   L   P   P   S   R   D   E   L   T   K   N   Q   V   S   L   T   C   L
541 TGTACACCCTGCCCCCATCCCGGGATGAGCTGACCAAGAACCAGGTCAGCCTGACCTGCC 201   V   K   G   F   Y   P   S   D   I   A   V   E   W   E   S   N   G   Q   P   E
601 TGGTCAAAGGCTTCTATCCCAGCGACATCGCCGTGGAGTGGGAGAGCAATGGGCAGCCGG 221   N   N   Y   K   T   T   P   P   V   L   D   S   D   G   S   F   F   L   Y   S
661 AGAACAACTACAAGACCACGCCTCCCGTGCTGGACTCCGACGGCTCCTTCTTCCTCTACA 241   K   L   T   V   D   K   S   R   W   Q   Q   G   N   V   F   S   C   S   V   M
721 GCAAGCTCACCGTGGACAAGAGCAGGTGGCAGCAGGGGAACGTCTTCTCATGCTCCGTGA 261   H   E   A   L   H   N   H   Y   T   Q   K   S   L   S   L   S   P   G   K   S
781 TGCATGAGGCTCTGCACAACCACTACACGCAGAAGAGCCTCTCCCTGTCTCCGGGTAAAA 281   L   D   P   K   S   C   D   K   T   H   T   C   P   P   C   P   A   P   E   L
841 GTCTAGACCCCAAATCTTGTGACAAAACTCACACATGCCCACCGTGCCCAGCACCTGAAC
        XbaI 301   L   G   G   P   S   V   F   L   F   P   P   K   P   K   D   T   L   M   I   S
901 TCCTGGGGGGACCGTCAGTCTTCCTCTTCCCCCCAAAACCCAAGGACACCCTCATGATCT 321   R   T   P   E   V   T   C   V   V   V   D   V   S   H   E   D   P   E   V   K
961 CCCGGACCCCTGAGGTCACATGCGTGGTGGTGGACGTGAGCCACGAAGACCCTGAGGTCA
```

FIG. 16 Continued

```
341  F  N  W  Y  V  D  G  V  E  V  H  N  A  K  T  K  P  R  E  E
1021 AGTTCAACTGGTACGTGGACGGCGTGGAGGTGCATAATGCCAAGACAAAGCCGCGGGAGG

361  Q  Y  N  S  T  Y  R  V  V  S  V  L  T  V  L  H  Q  D  W  L
1081 AGCAGTACAACAGCACGTACCGGGTGGTCAGCGTCCTCACCGTCCTGCACCAGGACTGGC

381  N  G  K  E  Y  K  C  K  V  S  N  K  A  L  P  A  P  I  E  K
1141 TGAATGGCAAGGAGTACAAGTGCAAGGTCTCCAACAAAGCCCTCCCAGCCCCCATCGAGA

401  T  I  S  K  A  K  G  Q  P  R  E  P  Q  V  Y  T  L  P  P  S
1201 AAACCATCTCCAAAGCCAAAGGGCAGCCCCGAGAACCACAGGTGTACACCCTGCCCCCAT

421  R  D  E  L  T  K  N  Q  V  S  L  T  C  L  V  K  G  F  Y  P
1261 CCCGGGATGAGCTGACCAAGAACCAGGTCAGCCTGACCTGCCTGGTCAAAGGCTTCTATC

441  S  D  I  A  V  E  W  E  S  N  G  Q  P  E  N  N  Y  K  T  T
1321 CCAGCGACATCGCCGTGGAGTGGGAGAGCAATGGGCAGCCGGAGAACAACTACAAGACCA

461  P  P  V  L  D  S  D  G  S  F  F  L  Y  S  K  L  T  V  D  K
1381 CGCCTCCCGTGCTGGACTCCGACGGCTCCTTCTTCCTCTACAGCAAGCTCACCGTGGACA

481  S  R  W  Q  Q  G  N  V  F  S  C  S  V  M  H  E  A  L  H  N
1441 AGAGCAGGTGGCAGCAGGGGAACGTCTTCTCATGCTCCGTGATGCATGAGGCTCTGCACA

501  H  Y  T  Q  K  S  L  S  L  S  P  G  K  T  G  *
1501 ACCACTACACGCAGAAGAGCCTCTCCCTGTCTCCGGGTAAAACCGGTTGACATCATCACC

1561 ATCACCATTGATGAGTTAAACCCGCTGA
```

Figure 17

IgG1 monomer - SEQ ID NO:19 and 20

RestEnzSites-IgK signal-RestEnzSites-IgG1(Hinge-CH2-CH3)-
RestEnzSites- epitope tags(V5 and His)-STOP

```
  1                                           M   E   T   D   T   L
  1 GTCAGTTAAGCTTGGTACCGAGCTCGGATCCAGTACCCTTCACCATGGAGACAGACACAC
           HindIII            BamHI
                 KpnI 21     L   L   W   V   L   L   W   V   P   G   S   T   G   D   A   A   D   I   Q
 61 TCCTGCTATGGGTACTGCTGCTCTGGGTTCCAGGTTCCACTGGTGACGCGGCAGATATCC
                                                                 EcoRV 41    H   S   G   G   R   S   S   E   P   K   S   C   D   K   T   H   T   C   P   P
121 AGCACAGTGGCGGCCGCTCGAGTGAGCCCAAATCTTGTGACAAAACTCACACATGCCCAC
               NotI    XhoI 61    C   P   A   P   E   L   L   G   G   P   S   V   F   L   F   P   P   K   P   K
181 CGTGCCCAGCACCTGAACTCCTGGGGGGACCGTCAGTCTTCCTCTTCCCCCCAAAACCCA 81    D   T   L   M   I   S   R   T   P   E   V   T   C   V   V   V   D   V   S   H
241 AGGACACCCTCATGATCTCCCGGACCCCTGAGGTCACATGCGTGGTGGTGGACGTGAGCC 101    E   D   P   E   V   K   F   N   W   Y   V   D   G   V   E   V   H   N   A   K
301 ACGAAGACCCTGAGGTCAAGTTCAACTGGTACGTGGACGGCGTGGAGGTGCATAATGCCA 121    T   K   P   R   E   E   Q   Y   N   S   T   Y   R   V   V   S   V   L   T   V
361 AGACAAAGCCGCGGGAGGAGCAGTACAACAGCACGTACCGGGTGGTCAGCGTCCTCACCG 141    L   H   Q   D   W   L   N   G   K   E   Y   K   C   K   V   S   N   K   A   L
421 TCCTGCACCAGGACTGGCTGAATGGCAAGGAGTACAAGTGCAAGGTCTCCAACAAAGCCC 161    P   A   P   I   E   K   T   I   S   K   A   K   G   Q   P   R   E   P   Q   V
481 TCCCAGCCCCCATCGAGAAAACCATCTCCAAAGCCAAAGGGCAGCCCCGAGAACCACAGG 181    Y   T   L   P   P   S   R   D   E   L   T   K   N   Q   V   S   L   T   C   L
541 TGTACACCCTGCCCCCATCCCGGGATGAGCTGACCAAGAACCAGGTCAGCCTGACCTGCC 201    V   K   G   F   Y   P   S   D   I   A   V   E   W   E   S   N   G   Q   P   E
601 TGGTCAAAGGCTTCTATCCCAGCGACATCGCCGTGGAGTGGGAGAGCAATGGGCAGCCGG 221    N   N   Y   K   T   T   P   P   V   L   D   S   D   G   S   F   F   L   Y   S
661 AGAACAACTACAAGACCACGCCTCCCGTGCTGGACTCCGACGGCTCCTTCTTCCTCTACA 241    K   L   T   V   D   K   S   R   W   Q   Q   G   N   V   F   S   C   S   V   M
721 GCAAGCTCACCGTGGACAAGAGCAGGTGGCAGCAGGGGAACGTCTTCTCATGCTCCGTGA 261    H   E   A   L   H   N   H   Y   T   Q   K   S   L   S   L   S   P   G   K   S
781 TGCATGAGGCTCTGCACAACCACTACACGCAGAAGAGCCTCTCCCTGTCTCCGGGTAAAA 281    L   E   G   P   R   F   E   G   K   P   I   P   N   P   L   L   G   L   D   S
841 GTCTAGAGGGCCCGCGGTTCGAAGGTAAGCCTATCCCTAACCCTCTCCTCGGTCTCGATT
        XbaI            BstBI 301    T   R   T   G   H   H   H   H   H   H
901 CTACGCGTACCGGTCATCATCACCATCACCATTGATGAGTTAAACCCGCTGA
              AgeI
```

FIG. 18

IgG1 dimer sequence without tags - SEQ ID NO:21 and 22

RestEnzSites-IgK signal-RestEnzSites-IgG1(Hinge-CH2-CH3)-XbaI site-
IgG1(Hinge-CH2-CH3)-STOP

```
  1                                          M   E   T   D   T   L
  1 GTCAGTTAAGCTTGGTACCGAGCTCGGATCCAGTACCCTTCACCATGGAGACAGACACAC
            HindIII              BamHI
                KpnI 21   L   L   W   V   L   L   L   W   V   P   G   S   T   G   D   A   A   D   I   Q
 61 TCCTGCTATGGGTACTGCTGCTCTGGGTTCCAGGTTCCACTGGTGACGCGGCAGATATCC
                                                                        EcoRV 41   H   S   G   G   R   S   S   E   P   K   S   C   D   K   T   H   T   C   P   P
121 AGCACAGTGGCGGCCGCTCGAGTGAGCCCAAATCTTGTGACAAAACTCACACATGCCCAC
              NotI   XhoI 61   C   P   A   P   E   L   L   G   G   P   S   V   F   L   F   P   P   K   P   K
181 CGTGCCCAGCACCTGAACTCCTGGGGGGACCGTCAGTCTTCCTCTTCCCCCCAAAACCCA 81   D   T   L   M   I   S   R   T   P   E   V   T   C   V   V   V   D   V   S   H
241 AGGACACCCTCATGATCTCCCGGACCCCTGAGGTCACATGCGTGGTGGTGGACGTGAGCC 101   E   D   P   E   V   K   F   N   W   Y   V   D   G   V   E   V   H   N   A   K
301 ACGAAGACCCTGAGGTCAAGTTCAACTGGTACGTGGACGGCGTGGAGGTGCATAATGCCA 121   T   K   P   R   E   E   Q   Y   N   S   T   Y   R   V   V   S   V   L   T   V
361 AGACAAAGCCGCGGGAGGAGCAGTACAACAGCACGTACCGGGTGGTCAGCGTCCTCACCG 141   L   H   Q   D   W   L   N   G   K   E   Y   K   C   K   V   S   N   K   A   L
421 TCCTGCACCAGGACTGGCTGAATGGCAAGGAGTACAAGTGCAAGGTCTCCAACAAAGCCC 161   P   A   P   I   E   K   T   I   S   K   A   K   G   Q   P   R   E   P   Q   V
481 TCCCAGCCCCCATCGAGAAAACCATCTCCAAAGCCAAAGGGCAGCCCCGAGAACCACAGG 181   Y   T   L   P   P   S   R   D   E   L   T   K   N   Q   V   S   L   T   C   L
541 TGTACACCCTGCCCCCATCCCGGGATGAGCTGACCAAGAACCAGGTCAGCCTGACCTGCC 201   V   K   G   F   Y   P   S   D   I   A   V   E   W   E   S   N   G   Q   P   E
601 TGGTCAAAGGCTTCTATCCCAGCGACATCGCCGTGGAGTGGGAGAGCAATGGGCAGCCGG 221   N   N   Y   K   T   T   P   P   V   L   D   S   D   G   S   F   F   L   Y   S
661 AGAACAACTACAAGACCACGCCTCCCGTGCTGGACTCCGACGGCTCCTTCTTCCTCTACA 241   K   L   T   V   D   K   S   R   W   Q   Q   G   N   V   F   S   C   S   V   M
721 GCAAGCTCACCGTGGACAAGAGCAGGTGGCAGCAGGGGAACGTCTTCTCATGCTCCGTGA 261   H   E   A   L   H   N   H   Y   T   Q   K   S   L   S   L   S   P   G   K   S
781 TGCATGAGGCTCTGCACAACCACTACACGCAGAAGAGCCTCTCCCTGTCTCCGGGTAAAA 281   L   D   P   K   S   C   D   K   T   H   T   C   P   P   C   P   A   P   E   L
841 GTCTAGACCCCAAATCTTGTGACAAAACTCACACATGCCCACCGTGCCCAGCACCTGAAC
        XbaI 301   L   G   G   P   S   V   F   L   F   P   P   K   P   K   D   T   L   M   I   S
901 TCCTGGGGGGACCGTCAGTCTTCCTCTTCCCCCCAAAACCCAAGGACACCCTCATGATCT 321   R   T   P   E   V   T   C   V   V   V   D   V   S   H   E   D   P   E   V   K
```

FIG. 18 Continued

```
 961 CCCGGACCCCTGAGGTCACATGCGTGGTGGTGGACGTGAGCCACGAAGACCCTGAGGTCA

341       F  N  W  Y  V  D  G  V  E  V  H  N  A  K  T  K  P  R  E  E
1021 AGTTCAACTGGTACGTGGACGGCGTGGAGGTGCATAATGCCAAGACAAAGCCGCGGGAGG

361       Q  Y  N  S  T  Y  R  V  V  S  V  L  T  V  L  H  Q  D  W  L
1081 AGCAGTACAACAGCACGTACCGGGTGGTCAGCGTCCTCACCGTCCTGCACCAGGACTGGC

381       N  G  K  E  Y  K  C  K  V  S  N  K  A  L  P  A  P  I  E  K
1141 TGAATGGCAAGGAGTACAAGTGCAAGGTCTCCAACAAAGCCCTCCCAGCCCCCATCGAGA

401       T  I  S  K  A  K  G  Q  P  R  E  P  Q  V  Y  T  L  P  P  S
1201 AAACCATCTCCAAAGCCAAAGGGCAGCCCCGAGAACCACAGGTGTACACCCTGCCCCCAT

421       R  D  E  L  T  K  N  Q  V  S  L  T  C  L  V  K  G  F  Y  P
1261 CCCGGGATGAGCTGACCAAGAACCAGGTCAGCCTGACCTGCCTGGTCAAAGGCTTCTATC

441       S  D  I  A  V  E  W  E  S  N  G  Q  P  E  N  N  Y  K  T  T
1321 CCAGCGACATCGCCGTGGAGTGGGAGAGCAATGGGCAGCCGGAGAACAACTACAAGACCA

461       P  P  V  L  D  S  D  G  S  F  F  L  Y  S  K  L  T  V  D  K
1381 CGCCTCCCGTGCTGGACTCCGACGGCTCCTTCTTCCTCTACAGCAAGCTCACCGTGGACA

481       S  R  W  Q  Q  G  N  V  F  S  C  S  V  M  H  E  A  L  H  N
1441 AGAGCAGGTGGCAGCAGGGGAACGTCTTCTCATGCTCCGTGATGCATGAGGCTCTGCACA

501       H  Y  T  Q  K  S  L  S  L  S  P  G  K  T  G
1501 ACCACTACACGCAGAAGAGCCTCTCCCTGTCTCCGGGTAAAACCGGTTGACATCATCACC

1561 ATCACCATTGATGAGTTAAACCCGCTGA
```

FIG. 19

IgG1 dimer sequence with epitope tags - SEQ ID NO:23 and 24

RestEnzSites-IgK signal-RestEnzSites-IgG1(Hinge-CH2-CH3)-XbaI site-
IgG1(Hinge-CH2-CH3)-RestEnzSites-epitope tags(V5 and His)-STOP

```
  1                                                    M   E   T   D   T   L
  1 GTCAGTTAAGCTTGGTACCGAGCTCGGATCCAGTACCCTTCACCATGGAGACAGACACAC
             HindIII              BamHI
                 KpnI 21   L   L   W   V   L   L   L   W   V   P   G   S   T   G   D   A   A   D   I   Q
 61 TCCTGCTATGGGTACTGCTGCTCTGGGTTCCAGGTTCCACTGGTGACGCGGCAGATATCC
                                                               EcoRV 41   H   S   G   G   R   S   S   E   P   K   S   C   D   K   T   H   T   C   P   P
121 AGCACAGTGGCGGCCGCTCGAGTGAGCCCAAATCTTGTGACAAAACTCACACATGCCCAC
              NotI   XhoI 61   C   P   A   P   E   L   L   G   G   P   S   V   F   L   F   P   P   K   P   K
181 CGTGCCCAGCACCTGAACTCCTGGGGGGACCGTCAGTCTTCCTCTTCCCCCCAAAACCCA 81   D   T   L   M   I   S   R   T   P   E   V   T   C   V   V   V   D   V   S   H
241 AGGACACCCTCATGATCTCCCGGACCCCTGAGGTCACATGCGTGGTGGTGGACGTGAGCC 101   E   D   P   E   V   K   F   N   W   Y   V   D   G   V   E   V   H   N   A   K
301 ACGAAGACCCTGAGGTCAAGTTCAACTGGTACGTGGACGGCGTGGAGGTGCATAATGCCA 121   T   K   P   R   E   E   Q   Y   N   S   T   Y   R   V   V   S   V   L   T   V
361 AGACAAAGCCGCGGGAGGAGCAGTACAACAGCACGTACCGGGTGGTCAGCGTCCTCACCG 141   L   H   Q   D   W   L   N   G   K   E   Y   K   C   K   V   S   N   K   A   L
421 TCCTGCACCAGGACTGGCTGAATGGCAAGGAGTACAAGTGCAAGGTCTCCAACAAAGCCC 161   P   A   P   I   E   K   T   I   S   K   A   K   G   Q   P   R   E   P   Q   V
481 TCCCAGCCCCCATCGAGAAAACCATCTCCAAAGCCAAAGGGCAGCCCCGAGAACCACAGG 181   Y   T   L   P   P   S   R   D   E   L   T   K   N   Q   V   S   L   T   C   L
541 TGTACACCCTGCCCCCATCCCGGGATGAGCTGACCAAGAACCAGGTCAGCCTGACCTGCC 201   V   K   G   F   Y   P   S   D   I   A   V   E   W   E   S   N   G   Q   P   E
601 TGGTCAAAGGCTTCTATCCCAGCGACATCGCCGTGGAGTGGGAGAGCAATGGGCAGCCGG 221   N   N   Y   K   T   T   P   P   V   L   D   S   D   G   S   F   F   L   Y   S
661 AGAACAACTACAAGACCACGCCTCCCGTGCTGGACTCCGACGGCTCCTTCTTCCTCTACA 241   K   L   T   V   D   K   S   R   W   Q   Q   G   N   V   F   S   C   S   V   M
721 GCAAGCTCACCGTGGACAAGAGCAGGTGGCAGCAGGGGAACGTCTTCTCATGCTCCGTGA 261   H   E   A   L   H   N   H   Y   T   Q   K   S   L   S   L   S   P   G   K   S
781 TGCATGAGGCTCTGCACAACCACTACACGCAGAAGAGCCTCTCCCTGTCTCCGGGTAAAA 281   L   D   P   K   S   C   D   K   T   H   T   C   P   P   C   P   A   P   E   L
841 GTCTAGACCCCAAATCTTGTGACAAAACTCACACATGCCCACCGTGCCCAGCACCTGAAC
       XbaI 301   L   G   G   P   S   V   F   L   F   P   P   K   P   K   D   T   L   M   I   S
901 TCCTGGGGGGACCGTCAGTCTTCCTCTTCCCCCCAAAACCCAAGGACACCCTCATGATCT
```

FIG. 20A

FcgRIIIa (F at 176) SEQ ID NO: 31 and 32

```
ATGTGGCAGCTGCTCCTCCCAACTGCTCTGCTACTTCTAGTTTCAGCTGGCATGCGGACT
 M  W  Q  L  L  L  P  T  A  L  L  L  L  V  S  A  G  M  R  T
GAAGATCTCCCAAAGGCTGTGGTGTTCCTGGAGCCTCAATGGTACAGGGTGCTCGAGAAG
 E  D  L  P  K  A  V  V  F  L  E  P  Q  W  Y  R  V  L  E  K
GACAGTGTGACTCTGAAGTGCCAGGGAGCCTACTCCCCTGAGGACAATTCCACACAGTGG
 D  S  V  T  L  K  C  Q  G  A  Y  S  P  E  D  N  S  T  Q  W
TTTCACAATGAGAGCCTCATCTCAAGCCAGGCCTCGAGCTACTTCATTGACGCTGCCACA
 F  H  N  E  S  L  I  S  S  Q  A  S  S  Y  F  I  D  A  A  T
GTCGACGACAGTGGAGAGTACAGGTGCCAGACAAACCTCTCCACCCTCAGTGACCCGGTG
 V  D  D  S  G  E  Y  R  C  Q  T  N  L  S  T  L  S  D  P  V
CAGCTAGAAGTCCATATCGGCTGGCTGTTGCTCCAGGCCCCTCGGTGGGTGTTCAAGGAG
 Q  L  E  V  H  I  G  W  L  L  L  Q  A  P  R  W  V  F  K  E
GAAGACCCTATTCACCTGAGGTGTCACAGCTGGAAGAACACTGCTCTGCATAAGGTCACA
 E  D  P  I  H  L  R  C  H  S  W  K  N  T  A  L  H  K  V  T
TATTTACAGAATGGCAAAGGCAGGAAGTATTTTCATCATAATTCTGACTTCTACATTCCA
 Y  L  Q  N  G  K  G  R  K  Y  F  H  H  N  S  D  F  Y  I  P
AAAGCCACACTCAAAGACAGCGGCTCCTACTTCTGCAGGGGGCTTTTTGGGAGTAAAAAT
 K  A  T  L  K  D  S  G  S  Y  F  C  R  G  L  F G  S  K  N
GTGTCTTCAGAGACTGTGAACATCACCATCACTCAAGGTTTG cat cat cac cat cat
 V  S  S  E  T  V  N  I  T  I  T  Q  G  L   h   h   h   h   h
cat TAG
 h   *
```

FIG. 20B

FcgRIIIa (V at 176) SEQ ID NO: 33 and 34

```
ATGTGGCAGCTGCTCCTCCCAACTGCTCTGCTACTTCTAGTTTCAGCTGGCATGCGGACT
 M  W  Q  L  L  L  P  T  A  L  L  L  L  V  S  A  G  M  R  T
GAAGATCTCCCAAAGGCTGTGGTGTTCCTGGAGCCTCAATGGTACAGGGTGCTCGAGAAG
 E  D  L  P  K  A  V  V  F  L  E  P  Q  W  Y  R  V  L  E  K
GACAGTGTGACTCTGAAGTGCCAGGGAGCCTACTCCCCTGAGGACAATTCCACACAGTGG
 D  S  V  T  L  K  C  Q  G  A  Y  S  P  E  D  N  S  T  Q  W
TTTCACAATGAGAGCCTCATCTCAAGCCAGGCCTCGAGCTACTTCATTGACGCTGCCACA
 F  H  N  E  S  L  I  S  S  Q  A  S  S  Y  F  I  D  A  A  T
GTCGACGACAGTGGAGAGTACAGGTGCCAGACAAACCTCTCCACCCTCAGTGACCCGGTG
 V  D  D  S  G  E  Y  R  C  Q  T  N  L  S  T  L  S  D  P  V
CAGCTAGAAGTCCATATCGGCTGGCTGTTGCTCCAGGCCCCTCGGTGGGTGTTCAAGGAG
 Q  L  E  V  H  I  G  W  L  L  L  Q  A  P  R  W  V  F  K  E
GAAGACCCTATTCACCTGAGGTGTCACAGCTGGAAGAACACTGCTCTGCATAAGGTCACA
 E  D  P  I  H  L  R  C  H  S  W  K  N  T  A  L  H  K  V  T
TATTTACAGAATGGCAAAGGCAGGAAGTATTTTCATCATAATTCTGACTTCTACATTCCA
 Y  L  Q  N  G  K  G  R  K  Y  F  H  H  N  S  D  F  Y  I  P
AAAGCCACACTCAAAGACAGCGGCTCCTACTTCTGCAGGGGGCTTGTTGGGAGTAAAAAT
 K  A  T  L  K  D  S  G  S  Y  F  C  R  G  L  V G  S  K  N
GTGTCTTCAGAGACTGTGAACATCACCATCACTCAAGGTTTG cat cat cac cat cat
 V  S  S  E  T  V  N  I  T  I  T  Q  G  L   h   h   h   h   h
cac TAG
 h   *
```

FIG. 21

IgG3/IgG1 dimer sequence with epitope tags - SEQ ID NO:25 and 26

RestEnzSites-IgK  signal-EcoRV  Site-IgG3(hinge-CH2-CH3)-IgG1(Hinge-CH2-CH3)-RestEnzSites-epitope tags(V5 and His)-STOP

```
  1                                              M   E   T   D   T   L
  1 GTCAGTTAAGCTTGGTACCGAGCTCGGATCCAGTACCCTTCACCATGGAGACAGACACAC
           HindIII          BamHI
                KpnI 21   L   L   W   V   L   L   L   W   V   P   G   S   T   G   D   A   A   D   I   E
 61 TCCTGCTATGGGTACTGCTGCTCTGGGTTCCAGGTTCCACTGGTGACGCGGCAGATATCG
                                                                       EcoRV 41   L   K   T   P   L   G   D   T   T   H   T   C   P   R   C   P   E   P   K   S
121 AGCTCAAAACCCCACTTGGTGACACAACTCACACATGCCCACGGTGCCCAGAGCCCAAAT 61   C   D   T   P   P   P   C   P   R   C   P   E   P   K   S   C   D   T   P   P
181 CTTGTGACACACCTCCCCCGTGCCCACGGTGCCCAGAGCCCAAATCTTGTGACACACCTC 81   P   C   P   R   C   P   E   P   K   S   C   D   T   P   P   P   C   P   R   C
241 CCCCATGCCCACGGTGCCCAGAGCCCAAATCTTGTGACACACCTCCCCCATGCCCACGGT 101   P   A   P   E   L   L   G   G   P   S   V   F   L   F   P   P   K   P   K   D
301 GCCCAGCACCTGAACTCCTGGGAGGACCGTCAGTCTTCCTCTTCCCCCCAAAACCCAAGG 121   T   L   M   I   S   R   T   P   E   V   T   C   V   V   V   D   V   S   H   E
361 ATACCCTTATGATTTCCCGGACCCCTGAGGTCACGTGCGTGGTGGTGGACGTGAGCCACG 141   D   P   E   V   Q   F   K   W   Y   V   D   G   V   E   V   H   N   A   K   T
421 AAGACCCCGAGGTCCAGTTCAAGTGGTACGTGGACGGCGTGGAGGTGCATAATGCCAAGA 161   K   P   R   E   E   Q   F   N   S   T   F   R   V   V   S   V   L   T   V   L
481 CAAAGCCGCGGGAGGAGCAGTTCAACAGCACGTTCCGTGTGGTCAGCGTCCTCACCGTCC 181   H   Q   D   W   L   N   G   K   E   Y   K   C   K   V   S   N   K   A   L   P
541 TGCACCAGGACTGGCTGAACGGCAAGGAGTACAAGTGCAAGGTCTCCAACAAAGCCCTCC 201   A   P   I   E   K   T   I   S   K   T   K   G   Q   P   R   E   P   Q   V   Y
601 CAGCCCCCATCGAGAAAACCATCTCCAAAACCAAAGGACAGCCCCGAGAACCACAGGTGT 221   T   L   P   P   S   R   E   E   M   T   K   N   Q   V   S   L   T   C   L   V
661 ACACCCTGCCCCCATCCCGGGAGGAGATGACCAAGAACCAGGTCAGCCTGACCTGCCTGG 241   K   G   F   Y   P   S   D   I   A   V   E   W   E   S   S   G   Q   P   E   N
721 TCAAAGGCTTCTACCCCAGCGACATCGCCGTGGAGTGGGAGAGCAGCGGGCAGCCGGAGA 261   N   Y   N   T   T   P   P   M   L   D   S   D   G   S   F   F   L   Y   S   K
781 ACAACTACAACACCACGCCTCCCATGCTGGACTCCGACGGCTCCTTCTTCCTCTACAGCA 281   L   T   V   D   K   S   R   W   Q   Q   G   N   I   F   S   C   S   V   M   H
841 AGCTCACCGTGGACAAGAGCAGGTGGCAGCAGGGGAACATCTTCTCATGCTCCGTGATGC 301   E   A   L   H   N   R   F   T   Q   K   S   L   S   L   S   P   G   K   G   G
901 ATGAGGCTCTGCACAACCGCTTCACGCAGAAGAGCCTCTCCCTGTCTCCGGGTAAAGGCG
```

FIG. 21 Continued

NotI

```
321    R   S   S   E   P   K   S   C   D   K   T   H   T   C   P   P   C   P   A   P
961  GCCGCTCGAGTGAGCCCAAATCTTGTGACAAAACTCACACATGCCCACCGTGCCCAGCAC
             XhoI

341    E   L   L   G   G   P   S   V   F   L   F   P   P   K   P   K   D   T   L   M
1021 CTGAACTCCTGGGGGGACCGTCAGTCTTCCTCTTCCCCCCAAAACCCAAGGACACCCTCA

361    I   S   R   T   P   E   V   T   C   V   V   V   D   V   S   H   E   D   P   E
1081 TGATCTCCCGGACCCCTGAGGTCACATGCGTGGTGGTGGACGTGAGCCACGAAGACCCTG

381    V   K   F   N   W   Y   V   D   G   V   E   V   H   N   A   K   T   K   P   R
1141 AGGTCAAGTTCAACTGGTACGTGGACGGCGTGGAGGTGCATAATGCCAAGACAAAGCCGC

401    E   E   Q   Y   N   S   T   Y   R   V   V   S   V   L   T   V   L   H   Q   D
1201 GGGAGGAGCAGTACAACAGCACGTACCGGGTGGTCAGCGTCCTCACCGTCCTGCACCAGG

421    W   L   N   G   K   E   Y   K   C   K   V   S   N   K   A   L   P   A   P   I
1261 ACTGGCTGAATGGCAAGGAGTACAAGTGCAAGGTCTCCAACAAAGCCCTCCCAGCCCCCA

441    E   K   T   I   S   K   A   K   G   Q   P   R   E   P   Q   V   Y   T   L   P
1321 TCGAGAAAACCATCTCCAAAGCCAAAGGGCAGCCCCGAGAACCACAGGTGTACACCCTGC

461    P   S   R   D   E   L   T   K   N   Q   V   S   L   T   C   L   V   K   G   F
1381 CCCCATCCCGGGATGAGCTGACCAAGAACCAGGTCAGCCTGACCTGCCTGGTCAAAGGCT

481    Y   P   S   D   I   A   V   E   W   E   S   N   G   Q   P   E   N   N   Y   K
1441 TCTATCCCAGCGACATCGCCGTGGAGTGGGAGAGCAATGGGCAGCCGGAGAACAACTACA

501    T   T   P   P   V   L   D   S   D   G   S   F   F   L   Y   S   K   L   T   V
1501 AGACCACGCCTCCCGTGCTGGACTCCGACGGCTCCTTCTTCCTCTACAGCAAGCTCACCG

521    D   K   S   R   W   Q   Q   G   N   V   F   S   C   S   V   M   H   E   A   L
1561 TGGACAAGAGCAGGTGGCAGCAGGGGAACGTCTTCTCATGCTCCGTGATGCATGAGGCTC

541    H   N   H   Y   T   Q   K   S   L   S   L   S   P   G   K   S   L   E   G   P
1621 TGCACAACCACTACACGCAGAAGAGCCTCTCCCTGTCTCCGGGTAAAAGTCTAGAGGGCC
                                                               XbaI

561    R   F   E   G   K   P   I   P   N   P   L   L   G   L   D   S   T   R   T   G
1681 CGCGGTTCGAAGGTAAGCCTATCCCTAACCCTCTCCTCGGTCTCGATTCTACGCGTACCG
            BstBI                                              AgeI

581    H   H   H   H   H   H   *
1741 GTCATCATCACCATCACCATTGA
```

FIG. 22

IgE (CH2)/IgG1 (hinge CH2 CH3)/IgG1 (Hinge CH2)-IgE(CH4) fusion without tags - SEQ ID NO:27 and 28

RestEnzSites-IgK signal-EcoRV Site-IgE(CH2)-IgG1(Hinge-CH2-CH3)-IgG1 (Hinge-CH2)-IgE(CH4)-STOP

```
  1                                            M   E   T   D   T   L
  1 GTCAGTTAAGCTTGGTACCGAGCTCGGATCCAGTACCCTTCACCATGGAGACAGACACAC
             HindIII          BamHI
               KpnI 21   L   L   W   V   L   L   L   W   V   P   G   S   T   G   D   A   A   D   I   V
 61 TCCTGCTATGGGTACTGCTGCTCTGGGTTCCAGGTTCCACTGGTGACGCGGCAGATATCG
                                                              EcoRV 41   C   S   R   D   F   T   P   P   T   V   K   I   L   Q   S   S   C   D   G   G
121 TCTGCTCCAGGGACTTCACCCCGCCCACCGTGAAGATCTTACAGTCGTCCTGCGACGGCG 61   G   H   F   P   P   T   I   Q   L   L   C   L   V   S   G   Y   T   P   G   T
181 GCGGGCACTTCCCCCCGACCATCCAGCTCCTGTGCCTCGTCTCTGGGTACACCCCAGGGA 81   I   N   I   T   W   L   E   D   G   Q   V   M   D   V   D   L   S   T   A   S
241 CTATCAACATCACCTGGCTGGAGGACGGGCAGGTCATGGACGTGGACTTGTCCACCGCCT 101   T   T   Q   E   G   E   L   A   S   T   Q   S   E   L   T   L   S   Q   K   H
301 CTACCACGCAGGAGGGTGAGCTGGCCTCCACACAAAGCGAGCTCACCCTCAGCCAGAAGC 121   W   L   S   D   R   T   Y   T   C   Q   V   T   Y   Q   G   H   T   F   E   D
361 ACTGGCTGTCAGACCGCACCTACACCTGCCAGGTCACCTATCAAGGTCACACCTTTGAGG 141   S   T   K   K   C   A   G   G   R   S   S   E   P   K   S   C   D   K   T   H
421 ACAGCACCAAGAAGTGTGCAGGCGGCCGCTCGAGTGAGCCCAAATCTTGTGACAAAACTC
                              NotI   XhoI 161   T   C   P   P   C   P   A   P   E   L   L   G   G   P   S   V   F   L   F   P
481 ACACATGCCCACCGTGCCCAGCACCTGAACTCCTGGGGGGACCGTCAGTCTTCCTCTTCC 181   P   K   P   K   D   T   L   M   I   S   R   T   P   E   V   T   C   V   V   V
541 CCCCAAAACCCAAGGACACCCTCATGATCTCCCGGACCCCTGAGGTCACATGCGTGGTGG 201   D   V   S   H   E   D   P   E   V   K   F   N   W   Y   V   D   G   V   E   V
601 TGGACGTGAGCCACGAAGACCCTGAGGTCAAGTTCAACTGGTACGTGGACGGCGTGGAGG 221   H   N   A   K   T   K   P   R   E   E   Q   Y   N   S   T   Y   R   V   V   S
661 TGCATAATGCCAAGACAAAGCCGCGGGAGGAGCAGTACAACAGCACGTACCGGGTGGTCA 241   V   L   T   V   L   H   Q   D   W   L   N   G   K   E   Y   K   C   K   V   S
721 GCGTCCTCACCGTCCTGCACCAGGACTGGCTGAATGGCAAGGAGTACAAGTGCAAGGTCT 261   N   K   A   L   P   A   P   I   E   K   T   I   S   K   A   K   G   Q   P   R
781 CCAACAAAGCCCTCCCAGCCCCCATCGAGAAAACCATCTCCAAAGCCAAAGGGCAGCCCC 281   E   P   Q   V   Y   T   L   P   P   S   R   D   E   L   T   K   N   Q   V   S
841 GAGAACCACAGGTGTACACCCTGCCCCCATCCCGGGATGAGCTGACCAAGAACCAGGTCA 301   L   T   C   L   V   K   G   F   Y   P   S   D   I   A   V   E   W   E   S   N
901 GCCTGACCTGCCTGGTCAAAGGCTTCTATCCCAGCGACATCGCCGTGGAGTGGGAGAGCA
```

FIG. 22 Continued

```
 321    G   Q   P   E   N   N   Y   K   T   T   P   P   V   L   D   S   D   G   S   F
 961  ATGGGCAGCCGGAGAACAACTACAAGACCACGCCTCCCGTGCTGGACTCCGACGGCTCCT

341    F   L   Y   S   K   L   T   V   D   K   S   R   W   Q   Q   G   N   V   F   S
1021  TCTTCCTCTACAGCAAGCTCACCGTGGACAAGAGCAGGTGGCAGCAGGGGAACGTCTTCT

361    C   S   V   M   H   E   A   L   H   N   H   Y   T   Q   K   S   L   S   L   S
1081  CATGCTCCGTGATGCATGAGGCTCTGCACAACCACTACACGCAGAAGAGCCTCTCCCTGT

381    P   G   K   S   L   D   P   K   S   C   D   K   T   H   T   C   P   P   C   P
1141  CTCCGGGTAAAAGTCTAGACCCCAAATCTTGTGACAAAACTCACACATGCCCACCGTGCC
                      XbaI

401    A   P   E   L   L   G   G   P   S   V   F   L   F   P   P   K   P   K   D   T
1201  CAGCACCTGAACTCCTGGGGGGACCGTCAGTCTTCCTCTTCCCCCCAAAACCCAAGGACA

421    L   M   I   S   R   T   P   E   V   T   C   V   V   V   D   V   S   H   E   D
1261  CCCTCATGATCTCCCGGACCCCTGAGGTCACATGCGTGGTGGTGGACGTGAGCCACGAAG

441    P   E   V   K   F   N   W   Y   V   D   G   V   E   V   H   N   A   K   T   K
1321  ACCCTGAGGTCAAGTTCAACTGGTACGTGGACGGCGTGGAGGTGCATAATGCCAAGACAA

461    P   R   E   E   Q   Y   N   S   T   Y   R   V   V   S   V   L   T   V   L   H
1381  AGCCGCGGGAGGAGCAGTACAACAGCACGTACCGGGTGGTCAGCGTCCTCACCGTCCTGC

481    Q   D   W   L   N   G   K   E   Y   K   C   K   V   S   N   K   A   L   P   A
1441  ACCAGGACTGGCTGAATGGCAAGGAGTACAAGTGCAAGGTCTCCAACAAAGCCCTCCCAG

501    P   I   E   K   T   I   S   K   A   K   G   Q   P   R   E   P   Q   V   Y   T
1501  CCCCCATCGAGAAAACCATCTCCAAAGCCAAAGGGCAGCCCCGAGAACCACAGGTGTACA

521    L   P   P   S   R   D   E   L   T   K   N   Q   V   S   L   T   C   L   V   K
1561  CCCTGCCCCCATCCCGGGATGAGCTGACCAAGAACCAGGTCAGCCTGACCTGCCTGGTCA

541    G   F   Y   P   S   D   I   A   V   E   W   E   S   N   G   Q   P   E   N   N
1621  AAGGCTTCTATCCCAGCGACATCGCCGTGGAGTGGGAGAGCAATGGGCAGCCGGAGAACA

561    Y   K   T   T   P   P   V   L   D   S   D   G   S   F   F   L   Y   S   K   L
1681  ACTACAAGACCACGCCTCCCGTGCTGGACTCCGACGGCTCCTTCTTCCTCTACAGCAAGC

581    T   V   D   K   S   R   W   Q   Q   G   N   V   F   S   C   S   V   M   H   E
1741  TCACCGTGGACAAGAGCAGGTGGCAGCAGGGGAACGTCTTCTCATGCTCCGTGATGCATG

601    A   L   H   N   H   Y   T   Q   K   S   L   S   L   S   P   G   K   G   P   R
1801  AGGCTCTGCACAACCACTACACGCAGAAGAGCCTCTCCCTGTCTCCGGGTAAAGGCCCGC

621    A   A   P   E   V   Y   A   F   A   T   P   E   W   P   G   S   R   D   K   R
1861  GTGCTGCCCCGGAAGTCTATGCGTTTGCGACGCCGGAGTGGCCGGGGAGCCGGGACAAGC

641    T   L   A   C   L   I   Q   N   F   M   P   E   D   I   S   V   Q   W   L   H
1921  GCACCCTCGCCTGCCTGATCCAGAACTTCATGCCTGAGGACATCTCGGTGCAGTGGCTGC

661    N   E   V   Q   L   P   D   A   R   H   S   T   T   Q   P   R   K   T   K   G
1981  ACAACGAGGTGCAGCTCCCGGACGCCCGGCACAGCACGACGCAGCCCCGCAAGACCAAGG

681    S   G   F   F   V   F   S   R   L   E   V   T   R   A   E   W   E   Q   K   D
2041  GCTCCGGCTTCTTCGTCTTCAGCCGCCTGGAGGTGACCAGGGCCGAATGGGAGCAGAAAG

701    E   F   I   C   R   A   V   H   E   A   A   S   P   S   Q   T   V   Q   R   A
2101  ATGAGTTCATCTGCCGTGCAGTCCATGAGGCAGCGAGCCCCTCACAGACCGTCCAGCGAG
```

FIG. 22 Continued

```
721  V   S   V   N   P   G   K
2161 CGGTGTCTGTAAATCCCGGTAAATGACATCATCACCATCACCATTGATGAGTTAAACCCG 741
2221 CTGA
```

Serial Stradomer

FIG. 23C
Core Stradomer
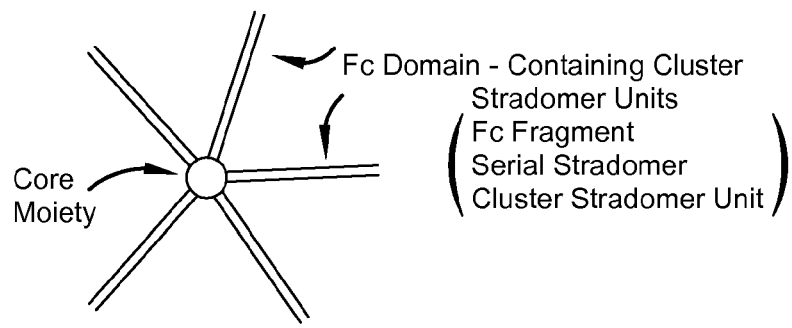
FIG. 23D
Cluster Stradomer
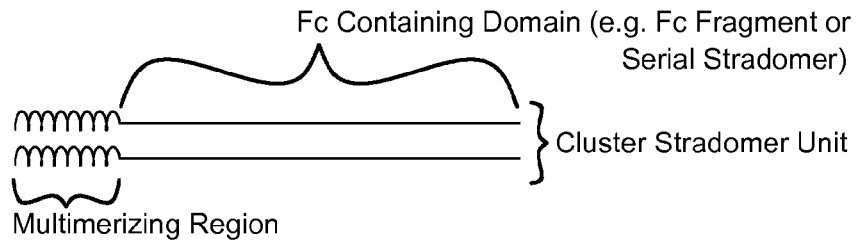
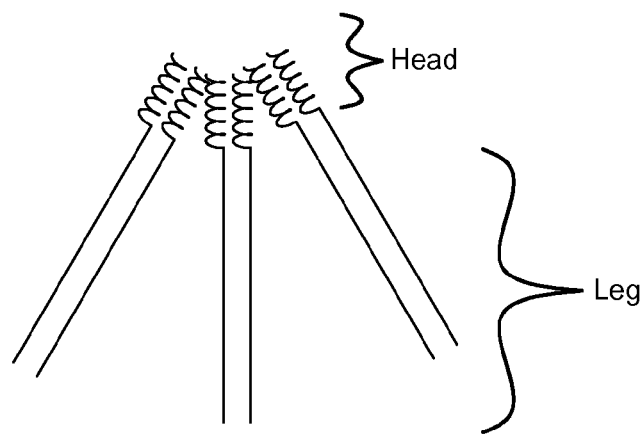

FIG. 24

SERIAL STRADOMER AMINO ACID SEQUENCES

G-003 WITH TAGS (SEQ ID NO:38)
METDTLLLWVLLLWVPGSTGDAADIQHGGRSSEPKSCDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLT
VDKSRWQQGNVFSCSVMHEALHNHYTQKSLSLSPGK*SLD*EPKSCDKTHTCPPCPAPE
LLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGKFEGKPIPNPLLGLD
STRTGHHHHHH

G-004 WITHOUT TAGS (SEQ ID NO:39)
METDTLLLWVLLLWVPGSTGDAADIQHGGRSSEPKSCDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLT
VDKSRWQQGNVFSCSVMHEALHNHYTQKSLSLSPGKSLEEPKSCDKTHTCPPCPAPE
LLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

G-007 WITH TAGS (SEQ ID NO:40)
METDTLLLWVLLLWVPGSTGDAADIVCSRDFTPPTVKILQSSCDGGGHFPPTIQLLC
LVSGYTPGTINITWLEDGQVMDVDLSTASTTQEGELASTQSELTLSQKHWLSDRTYT
CQVTYQGHTFEDSTKKCAGGRSSEPKSCDKTHTCPPCPAPELLGGPSVFLFPPKPKD
TLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQG
NVFSCSVMHEALHNHYTQKSLSLSPGKEPKSCDKTHTCPPCPAPELLGGPSVFLFPP
KPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGPRAAPEVYAFATPEWPGR
DKRTLACLIQNFMPEDISVQWLHNEVQLPDARHSTTQPRKTKGSGFFVFSRLEVTRA
EWEQKDEFICRAVHEAASPSQTVQRAVSVNPGKFEGKPIPNPLLGLDSTRTGHHHHH
H

G-011 WITH TAGS (SEQ ID NO:41)
METDTLLLWVLLLWVPGSTGDAADIVCSRDFTPPTVKILQSSCDGGGHFPPTIQLLC
LVSGYTPGTINITWLEDGQVMDVDLSTASTTQEGELASTQSELTLSQKHWLSDRTYT
CQVTYQGHTFEDSTKKCGGGRSSEPKSCDKTHTCPPCPAPELLGGPSVFLFPPKPKD
TLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQG

FIG. 24 Continued

NVFSCSVMHEALHNHYTQKSLSLSPGK*SLD*EPKSCDKTHTCPPCPAPELLGGPSVFL
FPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVD
KSRWQQGNVFSCSVMHEALHNHYTQKSLSLSPGKFEGKPIPNPLLGLDSTRTGHHHH
HH

G-012 WITHOUT TAGS (SEQ ID NO:42)
METDTLLLWVLLLWVPGSTGDAADIVCSRDFTPPTVKILQSSCDGGGHFPPTIQLLC
LVSGYTPGTINITWLEDGQVMDVDLSTASTTQEGELASTQSELTLSQKHWLSDRTYT
CQVTYQGHTFEDSTKKCGGGRSSEPKSCDKTHTCPPCPAPELLGGPSVFLFPPKPKD
TLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQG
NVFSCSVMHEALHNHYTQKSLSLSPGK*SLD*EPKSCDKTHTCPPCPAPELLGGPSVFL
FPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVD
KSRWQQGNVFSCSVMHEALHNHYTQKSLSLSPGKGPRAAPEVYAFATPEWPGRDKRT
LACLIQNFMPEDISVQWLHNEVQLPDARHSTTQPRKTKGSGFFVFSRLEVTRAEWEQ
KDEFICRAVHEAASPSQTVQRAVSVNPGK

G-014 WITHOUT TAGS (SEQ ID NO:43)
METDTLLLWVLLLWVPGSTGDAADIQHGGRSSEPKSCDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLT
VDKSRWQQGNVFSCSVMHEALHNHYTQKSLSLSPGK*SLD*EPKSCDKTHTCPPCPAPE
LLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGKFEEPKSCDKTHTCP
PCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

G-016 WITH TAGS (SEQ ID NO:44)
METDTLLLWVLLLWVPGSTGDAADISSKPHLVTQLTHAHGCPEPKSCDTPPPCPRCP
EPKSCDTPPPCPRCPEPKSCDTPPPCPRCPAPELLGGPSVFLFPPKPKDTLMISRTP
EVTCVVVDVSHEDPEVQFKWYVDGVEVHNAKTKLREEQYNSTFRVVSVLTVLHQDWL
NGKEYKCKVSNKALPAPIEKTISKTKGQPREPQVYTLPPSREEMTKNQVSLTCLVKG
FYPSDIAVEWESNGQPENNYNTTPPMLDSDGSFFLYSKLTVDKSRWQQGNIFSCSVM
HEALHNRYTQKSLSLSPGKGGRSSEPKSCDKTHTCPPCPAPELLGGPSVFLFPPKPK
DTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQ
GNVFSCSVMHEALHNHYTQKSLSLSPGKFEGKPIPNPLLGLDSTRTGHHHHHH

FIG. 24 Continued

G-017 WITH TAGS (SEQ ID NO:45)
METDTLLLWVLLLWVPGSTGDAADIQHGGRSSEPKSCDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLT
VDKSRWQQGNVFSCSVMHEALHNHYTQKSLSLSPGK*SLEGPRFEE*PKSCDKTHTCPP
CPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGKFEGKPIPNP
LLGLDSTRTGHHHHHH

G-023 WITHOUT TAGS (SEQ ID NO:46)
METDTLLLWVLLLWVPGSTGDAADIELKTPLGDTTHTCPRCPEPKSCDTPPPCPRCP
EPKSCDTPPPCPRCPEPKSCDTPPPCPRCPGGRSSEPKSCDKTHTCPPCPAPELLGG
PSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGK*SLDE*PKSCDKTHTCPPCP
APELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK

G-024 WITH TAGS (SEQ ID NO:47)
METDTLLLWVLLLWVPGSTGDAADIELKTPLGDTTHTCPRCPEPKSCDTPPPCPRCP
EPKSCDTPPPCPRCPEPKSCDTPPPCPRCPAPELLGGPSVFLFPPKPKDTLMISRTP
EVTCVVVDVSHEDPEVQFKWYVDGVEVHNAKTKLREEQYNSTFRVVSVLTVLHQDWL
NGKEYKCKVSNKALPAPIEKTISKTKGQPREPQVYTLPPSREEMTKNQVSLTCLVKG
FYPSDIAVEWESNGQPENNYNTTPPMLDSDGSFFLYSKLTVDKSRWQQGNIFSCSVM
HEALHNRYTQKSLSLSPGKGGRSSEPKSCDKTHTCPPCPAPELLGGPSVFLFPPKPK
DTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQ
GNVFSCSVMHEALHNHYTQKSLSLSPGK*SLEGPRFEE*PKSCDKTHTCPPCPAPELLG
GPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGKFEGKPIPNPLLGLDSTR
TGHHHHHH

G-025 WITH TAGS (SEQ ID NO:48)
METDTLLLWVLLLWVPGSTGDAADIEDTCGELEFQNDEIVKTISVKVIDDEEYEKNK
TFFLEIGKPRLVEMSEKKALLLNELGGFTITGKYLFGQPVFRKVHAREHPILSTVIT
IADEYDDKQPLTSKEKEEGGRSSEPKSCDKTHTCPPCPAPELLGGPSVFLFPPKPKD
TLMISRTPEVTCVVVDVSHEDPEVKFNWYVDGVEVHNAKTKPREEQYNSTYRVVSVL

FIG. 24 Continued

TVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQG
NVFSCSVMHEALHNHYTQKSLSLSPGKFEGKPIPNPLLGLDSTRTGHHHHHH

G-026 WITH TAGS (SEQ ID NO:49)
METDTLLLWVLLLWVPGSTGDAADIEDTCGELEFQNDEIVKTISVKVIDDEEYEKNK
TFFLEIGKPRLVEMSEKKALLLNELGGFTITGKYLFGQPVFRKVHAREHPILSTVIT
IADEYDDKQPLTSKEKEEGGRSSEPKSCDKTHTCPPCPAPELLGGPSVFLFPPKPKD
TLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQG
NVFSCSVMHEALHNHYTQKSLSLSPGK*SLEGPRFEE*PKSCDKTHTCPPCPAPELLGG
PSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGKFEGKPIPNPLLGLDSTRT
GHHHHHH

CORE STRADOMERS

G-002 IGG1 FC WITH TAGS (SEQ ID NO:50)
METDTLLLWVLLLWVPGSTGDAADIQHSGGRSSEPKSCDKTHTCPPCPAPELLGGPS
VFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKL
TVDKSRWQQGNVFSCSVMHEALHNHYTQKSLSLSPGKSLEGPRFEGKPIPNPLLGLD
STRTGHHHHHH

G-002 IGG1 FC WITHOUT TAGS WITHOUT RESTRICTION ENZYME
SITES (SEQ ID NO:51)
METDTLLLWVLLLWVPGSTGEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSRWQQGNVF
SCSVMHEALHNHYTQKSLSLSPGK

G-022 WITHOUT TAGS (SEQ ID NO:52)
METDTLLLWVLLLWVPGSTGDAADIQHSGGRSSEPKSCDKTHTCPPCPAPELLGGPS
VFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKL
TVDKSRWQQGNVFSCSVMHEALHNHYTQKSLSLSPGKSLEGPRFEELKTPLGDTTHT
CPRCPEPKSCDTPPPCPRCPEPKSCDTPPPCPRCPEPKSCDTPPPCPRCPA

CLUSTER STRADOMERS
G-008 WITHOUT TAGS (SEQ ID NO:53)
METDTLLLWVLLLWVPGSTGDAADIQHGGRSSEPKSCDKTHTCPPCPAPELLGGPSV
FLFPPKPKDTLMISRTPEVTCVVVDVSHEDPEVKFNWYVDGVEVHNAKTKPREEQYN

FIG. 24 Continued

```
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLT
VDKSRWQQGNVFSCSVMHEALHNHYTQKSLSLSPGKSLDEPKSCDKTHTCPPCPAPE
LLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGKFEDQDIAIRVFAIP
PSFASIFLTKSTKLTCLVTDLTTYDSVTISWTRQNGEAVKTHTNISESHPNATFSAV
GEASICEDDWNSGERFTCTVTHTDLPSPLKQTISRPKGVALHRPDVYLLPPAREQLN
LRESATITCLVTGFSPADVFVQWMQRGQPLSPEKYVTSAPMPEPQAPGRYFAHSILT
VSEEEWNTGETYTCVVAHEALPNRVTERTVDKSTGKPTLYNVSLVMSDTAGTCY

G-009 WITHOUT TAGS (SEQ ID NO:54)
METDTLLLWVLLLWVPGSTGDAADIQHSGGRSSEPKSCDKTHTCPPCPAPELLGGPS
VFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKL
TVDKSRWQQGNVFSCSVMHEALHNHYTQKSLSLSPGKSLEGPRFEDQDIAIRVFAIP
PSFASIFLTKSTKLTCLVTDLTTYDSVTISWTRQNGEAVKTHTNISESHPNATFSAV
GEASICEDDWNSGERFTCTVTHTDLPSPLKQTISRPKGVALHRPDVYLLPPAREQLN
LRESATITCLVTGFSPADVFVQWMQRGQPLSPEKYVTSAPMPEPQAPGRYFAHSILT
VSEEEWNTGETYTCVVAHEALPNRVTERTVDKSTGKPTLYNVSLVMSDTAGTCY

G-010 WITH TAGS (SEQ ID NO:55)
METDTLLLWVLLLWVPGSTGDAADIVCSRDFTPPTVKILQSSCDGGGHFPPTIQLLC
LVSGYTPGTINITWLEDGQVMDVDLSTASTTQEGELASTQSELTLSQKHWLSDRTYT
CQVTYQGHTFEDSTKKCGGGRSSEPKSCDKTHTCPPCPAPELLGGPSVFLFPPKPKD
TLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQG
NVFSCSVMHEALHNHYTQKSLSLSPGKFEGKPIPNPLLGLDSTRTGHHHHHH

WITHOUT TAGS WITHOUT RESTRICTION ENZYME SITES (SEQ ID
NO:56)
METDTLLLWVLLLWVPGSTGVCSRDFTPPTVKILQSSCDGGGHFPPTIQLLCLVSGY
TPGTINITWLEDGQVMDVDLSTASTTQEGELASTQSELTLSQKHWLSDRTYTCQVTY
QGHTFEDSTKKCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEA
LHNHYTQKSLSLSPGKFEGK

G-018
WITH TAG. (SEQ ID NO:57)
METDTLLLWVLLLWVPGSTGDAADIERKCCVECPPCPAPPVAGPSVFLFPPKPKDTL
MISRTPEVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREEMTKNQVSL
TCLVKGFYPSDIAVEWESNGQPENNYKTTPPMLDSDGSFFLYSKLTVDKSRWQQGNV
FSCSVMHEALHNHYTQKSLSLSPGKRSSEPKSCDKTHTCPPCPAPELLGGPSVFLFP
```

FIG. 24 Continued

PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKS
RWQQGNVFSCSVMHEALHNHYTQKSLSLSPGKSLEGPRFEGKPIPNPLLGLDSTRTG
HHHHHH.

WITHOUT TAG. (SEQ ID NO:58)
METDTLLLWVLLLWVPGSTGDAADIERKCCVECPPCPAPPVAGPSVFLFPPKPKDTL
MISRTPEVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREEMTKNQVSL
TCLVKGFYPSDIAVEWESNGQPENNYKTTPPMLDSDGSFFLYSKLTVDKSRWQQGNV
FSCSVMHEALHNHYTQKSLSLSPGKRSSEPKSCDKTHTCPPCPAPELLGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKS
RWQQGNVFSCSVMHEALHNHYTQKSLSLSPGK.

G-019
WITH TAG (SEQ ID NO:59)
METDTLLLWVLLLWVPGSTGDAADIERKCCVECPPCPRSSEPKSCDKTHTCPPCPAP
ELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGKSLEGPRFEGKPIP
NPLLGLDSTRTGHHHHHH.

WITHOUT TAG (SEQ ID NO:60)
METDTLLLWVLLLWVPGSTGDAADIERKCCVECPPCPRSSEPKSCDKTHTCPPCPAP
ELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK.

WITHOUT TAGS WITHOUT RESTRICTION ENZYME SITES (SEQ ID NO:61)
METDTLLLWVLLLWVPGSTGERKCCVECPPCPEPKSCDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLT
VDKSRWQQGNVFSCSVMHEALHNHYTQKSLSLSPGK

G-020.

WITH TAG (SEQ ID NO:62)
METDTLLLWVLLLWVPGSTGDAADIERKCCVECPPCPRSSEPKSCDKTHTCPPCPAP
ELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGKSLDEPKSCDKTHT
CPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKA

FIG. 24 Continued

KGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGKSLEGPR
FEGKPIPNPLLGLDSTRTGHHHHHH.

WITH OUT TAG (SEQ ID NO:63)
METDTLLLWVLLLWVPGSTGDAADIERKCCVECPPCPRSSEPKSCDKTHTCPPCPAP
ELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGKSLDEPKSCDKTHT
CPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK.

G-027
WITH TAG (SEQ ID NO:64)
METDTLLLWVLLLWVPGSTGDAADIVCSRDFTPPTVKILQSSCDGGGHFPPTIQLLC
LVSGYTPGTINITWLEDGQVMDVDLSTASTTQEGELASTQSELTLSQKHWLSDRTYT
CQVTYQGHTFEDSTKKCGGGDIVCSRDFTPPTVKILQSSCDGGGHFPPTIQLLCLVS
GYTPGTINITWLEDGQVMDVDLSTASTTQEGELASTQSELTLSQKHWLSDRTYTCQV
TYQGHTFEDSTKKCGGGRSSEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVF
SCSVMHEALHNHYTQKSLSLSPGKSLEGPRFEGKPIPNPLLGLDSTRTGHHHHHH.

WITH OUT TAG (SEQ ID NO:65)
METDTLLLWVLLLWVPGSTGDAADIVCSRDFTPPTVKILQSSCDGGGHFPPTIQLLC
LVSGYTPGTINITWLEDGQVMDVDLSTASTTQEGELASTQSELTLSQKHWLSDRTYT
CQVTYQGHTFEDSTKKCGGGDIVCSRDFTPPTVKILQSSCDGGGHFPPTIQLLCLVS
GYTPGTINITWLEDGQVMDVDLSTASTTQEGELASTQSELTLSQKHWLSDRTYTCQV
TYQGHTFEDSTKKCGGGRSSEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVF
SCSVMHEALHNHYTQKSLSLSPGK.

G-028
WITH TAG (SEQ ID NO:66)
METDTLLLWVLLLWVPGSTGDAADILGGGSIKQIEDKIEEILSKIYHIENEIARIKK
LIGERGHGGGSSEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCSVMHEA
LHNHYTQKSLSLSPGKSLEGPRFEGKPIPNPLLGLDSTRTGHHHHHH

WITHOUT TAG (SEQ ID NO:67)
METDTLLLWVLLLWVPGSTGDAADILGGGSIKQIEDKIEEILSKIYHIENEIARIKK
LIGERGHGGGSSEPKSCDKTHTCPPCPAPELLGGPSVFLFPPKPKDTLMISRTPEVT

FIG. 24 Continued

CVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCSVMHEA
LHNHYTQKSLSLSPGK.

G-029 (SEQ ID NO:68)
METDTLLLWVLLLWVPGSTGDAADILGGGSIKQIEDKIEEILSKIYHIENEIARIKK
LIGERGHGGGDIVCSRDFTPPTVKILQSSCDGGGHFPPTIQLLCLVSGYTPGTINIT
WLEDGQVMDVDLSTASTTQEGELASTQSELTLSQKHWLSDRTYTCQVTYQGHTFEDS
TKKCGGGRSSEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALH
NHYTQKSLSLSPGKSLEGPRFEGKPIPNPLLGLDSTRTGHHHHHH.

WITH OUT TAG (SEQ ID NO:69)
METDTLLLWVLLLWVPGSTGDAADILGGGSIKQIEDKIEEILSKIYHIENEIARIKK
LIGERGHGGGDIVCSRDFTPPTVKILQSSCDGGGHFPPTIQLLCLVSGYTPGTINIT
WLEDGQVMDVDLSTASTTQEGELASTQSELTLSQKHWLSDRTYTCQVTYQGHTFEDS
TKKCGGGRSSEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALH
NHYTQKSLSLSPGK.

G-030
WITH TAG. (SEQ ID NO:70)
METDTLLLWVLLLWVPGSTGDAADILGGGSIKQIEDKIEEILSKIYHIENEIARIKK
LIGERGHILGGGDIERKCCVECPPCPAPPVAGPSVFLFPPKPKDTLMISRTPEVTCV
VVDVSHEDPEVQFNWYVDGVEVHNAKTKPREEQFNSTFRVVSVLTVVHQDWLNGKEY
KCKVSNKGLPAPIEKTISKTKGQPREPQVYTLPPSREEMTKNQVSLTCLVKGFYPSD
IAVEWESNGQPENNYKTTPPMLDSDGSFFLYSKLTVDKSRWQQGNVFSCSVMHEALH
NHYTQKSLSLSPGKRSSEPKSCDKTHTCPPCPAPELLGGPSVFLFPPKPKDTLMISR
TPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCS
VMHEALHNHYTQKSLSLSPGKSLEGPRFEGKPIPNPLLGLDSTRTGHHHHHH.

WITHOUT TAG. (SEQ ID NO:71)
METDTLLLWVLLLWVPGSTGDAADILGGGSIKQIEDKIEEILSKIYHIENEIARIKK
LIGERGHILGGGDIERKCCVECPPCPAPPVAGPSVFLFPPKPKDTLMISRTPEVTCV
VVDVSHEDPEVQFNWYVDGVEVHNAKTKPREEQFNSTFRVVSVLTVVHQDWLNGKEY
KCKVSNKGLPAPIEKTISKTKGQPREPQVYTLPPSREEMTKNQVSLTCLVKGFYPSD
IAVEWESNGQPENNYKTTPPMLDSDGSFFLYSKLTVDKSRWQQGNVFSCSVMHEALH
NHYTQKSLSLSPGKRSSEPKSCDKTHTCPPCPAPELLGGPSVFLFPPKPKDTLMISR
TPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCS
VMHEALHNHYTQKSLSLSPGK.

FIG. 24 Continued

G-031
WITH TAG (SEQ ID NO:72)
METDTLLLWVLLLWVPGSTGDAADILGGGSIKQIEDKIEEILSKIYHIENEIARIKK
LIGERGHDIERKCCVECPPCPRSSEPKSCDKTHTCPPCPAPELLGGPSVFLFPPKPK
DTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQ
GNVFSCSVMHEALHNHYTQKSLSLSPGKSLEGPRFEGKPIPNPLLGLDSTRTGHHHH
HH.

WITHOUT TAG (SEQ ID NO:73)
METDTLLLWVLLLWVPGSTGDAADILGGGSIKQIEDKIEEILSKIYHIENEIARIKK
LIGERGHDIERKCCVECPPCPRSSEPKSCDKTHTCPPCPAPELLGGPSVFLFPPKPK
DTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQ
GNVFSCSVMHEALHNHYTQKSLSLSPGK.

G-032
WITH TAG (SEQ ID NO:74)
METDTLLLWVLLLWVPGSTGDAADILGGGSIKQIEDKIEEILSKIYHIENEIARIKK
LIGERGHILGGGSIKQIEDKIEEILSKIYHIENEIARIKKLIGERGHGGGSSEPKSC
DKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGKS
LEGPRFEGKPIPNPLLGLDSTRTGHHHHHH

WITHOUT TAG (SEQ ID NO:75)
METDTLLLWVLLLWVPGSTGDAADILGGGSIKQIEDKIEEILSKIYHIENEIARIKK
LIGERGHILGGGSIKQIEDKIEEILSKIYHIENEIARIKKLIGERGHGGGSSEPKSC
DKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK.

G-033
WITH TAG (SEQ ID NO:76)
METDTLLLWVLLLWVPGSTGDAAERKCCVECPPCPDIVCSRDFTPPTVKILQSSCDG
GGHFPPTIQLLCLVSGYTPGTINITWLEDGQVMDVDLSTASTTQEGELASTQSELTL
SQKHWLSDRTYTCQVTYQGHTFEDSTKKCGGGRSSEPKSCDKTHTCPPCPAPELLGG
PSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGKSLEGPRFEGKPIPNPLLG
LDSTRTGHHHHHH.

WITH OUT TAG (SEQ ID NO:77)
METDTLLLWVLLLWVPGSTGDAAERKCCVECPPCPDIVCSRDFTPPTVKILQSSCDG
GGHFPPTIQLLCLVSGYTPGTINITWLEDGQVMDVDLSTASTTQEGELASTQSELTL

FIG. 24 Continued

SQKHWLSDRTYTCQVTYQGHTFEDSTKKCGGGRSSEPKSCDKTHTCPPCPAPELLGG
PSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK.

G-034
WITH TAG (SEQ ID NO:78)
METDTLLLWVLLLWVPGSTGDAAERKCCVECPPCPDILGGGSIKQIEDKIEEILSKI
YHIENEIARIKKLIGERGHGGGSSERKCCVECPPCPAPPVAGPSVFLFPPKPKDTLM
ISRTPEVTCVVVDVSHEDPEVQFNWYVDGVEVHNAKTKPREEQFNSTFRVVSVLTVV
HQDWLNGKEYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDKSRWQQGNVF
SCSVMHEALHNHYTQKSLSLSPGKRSSEPKSCDKTHTCPPCPAPELLGGPSVFLFPP
KPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSR
WQQGNVFSCSVMHEALHNHYTQKSLSLSPGKSLEGPRFEGKPIPNPLLGLDSTRTGH
HHHHH

WITH OUT TAG (SEQ ID NO:79)
METDTLLLWVLLLWVPGSTGDAAERKCCVECPPCPDILGGGSIKQIEDKIEEILSKI
YHIENEIARIKKLIGERGHGGGSSERKCCVECPPCPAPPVAGPSVFLFPPKPKDTLM
ISRTPEVTCVVVDVSHEDPEVQFNWYVDGVEVHNAKTKPREEQFNSTFRVVSVLTVV
HQDWLNGKEYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDKSRWQQGNVF
SCSVMHEALHNHYTQKSLSLSPGKRSSEPKSCDKTHTCPPCPAPELLGGPSVFLFPP
KPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSR
WQQGNVFSCSVMHEALHNHYTQKSLSLSPGK.

G-035
WITH TAG (SEQ ID NO:80)
METDTLLLWVLLLWVPGSTGDAAERKCCVECPPCPDIERKCCVECPPCPRSSEPKSC
DKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGKS
LEGPRFEGKPIPNPLLGLDSTRTGHHHHHH.

WITH OUT TAG (SEQ ID NO:81)
METDTLLLWVLLLWVPGSTGDAAERKCCVECPPCPDIERKCCVECPPCPRSSEPKSC
DKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK.

WITH TAG (SEQ ID NO:82)
METDTLLLWVLLLWVPGSTGDAAERKCCVECPPCPDILGGGSIKQIEDKIEEILSKI
YHIENEIARIKKLIGERGHGGGSSEPKSCDKTHTCPPCPAPELLGGPSVFLFPPKPK
DTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQ
GNVFSCSVMHEALHNHYTQKSLSLSPGKSLEGPRFEGKPIPNPLLGLDSTRTGHHHH
HH.

WITH OUT TAG (SEQ ID NO:83)
METDTLLLWVLLLWVPGSTGDAAERKCCVECPPCPDILGGGSIKQIEDKIEEILSKI
YHIENEIARIKKLIGERGHGGGSSEPKSCDKTHTCPPCPAPELLGGPSVFLFPPKPK
DTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQ
GNVFSCSVMHEALHNHYTQKSLSLSPGK.

G-037
WITH TAG (SEQ ID NO:84)
METDTLLLWVLLLWVPGSTGDAAERKCCVECPPCPDIERKCCVECPPCPAPPVAGPS
VFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPP
SREEMTKNQVSLTCLVKGFYPSDIAVEWESNGQPENNYKTTPPMLDSDGSFFLYSKL
TVDKSRWQQGNVFSCSVMHEALHNHYTQKSLSLSPGKRSSEPKSCDKTHTCPPCPAP
ELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGKSLEGPRFEGKPIP
NPLLGLDSTRTGHHHHHH.

WITHOUT TAG (SEQ ID NO:85)
METDTLLLWVLLLWVPGSTGDAAERKCCVECPPCPDIERKCCVECPPCPAPPVAGPS
VFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPP
SREEMTKNQVSLTCLVKGFYPSDIAVEWESNGQPENNYKTTPPMLDSDGSFFLYSKL
TVDKSRWQQGNVFSCSVMHEALHNHYTQKSLSLSPGKRSSEPKSCDKTHTCPPCPAP
ELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK.

OTHER SEQUENCES

G-106 J CHAIN (SEQ ID NO:86)

MKNHLLFWGVLAVFIKAVHVKAQEDERIVLVDNKCKCARITSRIIRSSEDPNEDIVE
RNIRIIVPLNNRENISDPTSPLRTRFVYHLSDLCKKCDPTEVELDNQIVTATQSNIC
DEDSATETCYTYDRNKCYTAVVPLVYGGETKMVETALTPDACYPD

Figure 25

Human IgG1
Hinge-EPKSCDKTHTCPPCP (SEQ ID NO:87)

CH2- APELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAK (SEQ ID NO:88)

CH3- GQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYT
QKSLSLSPGK (SEQ ID NO:89)

Human IgG2
Hinge- RKCCVECPPCP (SEQ ID NO:90)

CH2- APPVAGPSVFLFPPKPKDTLMISRTPEVTCVVVDVSHEDPEVQFNWY
VDGMEVHNAKTKPREEQFNSTFRVVSVLTVVHQDWLNGKEYKCKVSNKGL
PAPIEKTISKTK (SEQ ID NO:91)

CH3- GQPREPQVYTLPPSREEMTKNQVSLTCLVKGFYPSDIAVEWESNGQP
ENNYKTTPPMLDSDGSFFLYSKLTVDKSRWQQGNVFSCSVMHEALHNHYTQ
KSLSLSPGK (SEQ ID NO:92)

Human IgG3
Hinge- ELKTPLGDTTHTCPRCPEPKSCDTPPPCPRCPEPKSCDTPPPCPRCPEPK
SCDTPPPCPRCP (SEQ ID NO:93)

CH2- APELLGGPSVFLFPPKPKDTLMISRTPEVTCVVVDVSHEDPEVQF
KWYV DGVEVHNAKTKPREEQFNSTFRVVSVLTVLHQDWLNGKEYKCKVSN
KALPAPIEKTISKTK (SEQ ID NO:94)

CH3- GQPREPQVYTLPPSREEMTKNQVSLTCLVKGFYPSDIAVEWESSGQP
ENNYNTTPPMLDSDGSFFLYSKLTVDKSRWQQGNIFSCSVMHEALHNRFTQK
SLSLSPGK (SEQ ID NO:95)

Human IgG4
Hinge- ESKYGPPCPSCP (SEQ ID NO:96)

CH2- APEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVSN
KGLPSSIEKTISKAK (SEQ ID NO:97)

CH3- GQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQ
KSLSLSLGK (SEQ ID NO:98)

SEQUENCE LISTING

```
<160> NUMBER OF SEQ ID NOS: 98

<210> SEQ ID NO 1
<211> LENGTH: 699
<212> TYPE: DNA
<213> ORGANISM: Homo sapiens
<220> FEATURE:
<221> NAME/KEY: misc_feature
<223> OTHER INFORMATION: IgG1 Fc domain
<220> FEATURE:
<221> NAME/KEY: CDS
<222> LOCATION: (1)..(699)

<400> SEQUENCE: 1 agt gag ccc aaa tct tgt gac aaa act cac aca tgc cca ccg tgc cca      48
Ser Glu Pro Lys Ser Cys Asp Lys Thr His Thr Cys Pro Pro Cys Pro
1               5                   10                  15 gca cct gaa ctc ctg ggg gga ccg tca gtc ttc ctc ttc ccc cca aaa     96
Ala Pro Glu Leu Leu Gly Gly Pro Ser Val Phe Leu Phe Pro Pro Lys
            20                  25                  30 ccc aag gac acc ctc atg atc tcc cgg acc cct gag gtc aca tgc gtg    144
Pro Lys Asp Thr Leu Met Ile Ser Arg Thr Pro Glu Val Thr Cys Val
        35                  40                  45 gtg gtg gac gtg agc cac gaa gac cct gag gtc aag ttc aac tgg tac    192
Val Val Asp Val Ser His Glu Asp Pro Glu Val Lys Phe Asn Trp Tyr
    50                  55                  60
```

```
gtg gac ggc gtg gag gtg cat aat gcc aag aca aag ccg cgg gag gag      240
Val Asp Gly Val Glu Val His Asn Ala Lys Thr Lys Pro Arg Glu Glu
 65                  70                  75                  80 cag tac aac agc acg tac cgg gtg gtc agc gtc ctc acc gtc ctg cac      288
Gln Tyr Asn Ser Thr Tyr Arg Val Val Ser Val Leu Thr Val Leu His
             85                  90                  95 cag gac tgg ctg aat ggc aag gag tac aag tgc aag gtc tcc aac aaa      336
Gln Asp Trp Leu Asn Gly Lys Glu Tyr Lys Cys Lys Val Ser Asn Lys
        100                 105                 110 gcc ctc cca gcc ccc atc gag aaa acc atc tcc aaa gcc aaa ggg cag      384
Ala Leu Pro Ala Pro Ile Glu Lys Thr Ile Ser Lys Ala Lys Gly Gln
    115                 120                 125 ccc cga gaa cca cag gtg tac acc ctg ccc cca tcc cgg gat gag ctg      432
Pro Arg Glu Pro Gln Val Tyr Thr Leu Pro Pro Ser Arg Asp Glu Leu
130                 135                 140 acc aag aac cag gtc agc ctg acc tgc ctg gtc aaa ggc ttc tat ccc      480
Thr Lys Asn Gln Val Ser Leu Thr Cys Leu Val Lys Gly Phe Tyr Pro
145                 150                 155                 160 agc gac atc gcc gtg gag tgg gag agc aat ggg cag ccg gag aac aac      528
Ser Asp Ile Ala Val Glu Trp Glu Ser Asn Gly Gln Pro Glu Asn Asn
                165                 170                 175 tac aag acc acg cct ccc gtg ctg gac tcc gac ggc tcc ttc ttc ctc      576
Tyr Lys Thr Thr Pro Pro Val Leu Asp Ser Asp Gly Ser Phe Phe Leu
            180                 185                 190 tac agc aag ctc acc gtg gac aag agc agg tgg cag cag ggg aac gtc      624
Tyr Ser Lys Leu Thr Val Asp Lys Ser Arg Trp Gln Gln Gly Asn Val
        195                 200                 205 ttc tca tgc tcc gtg atg cat gag gct ctg cac aac cac tac acg cag      672
Phe Ser Cys Ser Val Met His Glu Ala Leu His Asn His Tyr Thr Gln
    210                 215                 220 aag agc ctc tcc ctg tct ccg ggt aaa                                  699
Lys Ser Leu Ser Leu Ser Pro Gly Lys
225                 230

<210> SEQ ID NO 2
<211> LENGTH: 233
<212> TYPE: PRT
<213> ORGANISM: Homo sapiens

<400> SEQUENCE: 2

Ser Glu Pro Lys Ser Cys Asp Lys Thr His Thr Cys Pro Pro Cys Pro
  1               5                  10                  15

Ala Pro Glu Leu Leu Gly Gly Pro Ser Val Phe Leu Phe Pro Pro Lys
             20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
             85                  90                  95

Gln Asp Trp Leu Asn Gly Lys Glu Tyr Lys Cys Lys Val Ser Asn Lys
        100                 105                 110

Ala Leu Pro Ala Pro Ile Glu Lys Thr Ile Ser Lys Ala Lys Gly Gln
    115                 120                 125

Pro Arg Glu Pro Gln Val Tyr Thr Leu Pro Pro Ser Arg Asp Glu Leu
130                 135                 140
```

```
Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 3
<211> LENGTH: 684
<212> TYPE: DNA
<213> ORGANISM: Homo sapiens
<220> FEATURE:
<221> NAME/KEY: misc_feature
<223> OTHER INFORMATION: IgG2 Fc domain
<220> FEATURE:
<221> NAME/KEY: CDS
<222> LOCATION: (1)..(684)

<400> SEQUENCE: 3
```

| | | | | | | | | | | | | | | | | |
|---|---|---|---|---|---|---|---|---|---|---|---|---|---|---|---|---|
| gag | cgc | aaa | tgt | tgt | gtc | gag | tgc | cca | ccg | tgc | cca | gca | cca | cct | gtg | 48 |
| Glu | Arg | Lys | Cys | Cys | Val | Glu | Cys | Pro | Pro | Cys | Pro | Ala | Pro | Pro | Val | |
| 1 | | | | 5 | | | | | 10 | | | | | 15 | | |
| gca | gga | ccg | tca | gtc | ttc | ctc | ttc | ccc | cca | aaa | ccc | aag | gac | acc | ctc | 96 |
| Ala | Gly | Pro | Ser | Val | Phe | Leu | Phe | Pro | Pro | Lys | Pro | Lys | Asp | Thr | Leu | |
| | | | 20 | | | | | 25 | | | | | 30 | | | |
| atg | atc | tcc | cgg | acc | cct | gag | gtc | acg | tgc | gtg | gtg | gtg | gac | gtg | agc | 144 |
| Met | Ile | Ser | Arg | Thr | Pro | Glu | Val | Thr | Cys | Val | Val | Val | Asp | Val | Ser | |
| | | | 35 | | | | | 40 | | | | | 45 | | | |
| cac | gaa | gac | ccc | gag | gtc | cag | ttc | aac | tgg | tac | gtg | gac | ggc | gtg | gag | 192 |
| His | Glu | Asp | Pro | Glu | Val | Gln | Phe | Asn | Trp | Tyr | Val | Asp | Gly | Val | Glu | |
| 50 | | | | | 55 | | | | | 60 | | | | | | |
| gtg | cat | aat | gcc | aag | aca | aag | cca | cgg | gag | gag | cag | ttc | aac | agc | acg | 240 |
| Val | His | Asn | Ala | Lys | Thr | Lys | Pro | Arg | Glu | Glu | Gln | Phe | Asn | Ser | Thr | |
| 65 | | | | 70 | | | | | 75 | | | | | 80 | | |
| ttc | cgt | gtg | gtc | agc | gtc | ctc | acc | gtt | gtg | cac | cag | gac | tgg | ctg | aac | 288 |
| Phe | Arg | Val | Val | Ser | Val | Leu | Thr | Val | Val | His | Gln | Asp | Trp | Leu | Asn | |
| | | | | 85 | | | | | 90 | | | | | 95 | | |
| ggc | aag | gag | tac | aag | tgc | aag | gtc | tcc | aac | aaa | ggc | ctc | cca | gcc | ccc | 336 |
| Gly | Lys | Glu | Tyr | Lys | Cys | Lys | Val | Ser | Asn | Lys | Gly | Leu | Pro | Ala | Pro | |
| | | | | 100 | | | | | 105 | | | | | 110 | | |
| atc | gag | aaa | acc | atc | tcc | aaa | acc | aaa | ggg | cag | ccc | cga | gaa | cca | cag | 384 |
| Ile | Glu | Lys | Thr | Ile | Ser | Lys | Thr | Lys | Gly | Gln | Pro | Arg | Glu | Pro | Gln | |
| | | | | 115 | | | | | 120 | | | | | 125 | | |
| gtg | tac | acc | ctg | ccc | cca | tcc | cgg | gag | gag | atg | acc | aag | aac | cag | gtc | 432 |
| Val | Tyr | Thr | Leu | Pro | Pro | Ser | Arg | Glu | Glu | Met | Thr | Lys | Asn | Gln | Val | |
| | | | 130 | | | | | 135 | | | | | 140 | | | |
| agc | ctg | acc | tgc | ctg | gtc | aaa | ggc | ttc | tac | ccc | agc | gac | atc | gcc | gtg | 480 |
| Ser | Leu | Thr | Cys | Leu | Val | Lys | Gly | Phe | Tyr | Pro | Ser | Asp | Ile | Ala | Val | |
| 145 | | | | | 150 | | | | | 155 | | | | | 160 | |
| gag | tgg | gag | agc | aat | ggg | cag | ccg | gag | aac | aac | tac | aag | acc | aca | cct | 528 |
| Glu | Trp | Glu | Ser | Asn | Gly | Gln | Pro | Glu | Asn | Asn | Tyr | Lys | Thr | Thr | Pro | |
| | | | | 165 | | | | | 170 | | | | | 175 | | |
| ccc | atg | ctg | gac | tcc | gac | ggc | tcc | ttc | ttc | ctc | tac | agc | aag | ctc | acc | 576 |
| Pro | Met | Leu | Asp | Ser | Asp | Gly | Ser | Phe | Phe | Leu | Tyr | Ser | Lys | Leu | Thr | |

```
gtg gac aag agc agg tgg cag cag ggg aac gtc ttc tca tgc tcc gtg      624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg      672
Met His Glu Ala Leu His Asn His Tyr Thr Gln Lys Ser Leu Ser Leu
210                 215                 220 tct ccg ggt aaa                                                      684
Ser Pro Gly Lys
225

<210> SEQ ID NO 4
<211> LENGTH: 228
<212> TYPE: PRT
<213> ORGANISM: Homo sapiens

<400> SEQUENCE: 4

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 5
<211> LENGTH: 837
<212> TYPE: DNA
<213> ORGANISM: Homo sapiens
<220> FEATURE:
<221> NAME/KEY: misc_feature
<223> OTHER INFORMATION: IgG3 Fc domain
<220> FEATURE:
<221> NAME/KEY: CDS
<222> LOCATION: (1)..(837)
```

<400> SEQUENCE: 5

```
gag ctc aaa acc cca ctt ggt gac aca act cac aca tgc cca cgg tgc      48
Glu Leu Lys Thr Pro Leu Gly Asp Thr Thr His Thr Cys Pro Arg Cys
1               5                   10                  15 cca gag ccc aaa tct tgt gac aca cct ccc ccg tgc cca cgg tgc cca      96
Pro Glu Pro Lys Ser Cys Asp Thr Pro Pro Pro Cys Pro Arg Cys Pro
            20                  25                  30 gag ccc aaa tct tgt gac aca cct ccc cca tgc cca cgg tgc cca gag     144
Glu Pro Lys Ser Cys Asp Thr Pro Pro Pro Cys Pro Arg Cys Pro Glu
        35                  40                  45 ccc aaa tct tgt gac aca cct ccc cca tgc cca cgg tgc cca gca cct     192
Pro Lys Ser Cys Asp Thr Pro Pro Pro Cys Pro Arg Cys Pro Ala Pro
    50                  55                  60 gaa ctc ctg gga gga ccg tca gtc ttc ctc ttc ccc cca aaa ccc aag     240
Glu Leu Leu Gly Gly Pro Ser Val Phe Leu Phe Pro Pro Lys Pro Lys
65                  70                  75                  80 gat acc ctt atg att tcc cgg acc cct gag gtc acg tgc gtg gtg gtg     288
Asp Thr Leu Met Ile Ser Arg Thr Pro Glu Val Thr Cys Val Val Val
                85                  90                  95 gac gtg agc cac gaa gac ccc gag gtc cag ttc aag tgg tac gtg gac     336
Asp Val Ser His Glu Asp Pro Glu Val Gln Phe Lys Trp Tyr Val Asp
            100                 105                 110 ggc gtg gag gtg cat aat gcc aag aca aag ccg cgg gag gag cag ttc     384
Gly Val Glu Val His Asn Ala Lys Thr Lys Pro Arg Glu Glu Gln Phe
        115                 120                 125 aac agc acg ttc cgt gtg gtc agc gtc ctc acc gtc ctg cac cag gac     432
Asn Ser Thr Phe Arg Val Val Ser Val Leu Thr Val Leu His Gln Asp
    130                 135                 140 tgg ctg aac ggc aag gag tac aag tgc aag gtc tcc aac aaa gcc ctc     480
Trp Leu Asn Gly Lys Glu Tyr Lys Cys Lys Val Ser Asn Lys Ala Leu
145                 150                 155                 160 cca gcc ccc atc gag aaa acc atc tcc aaa acc aaa gga cag ccc cga     528
Pro Ala Pro Ile Glu Lys Thr Ile Ser Lys Thr Lys Gly Gln Pro Arg
                165                 170                 175 gaa cca cag gtg tac acc ctg ccc cca tcc cgg gag gag atg acc aag     576
Glu Pro Gln Val Tyr Thr Leu Pro Pro Ser Arg Glu Glu Met Thr Lys
            180                 185                 190 aac cag gtc agc ctg acc tgc ctg gtc aaa ggc ttc tac ccc agc gac     624
Asn Gln Val Ser Leu Thr Cys Leu Val Lys Gly Phe Tyr Pro Ser Asp
        195                 200                 205 atc gcc gtg gag tgg gag agc agc ggg cag ccg gag aac aac tac aac     672
Ile Ala Val Glu Trp Glu Ser Ser Gly Gln Pro Glu Asn Asn Tyr Asn
    210                 215                 220 acc acg cct ccc atg ctg gac tcc gac ggc tcc ttc ttc ctc tac agc     720
Thr Thr Pro Pro Met Leu Asp Ser Asp Gly Ser Phe Phe Leu Tyr Ser
225                 230                 235                 240 aag ctc acc gtg gac aag agc agg tgg cag cag ggg aac atc ttc tca     768
Lys Leu Thr Val Asp Lys Ser Arg Trp Gln Gln Gly Asn Ile Phe Ser
                245                 250                 255 tgc tcc gtg atg cat gag gct ctg cac aac cgc ttc acg cag aag agc     816
Cys Ser Val Met His Glu Ala Leu His Asn Arg Phe Thr Gln Lys Ser
            260                 265                 270 ctc tcc ctg tct ccg ggt aaa                                         837
Leu Ser Leu Ser Pro Gly Lys
        275
```

<210> SEQ ID NO 6
<211> LENGTH: 279
<212> TYPE: PRT
<213> ORGANISM: Homo sapiens

<400> SEQUENCE: 6

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Phe
            115                 120                 125

Asn Ser Thr Phe Arg Val Val Ser Val Leu Thr Val Leu His Gln Asp
130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 7
<211> LENGTH: 687
<212> TYPE: DNA
<213> ORGANISM: Homo sapiens
<220> FEATURE:
<221> NAME/KEY: misc_feature
<223> OTHER INFORMATION: IgG4 Fc domain
<220> FEATURE:
<221> NAME/KEY: CDS
<222> LOCATION: (1)..(687)

<400> SEQUENCE: 7 gag tcc aaa tat ggt ccc ccg tgc cca tca tgc cca gca cct gag ttc     48
Glu Ser Lys Tyr Gly Pro Pro Cys Pro Ser Cys Pro Ala Pro Glu Phe
1               5                   10                  15 ctg ggg gga cca tca gtc ttc ctg ttc ccc cca aaa ccc aag gac act     96
Leu Gly Gly Pro Ser Val Phe Leu Phe Pro Pro Lys Pro Lys Asp Thr
            20                  25                  30

```
ctc atg atc tcc cgg acc cct gag gtc acg tgc gtg gtg gtg gac gtg      144
Leu Met Ile Ser Arg Thr Pro Glu Val Thr Cys Val Val Val Asp Val
        35                  40                  45 agc cag gaa gac ccc gag gtc cag ttc aac tgg tac gtg gat ggc gtg      192
Ser Gln Glu Asp Pro Glu Val Gln Phe Asn Trp Tyr Val Asp Gly Val
 50                  55                  60 gag gtg cat aat gcc aag aca aag ccg cgg gag gag cag ttc aac agc      240
Glu Val His Asn Ala Lys Thr Lys Pro Arg Glu Glu Gln Phe Asn Ser
 65                  70                  75                  80 acg tac cgt gtg gtc agc gtc ctc acc gtc gtg cac cag gac tgg ctg      288
Thr Tyr Arg Val Val Ser Val Leu Thr Val Val His Gln Asp Trp Leu
                 85                  90                  95 aac ggc aag gag tac aag tgc aag gtc tcc aac aaa ggc ctc ccg tcc      336
Asn Gly Lys Glu Tyr Lys Cys Lys Val Ser Asn Lys Gly Leu Pro Ser
            100                 105                 110 tcc atc gag aaa acc atc tcc aaa gcc aaa ggg cag ccc cga gag cca      384
Ser Ile Glu Lys Thr Ile Ser Lys Ala Lys Gly Gln Pro Arg Glu Pro
        115                 120                 125 cag gtg tac acc ctg ccc cca tcc cag gag gag atg acc aag aac cag      432
Gln Val Tyr Thr Leu Pro Pro Ser Gln Glu Glu Met Thr Lys Asn Gln
130                 135                 140 gtc agc ctg acc tgc ctg gtc aaa ggc ttc tac ccc agc gac atc gcc      480
Val Ser Leu Thr Cys Leu Val Lys Gly Phe Tyr Pro Ser Asp Ile Ala
145                 150                 155                 160 gtg gag tgg gag agc aat ggg cag ccg gag aac aac tac aag acc acg      528
Val Glu Trp Glu Ser Asn Gly Gln Pro Glu Asn Asn Tyr Lys Thr Thr
                165                 170                 175 cct ccc gtg ctg gac tcc gac ggc tcc ttc ttc ctc tac agc agg cta      576
Pro Pro Val Leu Asp Ser Asp Gly Ser Phe Phe Leu Tyr Ser Arg Leu
            180                 185                 190 acc gtg gac aag agc agg tgg cag gag ggg aat gtc ttc tca tgc tcc      624
Thr Val Asp Lys Ser Arg Trp Gln Glu Gly Asn Val Phe Ser Cys Ser
        195                 200                 205 gtg atg cat gag gct ctg cac aac cac tac acg cag aag agc ctc tcc      672
Val Met His Glu Ala Leu His Asn His Tyr Thr Gln Lys Ser Leu Ser
    210                 215                 220 ctg tct ctg ggt aaa                                                   687
Leu Ser Leu Gly Lys
225

<210> SEQ ID NO 8
<211> LENGTH: 229
<212> TYPE: PRT
<213> ORGANISM: Homo sapiens

<400> SEQUENCE: 8

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Val His Gln Asp Trp Leu
                 85                  90                  95

Asn Gly Lys Glu Tyr Lys Cys Lys Val Ser Asn Lys Gly Leu Pro Ser
```

```
                  100                 105                 110
Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 9
<211> LENGTH: 48
<212> TYPE: DNA
<213> ORGANISM: Homo sapiens
<220> FEATURE:
<221> NAME/KEY: misc_feature
<223> OTHER INFORMATION: IgG1 hinge region
<220> FEATURE:
<221> NAME/KEY: CDS
<222> LOCATION: (1)..(48)

<400> SEQUENCE: 9 agt gag ccc aaa tct tgt gac aaa act cac aca tgc cca ccg tgc cca      48
Ser Glu Pro Lys Ser Cys Asp Lys Thr His Thr Cys Pro Pro Cys Pro
1               5                   10                  15

<210> SEQ ID NO 10
<211> LENGTH: 16
<212> TYPE: PRT
<213> ORGANISM: Homo sapiens

<400> SEQUENCE: 10

Ser Glu Pro Lys Ser Cys Asp Lys Thr His Thr Cys Pro Pro Cys Pro
1               5                   10                  15

<210> SEQ ID NO 11
<211> LENGTH: 36
<212> TYPE: DNA
<213> ORGANISM: Homo sapiens
<220> FEATURE:
<221> NAME/KEY: misc_feature
<223> OTHER INFORMATION: IgG2 hinge region
<220> FEATURE:
<221> NAME/KEY: CDS
<222> LOCATION: (1)..(36)

<400> SEQUENCE: 11 gag cgc aaa tgt tgt gtc gag tgc cca ccg tgc cca                      36
Glu Arg Lys Cys Cys Val Glu Cys Pro Pro Cys Pro
1               5                   10

<210> SEQ ID NO 12
<211> LENGTH: 12
<212> TYPE: PRT
<213> ORGANISM: Homo sapiens
```

<400> SEQUENCE: 12

Glu Arg Lys Cys Cys Val Glu Cys Pro Pro Cys Pro
1               5                  10

<210> SEQ ID NO 13
<211> LENGTH: 186
<212> TYPE: DNA
<213> ORGANISM: Homo sapiens
<220> FEATURE:
<221> NAME/KEY: misc_feature
<223> OTHER INFORMATION: IgG3 hinge region
<220> FEATURE:
<221> NAME/KEY: CDS
<222> LOCATION: (1)..(186)

<400> SEQUENCE: 13

```
gag ctc aaa acc cca ctt ggt gac aca act cac aca tgc cca cgg tgc    48
Glu Leu Lys Thr Pro Leu Gly Asp Thr Thr His Thr Cys Pro Arg Cys
1               5                  10                  15 cca gag ccc aaa tct tgt gac aca cct ccc ccg tgc cca cgg tgc cca    96
Pro Glu Pro Lys Ser Cys Asp Thr Pro Pro Pro Cys Pro Arg Cys Pro
            20                  25                  30 gag ccc aaa tct tgt gac aca cct ccc cca tgc cca cgg tgc cca gag   144
Glu Pro Lys Ser Cys Asp Thr Pro Pro Pro Cys Pro Arg Cys Pro Glu
        35                  40                  45 ccc aaa tct tgt gac aca cct ccc cca tgc cca cgg tgc cca             186
Pro Lys Ser Cys Asp Thr Pro Pro Pro Cys Pro Arg Cys Pro
    50                  55                  60
```

<210> SEQ ID NO 14
<211> LENGTH: 62
<212> TYPE: PRT
<213> ORGANISM: Homo sapiens

<400> SEQUENCE: 14

Glu Leu Lys Thr Pro Leu Gly Asp Thr Thr His Thr Cys Pro Arg Cys
1               5                  10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro
    50                  55                  60

<210> SEQ ID NO 15
<211> LENGTH: 36
<212> TYPE: DNA
<213> ORGANISM: Homo sapiens
<220> FEATURE:
<221> NAME/KEY: misc_feature
<223> OTHER INFORMATION: IgG4 hinge region
<220> FEATURE:
<221> NAME/KEY: CDS
<222> LOCATION: (1)..(36)

<400> SEQUENCE: 15

```
gag tcc aaa tat ggt ccc ccg tgc cca tca tgc cca                     36
Glu Ser Lys Tyr Gly Pro Pro Cys Pro Ser Cys Pro
1               5                  10
```

<210> SEQ ID NO 16
<211> LENGTH: 12
<212> TYPE: PRT
<213> ORGANISM: Homo sapiens -continued

```
<400> SEQUENCE: 16

Glu Ser Lys Tyr Gly Pro Pro Cys Pro Ser Cys Pro
1               5                   10

<210> SEQ ID NO 17
<211> LENGTH: 1588
<212> TYPE: DNA
<213> ORGANISM: Artificial Sequence
<220> FEATURE:
<223> OTHER INFORMATION: IgK/IgG1 Fc/IgG1 Fc
<220> FEATURE:
<221> NAME/KEY: CDS
<222> LOCATION: (45)..(1550)

<400> SEQUENCE: 17
gtcagttaag cttggtaccg agctcggatc cagtacccett cacc atg gag aca gac      56
                                                 Met Glu Thr Asp
                                                 1 aca ctc ctg cta tgg gta ctg ctg ctc tgg gtt cca ggt tcc act ggt      104
Thr Leu Leu Leu Trp Val Leu Leu Leu Trp Val Pro Gly Ser Thr Gly
5                   10                  15                  20 gac gcg gca gat atc cag cac agt ggc ggc cgc tcg agt gag ccc aaa      152
Asp Ala Ala Asp Ile Gln His Ser Gly Gly Arg Ser Ser Glu Pro Lys
                25                  30                  35 tct tgt gac aaa act cac aca tgc cca ccg tgc cca gca cct gaa ctc      200
Ser Cys Asp Lys Thr His Thr Cys Pro Pro Cys Pro Ala Pro Glu Leu
            40                  45                  50 ctg ggg gga ccg tca gtc ttc ctc ttc ccc cca aaa ccc aag gac acc      248
Leu Gly Gly Pro Ser Val Phe Leu Phe Pro Pro Lys Pro Lys Asp Thr
        55                  60                  65 ctc atg atc tcc cgg acc cct gag gtc aca tgc gtg gtg gtg gac gtg      296
Leu Met Ile Ser Arg Thr Pro Glu Val Thr Cys Val Val Val Asp Val
70                  75                  80 agc cac gaa gac cct gag gtc aag ttc aac tgg tac gtg gac ggc gtg      344
Ser His Glu Asp Pro Glu Val Lys Phe Asn Trp Tyr Val Asp Gly Val
85                  90                  95                 100 gag gtg cat aat gcc aag aca aag ccg cgg gag gag cag tac aac agc      392
Glu Val His Asn Ala Lys Thr Lys Pro Arg Glu Glu Gln Tyr Asn Ser
                105                 110                 115 acg tac cgg gtg gtc agc gtc ctc acc gtc ctg cac cag gac tgg ctg      440
Thr Tyr Arg Val Val Ser Val Leu Thr Val Leu His Gln Asp Trp Leu
            120                 125                 130 aat ggc aag gag tac aag tgc aag gtc tcc aac aaa gcc ctc cca gcc      488
Asn Gly Lys Glu Tyr Lys Cys Lys Val Ser Asn Lys Ala Leu Pro Ala
        135                 140                 145 ccc atc gag aaa acc atc tcc aaa gcc aaa ggg cag ccc cga gaa cca      536
Pro Ile Glu Lys Thr Ile Ser Lys Ala Lys Gly Gln Pro Arg Glu Pro
    150                 155                 160 cag gtg tac acc ctg ccc cca tcc cgg gat gag ctg acc aag aac cag      584
Gln Val Tyr Thr Leu Pro Pro Ser Arg Asp Glu Leu Thr Lys Asn Gln
165                 170                 175                 180 gtc agc ctg acc tgc ctg gtc aaa ggc ttc tat ccc agc gac atc gcc      632
Val Ser Leu Thr Cys Leu Val Lys Gly Phe Tyr Pro Ser Asp Ile Ala
                185                 190                 195 gtg gag tgg gag agc aat ggg cag ccg gag aac aac tac aag acc acg      680
Val Glu Trp Glu Ser Asn Gly Gln Pro Glu Asn Asn Tyr Lys Thr Thr
            200                 205                 210 cct ccc gtg ctg gac tcc gac ggc tcc ttc ttc ctc tac agc aag ctc      728
Pro Pro Val Leu Asp Ser Asp Gly Ser Phe Phe Leu Tyr Ser Lys Leu
        215                 220                 225 acc gtg gac aag agc agg tgg cag cag ggg aac gtc ttc tca tgc tcc      776
Thr Val Asp Lys Ser Arg Trp Gln Gln Gly Asn Val Phe Ser Cys Ser
```

```
Thr Val Asp Lys Ser Arg Trp Gln Gln Gly Asn Val Phe Ser Cys Ser
    230                 235                 240 gtg atg cat gag gct ctg cac aac cac tac acg cag aag agc ctc tcc      824
Val Met His Glu Ala Leu His Asn His Tyr Thr Gln Lys Ser Leu Ser
245                 250                 255                 260 ctg tct ccg ggt aaa agt cta gac ccc aaa tct tgt gac aaa act cac      872
Leu Ser Pro Gly Lys Ser Leu Asp Pro Lys Ser Cys Asp Lys Thr His
                265                 270                 275 aca tgc cca ccg tgc cca gca cct gaa ctc ctg ggg gga ccg tca gtc      920
Thr Cys Pro Pro Cys Pro Ala Pro Glu Leu Leu Gly Gly Pro Ser Val
            280                 285                 290 ttc ctc ttc ccc cca aaa ccc aag gac acc ctc atg atc tcc cgg acc      968
Phe Leu Phe Pro Pro Lys Pro Lys Asp Thr Leu Met Ile Ser Arg Thr
        295                 300                 305 cct gag gtc aca tgc gtg gtg gtg gac gtg agc cac gaa gac cct gag     1016
Pro Glu Val Thr Cys Val Val Val Asp Val Ser His Glu Asp Pro Glu
    310                 315                 320 gtc aag ttc aac tgg tac gtg gac ggc gtg gag gtg cat aat gcc aag     1064
Val Lys Phe Asn Trp Tyr Val Asp Gly Val Glu Val His Asn Ala Lys
325                 330                 335                 340 aca aag ccg cgg gag gag cag tac aac agc acg tac cgg gtg gtc agc     1112
Thr Lys Pro Arg Glu Glu Gln Tyr Asn Ser Thr Tyr Arg Val Val Ser
                345                 350                 355 gtc ctc acc gtc ctg cac cag gac tgg ctg aat ggc aag gag tac aag     1160
Val Leu Thr Val Leu His Gln Asp Trp Leu Asn Gly Lys Glu Tyr Lys
            360                 365                 370 tgc aag gtc tcc aac aaa gcc ctc cca gcc ccc atc gag aaa acc atc     1208
Cys Lys Val Ser Asn Lys Ala Leu Pro Ala Pro Ile Glu Lys Thr Ile
        375                 380                 385 tcc aaa gcc aaa ggg cag ccc cga gaa cca cag gtg tac acc ctg ccc     1256
Ser Lys Ala Lys Gly Gln Pro Arg Glu Pro Gln Val Tyr Thr Leu Pro
    390                 395                 400 cca tcc cgg gat gag ctg acc aag aac cag gtc agc ctg acc tgc ctg     1304
Pro Ser Arg Asp Glu Leu Thr Lys Asn Gln Val Ser Leu Thr Cys Leu
405                 410                 415                 420 gtc aaa ggc ttc tat ccc agc gac atc gcc gtg gag tgg gag agc aat     1352
Val Lys Gly Phe Tyr Pro Ser Asp Ile Ala Val Glu Trp Glu Ser Asn
                425                 430                 435 ggg cag ccg gag aac aac tac aag acc acg cct ccc gtg ctg gac tcc     1400
Gly Gln Pro Glu Asn Asn Tyr Lys Thr Thr Pro Pro Val Leu Asp Ser
            440                 445                 450 gac ggc tcc ttc ttc ctc tac agc aag ctc acc gtg gac aag agc agg     1448
Asp Gly Ser Phe Phe Leu Tyr Ser Lys Leu Thr Val Asp Lys Ser Arg
        455                 460                 465 tgg cag cag ggg aac gtc ttc tca tgc tcc gtg atg cat gag gct ctg     1496
Trp Gln Gln Gly Asn Val Phe Ser Cys Ser Val Met His Glu Ala Leu
    470                 475                 480 cac aac cac tac acg cag aag agc ctc tcc ctg tct ccg ggt aaa acc     1544
His Asn His Tyr Thr Gln Lys Ser Leu Ser Leu Ser Pro Gly Lys Thr
485                 490                 495                 500 ggt tga catcatcacc atcaccattg atgagttaaa cccgctga                   1588
Gly

<210> SEQ ID NO 18
<211> LENGTH: 501
<212> TYPE: PRT
<213> ORGANISM: Artificial Sequence
<220> FEATURE:
<223> OTHER INFORMATION: Synthetic Construct

<400> SEQUENCE: 18
```

-continued

```
Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
            20                  25                  30

Ser Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
50                      55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
                100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
                180                 185                 190

Ser Asp Ile Ala Val Glu Trp Glu Ser Asn Gly Gln Pro Glu Asn Asn
                195                 200                 205

Tyr Lys Thr Thr Pro Pro Val Leu Asp Ser Asp Gly Ser Phe Phe Leu
        210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys Ser Leu Asp Pro Lys Ser Cys
                260                 265                 270

Asp Lys Thr His Thr Cys Pro Pro Cys Pro Ala Pro Glu Leu Leu Gly
            275                 280                 285

Gly Pro Ser Val Phe Leu Phe Pro Pro Lys Pro Lys Asp Thr Leu Met
        290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
            355                 360                 365

Lys Glu Tyr Lys Cys Lys Val Ser Asn Lys Ala Leu Pro Ala Pro Ile
        370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415
```

```
Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Thr Gly
            500

<210> SEQ ID NO 19
<211> LENGTH: 952
<212> TYPE: DNA
<213> ORGANISM: Artificial Sequence
<220> FEATURE:
<223> OTHER INFORMATION: IgG1 monomer sequence
<220> FEATURE:
<221> NAME/KEY: CDS
<222> LOCATION: (45)..(932)

<400> SEQUENCE: 19
gtcagttaag cttggtaccg agctcggatc cagtacccgtt cacc atg gag aca gac      56
                                                  Met Glu Thr Asp
                                                   1 aca ctc ctg cta tgg gta ctg ctg ctc tgg gtt cca ggt tcc act ggt     104
Thr Leu Leu Leu Trp Val Leu Leu Leu Trp Val Pro Gly Ser Thr Gly
 5                  10                  15                  20 gac gcg gca gat atc cag cac agt ggc ggc cgc tcg agt gag ccc aaa     152
Asp Ala Ala Asp Ile Gln His Ser Gly Gly Arg Ser Ser Glu Pro Lys
                25                  30                  35 tct tgt gac aaa act cac aca tgc cca ccg tgc cca gca cct gaa ctc     200
Ser Cys Asp Lys Thr His Thr Cys Pro Pro Cys Pro Ala Pro Glu Leu
            40                  45                  50 ctg ggg gga ccg tca gtc ttc ctc ttc ccc cca aaa ccc aag gac acc     248
Leu Gly Gly Pro Ser Val Phe Leu Phe Pro Pro Lys Pro Lys Asp Thr
        55                  60                  65 ctc atg atc tcc cgg acc cct gag gtc aca tgc gtg gtg gtg gac gtg     296
Leu Met Ile Ser Arg Thr Pro Glu Val Thr Cys Val Val Val Asp Val
 70                  75                  80 agc cac gaa gac cct gag gtc aag ttc aac tgg tac gtg gac ggc gtg     344
Ser His Glu Asp Pro Glu Val Lys Phe Asn Trp Tyr Val Asp Gly Val
 85                  90                  95                 100 gag gtg cat aat gcc aag aca aag ccg cgg gag gag cag tac aac agc     392
Glu Val His Asn Ala Lys Thr Lys Pro Arg Glu Glu Gln Tyr Asn Ser
                105                 110                 115 acg tac cgg gtg gtc agc gtc ctc acc gtc ctg cac cag gac tgg ctg     440
Thr Tyr Arg Val Val Ser Val Leu Thr Val Leu His Gln Asp Trp Leu
            120                 125                 130 aat ggc aag gag tac aag tgc aag gtc tcc aac aaa gcc ctc cca gcc     488
Asn Gly Lys Glu Tyr Lys Cys Lys Val Ser Asn Lys Ala Leu Pro Ala
        135                 140                 145 ccc atc gag aaa acc atc tcc aaa gcc aaa ggg cag ccc cga gaa cca     536
Pro Ile Glu Lys Thr Ile Ser Lys Ala Lys Gly Gln Pro Arg Glu Pro
    150                 155                 160 cag gtg tac acc ctg ccc cca tcc cgg gat gag ctg acc aag aac cag     584
Gln Val Tyr Thr Leu Pro Pro Ser Arg Asp Glu Leu Thr Lys Asn Gln
165                 170                 175                 180
```

```
gtc agc ctg acc tgc ctg gtc aaa ggc ttc tat ccc agc gac atc gcc      632
Val Ser Leu Thr Cys Leu Val Lys Gly Phe Tyr Pro Ser Asp Ile Ala
            185                 190                 195 gtg gag tgg gag agc aat ggg cag ccg gag aac aac tac aag acc acg      680
Val Glu Trp Glu Ser Asn Gly Gln Pro Glu Asn Asn Tyr Lys Thr Thr
        200                 205                 210 cct ccc gtg ctg gac tcc gac ggc tcc ttc ttc ctc tac agc aag ctc      728
Pro Pro Val Leu Asp Ser Asp Gly Ser Phe Phe Leu Tyr Ser Lys Leu
    215                 220                 225 acc gtg gac aag agc agg tgg cag cag ggg aac gtc ttc tca tgc tcc      776
Thr Val Asp Lys Ser Arg Trp Gln Gln Gly Asn Val Phe Ser Cys Ser
230                 235                 240 gtg atg cat gag gct ctg cac aac cac tac acg cag aag agc ctc tcc      824
Val Met His Glu Ala Leu His Asn His Tyr Thr Gln Lys Ser Leu Ser
245                 250                 255                 260 ctg tct ccg ggt aaa agt cta gag ggc ccg cgg ttc gaa ggt aag cct      872
Leu Ser Pro Gly Lys Ser Leu Glu Gly Pro Arg Phe Glu Gly Lys Pro
                265                 270                 275 atc cct aac cct ctc ctc ggt ctc gat tct acg cgt acc ggt cat cat      920
Ile Pro Asn Pro Leu Leu Gly Leu Asp Ser Thr Arg Thr Gly His His
            280                 285                 290 cac cat cac cat tgatgagtta aacccgctga                                952
His His His His
            295

<210> SEQ ID NO 20
<211> LENGTH: 296
<212> TYPE: PRT
<213> ORGANISM: Artificial Sequence
<220> FEATURE:
<223> OTHER INFORMATION: Synthetic Construct

<400> SEQUENCE: 20

Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
                20                  25                  30

Ser Glu Pro Lys Ser Cys Asp Lys Thr His Thr Cys Pro Pro Cys Pro
            35                  40                  45

Ala Pro Glu Leu Leu Gly Gly Pro Ser Val Phe Leu Phe Pro Pro Lys
        50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
```

```
                    195                 200                 205
Tyr Lys Thr Thr Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys Ser Leu Glu Gly Pro Arg Phe
            260                 265                 270

Glu Gly Lys Pro Ile Pro Asn Pro Leu Leu Gly Leu Asp Ser Thr Arg
        275                 280                 285

Thr Gly His His His His His His
    290                 295

<210> SEQ ID NO 21
<211> LENGTH: 1588
<212> TYPE: DNA
<213> ORGANISM: Artificial Sequence
<220> FEATURE:
<223> OTHER INFORMATION: IgG1 dimer sequence without tags
<220> FEATURE:
<221> NAME/KEY: CDS
<222> LOCATION: (45)..(1550)

<400> SEQUENCE: 21
gtcagttaag cttggtaccg agctcggatc cagtacccett cacc atg gag aca gac     56
                                                 Met Glu Thr Asp
                                                   1 aca ctc ctg cta tgg gta ctg ctg ctc tgg gtt cca ggt tcc act ggt      104
Thr Leu Leu Leu Trp Val Leu Leu Leu Trp Val Pro Gly Ser Thr Gly
  5               10                  15                  20 gac gcg gca gat atc cag cac agt ggc ggc cgc tcg agt gag ccc aaa      152
Asp Ala Ala Asp Ile Gln His Ser Gly Gly Arg Ser Ser Glu Pro Lys
                 25                  30                  35 tct tgt gac aaa act cac aca tgc cca ccg tgc cca gca cct gaa ctc      200
Ser Cys Asp Lys Thr His Thr Cys Pro Pro Cys Pro Ala Pro Glu Leu
             40                  45                  50 ctg ggg gga ccg tca gtc ttc ctc ttc ccc cca aaa ccc aag gac acc      248
Leu Gly Gly Pro Ser Val Phe Leu Phe Pro Pro Lys Pro Lys Asp Thr
         55                  60                  65 ctc atg atc tcc cgg acc cct gag gtc aca tgc gtg gtg gtg gac gtg      296
Leu Met Ile Ser Arg Thr Pro Glu Val Thr Cys Val Val Val Asp Val
 70                  75                  80 agc cac gaa gac cct gag gtc aag ttc aac tgg tac gtg gac ggc gtg      344
Ser His Glu Asp Pro Glu Val Lys Phe Asn Trp Tyr Val Asp Gly Val
 85                  90                  95                 100 gag gtg cat aat gcc aag aca aag ccg cgg gag gag cag tac aac agc      392
Glu Val His Asn Ala Lys Thr Lys Pro Arg Glu Glu Gln Tyr Asn Ser
                105                 110                 115 acg tac cgg gtg gtc agc gtc ctc acc gtc ctg cac cag gac tgg ctg      440
Thr Tyr Arg Val Val Ser Val Leu Thr Val Leu His Gln Asp Trp Leu
            120                 125                 130 aat ggc aag gag tac aag tgc aag gtc tcc aac aaa gcc ctc cca gcc      488
Asn Gly Lys Glu Tyr Lys Cys Lys Val Ser Asn Lys Ala Leu Pro Ala
        135                 140                 145 ccc atc gag aaa acc atc tcc aaa gcc aaa ggg cag ccc cga gaa cca      536
Pro Ile Glu Lys Thr Ile Ser Lys Ala Lys Gly Gln Pro Arg Glu Pro
    150                 155                 160 cag gtg tac acc ctg ccc cca tcc cgg gat gag ctg acc aag aac cag      584
Gln Val Tyr Thr Leu Pro Pro Ser Arg Asp Glu Leu Thr Lys Asn Gln
```

```
                                                          165                 170                 175                 180
gtc agc ctg acc tgc ctg gtc aaa ggc ttc tat ccc agc gac atc gcc        632
Val Ser Leu Thr Cys Leu Val Lys Gly Phe Tyr Pro Ser Asp Ile Ala
                185                 190                 195 gtg gag tgg gag agc aat ggg cag ccg gag aac aac tac aag acc acg        680
Val Glu Trp Glu Ser Asn Gly Gln Pro Glu Asn Asn Tyr Lys Thr Thr
        200                 205                 210 cct ccc gtg ctg gac tcc gac ggc tcc ttc ttc ctc tac agc aag ctc        728
Pro Pro Val Leu Asp Ser Asp Gly Ser Phe Phe Leu Tyr Ser Lys Leu
            215                 220                 225 acc gtg gac aag agc agg tgg cag cag ggg aac gtc ttc tca tgc tcc        776
Thr Val Asp Lys Ser Arg Trp Gln Gln Gly Asn Val Phe Ser Cys Ser
        230                 235                 240 gtg atg cat gag gct ctg cac aac cac tac acg cag aag agc ctc tcc        824
Val Met His Glu Ala Leu His Asn His Tyr Thr Gln Lys Ser Leu Ser
245                 250                 255                 260 ctg tct ccg ggt aaa agt cta gac ccc aaa tct tgt gac aaa act cac        872
Leu Ser Pro Gly Lys Ser Leu Asp Pro Lys Ser Cys Asp Lys Thr His
                265                 270                 275 aca tgc cca ccg tgc cca gca cct gaa ctc ctg ggg gga ccg tca gtc        920
Thr Cys Pro Pro Cys Pro Ala Pro Glu Leu Leu Gly Gly Pro Ser Val
            280                 285                 290 ttc ctc ttc ccc cca aaa ccc aag gac acc ctc atg atc tcc cgg acc        968
Phe Leu Phe Pro Pro Lys Pro Lys Asp Thr Leu Met Ile Ser Arg Thr
        295                 300                 305 cct gag gtc aca tgc gtg gtg gtg gac gtg agc cac gaa gac cct gag       1016
Pro Glu Val Thr Cys Val Val Val Asp Val Ser His Glu Asp Pro Glu
    310                 315                 320 gtc aag ttc aac tgg tac gtg gac ggc gtg gag gtg cat aat gcc aag       1064
Val Lys Phe Asn Trp Tyr Val Asp Gly Val Glu Val His Asn Ala Lys
325                 330                 335                 340 aca aag ccg cgg gag gag cag tac aac agc acg tac cgg gtg gtc agc       1112
Thr Lys Pro Arg Glu Glu Gln Tyr Asn Ser Thr Tyr Arg Val Val Ser
                345                 350                 355 gtc ctc acc gtc ctg cac cag gac tgg ctg aat ggc aag gag tac aag       1160
Val Leu Thr Val Leu His Gln Asp Trp Leu Asn Gly Lys Glu Tyr Lys
            360                 365                 370 tgc aag gtc tcc aac aaa gcc ctc cca gcc ccc atc gag aaa acc atc       1208
Cys Lys Val Ser Asn Lys Ala Leu Pro Ala Pro Ile Glu Lys Thr Ile
        375                 380                 385 tcc aaa gcc aaa ggg cag ccc cga gaa cca cag gtg tac acc ctg ccc       1256
Ser Lys Ala Lys Gly Gln Pro Arg Glu Pro Gln Val Tyr Thr Leu Pro
    390                 395                 400 cca tcc cgg gat gag ctg acc aag aac cag gtc agc ctg acc tgc ctg       1304
Pro Ser Arg Asp Glu Leu Thr Lys Asn Gln Val Ser Leu Thr Cys Leu
405                 410                 415                 420 gtc aaa ggc ttc tat ccc agc gac atc gcc gtg gag tgg gag agc aat       1352
Val Lys Gly Phe Tyr Pro Ser Asp Ile Ala Val Glu Trp Glu Ser Asn
                425                 430                 435 ggg cag ccg gag aac aac tac aag acc acg cct ccc gtg ctg gac tcc       1400
Gly Gln Pro Glu Asn Asn Tyr Lys Thr Thr Pro Pro Val Leu Asp Ser
            440                 445                 450 gac ggc tcc ttc ttc ctc tac agc aag ctc acc gtg gac aag agc agg       1448
Asp Gly Ser Phe Phe Leu Tyr Ser Lys Leu Thr Val Asp Lys Ser Arg
        455                 460                 465 tgg cag cag ggg aac gtc ttc tca tgc tcc gtg atg cat gag gct ctg       1496
Trp Gln Gln Gly Asn Val Phe Ser Cys Ser Val Met His Glu Ala Leu
    470                 475                 480 cac aac cac tac acg cag aag agc ctc tcc ctg tct ccg ggt aaa acc       1544
```

```
His Asn His Tyr Thr Gln Lys Ser Leu Ser Leu Ser Pro Gly Lys Thr
485                 490                 495                 500 ggt tga catcatcacc atcaccattg atgagttaaa cccgctga            1588
Gly
```

<210> SEQ ID NO 22
<211> LENGTH: 501
<212> TYPE: PRT
<213> ORGANISM: Artificial Sequence
<220> FEATURE:
<223> OTHER INFORMATION: Synthetic Construct

<400> SEQUENCE: 22

```
Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
                20                  25                  30

Ser Glu Pro Lys Ser Cys Asp Lys Thr His Thr Cys Pro Pro Cys Pro
            35                  40                  45

Ala Pro Glu Leu Leu Gly Gly Pro Ser Val Phe Leu Phe Pro Pro Lys
        50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys Ser Leu Asp Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335
```

```
His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
                355                 360                 365

Lys Glu Tyr Lys Cys Lys Val Ser Asn Lys Ala Leu Pro Ala Pro Ile
            370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
            435                 440                 445

Val Leu Asp Ser Asp Gly Ser Phe Phe Leu Tyr Ser Lys Leu Thr Val
            450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Thr Gly
            500

<210> SEQ ID NO 23
<211> LENGTH: 1636
<212> TYPE: DNA
<213> ORGANISM: Artificial Sequence
<220> FEATURE:
<223> OTHER INFORMATION: IgG1 dimer sequence with epitope tags
<220> FEATURE:
<221> NAME/KEY: CDS
<222> LOCATION: (45)..(1616)

<400> SEQUENCE: 23
gtcagttaag cttggtaccg agctcggatc cagtacccct tcacc atg gag aca gac       56
                                                  Met Glu Thr Asp
                                                    1 aca ctc ctg cta tgg gta ctg ctg ctc tgg gtt cca ggt tcc act ggt      104
Thr Leu Leu Leu Trp Val Leu Leu Leu Trp Val Pro Gly Ser Thr Gly
  5                  10                  15                  20 gac gcg gca gat atc cag cac agt ggc ggc cgc tcg agt gag ccc aaa      152
Asp Ala Ala Asp Ile Gln His Ser Gly Gly Arg Ser Ser Glu Pro Lys
                 25                  30                  35 tct tgt gac aaa act cac aca tgc cca ccg tgc cca gca cct gaa ctc      200
Ser Cys Asp Lys Thr His Thr Cys Pro Pro Cys Pro Ala Pro Glu Leu
             40                  45                  50 ctg ggg gga ccg tca gtc ttc ctc ttc ccc cca aaa ccc aag gac acc      248
Leu Gly Gly Pro Ser Val Phe Leu Phe Pro Pro Lys Pro Lys Asp Thr
         55                  60                  65 ctc atg atc tcc cgg acc cct gag gtc aca tgc gtg gtg gtg gac gtg      296
Leu Met Ile Ser Arg Thr Pro Glu Val Thr Cys Val Val Val Asp Val
 70                  75                  80 agc cac gaa gac cct gag gtc aag ttc aac tgg tac gtg gac ggc gtg      344
Ser His Glu Asp Pro Glu Val Lys Phe Asn Trp Tyr Val Asp Gly Val
 85                  90                  95                 100 gag gtg cat aat gcc aag aca aag ccg cgg gag gag cag tac aac agc      392
Glu Val His Asn Ala Lys Thr Lys Pro Arg Glu Glu Gln Tyr Asn Ser
                105                 110                 115 acg tac cgg gtg gtc agc gtc ctc acc gtc ctg cac cag gac tgg ctg      440
```

-continued

```
                    Thr Tyr Arg Val Val Ser Val Leu Thr Val Leu His Gln Asp Trp Leu
                                120                 125                 130 aat ggc aag gag tac aag tgc aag gtc tcc aac aaa gcc ctc cca gcc              488
Asn Gly Lys Glu Tyr Lys Cys Lys Val Ser Asn Lys Ala Leu Pro Ala
        135                 140                 145 ccc atc gag aaa acc atc tcc aaa gcc aaa ggg cag ccc cga gaa cca              536
Pro Ile Glu Lys Thr Ile Ser Lys Ala Lys Gly Gln Pro Arg Glu Pro
    150                 155                 160 cag gtg tac acc ctg ccc cca tcc cgg gat gag ctg acc aag aac cag              584
Gln Val Tyr Thr Leu Pro Pro Ser Arg Asp Glu Leu Thr Lys Asn Gln
165                 170                 175                 180 gtc agc ctg acc tgc ctg gtc aaa ggc ttc tat ccc agc gac atc gcc              632
Val Ser Leu Thr Cys Leu Val Lys Gly Phe Tyr Pro Ser Asp Ile Ala
                185                 190                 195 gtg gag tgg gag agc aat ggg cag ccg gag aac aac tac aag acc acg              680
Val Glu Trp Glu Ser Asn Gly Gln Pro Glu Asn Asn Tyr Lys Thr Thr
            200                 205                 210 cct ccc gtg ctg gac tcc gac ggc tcc ttc ttc ctc tac agc aag ctc              728
Pro Pro Val Leu Asp Ser Asp Gly Ser Phe Phe Leu Tyr Ser Lys Leu
        215                 220                 225 acc gtg gac aag agc agg tgg cag cag ggg aac gtc ttc tca tgc tcc              776
Thr Val Asp Lys Ser Arg Trp Gln Gln Gly Asn Val Phe Ser Cys Ser
    230                 235                 240 gtg atg cat gag gct ctg cac aac cac tac acg cag aag agc ctc tcc              824
Val Met His Glu Ala Leu His Asn His Tyr Thr Gln Lys Ser Leu Ser
245                 250                 255                 260 ctg tct ccg ggt aaa agt cta gac ccc aaa tct tgt gac aaa act cac              872
Leu Ser Pro Gly Lys Ser Leu Asp Pro Lys Ser Cys Asp Lys Thr His
                265                 270                 275 aca tgc cca ccg tgc cca gca cct gaa ctc ctg ggg gga ccg tca gtc              920
Thr Cys Pro Pro Cys Pro Ala Pro Glu Leu Leu Gly Gly Pro Ser Val
            280                 285                 290 ttc ctc ttc ccc cca aaa ccc aag gac acc ctc atg atc tcc cgg acc              968
Phe Leu Phe Pro Pro Lys Pro Lys Asp Thr Leu Met Ile Ser Arg Thr
        295                 300                 305 cct gag gtc aca tgc gtg gtg gtg gac gtg agc cac gaa gac cct gag             1016
Pro Glu Val Thr Cys Val Val Val Asp Val Ser His Glu Asp Pro Glu
    310                 315                 320 gtc aag ttc aac tgg tac gtg gac ggc gtg gag gtg cat aat gcc aag             1064
Val Lys Phe Asn Trp Tyr Val Asp Gly Val Glu Val His Asn Ala Lys
325                 330                 335                 340 aca aag ccg cgg gag gag cag tac aac agc acg tac cgg gtg gtc agc             1112
Thr Lys Pro Arg Glu Glu Gln Tyr Asn Ser Thr Tyr Arg Val Val Ser
                345                 350                 355 gtc ctc acc gtc ctg cac cag gac tgg ctg aat ggc aag gag tac aag             1160
Val Leu Thr Val Leu His Gln Asp Trp Leu Asn Gly Lys Glu Tyr Lys
            360                 365                 370 tgc aag gtc tcc aac aaa gcc ctc cca gcc ccc atc gag aaa acc atc             1208
Cys Lys Val Ser Asn Lys Ala Leu Pro Ala Pro Ile Glu Lys Thr Ile
        375                 380                 385 tcc aaa gcc aaa ggg cag ccc cga gaa cca cag gtg tac acc ctg ccc             1256
Ser Lys Ala Lys Gly Gln Pro Arg Glu Pro Gln Val Tyr Thr Leu Pro
    390                 395                 400 cca tcc cgg gat gag ctg acc aag aac cag gtc agc ctg acc tgc ctg             1304
Pro Ser Arg Asp Glu Leu Thr Lys Asn Gln Val Ser Leu Thr Cys Leu
405                 410                 415                 420 gtc aaa ggc ttc tat ccc agc gac atc gcc gtg gag tgg gag agc aat             1352
Val Lys Gly Phe Tyr Pro Ser Asp Ile Ala Val Glu Trp Glu Ser Asn
                425                 430                 435
```

```
ggg cag ccg gag aac aac tac aag acc acg cct ccc gtg ctg gac tcc       1400
Gly Gln Pro Glu Asn Asn Tyr Lys Thr Thr Pro Pro Val Leu Asp Ser
            440                 445                 450 gac ggc tcc ttc ttc ctc tac agc aag ctc acc gtg gac aag agc agg       1448
Asp Gly Ser Phe Phe Leu Tyr Ser Lys Leu Thr Val Asp Lys Ser Arg
        455                 460                 465 tgg cag cag ggg aac gtc ttc tca tgc tcc gtg atg cat gag gct ctg       1496
Trp Gln Gln Gly Asn Val Phe Ser Cys Ser Val Met His Glu Ala Leu
470                 475                 480 cac aac cac tac acg cag aag agc ctc tcc ctg tct ccg ggt aaa ttc       1544
His Asn His Tyr Thr Gln Lys Ser Leu Ser Leu Ser Pro Gly Lys Phe
485                 490                 495                 500 gaa ggt aag cct atc cct aac cct ctc ctc ggt ctc gat tct acg cgt       1592
Glu Gly Lys Pro Ile Pro Asn Pro Leu Leu Gly Leu Asp Ser Thr Arg
                505                 510                 515 acc ggt cat cat cac cat cac cat tgatgagtta aacccgctga                 1636
Thr Gly His His His His His His
            520

<210> SEQ ID NO 24
<211> LENGTH: 524
<212> TYPE: PRT
<213> ORGANISM: Artificial Sequence
<220> FEATURE:
<223> OTHER INFORMATION: Synthetic Construct

<400> SEQUENCE: 24

Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
            20                  25                  30

Ser Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240
```

```
Phe Ser Cys Ser Val Met His Glu Ala Leu His Asn His Tyr Thr Gln
            245                 250                 255
Lys Ser Leu Ser Leu Ser Pro Gly Lys Ser Leu Asp Pro Lys Ser Cys
        260                 265                 270
Asp Lys Thr His Thr Cys Pro Pro Cys Pro Ala Pro Glu Leu Leu Gly
        275                 280                 285
Gly Pro Ser Val Phe Leu Phe Pro Pro Lys Pro Lys Asp Thr Leu Met
        290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
            325                 330                 335
His Asn Ala Lys Thr Lys Pro Arg Glu Glu Gln Tyr Asn Ser Thr Tyr
            340                 345                 350
Arg Val Val Ser Val Leu Thr Val Leu His Gln Asp Trp Leu Asn Gly
            355                 360                 365
Lys Glu Tyr Lys Cys Lys Val Ser Asn Lys Ala Leu Pro Ala Pro Ile
        370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
            405                 410                 415
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
            435                 440                 445
Val Leu Asp Ser Asp Gly Ser Phe Phe Leu Tyr Ser Lys Leu Thr Val
        450                 455                 460
Asp Lys Ser Arg Trp Gln Gln Gly Asn Val Phe Ser Cys Ser Val Met
465                 470                 475                 480
His Glu Ala Leu His Asn His Tyr Thr Gln Lys Ser Leu Ser Leu Ser
            485                 490                 495
Pro Gly Lys Phe Glu Gly Lys Pro Ile Pro Asn Pro Leu Leu Gly Leu
        500                 505                 510
Asp Ser Thr Arg Thr Gly His His His His His
        515                 520
```

<210> SEQ ID NO 25
<211> LENGTH: 1763
<212> TYPE: DNA
<213> ORGANISM: Artificial Sequence
<220> FEATURE:
<223> OTHER INFORMATION: IgG3/IgG1 dimer sequence with epitope tags
<220> FEATURE:
<221> NAME/KEY: CDS
<222> LOCATION: (45)..(1760)

<400> SEQUENCE: 25

```
gtcagttaag cttggtaccg agctcggatc cagtacccett cacc atg gag aca gac        56
                                                Met Glu Thr Asp
                                                  1 aca ctc ctg cta tgg gta ctg ctg ctc tgg gtt cca ggt tcc act ggt      104
Thr Leu Leu Leu Trp Val Leu Leu Leu Trp Val Pro Gly Ser Thr Gly
  5                  10                  15                  20 gac gcg gca gat atc gag ctc aaa acc cca ctt ggt gac aca act cac      152
Asp Ala Ala Asp Ile Glu Leu Lys Thr Pro Leu Gly Asp Thr Thr His
                 25                  30                  35
```

| | | |
|---|---|---|
| aca tgc cca cgg tgc cca gag ccc aaa tct tgt gac aca cct ccc ccg<br>Thr Cys Pro Arg Cys Pro Glu Pro Lys Ser Cys Asp Thr Pro Pro Pro<br>          40                         45                       50 | 200 |
| tgc cca cgg tgc cca gag ccc aaa tct tgt gac aca cct ccc cca tgc<br>Cys Pro Arg Cys Pro Glu Pro Lys Ser Cys Asp Thr Pro Pro Pro Cys<br>          55                       60                       65 | 248 |
| cca cgg tgc cca gag ccc aaa tct tgt gac aca cct ccc cca tgc cca<br>Pro Arg Cys Pro Glu Pro Lys Ser Cys Asp Thr Pro Pro Pro Cys Pro<br>70                       75                      80 | 296 |
| cgg tgc cca gca cct gaa ctc ctg gga gga ccg tca gtc ttc ctc ttc<br>Arg Cys Pro Ala Pro Glu Leu Leu Gly Gly Pro Ser Val Phe Leu Phe<br>85                      90                      95                 100 | 344 |
| ccc cca aaa ccc aag gat acc ctt atg att tcc cgg acc cct gag gtc<br>Pro Pro Lys Pro Lys Asp Thr Leu Met Ile Ser Arg Thr Pro Glu Val<br>                    105                    110                    115 | 392 |
| acg tgc gtg gtg gtg gac gtg agc cac gaa gac ccc gag gtc cag ttc<br>Thr Cys Val Val Val Asp Val Ser His Glu Asp Pro Glu Val Gln Phe<br>               120                    125                    130 | 440 |
| aag tgg tac gtg gac ggc gtg gag gtg cat aat gcc aag aca aag ccg<br>Lys Trp Tyr Val Asp Gly Val Glu Val His Asn Ala Lys Thr Lys Pro<br>          135                    140                    145 | 488 |
| cgg gag gag cag ttc aac agc acg ttc cgt gtg gtc agc gtc ctc acc<br>Arg Glu Glu Gln Phe Asn Ser Thr Phe Arg Val Val Ser Val Leu Thr<br>150                    155                    160 | 536 |
| gtc ctg cac cag gac tgg ctg aac ggc aag gag tac aag tgc aag gtc<br>Val Leu His Gln Asp Trp Leu Asn Gly Lys Glu Tyr Lys Cys Lys Val<br>165                    170                  175              180 | 584 |
| tcc aac aaa gcc ctc cca gcc ccc atc gag aaa acc atc tcc aaa acc<br>Ser Asn Lys Ala Leu Pro Ala Pro Ile Glu Lys Thr Ile Ser Lys Thr<br>               185                    190                    195 | 632 |
| aaa gga cag ccc cga gaa cca cag gtg tac acc ctg ccc cca tcc cgg<br>Lys Gly Gln Pro Arg Glu Pro Gln Val Tyr Thr Leu Pro Pro Ser Arg<br>200                    205                    210 | 680 |
| gag gag atg acc aag aac cag gtc agc ctg acc tgc ctg gtc aaa ggc<br>Glu Glu Met Thr Lys Asn Gln Val Ser Leu Thr Cys Leu Val Lys Gly<br>215                    220                    225 | 728 |
| ttc tac ccc agc gac atc gcc gtg gag tgg gag agc agc ggg cag ccg<br>Phe Tyr Pro Ser Asp Ile Ala Val Glu Trp Glu Ser Ser Gly Gln Pro<br>230                      235                    240 | 776 |
| gag aac aac tac aac acc acg cct ccc atg ctg gac tcc gac ggc tcc<br>Glu Asn Asn Tyr Asn Thr Thr Pro Pro Met Leu Asp Ser Asp Gly Ser<br>245                    250                    255              260 | 824 |
| ttc ttc ctc tac agc aag ctc acc gtg gac aag agc agg tgg cag cag<br>Phe Phe Leu Tyr Ser Lys Leu Thr Val Asp Lys Ser Arg Trp Gln Gln<br>               265                    270                    275 | 872 |
| ggg aac atc ttc tca tgc tcc gtg atg cat gag gct ctg cac aac cgc<br>Gly Asn Ile Phe Ser Cys Ser Val Met His Glu Ala Leu His Asn Arg<br>               280                    285                    290 | 920 |
| ttc acg cag aag agc ctc tcc ctg tct ccg ggt aaa ggc ggc cgc tcg<br>Phe Thr Gln Lys Ser Leu Ser Leu Ser Pro Gly Lys Gly Gly Arg Ser<br>295                    300                    305 | 968 |
| agt gag ccc aaa tct tgt gac aaa act cac aca tgc cca ccg tgc cca<br>Ser Glu Pro Lys Ser Cys Asp Lys Thr His Thr Cys Pro Pro Cys Pro<br>310                    315                    320 | 1016 |
| gca cct gaa ctc ctg ggg gga ccg tca gtc ttc ctc ttc ccc cca aaa<br>Ala Pro Glu Leu Leu Gly Gly Pro Ser Val Phe Leu Phe Pro Pro Lys<br>325                    330                    335              340 | 1064 |
| ccc aag gac acc ctc atg atc tcc cgg acc cct gag gtc aca tgc gtg<br>Pro Lys Asp Thr Leu Met Ile Ser Arg Thr Pro Glu Val Thr Cys Val<br>               345                    350                    355 | 1112 |

```
gtg gtg gac gtg agc cac gaa gac cct gag gtc aag ttc aac tgg tac      1160
Val Val Asp Val Ser His Glu Asp Pro Glu Val Lys Phe Asn Trp Tyr
            360                 365                 370 gtg gac ggc gtg gag gtg cat aat gcc aag aca aag ccg cgg gag gag      1208
Val Asp Gly Val Glu Val His Asn Ala Lys Thr Lys Pro Arg Glu Glu
        375                 380                 385 cag tac aac agc acg tac cgg gtg gtc agc gtc ctc acc gtc ctg cac      1256
Gln Tyr Asn Ser Thr Tyr Arg Val Val Ser Val Leu Thr Val Leu His
    390                 395                 400 cag gac tgg ctg aat ggc aag gag tac aag tgc aag gtc tcc aac aaa      1304
Gln Asp Trp Leu Asn Gly Lys Glu Tyr Lys Cys Lys Val Ser Asn Lys
405                 410                 415                 420 gcc ctc cca gcc ccc atc gag aaa acc atc tcc aaa gcc aaa ggg cag      1352
Ala Leu Pro Ala Pro Ile Glu Lys Thr Ile Ser Lys Ala Lys Gly Gln
                425                 430                 435 ccc cga gaa cca cag gtg tac acc ctg ccc cca tcc cgg gat gag ctg      1400
Pro Arg Glu Pro Gln Val Tyr Thr Leu Pro Pro Ser Arg Asp Glu Leu
            440                 445                 450 acc aag aac cag gtc agc ctg acc tgc ctg gtc aaa ggc ttc tat ccc      1448
Thr Lys Asn Gln Val Ser Leu Thr Cys Leu Val Lys Gly Phe Tyr Pro
        455                 460                 465 agc gac atc gcc gtg gag tgg gag agc aat ggg cag ccg gag aac aac      1496
Ser Asp Ile Ala Val Glu Trp Glu Ser Asn Gly Gln Pro Glu Asn Asn
    470                 475                 480 tac aag acc acg cct ccc gtg ctg gac tcc gac ggc tcc ttc ttc ctc      1544
Tyr Lys Thr Thr Pro Pro Val Leu Asp Ser Asp Gly Ser Phe Phe Leu
485                 490                 495                 500 tac agc aag ctc acc gtg gac aag agc agg tgg cag cag ggg aac gtc      1592
Tyr Ser Lys Leu Thr Val Asp Lys Ser Arg Trp Gln Gln Gly Asn Val
                505                 510                 515 ttc tca tgc tcc gtg atg cat gag gct ctg cac aac cac tac acg cag      1640
Phe Ser Cys Ser Val Met His Glu Ala Leu His Asn His Tyr Thr Gln
            520                 525                 530 aag agc ctc tcc ctg tct ccg ggt aaa agt cta gag ggc ccg cgg ttc      1688
Lys Ser Leu Ser Leu Ser Pro Gly Lys Ser Leu Glu Gly Pro Arg Phe
        535                 540                 545 gaa ggt aag cct atc cct aac cct ctc ctc ggt ctc gat tct acg cgt      1736
Glu Gly Lys Pro Ile Pro Asn Pro Leu Leu Gly Leu Asp Ser Thr Arg
550                 555                 560 acc ggt cat cat cac cat cac cat tga                                  1763
Thr Gly His His His His His His
565                 570

<210> SEQ ID NO 26
<211> LENGTH: 572
<212> TYPE: PRT
<213> ORGANISM: Artificial Sequence
<220> FEATURE:
<223> OTHER INFORMATION: Synthetic Construct

<400> SEQUENCE: 26

Met Glu Thr Asp Thr Leu Leu Leu Trp Val Leu Leu Leu Trp Val Pro
1               5                   10                  15

Gly Ser Thr Gly Asp Ala Ala Asp Ile Glu Leu Lys Thr Pro Leu Gly
            20                  25                  30

Asp Thr Thr His Thr Cys Pro Arg Cys Pro Glu Pro Lys Ser Cys Asp
        35                  40                  45

Thr Pro Pro Pro Cys Pro Arg Cys Pro Glu Pro Lys Ser Cys Asp Thr
    50                  55                  60
```

-continued

```
Pro Pro Pro Cys Pro Arg Cys Pro Glu Pro Lys Ser Cys Asp Thr Pro
 65                  70                  75                  80

Pro Pro Cys Pro Arg Cys Pro Ala Pro Glu Leu Leu Gly Gly Pro Ser
                 85                  90                  95

Val Phe Leu Phe Pro Pro Lys Pro Lys Asp Thr Leu Met Ile Ser Arg
            100                 105                 110

Thr Pro Glu Val Thr Cys Val Val Val Asp Val Ser His Glu Asp Pro
        115                 120                 125

Glu Val Gln Phe Lys Trp Tyr Val Asp Gly Val Glu Val His Asn Ala
    130                 135                 140

Lys Thr Lys Pro Arg Glu Glu Gln Phe Asn Ser Thr Phe Arg Val Val
145                 150                 155                 160

Ser Val Leu Thr Val Leu His Gln Asp Trp Leu Asn Gly Lys Glu Tyr
                165                 170                 175

Lys Cys Lys Val Ser Asn Lys Ala Leu Pro Ala Pro Ile Glu Lys Thr
            180                 185                 190

Ile Ser Lys Thr Lys Gly Gln Pro Arg Glu Pro Gln Val Tyr Thr Leu
        195                 200                 205

Pro Pro Ser Arg Glu Glu Met Thr Lys Asn Gln Val Ser Leu Thr Cys
    210                 215                 220

Leu Val Lys Gly Phe Tyr Pro Ser Asp Ile Ala Val Glu Trp Glu Ser
225                 230                 235                 240

Ser Gly Gln Pro Glu Asn Asn Tyr Asn Thr Thr Pro Pro Met Leu Asp
                245                 250                 255

Ser Asp Gly Ser Phe Phe Leu Tyr Ser Lys Leu Thr Val Asp Lys Ser
            260                 265                 270

Arg Trp Gln Gln Gly Asn Ile Phe Ser Cys Ser Val Met His Glu Ala
        275                 280                 285

Leu His Asn Arg Phe Thr Gln Lys Ser Leu Ser Leu Ser Pro Gly Lys
    290                 295                 300

Gly Gly Arg Ser Ser Glu Pro Lys Ser Cys Asp Lys Thr His Thr Cys
305                 310                 315                 320

Pro Pro Cys Pro Ala Pro Glu Leu Leu Gly Gly Pro Ser Val Phe Leu
                325                 330                 335

Phe Pro Pro Lys Pro Lys Asp Thr Leu Met Ile Ser Arg Thr Pro Glu
            340                 345                 350

Val Thr Cys Val Val Val Asp Val Ser His Glu Asp Pro Glu Val Lys
        355                 360                 365

Phe Asn Trp Tyr Val Asp Gly Val Glu Val His Asn Ala Lys Thr Lys
    370                 375                 380

Pro Arg Glu Glu Gln Tyr Asn Ser Thr Tyr Arg Val Val Ser Val Leu
385                 390                 395                 400

Thr Val Leu His Gln Asp Trp Leu Asn Gly Lys Glu Tyr Lys Cys Lys
                405                 410                 415

Val Ser Asn Lys Ala Leu Pro Ala Pro Ile Glu Lys Thr Ile Ser Lys
            420                 425                 430

Ala Lys Gly Gln Pro Arg Glu Pro Gln Val Tyr Thr Leu Pro Pro Ser
        435                 440                 445

Arg Asp Glu Leu Thr Lys Asn Gln Val Ser Leu Thr Cys Leu Val Lys
    450                 455                 460

Gly Phe Tyr Pro Ser Asp Ile Ala Val Glu Trp Glu Ser Asn Gly Gln
465                 470                 475                 480

Pro Glu Asn Asn Tyr Lys Thr Thr Pro Pro Val Leu Asp Ser Asp Gly
```

```
                    485                 490                 495
Ser Phe Phe Leu Tyr Ser Lys Leu Thr Val Asp Lys Ser Arg Trp Gln
                500                 505                 510

Gln Gly Asn Val Phe Ser Cys Ser Val Met His Glu Ala Leu His Asn
                515                 520                 525

His Tyr Thr Gln Lys Ser Leu Ser Leu Ser Pro Gly Lys Ser Leu Glu
                530                 535                 540

Gly Pro Arg Phe Glu Gly Lys Pro Ile Pro Asn Pro Leu Leu Gly Leu
545                 550                 555                 560

Asp Ser Thr Arg Thr Gly His His His His His
                565                 570

<210> SEQ ID NO 27
<211> LENGTH: 2224
<212> TYPE: DNA
<213> ORGANISM: Artificial Sequence
<220> FEATURE:
<223> OTHER INFORMATION: IgE(CH2)/IgG1(hinge-CH2-CH3)/IgG1
      (hinge-CH2)/IgE(CH4) fusion without epitope tags
<220> FEATURE:
<221> NAME/KEY: CDS
<222> LOCATION: (45)..(2183)

<400> SEQUENCE: 27
gtcagttaag cttggtaccg agctcggatc cagtacccct cacc atg gag aca gac       56
                                                Met Glu Thr Asp
                                                  1 aca ctc ctg cta tgg gta ctg ctg ctc tgg gtt cca ggt tcc act ggt      104
Thr Leu Leu Leu Trp Val Leu Leu Leu Trp Val Pro Gly Ser Thr Gly
  5                  10                  15                  20 gac gcg gca gat atc gtc tgc tcc agg gac ttc acc ccg ccc acc gtg      152
Asp Ala Ala Asp Ile Val Cys Ser Arg Asp Phe Thr Pro Pro Thr Val
                 25                  30                  35 aag atc tta cag tcg tcc tgc gac ggc ggc ggg cac ttc ccc ccg acc      200
Lys Ile Leu Gln Ser Ser Cys Asp Gly Gly Gly His Phe Pro Pro Thr
             40                  45                  50 atc cag ctc ctg tgc ctc gtc tct ggg tac acc cca ggg act atc aac      248
Ile Gln Leu Leu Cys Leu Val Ser Gly Tyr Thr Pro Gly Thr Ile Asn
         55                  60                  65 atc acc tgg ctg gag gac ggg cag gtc atg gac gtg gac ttg tcc acc      296
Ile Thr Trp Leu Glu Asp Gly Gln Val Met Asp Val Asp Leu Ser Thr
 70                  75                  80 gcc tct acc acg cag gag ggt gag ctg gcc tcc aca caa agc gag ctc      344
Ala Ser Thr Thr Gln Glu Gly Glu Leu Ala Ser Thr Gln Ser Glu Leu
 85                  90                  95                 100 acc ctc agc cag aag cac tgg ctg tca gac cgc acc tac acc tgc cag      392
Thr Leu Ser Gln Lys His Trp Leu Ser Asp Arg Thr Tyr Thr Cys Gln
                105                 110                 115 gtc acc tat caa ggt cac acc ttt gag gac agc acc aag aag tgt gca      440
Val Thr Tyr Gln Gly His Thr Phe Glu Asp Ser Thr Lys Lys Cys Ala
            120                 125                 130 ggc ggc cgc tcg agt gag ccc aaa tct tgt gac aaa act cac aca tgc      488
Gly Gly Arg Ser Ser Glu Pro Lys Ser Cys Asp Lys Thr His Thr Cys
        135                 140                 145 cca ccg tgc cca gca cct gaa ctc ctg ggg gga ccg tca gtc ttc ctc      536
Pro Pro Cys Pro Ala Pro Glu Leu Leu Gly Gly Pro Ser Val Phe Leu
    150                 155                 160 ttc ccc cca aaa ccc aag gac acc ctc atg atc tcc cgg acc cct gag      584
Phe Pro Pro Lys Pro Lys Asp Thr Leu Met Ile Ser Arg Thr Pro Glu
165                 170                 175                 180
```

```
                                                    -continued gtc aca tgc gtg gtg gtg gac gtg agc cac gaa gac cct gag gtc aag      632
Val Thr Cys Val Val Val Asp Val Ser His Glu Asp Pro Glu Val Lys
            185                 190                 195 ttc aac tgg tac gtg gac ggc gtg gag gtg cat aat gcc aag aca aag      680
Phe Asn Trp Tyr Val Asp Gly Val Glu Val His Asn Ala Lys Thr Lys
            200                 205                 210 ccg cgg gag gag cag tac aac agc acg tac cgg gtg gtc agc gtc ctc      728
Pro Arg Glu Glu Gln Tyr Asn Ser Thr Tyr Arg Val Val Ser Val Leu
            215                 220                 225 acc gtc ctg cac cag gac tgg ctg aat ggc aag gag tac aag tgc aag      776
Thr Val Leu His Gln Asp Trp Leu Asn Gly Lys Glu Tyr Lys Cys Lys
            230                 235                 240 gtc tcc aac aaa gcc ctc cca gcc ccc atc gag aaa acc atc tcc aaa      824
Val Ser Asn Lys Ala Leu Pro Ala Pro Ile Glu Lys Thr Ile Ser Lys
245             250                 255                 260 gcc aaa ggg cag ccc cga gaa cca cag gtg tac acc ctg ccc cca tcc      872
Ala Lys Gly Gln Pro Arg Glu Pro Gln Val Tyr Thr Leu Pro Pro Ser
                265                 270                 275 cgg gat gag ctg acc aag aac cag gtc agc ctg acc tgc ctg gtc aaa      920
Arg Asp Glu Leu Thr Lys Asn Gln Val Ser Leu Thr Cys Leu Val Lys
            280                 285                 290 ggc ttc tat ccc agc gac atc gcc gtg gag tgg gag agc aat ggg cag      968
Gly Phe Tyr Pro Ser Asp Ile Ala Val Glu Trp Glu Ser Asn Gly Gln
            295                 300                 305 ccg gag aac aac tac aag acc acg cct ccc gtg ctg gac tcc gac ggc     1016
Pro Glu Asn Asn Tyr Lys Thr Thr Pro Pro Val Leu Asp Ser Asp Gly
            310                 315                 320 tcc ttc ttc ctc tac agc aag ctc acc gtg gac aag agc agg tgg cag     1064
Ser Phe Phe Leu Tyr Ser Lys Leu Thr Val Asp Lys Ser Arg Trp Gln
325             330                 335                 340 cag ggg aac gtc ttc tca tgc tcc gtg atg cat gag gct ctg cac aac     1112
Gln Gly Asn Val Phe Ser Cys Ser Val Met His Glu Ala Leu His Asn
                345                 350                 355 cac tac acg cag aag agc ctc tcc ctg tct ccg ggt aaa agt cta gac     1160
His Tyr Thr Gln Lys Ser Leu Ser Leu Ser Pro Gly Lys Ser Leu Asp
            360                 365                 370 ccc aaa tct tgt gac aaa act cac aca tgc cca ccg tgc cca gca cct     1208
Pro Lys Ser Cys Asp Lys Thr His Thr Cys Pro Pro Cys Pro Ala Pro
            375                 380                 385 gaa ctc ctg ggg gga ccg tca gtc ttc ctc ttc ccc cca aaa ccc aag     1256
Glu Leu Leu Gly Gly Pro Ser Val Phe Leu Phe Pro Pro Lys Pro Lys
            390                 395                 400 gac acc ctc atg atc tcc cgg acc cct gag gtc aca tgc gtg gtg gtg     1304
Asp Thr Leu Met Ile Ser Arg Thr Pro Glu Val Thr Cys Val Val Val
405             410                 415                 420 gac gtg agc cac gaa gac cct gag gtc aag ttc aac tgg tac gtg gac     1352
Asp Val Ser His Glu Asp Pro Glu Val Lys Phe Asn Trp Tyr Val Asp
                425                 430                 435 ggc gtg gag gtg cat aat gcc aag aca aag ccg cgg gag gag cag tac     1400
Gly Val Glu Val His Asn Ala Lys Thr Lys Pro Arg Glu Glu Gln Tyr
            440                 445                 450 aac agc acg tac cgg gtg gtc agc gtc ctc acc gtc ctg cac cag gac     1448
Asn Ser Thr Tyr Arg Val Val Ser Val Leu Thr Val Leu His Gln Asp
            455                 460                 465 tgg ctg aat ggc aag gag tac aag tgc aag gtc tcc aac aaa gcc ctc     1496
Trp Leu Asn Gly Lys Glu Tyr Lys Cys Lys Val Ser Asn Lys Ala Leu
            470                 475                 480 cca gcc ccc atc gag aaa acc atc tcc aaa gcc aaa ggg cag ccc cga     1544
Pro Ala Pro Ile Glu Lys Thr Ile Ser Lys Ala Lys Gly Gln Pro Arg
485             490                 495                 500
```

```
gaa cca cag gtg tac acc ctg ccc cca tcc cgg gat gag ctg acc aag      1592
Glu Pro Gln Val Tyr Thr Leu Pro Pro Ser Arg Asp Glu Leu Thr Lys
            505                 510                 515 aac cag gtc agc ctg acc tgc ctg gtc aaa ggc ttc tat ccc agc gac      1640
Asn Gln Val Ser Leu Thr Cys Leu Val Lys Gly Phe Tyr Pro Ser Asp
        520                 525                 530 atc gcc gtg gag tgg gag agc aat ggg cag ccg gag aac aac tac aag      1688
Ile Ala Val Glu Trp Glu Ser Asn Gly Gln Pro Glu Asn Asn Tyr Lys
    535                 540                 545 acc acg cct ccc gtg ctg gac tcc gac ggc tcc ttc ttc ctc tac agc      1736
Thr Thr Pro Pro Val Leu Asp Ser Asp Gly Ser Phe Phe Leu Tyr Ser
550                 555                 560 aag ctc acc gtg gac aag agc agg tgg cag cag ggg aac gtc ttc tca      1784
Lys Leu Thr Val Asp Lys Ser Arg Trp Gln Gln Gly Asn Val Phe Ser
565                 570                 575                 580 tgc tcc gtg atg cat gag gct ctg cac aac cac tac acg cag aag agc      1832
Cys Ser Val Met His Glu Ala Leu His Asn His Tyr Thr Gln Lys Ser
            585                 590                 595 ctc tcc ctg tct ccg ggt aaa ggc ccg cgt gct gcc ccg gaa gtc tat      1880
Leu Ser Leu Ser Pro Gly Lys Gly Pro Arg Ala Ala Pro Glu Val Tyr
        600                 605                 610 gcg ttt gcg acg ccg gag tgg ccg ggg agc cgg gac aag cgc acc ctc      1928
Ala Phe Ala Thr Pro Glu Trp Pro Gly Ser Arg Asp Lys Arg Thr Leu
    615                 620                 625 gcc tgc ctg atc cag aac ttc atg cct gag gac atc tcg gtg cag tgg      1976
Ala Cys Leu Ile Gln Asn Phe Met Pro Glu Asp Ile Ser Val Gln Trp
630                 635                 640 ctg cac aac gag gtg cag ctc ccg gac gcc cgg cac agc acg acg cag      2024
Leu His Asn Glu Val Gln Leu Pro Asp Ala Arg His Ser Thr Thr Gln
645                 650                 655                 660 ccc cgc aag acc aag ggc tcc ggc ttc ttc gtc ttc agc cgc ctg gag      2072
Pro Arg Lys Thr Lys Gly Ser Gly Phe Phe Val Phe Ser Arg Leu Glu
            665                 670                 675 gtg acc agg gcc gaa tgg gag cag aaa gat gag ttc atc tgc cgt gca      2120
Val Thr Arg Ala Glu Trp Glu Gln Lys Asp Glu Phe Ile Cys Arg Ala
        680                 685                 690 gtc cat gag gca gcg agc ccc tca cag acc gtc cag cga gcg gtg tct      2168
Val His Glu Ala Ala Ser Pro Ser Gln Thr Val Gln Arg Ala Val Ser
    695                 700                 705 gta aat ccc ggt aaa tgacatcatc accatcacca ttgatgagtt aaacccgctg a   2224
Val Asn Pro Gly Lys
        710

<210> SEQ ID NO 28
<211> LENGTH: 713
<212> TYPE: PRT
<213> ORGANISM: Artificial Sequence
<220> FEATURE:
<223> OTHER INFORMATION: Synthetic Construct

<400> SEQUENCE: 28

Met Glu Thr Asp Thr Leu Leu Leu Trp Val Leu Leu Trp Val Pro
1               5                   10                  15

Gly Ser Thr Gly Asp Ala Ala Asp Ile Val Cys Ser Arg Asp Phe Thr
            20                  25                  30

Pro Pro Thr Val Lys Ile Leu Gln Ser Ser Cys Asp Gly Gly Gly His
        35                  40                  45

Phe Pro Pro Thr Ile Gln Leu Leu Cys Leu Val Ser Gly Tyr Thr Pro
    50                  55                  60
```

```
Gly Thr Ile Asn Ile Thr Trp Leu Glu Asp Gly Gln Val Met Asp Val
 65                  70                  75                  80

Asp Leu Ser Thr Ala Ser Thr Thr Gln Glu Gly Glu Leu Ala Ser Thr
                 85                  90                  95

Gln Ser Glu Leu Thr Leu Ser Gln Lys His Trp Leu Ser Asp Arg Thr
            100                 105                 110

Tyr Thr Cys Gln Val Thr Tyr Gln Gly His Thr Phe Glu Asp Ser Thr
        115                 120                 125

Lys Lys Cys Ala Gly Gly Arg Ser Ser Glu Pro Lys Ser Cys Asp Lys
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
                180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
        210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
                260                 265                 270

Leu Pro Pro Ser Arg Asp Glu Leu Thr Lys Asn Gln Val Ser Leu Thr
            275                 280                 285

Cys Leu Val Lys Gly Phe Tyr Pro Ser Asp Ile Ala Val Glu Trp Glu
        290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys Ser Leu Asp Pro Lys Ser Cys Asp Lys Thr His Thr Cys Pro Pro
    370                 375                 380

Cys Pro Ala Pro Glu Leu Leu Gly Gly Pro Ser Val Phe Leu Phe Pro
385                 390                 395                 400

Pro Lys Pro Lys Asp Thr Leu Met Ile Ser Arg Thr Pro Glu Val Thr
                405                 410                 415

Cys Val Val Val Asp Val Ser His Glu Asp Pro Glu Val Lys Phe Asn
                420                 425                 430

Trp Tyr Val Asp Gly Val Glu Val His Asn Ala Lys Thr Lys Pro Arg
            435                 440                 445

Glu Glu Gln Tyr Asn Ser Thr Tyr Arg Val Val Ser Val Leu Thr Val
        450                 455                 460

Leu His Gln Asp Trp Leu Asn Gly Lys Glu Tyr Lys Cys Lys Val Ser
465                 470                 475                 480

Asn Lys Ala Leu Pro Ala Pro Ile Glu Lys Thr Ile Ser Lys Ala Lys
```

```
            485                 490                 495
Gly Gln Pro Arg Glu Pro Gln Val Tyr Thr Leu Pro Pro Ser Arg Asp
            500                 505                 510

Glu Leu Thr Lys Asn Gln Val Ser Leu Thr Cys Leu Val Lys Gly Phe
            515                 520                 525

Tyr Pro Ser Asp Ile Ala Val Glu Trp Glu Ser Asn Gly Gln Pro Glu
            530                 535                 540

Asn Asn Tyr Lys Thr Thr Pro Pro Val Leu Asp Ser Asp Gly Ser Phe
545                 550                 555                 560

Phe Leu Tyr Ser Lys Leu Thr Val Asp Lys Ser Arg Trp Gln Gln Gly
                565                 570                 575

Asn Val Phe Ser Cys Ser Val Met His Glu Ala Leu His Asn His Tyr
            580                 585                 590

Thr Gln Lys Ser Leu Ser Leu Ser Pro Gly Lys Gly Pro Arg Ala Ala
            595                 600                 605

Pro Glu Val Tyr Ala Phe Ala Thr Pro Glu Trp Pro Gly Ser Arg Asp
            610                 615                 620

Lys Arg Thr Leu Ala Cys Leu Ile Gln Asn Phe Met Pro Glu Asp Ile
625                 630                 635                 640

Ser Val Gln Trp Leu His Asn Glu Val Gln Leu Pro Asp Ala Arg His
                645                 650                 655

Ser Thr Thr Gln Pro Arg Lys Thr Lys Gly Ser Gly Phe Phe Val Phe
            660                 665                 670

Ser Arg Leu Glu Val Thr Arg Ala Glu Trp Glu Gln Lys Asp Glu Phe
            675                 680                 685

Ile Cys Arg Ala Val His Glu Ala Ala Ser Pro Ser Gln Thr Val Gln
            690                 695                 700

Arg Ala Val Ser Val Asn Pro Gly Lys
705                 710

<210> SEQ ID NO 29
<211> LENGTH: 31
<212> TYPE: DNA
<213> ORGANISM: Artificial Sequence
<220> FEATURE:
<223> OTHER INFORMATION: PCR primer

<400> SEQUENCE: 29
gtctctagag gagcccaaat cttgtgacaa a                             31

<210> SEQ ID NO 30
<211> LENGTH: 34
<212> TYPE: DNA
<213> ORGANISM: Artificial Sequence
<220> FEATURE:
<223> OTHER INFORMATION: PCR primer

<400> SEQUENCE: 30
gcgtaccggt tcatttaccc ggggacaggg agag                          34

<210> SEQ ID NO 31
<211> LENGTH: 603
<212> TYPE: DNA
<213> ORGANISM: Artificial Sequence
<220> FEATURE:
<223> OTHER INFORMATION: N-terminal Fc gamma receptor IIIa -
      phenylalanine polymorphic
      variant
<220> FEATURE:
<221> NAME/KEY: CDS
```

<220> LOCATION: (1)..(600)

<400> SEQUENCE: 31

```
atg tgg cag ctg ctc ctc cca act gct ctg cta ctt cta gtt tca gct     48
Met Trp Gln Leu Leu Leu Pro Thr Ala Leu Leu Leu Val Ser Ala
 1               5                  10                  15 ggc atg cgg act gaa gat ctc cca aag gct gtg gtg ttc ctg gag cct     96
Gly Met Arg Thr Glu Asp Leu Pro Lys Ala Val Val Phe Leu Glu Pro
             20                  25                  30 caa tgg tac agg gtg ctc gag aag gac agt gtg act ctg aag tgc cag    144
Gln Trp Tyr Arg Val Leu Glu Lys Asp Ser Val Thr Leu Lys Cys Gln
         35                  40                  45 gga gcc tac tcc cct gag gac aat tcc aca cag tgg ttt cac aat gag    192
Gly Ala Tyr Ser Pro Glu Asp Asn Ser Thr Gln Trp Phe His Asn Glu
     50                  55                  60 agc ctc atc tca agc cag gcc tcg agc tac ttc att gac gct gcc aca    240
Ser Leu Ile Ser Ser Gln Ala Ser Ser Tyr Phe Ile Asp Ala Ala Thr
 65                  70                  75                  80 gtc gac gac agt gga gag tac agg tgc cag aca aac ctc tcc acc ctc    288
Val Asp Asp Ser Gly Glu Tyr Arg Cys Gln Thr Asn Leu Ser Thr Leu
                 85                  90                  95 agt gac ccg gtg cag cta gaa gtc cat atc ggc tgg ctg ttg ctc cag    336
Ser Asp Pro Val Gln Leu Glu Val His Ile Gly Trp Leu Leu Leu Gln
            100                 105                 110 gcc cct cgg tgg gtg ttc aag gag gaa gac cct att cac ctg agg tgt    384
Ala Pro Arg Trp Val Phe Lys Glu Glu Asp Pro Ile His Leu Arg Cys
        115                 120                 125 cac agc tgg aag aac act gct ctg cat aag gtc aca tat tta cag aat    432
His Ser Trp Lys Asn Thr Ala Leu His Lys Val Thr Tyr Leu Gln Asn
    130                 135                 140 ggc aaa ggc agg aag tat ttt cat cat aat tct gac ttc tac att cca    480
Gly Lys Gly Arg Lys Tyr Phe His His Asn Ser Asp Phe Tyr Ile Pro
145                 150                 155                 160 aaa gcc aca ctc aaa gac agc ggc tcc tac ttc tgc agg ggg ctt ttt    528
Lys Ala Thr Leu Lys Asp Ser Gly Ser Tyr Phe Cys Arg Gly Leu Phe
                165                 170                 175 ggg agt aaa aat gtg tct tca gag act gtg aac atc acc atc act caa    576
Gly Ser Lys Asn Val Ser Ser Glu Thr Val Asn Ile Thr Ile Thr Gln
            180                 185                 190 ggt ttg cat cat cac cat cat cat tag                                603
Gly Leu His His His His His His
        195                 200
```

<210> SEQ ID NO 32
<211> LENGTH: 200
<212> TYPE: PRT
<213> ORGANISM: Artificial Sequence
<220> FEATURE:
<223> OTHER INFORMATION: Synthetic Construct

<400> SEQUENCE: 32

```
Met Trp Gln Leu Leu Leu Pro Thr Ala Leu Leu Leu Val Ser Ala
 1               5                  10                  15

Gly Met Arg Thr Glu Asp Leu Pro Lys Ala Val Val Phe Leu Glu Pro
             20                  25                  30

Gln Trp Tyr Arg Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
     50                  55                  60

Ser Leu Ile Ser Ser Gln Ala Ser Ser Tyr Phe Ile Asp Ala Ala Thr
```

```
                65                  70                  75                  80
Val Asp Asp Ser Gly Glu Tyr Arg Cys Gln Thr Asn Leu Ser Thr Leu
                        85                  90                  95

Ser Asp Pro Val Gln Leu Glu Val His Ile Gly Trp Leu Leu Leu Gln
                100                 105                 110

Ala Pro Arg Trp Val Phe Lys Glu Asp Pro Ile His Leu Arg Cys
                115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu His His His His His His
            195                 200

<210> SEQ ID NO 33
<211> LENGTH: 603
<212> TYPE: DNA
<213> ORGANISM: Artificial Sequence
<220> FEATURE:
<223> OTHER INFORMATION: N-terminal Fc gamma receptor IIIa - valine
      polymorphic variant
<220> FEATURE:
<221> NAME/KEY: CDS
<222> LOCATION: (1)..(600)

<400> SEQUENCE: 33 atg tgg cag ctg ctc ctc cca act gct ctg cta ctt cta gtt tca gct      48
Met Trp Gln Leu Leu Leu Pro Thr Ala Leu Leu Leu Leu Val Ser Ala
1               5                   10                  15 ggc atg cgg act gaa gat ctc cca aag gct gtg gtg ttc ctg gag cct      96
Gly Met Arg Thr Glu Asp Leu Pro Lys Ala Val Val Phe Leu Glu Pro
                20                  25                  30 caa tgg tac agg gtg ctc gag aag gac agt gtg act ctg aag tgc cag     144
Gln Trp Tyr Arg Val Leu Glu Lys Asp Ser Val Thr Leu Lys Cys Gln
            35                  40                  45 gga gcc tac tcc cct gag gac aat tcc aca cag tgg ttt cac aat gag     192
Gly Ala Tyr Ser Pro Glu Asp Asn Ser Thr Gln Trp Phe His Asn Glu
        50                  55                  60 agc ctc atc tca agc cag gcc tcg agc tac ttc att gac gct gcc aca     240
Ser Leu Ile Ser Ser Gln Ala Ser Ser Tyr Phe Ile Asp Ala Ala Thr
65                  70                  75                  80 gtc gac gac agt gga gag tac agg tgc cag aca aac ctc tcc acc ctc     288
Val Asp Asp Ser Gly Glu Tyr Arg Cys Gln Thr Asn Leu Ser Thr Leu
                    85                  90                  95 agt gac ccg gtg cag cta gaa gtc cat atc ggc tgg ctg ttg ctc cag     336
Ser Asp Pro Val Gln Leu Glu Val His Ile Gly Trp Leu Leu Leu Gln
                100                 105                 110 gcc cct cgg tgg gtg ttc aag gag gaa gac cct att cac ctg agg tgt     384
Ala Pro Arg Trp Val Phe Lys Glu Glu Asp Pro Ile His Leu Arg Cys
            115                 120                 125 cac agc tgg aag aac act gct ctg cat aag gtc aca tat tta cag aat     432
His Ser Trp Lys Asn Thr Ala Leu His Lys Val Thr Tyr Leu Gln Asn
        130                 135                 140 ggc aaa ggc agg aag tat ttt cat cat aat tct gac ttc tac att cca     480
Gly Lys Gly Arg Lys Tyr Phe His His Asn Ser Asp Phe Tyr Ile Pro
145                 150                 155                 160
```

-continued

```
aaa gcc aca ctc aaa gac agc ggc tcc tac ttc tgc agg ggg ctt gtt      528
Lys Ala Thr Leu Lys Asp Ser Gly Ser Tyr Phe Cys Arg Gly Leu Val
            165                 170                 175 ggg agt aaa aat gtg tct tca gag act gtg aac atc acc atc act caa      576
Gly Ser Lys Asn Val Ser Ser Glu Thr Val Asn Ile Thr Ile Thr Gln
        180                 185                 190 ggt ttg cat cat cac cat cat cac tag                                  603
Gly Leu His His His His His His
            195                 200
```

<210> SEQ ID NO 34
<211> LENGTH: 200
<212> TYPE: PRT
<213> ORGANISM: Artificial Sequence
<220> FEATURE:
<223> OTHER INFORMATION: Synthetic Construct

<400> SEQUENCE: 34

```
Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu His His His His His His
        195                 200
```

<210> SEQ ID NO 35
<211> LENGTH: 20
<212> TYPE: PRT
<213> ORGANISM: Homo sapiens
<220> FEATURE:
<221> NAME/KEY: MISC_FEATURE
<223> OTHER INFORMATION: IgK signal sequence

<400> SEQUENCE: 35

```
Met Glu Thr Asp Thr Leu Leu Leu Trp Val Leu Leu Leu Trp Val Pro
1               5                   10                  15

Gly Ser Thr Gly
            20
```

<210> SEQ ID NO 36
<211> LENGTH: 12
<212> TYPE: PRT
<213> ORGANISM: Homo sapiens

<400> SEQUENCE: 36

Glu Arg Lys Cys Cys Val Glu Cys Pro Pro Cys Pro
1               5                   10

<210> SEQ ID NO 37
<211> LENGTH: 88
<212> TYPE: PRT
<213> ORGANISM: Saccharomyces cerevisiae

<400> SEQUENCE: 37

Tyr Thr Gln Lys Ser Leu Ser Leu Ser Pro Gly Lys Glu Leu Leu Gly
1               5                   10                  15

Gly Gly Ser Ile Lys Gln Ile Glu Asp Lys Ile Glu Glu Ile Leu Ser
            20                  25                  30

Lys Ile Tyr His Ile Glu Asn Glu Ile Ala Arg Ile Lys Lys Leu Ile
        35                  40                  45

Gly Glu Arg Gly His Gly Gly Ser Asn Ser Gln Val Ser His Arg
    50                  55                  60

Tyr Pro Arg Phe Gln Ser Ile Lys Val Gln Phe Thr Glu Tyr Lys Lys
65                  70                  75                  80

Glu Lys Gly Phe Ile Leu Thr Ser
                85

<210> SEQ ID NO 38
<211> LENGTH: 524
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 38

Met Glu Thr Asp Thr Leu Leu Leu Trp Val Leu Leu Leu Trp Val Pro
1               5                   10                  15

Gly Ser Thr Gly Asp Ala Ala Asp Ile Gln His Gly Gly Arg Ser Ser
            20                  25                  30

Glu Pro Lys Ser Cys Asp Lys Thr His Thr Cys Pro Pro Cys Pro Ala
        35                  40                  45

Pro Glu Leu Leu Gly Gly Pro Ser Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Asp Glu Leu Thr
                165                 170                 175

Lys Asn Gln Val Ser Leu Thr Cys Leu Val Lys Gly Phe Tyr Pro Ser
                180                 185                 190

Asp Ile Ala Val Glu Trp Glu Ser Asn Gly Gln Pro Glu Asn Asn Tyr
                195                 200                 205

Lys Thr Thr Pro Pro Val Leu Asp Ser Asp Gly Ser Phe Phe Leu Tyr
            210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys Ser Leu Asp Glu Pro Lys Ser Cys
            260                 265                 270

Asp Lys Thr His Thr Cys Pro Pro Cys Pro Ala Pro Glu Leu Leu Gly
            275                 280                 285

Gly Pro Ser Val Phe Leu Phe Pro Pro Lys Pro Lys Asp Thr Leu Met
        290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Phe Glu Gly Lys Pro Ile Pro Asn Pro Leu Leu Gly Leu
            500                 505                 510

Asp Ser Thr Arg Thr Gly His His His His His
        515                 520

<210> SEQ ID NO 39
<211> LENGTH: 499
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 39

Met Glu Thr Asp Thr Leu Leu Leu Trp Val Leu Leu Leu Trp Val Pro
1               5                   10                  15

-continued

```
Gly Ser Thr Gly Asp Ala Ala Asp Ile Gln His Gly Gly Arg Ser Ser
            20                  25                  30
Glu Pro Lys Ser Cys Asp Lys Thr His Thr Cys Pro Pro Cys Pro Ala
        35                  40                  45
Pro Glu Leu Leu Gly Gly Pro Ser Val Phe Leu Phe Pro Pro Lys Pro
    50                  55                  60
Lys Asp Thr Leu Met Ile Ser Arg Thr Pro Glu Val Thr Cys Val Val
65                  70                  75                  80
Val Asp Val Ser His Glu Asp Pro Glu Val Lys Phe Asn Trp Tyr Val
                85                  90                  95
Asp Gly Val Glu Val His Asn Ala Lys Thr Lys Pro Arg Glu Glu Gln
            100                 105                 110
Tyr Asn Ser Thr Tyr Arg Val Val Ser Val Leu Thr Val Leu His Gln
        115                 120                 125
Asp Trp Leu Asn Gly Lys Glu Tyr Lys Cys Lys Val Ser Asn Lys Ala
    130                 135                 140
Leu Pro Ala Pro Ile Glu Lys Thr Ile Ser Lys Ala Lys Gly Gln Pro
145                 150                 155                 160
Arg Glu Pro Gln Val Tyr Thr Leu Pro Pro Ser Arg Asp Glu Leu Thr
                165                 170                 175
Lys Asn Gln Val Ser Leu Thr Cys Leu Val Lys Gly Phe Tyr Pro Ser
            180                 185                 190
Asp Ile Ala Val Glu Trp Glu Ser Asn Gly Gln Pro Glu Asn Asn Tyr
        195                 200                 205
Lys Thr Thr Pro Pro Val Leu Asp Ser Asp Gly Ser Phe Phe Leu Tyr
    210                 215                 220
Ser Lys Leu Thr Val Asp Lys Ser Arg Trp Gln Gln Gly Asn Val Phe
225                 230                 235                 240
Ser Cys Ser Val Met His Glu Ala Leu His Asn His Tyr Thr Gln Lys
                245                 250                 255
Ser Leu Ser Leu Ser Pro Gly Lys Ser Leu Glu Glu Pro Lys Ser Cys
            260                 265                 270
Asp Lys Thr His Thr Cys Pro Pro Cys Pro Ala Pro Glu Leu Leu Gly
        275                 280                 285
Gly Pro Ser Val Phe Leu Phe Pro Pro Lys Pro Lys Asp Thr Leu Met
    290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
                325                 330                 335
His Asn Ala Lys Thr Lys Pro Arg Glu Glu Gln Tyr Asn Ser Thr Tyr
            340                 345                 350
Arg Val Val Ser Val Leu Thr Val Leu His Gln Asp Trp Leu Asn Gly
        355                 360                 365
Lys Glu Tyr Lys Cys Lys Val Ser Asn Lys Ala Leu Pro Ala Pro Ile
    370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
                405                 410                 415
Leu Thr Cys Leu Val Lys Gly Phe Tyr Pro Ser Asp Ile Ala Val Glu
            420                 425                 430
```

```
Trp Glu Ser Asn Gly Gln Pro Glu Asn Asn Tyr Lys Thr Thr Pro Pro
            435                 440                 445

Val Leu Asp Ser Asp Gly Ser Phe Phe Leu Tyr Ser Lys Leu Thr Val
450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
            485                 490                 495

Pro Gly Lys

<210> SEQ ID NO 40
<211> LENGTH: 628
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 40

Met Glu Thr Asp Thr Leu Leu Leu Trp Val Leu Leu Leu Trp Val Pro
1               5                   10                  15

Gly Ser Thr Gly Asp Ala Ala Asp Ile Val Cys Ser Arg Asp Phe Thr
            20                  25                  30

Pro Pro Thr Val Lys Ile Leu Gln Ser Ser Cys Asp Gly Gly Gly His
        35                  40                  45

Phe Pro Pro Thr Ile Gln Leu Leu Cys Leu Val Ser Gly Tyr Thr Pro
    50                  55                  60

Gly Thr Ile Asn Ile Thr Trp Leu Glu Asp Gly Gln Val Met Asp Val
65                  70                  75                  80

Asp Leu Ser Thr Ala Ser Thr Thr Gln Glu Gly Glu Leu Ala Ser Thr
                85                  90                  95

Gln Ser Glu Leu Thr Leu Ser Gln Lys His Trp Leu Ser Asp Arg Thr
            100                 105                 110

Tyr Thr Cys Gln Val Thr Tyr Gln Gly His Thr Phe Glu Asp Ser Thr
        115                 120                 125

Lys Lys Cys Ala Gly Gly Arg Ser Ser Glu Pro Lys Ser Cys Asp Lys
130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Asp Glu Leu Thr Lys Asn Gln Val Ser Leu Thr
        275                 280                 285

Cys Leu Val Lys Gly Phe Tyr Pro Ser Asp Ile Ala Val Glu Trp Glu
```

```
            290                 295                 300
Ser Asn Gly Gln Pro Glu Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
                340                 345                 350

Ala Leu His Asn His Tyr Thr Gln Lys Ser Leu Ser Leu Ser Pro Gly
            355                 360                 365

Lys Glu Pro Lys Ser Cys Asp Lys Thr His Thr Cys Pro Pro Cys Pro
    370                 375                 380

Ala Pro Glu Leu Leu Gly Gly Pro Ser Val Phe Leu Phe Pro Pro Lys
385                 390                 395                 400

Pro Lys Asp Thr Leu Met Ile Ser Arg Thr Pro Glu Val Thr Cys Val
                405                 410                 415

Val Val Asp Val Ser His Glu Asp Pro Glu Val Lys Phe Asn Trp Tyr
                420                 425                 430

Val Asp Gly Val Glu Val His Asn Ala Lys Thr Lys Pro Arg Glu Glu
            435                 440                 445

Gln Tyr Asn Ser Thr Tyr Arg Val Val Ser Val Leu Thr Val Leu His
    450                 455                 460

Gln Asp Trp Leu Asn Gly Lys Glu Tyr Lys Cys Lys Val Ser Asn Lys
465                 470                 475                 480

Ala Leu Pro Ala Pro Ile Glu Lys Thr Ile Ser Lys Ala Lys Gly Pro
                485                 490                 495

Arg Ala Ala Pro Glu Val Tyr Ala Phe Ala Thr Pro Glu Trp Pro Gly
            500                 505                 510

Arg Asp Lys Arg Thr Leu Ala Cys Leu Ile Gln Asn Phe Met Pro Glu
    515                 520                 525

Asp Ile Ser Val Gln Trp Leu His Asn Glu Val Gln Leu Pro Asp Ala
530                 535                 540

Arg His Ser Thr Thr Gln Pro Arg Lys Thr Lys Gly Ser Gly Phe Phe
545                 550                 555                 560

Val Phe Ser Arg Leu Glu Val Thr Arg Ala Glu Trp Glu Gln Lys Asp
                565                 570                 575

Glu Phe Ile Cys Arg Ala Val His Glu Ala Ala Ser Pro Ser Gln Thr
                580                 585                 590

Val Gln Arg Ala Val Ser Val Asn Pro Gly Lys Phe Glu Gly Lys Pro
            595                 600                 605

Ile Pro Asn Pro Leu Leu Gly Leu Asp Ser Arg Thr Gly His His
    610                 615                 620

His His His His
625

<210> SEQ ID NO 41
<211> LENGTH: 629
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 41

Met Glu Thr Asp Thr Leu Leu Leu Trp Val Leu Leu Leu Trp Val Pro
1               5                   10                  15

Gly Ser Thr Gly Asp Ala Ala Asp Ile Val Cys Ser Arg Asp Phe Thr
```

-continued

```
                20                  25                  30
Pro Pro Thr Val Lys Ile Leu Gln Ser Ser Cys Asp Gly Gly His
            35                  40                  45
Phe Pro Pro Thr Ile Gln Leu Leu Cys Leu Val Ser Gly Tyr Thr Pro
        50                  55                  60
Gly Thr Ile Asn Ile Thr Trp Leu Glu Asp Gly Gln Val Met Asp Val
65                  70                  75                  80
Asp Leu Ser Thr Ala Ser Thr Thr Gln Glu Gly Glu Leu Ala Ser Thr
                85                  90                  95
Gln Ser Glu Leu Thr Leu Ser Gln Lys His Trp Leu Ser Asp Arg Thr
            100                 105                 110
Tyr Thr Cys Gln Val Thr Tyr Gln Gly His Thr Phe Glu Asp Ser Thr
        115                 120                 125
Lys Lys Cys Gly Gly Arg Ser Ser Glu Pro Lys Ser Cys Asp Lys
        130                 135                 140
Thr His Thr Cys Pro Pro Cys Pro Ala Pro Glu Leu Leu Gly Gly Pro
145                 150                 155                 160
Ser Val Phe Leu Phe Pro Pro Lys Pro Lys Asp Thr Leu Met Ile Ser
                165                 170                 175
Arg Thr Pro Glu Val Thr Cys Val Val Val Asp Val Ser His Glu Asp
            180                 185                 190
Pro Glu Val Lys Phe Asn Trp Tyr Val Asp Gly Val Glu Val His Asn
        195                 200                 205
Ala Lys Thr Lys Pro Arg Glu Glu Gln Tyr Asn Ser Thr Tyr Arg Val
        210                 215                 220
Val Ser Val Leu Thr Val Leu His Gln Asp Trp Leu Asn Gly Lys Glu
225                 230                 235                 240
Tyr Lys Cys Lys Val Ser Asn Lys Ala Leu Pro Ala Pro Ile Glu Lys
                245                 250                 255
Thr Ile Ser Lys Ala Lys Gly Gln Pro Arg Glu Pro Gln Val Tyr Thr
            260                 265                 270
Leu Pro Pro Ser Arg Asp Glu Leu Thr Lys Asn Gln Val Ser Leu Thr
        275                 280                 285
Cys Leu Val Lys Gly Phe Tyr Pro Ser Asp Ile Ala Val Glu Trp Glu
        290                 295                 300
Ser Asn Gly Gln Pro Glu Asn Asn Tyr Lys Thr Thr Pro Pro Val Leu
305                 310                 315                 320
Asp Ser Asp Gly Ser Phe Phe Leu Tyr Ser Lys Leu Thr Val Asp Lys
                325                 330                 335
Ser Arg Trp Gln Gln Gly Asn Val Phe Ser Cys Ser Val Met His Glu
            340                 345                 350
Ala Leu His Asn His Tyr Thr Gln Lys Ser Leu Ser Leu Ser Pro Gly
        355                 360                 365
Lys Ser Leu Asp Glu Pro Lys Ser Cys Asp Lys Thr His Thr Cys Pro
        370                 375                 380
Pro Cys Pro Ala Pro Glu Leu Leu Gly Gly Pro Ser Val Phe Leu Phe
385                 390                 395                 400
Pro Pro Lys Pro Lys Asp Thr Leu Met Ile Ser Arg Thr Pro Glu Val
                405                 410                 415
Thr Cys Val Val Val Asp Val Ser His Glu Asp Pro Glu Val Lys Phe
            420                 425                 430
Asn Trp Tyr Val Asp Gly Val Glu Val His Asn Ala Lys Thr Lys Pro
        435                 440                 445
```

```
Arg Glu Glu Gln Tyr Asn Ser Thr Tyr Arg Val Val Ser Val Leu Thr
            450                 455                 460

Val Leu His Gln Asp Trp Leu Asn Gly Lys Glu Tyr Lys Cys Lys Val
465                 470                 475                 480

Ser Asn Lys Ala Leu Pro Ala Pro Ile Glu Lys Thr Ile Ser Lys Ala
                485                 490                 495

Lys Gly Gln Pro Arg Glu Pro Gln Val Tyr Thr Leu Pro Pro Ser Arg
            500                 505                 510

Asp Glu Leu Thr Lys Asn Gln Val Ser Leu Thr Cys Leu Val Lys Gly
            515                 520                 525

Phe Tyr Pro Ser Asp Ile Ala Val Glu Trp Glu Ser Asn Gly Gln Pro
530                 535                 540

Glu Asn Asn Tyr Lys Thr Thr Pro Pro Val Leu Asp Ser Asp Gly Ser
545                 550                 555                 560

Phe Phe Leu Tyr Ser Lys Leu Thr Val Asp Lys Ser Arg Trp Gln Gln
                565                 570                 575

Gly Asn Val Phe Ser Cys Ser Val Met His Glu Ala Leu His Asn His
            580                 585                 590

Tyr Thr Gln Lys Ser Leu Ser Leu Ser Pro Gly Lys Phe Glu Gly Lys
            595                 600                 605

Pro Ile Pro Asn Pro Leu Leu Gly Leu Asp Ser Thr Arg Thr Gly His
            610                 615                 620

His His His His His
625

<210> SEQ ID NO 42
<211> LENGTH: 713
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 42

Met Glu Thr Asp Thr Leu Leu Leu Trp Val Leu Leu Leu Trp Val Pro
1               5                   10                  15

Gly Ser Thr Gly Asp Ala Ala Asp Ile Val Cys Ser Arg Asp Phe Thr
            20                  25                  30

Pro Pro Thr Val Lys Ile Leu Gln Ser Ser Cys Asp Gly Gly His
            35                  40                  45

Phe Pro Pro Thr Ile Gln Leu Leu Cys Leu Val Ser Gly Tyr Thr Pro
        50                  55                  60

Gly Thr Ile Asn Ile Thr Trp Leu Glu Asp Gly Gln Val Met Asp Val
65                  70                  75                  80

Asp Leu Ser Thr Ala Ser Thr Thr Gln Glu Gly Glu Leu Ala Ser Thr
                85                  90                  95

Gln Ser Glu Leu Thr Leu Ser Lys His Trp Leu Ser Asp Arg Thr
            100                 105                 110

Tyr Thr Cys Gln Val Thr Tyr Gln Gly His Thr Phe Glu Asp Ser Thr
            115                 120                 125

Lys Lys Cys Gly Gly Gly Arg Ser Ser Glu Pro Lys Ser Cys Asp Lys
        130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175
```

```
Arg Thr Pro Glu Val Thr Cys Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Asp Glu Leu Thr Lys Asn Gln Val Ser Leu Thr
            275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys Ser Leu Asp Glu Pro Lys Ser Cys Asp Lys Thr His Thr Cys Pro
    370                 375                 380

Pro Cys Pro Ala Pro Glu Leu Leu Gly Gly Pro Ser Val Phe Leu Phe
385                 390                 395                 400

Pro Pro Lys Pro Lys Asp Thr Leu Met Ile Ser Arg Thr Pro Glu Val
                405                 410                 415

Thr Cys Val Val Val Asp Val Ser His Glu Asp Pro Glu Val Lys Phe
            420                 425                 430

Asn Trp Tyr Val Asp Gly Val Glu Val His Asn Ala Lys Thr Lys Pro
            435                 440                 445

Arg Glu Glu Gln Tyr Asn Ser Thr Tyr Arg Val Val Ser Val Leu Thr
    450                 455                 460

Val Leu His Gln Asp Trp Leu Asn Gly Lys Glu Tyr Lys Cys Lys Val
465                 470                 475                 480

Ser Asn Lys Ala Leu Pro Ala Pro Ile Glu Lys Thr Ile Ser Lys Ala
                485                 490                 495

Lys Gly Gln Pro Arg Glu Pro Gln Val Tyr Thr Leu Pro Pro Ser Arg
            500                 505                 510

Asp Glu Leu Thr Lys Asn Gln Val Ser Leu Thr Cys Leu Val Lys Gly
            515                 520                 525

Phe Tyr Pro Ser Asp Ile Ala Val Glu Trp Glu Ser Asn Gly Gln Pro
    530                 535                 540

Glu Asn Asn Tyr Lys Thr Thr Pro Pro Val Leu Asp Ser Asp Gly Ser
545                 550                 555                 560

Phe Phe Leu Tyr Ser Lys Leu Thr Val Asp Lys Ser Arg Trp Gln Gln
                565                 570                 575

Gly Asn Val Phe Ser Cys Ser Val Met His Glu Ala Leu His Asn His
            580                 585                 590
```

-continued

```
Tyr Thr Gln Lys Ser Leu Ser Leu Ser Pro Gly Lys Gly Pro Arg Ala
            595                 600                 605

Ala Pro Glu Val Tyr Ala Phe Ala Thr Pro Glu Trp Pro Gly Arg Asp
610                 615                 620

Lys Arg Thr Leu Ala Cys Leu Ile Gln Asn Phe Met Pro Glu Asp Ile
625                 630                 635                 640

Ser Val Gln Trp Leu His Asn Glu Val Gln Leu Pro Asp Ala Arg His
            645                 650                 655

Ser Thr Thr Gln Pro Arg Lys Thr Lys Gly Ser Gly Phe Phe Val Phe
            660                 665                 670

Ser Arg Leu Glu Val Thr Arg Ala Glu Trp Glu Gln Lys Asp Glu Phe
            675                 680                 685

Ile Cys Arg Ala Val His Glu Ala Ala Ser Pro Ser Gln Thr Val Gln
            690                 695                 700

Arg Ala Val Ser Val Asn Pro Gly Lys
705                 710

<210> SEQ ID NO 43
<211> LENGTH: 733
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 43

Met Glu Thr Asp Thr Leu Leu Leu Trp Val Leu Leu Leu Trp Val Pro
1               5                   10                  15

Gly Ser Thr Gly Asp Ala Ala Asp Ile Gln His Gly Gly Arg Ser Ser
            20                  25                  30

Glu Pro Lys Ser Cys Asp Lys Thr His Thr Cys Pro Pro Cys Pro Ala
        35                  40                  45

Pro Glu Leu Leu Gly Gly Pro Ser Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Asp Glu Leu Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240
```

```
Ser Cys Ser Val Met His Glu Ala Leu His Asn His Tyr Thr Gln Lys
            245                 250                 255

Ser Leu Ser Leu Ser Pro Gly Lys Ser Leu Asp Glu Pro Lys Ser Cys
        260                 265                 270

Asp Lys Thr His Thr Cys Pro Pro Cys Pro Ala Pro Glu Leu Leu Gly
            275                 280                 285

Gly Pro Ser Val Phe Leu Phe Pro Pro Lys Pro Lys Asp Thr Leu Met
        290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Phe Glu Glu Pro Lys Ser Cys Asp Lys Thr His Thr Cys
        500                 505                 510

Pro Pro Cys Pro Ala Pro Glu Leu Leu Gly Gly Pro Ser Val Phe Leu
    515                 520                 525

Phe Pro Pro Lys Pro Lys Asp Thr Leu Met Ile Ser Arg Thr Pro Glu
530                 535                 540

Val Thr Cys Val Val Val Asp Val Ser His Glu Asp Pro Glu Val Lys
545                 550                 555                 560

Phe Asn Trp Tyr Val Asp Gly Val Glu Val His Asn Ala Lys Thr Lys
                565                 570                 575

Pro Arg Glu Glu Gln Tyr Asn Ser Thr Tyr Arg Val Val Ser Val Leu
            580                 585                 590

Thr Val Leu His Gln Asp Trp Leu Asn Gly Lys Glu Tyr Lys Cys Lys
        595                 600                 605

Val Ser Asn Lys Ala Leu Pro Ala Pro Ile Glu Lys Thr Ile Ser Lys
    610                 615                 620

Ala Lys Gly Gln Pro Arg Glu Pro Gln Val Tyr Thr Leu Pro Pro Ser
625                 630                 635                 640

Arg Asp Glu Leu Thr Lys Asn Gln Val Ser Leu Thr Cys Leu Val Lys
                645                 650                 655

Gly Phe Tyr Pro Ser Asp Ile Ala Val Glu Trp Glu Ser Asn Gly Gln
```

```
                    660                 665                 670
Pro Glu Asn Asn Tyr Lys Thr Thr Pro Pro Val Leu Asp Ser Asp Gly
                675                 680                 685
Ser Phe Phe Leu Tyr Ser Lys Leu Thr Val Asp Lys Ser Arg Trp Gln
            690                 695                 700
Gln Gly Asn Val Phe Ser Cys Ser Val Met His Glu Ala Leu His Asn
705                 710                 715                 720
His Tyr Thr Gln Lys Ser Leu Ser Leu Ser Pro Gly Lys
                725                 730

<210> SEQ ID NO 44
<211> LENGTH: 566
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 44

Met Glu Thr Asp Thr Leu Leu Leu Trp Val Leu Leu Leu Trp Val Pro
1               5                   10                  15
Gly Ser Thr Gly Asp Ala Ala Asp Ile Ser Ser Lys Pro His Leu Val
                20                  25                  30
Thr Gln Leu Thr His Ala His Gly Cys Pro Glu Pro Lys Ser Cys Asp
            35                  40                  45
Thr Pro Pro Cys Pro Arg Cys Pro Glu Pro Lys Ser Cys Asp Thr
        50                  55                  60
Pro Pro Pro Cys Pro Arg Cys Pro Glu Pro Lys Ser Cys Asp Thr Pro
65                  70                  75                  80
Pro Pro Cys Pro Arg Cys Pro Ala Pro Glu Leu Leu Gly Gly Pro Ser
                85                  90                  95
Val Phe Leu Phe Pro Pro Lys Pro Lys Asp Thr Leu Met Ile Ser Arg
                100                 105                 110
Thr Pro Glu Val Thr Cys Val Val Val Asp Val Ser His Glu Asp Pro
            115                 120                 125
Glu Val Gln Phe Lys Trp Tyr Val Asp Gly Val Glu Val His Asn Ala
        130                 135                 140
Lys Thr Lys Leu Arg Glu Glu Gln Tyr Asn Ser Thr Phe Arg Val Val
145                 150                 155                 160
Ser Val Leu Thr Val Leu His Gln Asp Trp Leu Asn Gly Lys Glu Tyr
                165                 170                 175
Lys Cys Lys Val Ser Asn Lys Ala Leu Pro Ala Pro Ile Glu Lys Thr
            180                 185                 190
Ile Ser Lys Thr Lys Gly Gln Pro Arg Glu Pro Gln Val Tyr Thr Leu
        195                 200                 205
Pro Pro Ser Arg Glu Glu Met Thr Lys Asn Gln Val Ser Leu Thr Cys
210                 215                 220
Leu Val Lys Gly Phe Tyr Pro Ser Asp Ile Ala Val Glu Trp Glu Ser
225                 230                 235                 240
Asn Gly Gln Pro Glu Asn Asn Tyr Asn Thr Thr Pro Pro Met Leu Asp
                245                 250                 255
Ser Asp Gly Ser Phe Phe Leu Tyr Ser Lys Leu Thr Val Asp Lys Ser
            260                 265                 270
Arg Trp Gln Gln Gly Asn Ile Phe Ser Cys Ser Val Met His Glu Ala
        275                 280                 285
Leu His Asn Arg Tyr Thr Gln Lys Ser Leu Ser Leu Ser Pro Gly Lys
```

```
                290                 295                 300
Gly Gly Arg Ser Ser Glu Pro Lys Ser Cys Asp Lys Thr His Thr Cys
305                 310                 315                 320

Pro Pro Cys Pro Ala Pro Glu Leu Leu Gly Gly Pro Ser Val Phe Leu
                325                 330                 335

Phe Pro Pro Lys Pro Lys Asp Thr Leu Met Ile Ser Arg Thr Pro Glu
                340                 345                 350

Val Thr Cys Val Val Val Asp Val Ser His Glu Asp Pro Glu Val Lys
                355                 360                 365

Phe Asn Trp Tyr Val Asp Gly Val Glu Val His Asn Ala Lys Thr Lys
                370                 375                 380

Pro Arg Glu Glu Gln Tyr Asn Ser Thr Tyr Arg Val Val Ser Val Leu
385                 390                 395                 400

Thr Val Leu His Gln Asp Trp Leu Asn Gly Lys Glu Tyr Lys Cys Lys
                405                 410                 415

Val Ser Asn Lys Ala Leu Pro Ala Pro Ile Glu Lys Thr Ile Ser Lys
                420                 425                 430

Ala Lys Gly Gln Pro Arg Glu Pro Gln Val Tyr Thr Leu Pro Pro Ser
                435                 440                 445

Arg Asp Glu Leu Thr Lys Asn Gln Val Ser Leu Thr Cys Leu Val Lys
450                 455                 460

Gly Phe Tyr Pro Ser Asp Ile Ala Val Glu Trp Glu Ser Asn Gly Gln
465                 470                 475                 480

Pro Glu Asn Asn Tyr Lys Thr Thr Pro Pro Val Leu Asp Ser Asp Gly
                485                 490                 495

Ser Phe Phe Leu Tyr Ser Lys Leu Thr Val Asp Lys Ser Arg Trp Gln
                500                 505                 510

Gln Gly Asn Val Phe Ser Cys Ser Val Met His Glu Ala Leu His Asn
                515                 520                 525

His Tyr Thr Gln Lys Ser Leu Ser Leu Ser Pro Gly Lys Phe Glu Gly
                530                 535                 540

Lys Pro Ile Pro Asn Pro Leu Leu Gly Leu Asp Ser Thr Arg Thr Gly
545                 550                 555                 560

His His His His His His
                565

<210> SEQ ID NO 45
<211> LENGTH: 529
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 45

Met Glu Thr Asp Thr Leu Leu Leu Trp Val Leu Leu Leu Trp Val Pro
1               5                   10                  15

Gly Ser Thr Gly Asp Ala Ala Asp Ile Gln His Gly Gly Arg Ser Ser
                20                  25                  30

Glu Pro Lys Ser Cys Asp Lys Thr His Thr Cys Pro Pro Cys Pro Ala
                35                  40                  45

Pro Glu Leu Leu Gly Gly Pro Ser Val Phe Leu Phe Pro Pro Lys Pro
                50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
```

-continued

```
                    85                  90                  95
Asp Gly Val Glu Val His Asn Ala Lys Thr Lys Pro Arg Glu Glu Gln
                100                 105                 110
Tyr Asn Ser Thr Tyr Arg Val Ser Val Leu Thr Val Leu His Gln
            115                 120                 125
Asp Trp Leu Asn Gly Lys Glu Tyr Lys Cys Lys Val Ser Asn Lys Ala
        130                 135                 140
Leu Pro Ala Pro Ile Glu Lys Thr Ile Ser Lys Ala Lys Gly Gln Pro
145                 150                 155                 160
Arg Glu Pro Gln Val Tyr Thr Leu Pro Pro Ser Arg Asp Glu Leu Thr
                165                 170                 175
Lys Asn Gln Val Ser Leu Thr Cys Leu Val Lys Gly Phe Tyr Pro Ser
            180                 185                 190
Asp Ile Ala Val Glu Trp Glu Ser Asn Gly Gln Pro Glu Asn Asn Tyr
        195                 200                 205
Lys Thr Thr Pro Pro Val Leu Asp Ser Asp Gly Ser Phe Phe Leu Tyr
210                 215                 220
Ser Lys Leu Thr Val Asp Lys Ser Arg Trp Gln Gln Gly Asn Val Phe
225                 230                 235                 240
Ser Cys Ser Val Met His Glu Ala Leu His Asn His Tyr Thr Gln Lys
                245                 250                 255
Ser Leu Ser Leu Ser Pro Gly Lys Ser Leu Glu Gly Pro Arg Phe Glu
            260                 265                 270
Glu Pro Lys Ser Cys Asp Lys Thr His Thr Cys Pro Pro Cys Pro Ala
        275                 280                 285
Pro Glu Leu Leu Gly Gly Pro Ser Val Phe Leu Phe Pro Pro Lys Pro
        290                 295                 300
Lys Asp Thr Leu Met Ile Ser Arg Thr Pro Glu Val Thr Cys Val Val
305                 310                 315                 320
Val Asp Val Ser His Glu Asp Pro Glu Val Lys Phe Asn Trp Tyr Val
                325                 330                 335
Asp Gly Val Glu Val His Asn Ala Lys Thr Lys Pro Arg Glu Glu Gln
            340                 345                 350
Tyr Asn Ser Thr Tyr Arg Val Val Ser Val Leu Thr Val Leu His Gln
        355                 360                 365
Asp Trp Leu Asn Gly Lys Glu Tyr Lys Cys Lys Val Ser Asn Lys Ala
    370                 375                 380
Leu Pro Ala Pro Ile Glu Lys Thr Ile Ser Lys Ala Lys Gly Gln Pro
385                 390                 395                 400
Arg Glu Pro Gln Val Tyr Thr Leu Pro Pro Ser Arg Asp Glu Leu Thr
                405                 410                 415
Lys Asn Gln Val Ser Leu Thr Cys Leu Val Lys Gly Phe Tyr Pro Ser
            420                 425                 430
Asp Ile Ala Val Glu Trp Glu Ser Asn Gly Gln Pro Glu Asn Asn Tyr
        435                 440                 445
Lys Thr Thr Pro Pro Val Leu Asp Ser Asp Gly Ser Phe Phe Leu Tyr
    450                 455                 460
Ser Lys Leu Thr Val Asp Lys Ser Arg Trp Gln Gln Gly Asn Val Phe
465                 470                 475                 480
Ser Cys Ser Val Met His Glu Ala Leu His Asn His Tyr Thr Gln Lys
                485                 490                 495
Ser Leu Ser Leu Ser Pro Gly Lys Phe Glu Gly Lys Pro Ile Pro Asn
            500                 505                 510
```

```
Pro Leu Leu Gly Leu Asp Ser Thr Arg Thr Gly His His His His
        515                 520                 525
His

<210> SEQ ID NO 46
<211> LENGTH: 559
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 46

Met Glu Thr Asp Thr Leu Leu Leu Trp Val Leu Leu Leu Trp Val Pro
1               5                   10                  15

Gly Ser Thr Gly Asp Ala Ala Asp Ile Glu Leu Lys Thr Pro Leu Gly
            20                  25                  30

Asp Thr Thr His Thr Cys Pro Arg Cys Pro Glu Pro Lys Ser Cys Asp
        35                  40                  45

Thr Pro Pro Pro Cys Pro Arg Cys Pro Glu Pro Lys Ser Cys Asp Thr
    50                  55                  60

Pro Pro Pro Cys Pro Arg Cys Pro Glu Pro Lys Ser Cys Asp Thr Pro
65                  70                  75                  80

Pro Pro Cys Pro Arg Cys Pro Gly Gly Arg Ser Ser Glu Pro Lys Ser
                85                  90                  95

Cys Asp Lys Thr His Thr Cys Pro Pro Cys Pro Ala Pro Glu Leu Leu
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175

Tyr Arg Val Val Ser Val Leu Thr Val Leu His Gln Asp Trp Leu Asn
            180                 185                 190

Gly Lys Glu Tyr Lys Cys Lys Val Ser Asn Lys Ala Leu Pro Ala Pro
        195                 200                 205

Ile Glu Lys Thr Ile Ser Lys Ala Lys Gly Gln Pro Arg Glu Pro Gln
    210                 215                 220

Val Tyr Thr Leu Pro Pro Ser Arg Asp Glu Leu Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
                260                 265                 270

Pro Val Leu Asp Ser Asp Gly Ser Phe Phe Leu Tyr Ser Lys Leu Thr
            275                 280                 285

Val Asp Lys Ser Arg Trp Gln Gln Gly Asn Val Phe Ser Cys Ser Val
        290                 295                 300

Met His Glu Ala Leu His Asn His Tyr Thr Gln Lys Ser Leu Ser Leu
305                 310                 315                 320

Ser Pro Gly Lys Ser Leu Asp Glu Pro Lys Ser Cys Asp Lys Thr His
                325                 330                 335
```

Thr Cys Pro Pro Cys Pro Ala Pro Glu Leu Gly Gly Pro Ser Val
            340             345             350

Phe Leu Phe Pro Lys Pro Lys Asp Thr Leu Met Ile Ser Arg Thr
        355             360             365

Pro Glu Val Thr Cys Val Val Val Asp Val Ser His Glu Asp Pro Glu
    370             375             380

Val Lys Phe Asn Trp Tyr Val Asp Gly Val Glu Val His Asn Ala Lys
385             390             395             400

Thr Lys Pro Arg Glu Glu Gln Tyr Asn Ser Thr Tyr Arg Val Val Ser
            405             410             415

Val Leu Thr Val Leu His Gln Asp Trp Leu Asn Gly Lys Glu Tyr Lys
        420             425             430

Cys Lys Val Ser Asn Lys Ala Leu Pro Ala Pro Ile Glu Lys Thr Ile
        435             440             445

Ser Lys Ala Lys Gly Gln Pro Arg Glu Pro Gln Val Tyr Thr Leu Pro
    450             455             460

Pro Ser Arg Asp Glu Leu Thr Lys Asn Gln Val Ser Leu Thr Cys Leu
465             470             475             480

Val Lys Gly Phe Tyr Pro Ser Asp Ile Ala Val Glu Trp Glu Ser Asn
            485             490             495

Gly Gln Pro Glu Asn Asn Tyr Lys Thr Thr Pro Pro Val Leu Asp Ser
        500             505             510

Asp Gly Ser Phe Phe Leu Tyr Ser Lys Leu Thr Val Asp Lys Ser Arg
        515             520             525

Trp Gln Gln Gly Asn Val Phe Ser Cys Ser Val Met His Glu Ala Leu
    530             535             540

His Asn His Tyr Thr Gln Lys Ser Leu Ser Leu Ser Pro Gly Lys
545             550             555

<210> SEQ ID NO 47
<211> LENGTH: 806
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 47

Met Glu Thr Asp Thr Leu Leu Leu Trp Val Leu Leu Leu Trp Val Pro
1               5                   10                  15

Gly Ser Thr Gly Asp Ala Ala Asp Ile Glu Leu Lys Thr Pro Leu Gly
            20                  25                  30

Asp Thr Thr His Thr Cys Pro Arg Cys Pro Glu Pro Lys Ser Cys Asp
        35                  40                  45

Thr Pro Pro Pro Cys Pro Arg Cys Pro Glu Pro Lys Ser Cys Asp Thr
    50                  55                  60

Pro Pro Pro Cys Pro Arg Cys Pro Glu Pro Lys Ser Cys Asp Thr Pro
65                  70                  75                  80

Pro Pro Cys Pro Arg Cys Pro Ala Pro Glu Leu Leu Gly Gly Pro Ser
            85                  90                  95

Val Phe Leu Phe Pro Lys Pro Lys Asp Thr Leu Met Ile Ser Arg
            100                 105                 110

Thr Pro Glu Val Thr Cys Val Val Val Asp Val Ser His Glu Asp Pro
        115                 120                 125

Glu Val Gln Phe Lys Trp Tyr Val Asp Gly Val Glu Val His Asn Ala
    130                 135                 140

-continued

```
Lys Thr Lys Leu Arg Glu Glu Gln Tyr Asn Ser Thr Phe Arg Val Val
145                 150                 155                 160

Ser Val Leu Thr Val Leu His Gln Asp Trp Leu Asn Gly Lys Glu Tyr
                165                 170                 175

Lys Cys Lys Val Ser Asn Lys Ala Leu Pro Ala Pro Ile Glu Lys Thr
            180                 185                 190

Ile Ser Lys Thr Lys Gly Gln Pro Arg Glu Pro Gln Val Tyr Thr Leu
        195                 200                 205

Pro Pro Ser Arg Glu Glu Met Thr Lys Asn Gln Val Ser Leu Thr Cys
210                 215                 220

Leu Val Lys Gly Phe Tyr Pro Ser Asp Ile Ala Val Glu Trp Glu Ser
225                 230                 235                 240

Asn Gly Gln Pro Glu Asn Asn Tyr Asn Thr Thr Pro Pro Met Leu Asp
                245                 250                 255

Ser Asp Gly Ser Phe Phe Leu Tyr Ser Lys Leu Thr Val Asp Lys Ser
            260                 265                 270

Arg Trp Gln Gln Gly Asn Ile Phe Ser Cys Ser Val Met His Glu Ala
        275                 280                 285

Leu His Asn Arg Tyr Thr Gln Lys Ser Leu Ser Leu Ser Pro Gly Lys
    290                 295                 300

Gly Gly Arg Ser Ser Glu Pro Lys Ser Cys Asp Lys Thr His Thr Cys
305                 310                 315                 320

Pro Pro Cys Pro Ala Pro Glu Leu Leu Gly Gly Pro Ser Val Phe Leu
                325                 330                 335

Phe Pro Pro Lys Pro Lys Asp Thr Leu Met Ile Ser Arg Thr Pro Glu
            340                 345                 350

Val Thr Cys Val Val Val Asp Val Ser His Glu Asp Pro Glu Val Lys
        355                 360                 365

Phe Asn Trp Tyr Val Asp Gly Val Glu Val His Asn Ala Lys Thr Lys
    370                 375                 380

Pro Arg Glu Glu Gln Tyr Asn Ser Thr Tyr Arg Val Val Ser Val Leu
385                 390                 395                 400

Thr Val Leu His Gln Asp Trp Leu Asn Gly Lys Glu Tyr Lys Cys Lys
                405                 410                 415

Val Ser Asn Lys Ala Leu Pro Ala Pro Ile Glu Lys Thr Ile Ser Lys
            420                 425                 430

Ala Lys Gly Gln Pro Arg Glu Pro Gln Val Tyr Thr Leu Pro Pro Ser
        435                 440                 445

Arg Asp Glu Leu Thr Lys Asn Gln Val Ser Leu Thr Cys Leu Val Lys
    450                 455                 460

Gly Phe Tyr Pro Ser Asp Ile Ala Val Glu Trp Glu Ser Asn Gly Gln
465                 470                 475                 480

Pro Glu Asn Asn Tyr Lys Thr Thr Pro Pro Val Leu Asp Ser Asp Gly
                485                 490                 495

Ser Phe Phe Leu Tyr Ser Lys Leu Thr Val Asp Lys Ser Arg Trp Gln
            500                 505                 510

Gln Gly Asn Val Phe Ser Cys Ser Val Met His Glu Ala Leu His Asn
        515                 520                 525

His Tyr Thr Gln Lys Ser Leu Ser Leu Ser Pro Gly Lys Ser Leu Glu
    530                 535                 540

Gly Pro Arg Phe Glu Glu Pro Lys Ser Cys Asp Lys Thr His Thr Cys
545                 550                 555                 560

Pro Pro Cys Pro Ala Pro Glu Leu Leu Gly Gly Pro Ser Val Phe Leu
```

```
                    565                 570                 575
Phe Pro Pro Lys Pro Lys Asp Thr Leu Met Ile Ser Arg Thr Pro Glu
                580                 585                 590

Val Thr Cys Val Val Val Asp Val Ser His Glu Asp Pro Glu Val Lys
            595                 600                 605

Phe Asn Trp Tyr Val Asp Gly Val Glu Val His Asn Ala Lys Thr Lys
        610                 615                 620

Pro Arg Glu Glu Gln Tyr Asn Ser Thr Tyr Arg Val Val Ser Val Leu
625                 630                 635                 640

Thr Val Leu His Gln Asp Trp Leu Asn Gly Lys Glu Tyr Lys Cys Lys
                645                 650                 655

Val Ser Asn Lys Ala Leu Pro Ala Pro Ile Glu Lys Thr Ile Ser Lys
            660                 665                 670

Ala Lys Gly Gln Pro Arg Glu Pro Gln Val Tyr Thr Leu Pro Pro Ser
        675                 680                 685

Arg Asp Glu Leu Thr Lys Asn Gln Val Ser Leu Thr Cys Leu Val Lys
690                 695                 700

Gly Phe Tyr Pro Ser Asp Ile Ala Val Glu Trp Glu Ser Asn Gly Gln
705                 710                 715                 720

Pro Glu Asn Asn Tyr Lys Thr Thr Pro Pro Val Leu Asp Ser Asp Gly
                725                 730                 735

Ser Phe Phe Leu Tyr Ser Lys Leu Thr Val Asp Lys Ser Arg Trp Gln
            740                 745                 750

Gln Gly Asn Val Phe Ser Cys Ser Val Met His Glu Ala Leu His Asn
        755                 760                 765

His Tyr Thr Gln Lys Ser Leu Ser Leu Ser Pro Gly Lys Phe Glu Gly
        770                 775                 780

Lys Pro Ile Pro Asn Pro Leu Leu Gly Leu Asp Ser Thr Arg Thr Gly
785                 790                 795                 800

His His His His His His
            805

<210> SEQ ID NO 48
<211> LENGTH: 394
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 48

Met Glu Thr Asp Thr Leu Leu Leu Trp Val Leu Leu Leu Trp Val Pro
1               5                   10                  15

Gly Ser Thr Gly Asp Ala Ala Asp Ile Glu Asp Thr Cys Gly Glu Leu
            20                  25                  30

Glu Phe Gln Asn Asp Glu Ile Val Lys Thr Ile Ser Val Lys Val Ile
        35                  40                  45

Asp Asp Glu Glu Tyr Glu Lys Asn Lys Thr Phe Phe Leu Glu Ile Gly
    50                  55                  60

Lys Pro Arg Leu Val Glu Met Ser Glu Lys Lys Ala Leu Leu Leu Asn
65                  70                  75                  80

Glu Leu Gly Gly Phe Thr Ile Thr Gly Lys Tyr Leu Phe Gly Gln Pro
                85                  90                  95

Val Phe Arg Lys Val His Ala Arg Glu His Pro Ile Leu Ser Thr Val
            100                 105                 110

Ile Thr Ile Ala Asp Glu Tyr Asp Asp Lys Gln Pro Leu Thr Ser Lys
```

```
                115                 120                 125
Glu Lys Glu Glu Gly Arg Ser Ser Glu Pro Lys Ser Cys Asp Lys
        130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Asp Glu Leu Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys Phe Glu Gly Lys Pro Ile Pro Asn Pro Leu Leu Gly Leu Asp Ser
    370                 375                 380

Thr Arg Thr Gly His His His His His His
385                 390

<210> SEQ ID NO 49
<211> LENGTH: 634
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 49

Met Glu Thr Asp Thr Leu Leu Leu Trp Val Leu Leu Leu Trp Val Pro
1               5                   10                  15

Gly Ser Thr Gly Asp Ala Ala Asp Ile Glu Asp Thr Cys Gly Glu Leu
            20                  25                  30

Glu Phe Gln Asn Asp Glu Ile Val Lys Thr Ile Ser Val Lys Val Ile
        35                  40                  45

Asp Asp Glu Glu Tyr Glu Lys Asn Lys Thr Phe Phe Leu Glu Ile Gly
    50                  55                  60

Lys Pro Arg Leu Val Glu Met Ser Glu Lys Lys Ala Leu Leu Leu Asn
65                  70                  75                  80

Glu Leu Gly Gly Phe Thr Ile Thr Gly Lys Tyr Leu Phe Gly Gln Pro
```

```
                   85                  90                  95
Val Phe Arg Lys Val His Ala Arg Glu His Pro Ile Leu Ser Thr Val
                100                 105                 110

Ile Thr Ile Ala Asp Glu Tyr Asp Asp Lys Gln Pro Leu Thr Ser Lys
            115                 120                 125

Glu Lys Glu Glu Gly Gly Arg Ser Ser Glu Pro Lys Ser Cys Asp Lys
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Asp Glu Leu Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys Ser Leu Glu Gly Pro Arg Phe Glu Pro Lys Ser Cys Asp Lys
    370                 375                 380

Thr His Thr Cys Pro Pro Cys Pro Ala Pro Glu Leu Leu Gly Gly Pro
385                 390                 395                 400

Ser Val Phe Leu Phe Pro Pro Lys Pro Lys Asp Thr Leu Met Ile Ser
                405                 410                 415

Arg Thr Pro Glu Val Thr Cys Val Val Val Asp Val Ser His Glu Asp
            420                 425                 430

Pro Glu Val Lys Phe Asn Trp Tyr Val Asp Gly Val Glu Val His Asn
        435                 440                 445

Ala Lys Thr Lys Pro Arg Glu Glu Gln Tyr Asn Ser Thr Tyr Arg Val
    450                 455                 460

Val Ser Val Leu Thr Val Leu His Gln Asp Trp Leu Asn Gly Lys Glu
465                 470                 475                 480

Tyr Lys Cys Lys Val Ser Asn Lys Ala Leu Pro Ala Pro Ile Glu Lys
                485                 490                 495

Thr Ile Ser Lys Ala Lys Gly Gln Pro Arg Glu Pro Gln Val Tyr Thr
            500                 505                 510
```

```
Leu Pro Pro Ser Arg Asp Glu Leu Thr Lys Asn Gln Val Ser Leu Thr
            515                 520                 525

Cys Leu Val Lys Gly Phe Tyr Pro Ser Asp Ile Ala Val Glu Trp Glu
        530                 535                 540

Ser Asn Gly Gln Pro Glu Asn Asn Tyr Lys Thr Thr Pro Pro Val Leu
545                 550                 555                 560

Asp Ser Asp Gly Ser Phe Phe Leu Tyr Ser Lys Leu Thr Val Asp Lys
                565                 570                 575

Ser Arg Trp Gln Gln Gly Asn Val Phe Ser Cys Ser Val Met His Glu
            580                 585                 590

Ala Leu His Asn His Tyr Thr Gln Lys Ser Leu Ser Leu Ser Pro Gly
        595                 600                 605

Lys Phe Glu Gly Lys Pro Ile Pro Asn Pro Leu Leu Gly Leu Asp Ser
    610                 615                 620

Thr Arg Thr Gly His His His His His His
625                 630

<210> SEQ ID NO 50
<211> LENGTH: 296
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 50

Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
            20                  25                  30

Ser Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240
```

```
Phe Ser Cys Ser Val Met His Glu Ala Leu His Asn His Tyr Thr Gln
                245                 250                 255

Lys Ser Leu Ser Leu Ser Pro Gly Lys Ser Leu Glu Gly Pro Arg Phe
            260                 265                 270

Glu Gly Lys Pro Ile Pro Asn Pro Leu Leu Gly Leu Asp Ser Thr Arg
            275                 280                 285

Thr Gly His His His His His His
            290                 295

<210> SEQ ID NO 51
<211> LENGTH: 252
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 51

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 52
<211> LENGTH: 336
<212> TYPE: PRT
<213> ORGANISM: ARTIFICIAL SEQUENCE
<220> FEATURE:
<223> OTHER INFORMATION: chemically-synthesized stradomer monomer
```

<400> SEQUENCE: 52

```
Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
            20                  25                  30

Ser Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys Ser Leu Glu Gly Pro Arg Phe
            260                 265                 270

Glu Glu Leu Lys Thr Pro Leu Gly Asp Thr Thr His Thr Cys Pro Arg
        275                 280                 285

Cys Pro Glu Pro Lys Ser Cys Asp Thr Pro Pro Cys Pro Arg Cys
    290                 295                 300

Pro Glu Pro Lys Ser Cys Asp Thr Pro Pro Cys Pro Arg Cys Pro
305                 310                 315                 320

Glu Pro Lys Ser Cys Asp Thr Pro Pro Cys Pro Arg Cys Pro Ala
                325                 330                 335
```

<210> SEQ ID NO 53
<211> LENGTH: 738
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 53

```
Met Glu Thr Asp Thr Leu Leu Leu Trp Val Leu Leu Leu Trp Val Pro
1               5                   10                  15

Gly Ser Thr Gly Asp Ala Ala Asp Ile Gln His Gly Gly Arg Ser Ser
```

-continued

```
                20                  25                  30
Glu Pro Lys Ser Cys Asp Lys Thr His Thr Cys Pro Pro Cys Pro Ala
             35                  40                  45

Pro Glu Leu Leu Gly Gly Pro Ser Val Phe Leu Phe Pro Pro Lys Pro
         50                  55                  60

Lys Asp Thr Leu Met Ile Ser Arg Thr Pro Glu Val Thr Cys Val Val
 65                  70                  75                  80

Val Asp Val Ser His Glu Asp Pro Glu Val Lys Phe Asn Trp Tyr Val
                 85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
            115                 120                 125

Asp Trp Leu Asn Gly Lys Glu Tyr Lys Cys Lys Val Ser Asn Lys Ala
        130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Asp Glu Leu Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys Ser Leu Asp Glu Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445
```

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Phe Glu Asp Gln Asp Ile Ala Ile Arg Val Phe Ala Ile
            500                 505                 510

Pro Pro Ser Phe Ala Ser Ile Phe Leu Thr Lys Ser Thr Lys Leu Thr
            515                 520                 525

Cys Leu Val Thr Asp Leu Thr Thr Tyr Asp Ser Val Thr Ile Ser Trp
    530                 535                 540

Thr Arg Gln Asn Gly Glu Ala Val Lys Thr His Thr Asn Ile Ser Glu
545                 550                 555                 560

Ser His Pro Asn Ala Thr Phe Ser Ala Val Gly Glu Ala Ser Ile Cys
                565                 570                 575

Glu Asp Asp Trp Asn Ser Gly Glu Arg Phe Thr Cys Thr Val Thr His
            580                 585                 590

Thr Asp Leu Pro Ser Pro Leu Lys Gln Thr Ile Ser Arg Pro Lys Gly
            595                 600                 605

Val Ala Leu His Arg Pro Asp Val Tyr Leu Leu Pro Pro Ala Arg Glu
    610                 615                 620

Gln Leu Asn Leu Arg Glu Ser Ala Thr Ile Thr Cys Leu Val Thr Gly
625                 630                 635                 640

Phe Ser Pro Ala Asp Val Phe Val Gln Trp Met Gln Arg Gly Gln Pro
                645                 650                 655

Leu Ser Pro Glu Lys Tyr Val Thr Ser Ala Pro Met Pro Glu Pro Gln
            660                 665                 670

Ala Pro Gly Arg Tyr Phe Ala His Ser Ile Leu Thr Val Ser Glu Glu
            675                 680                 685

Glu Trp Asn Thr Gly Glu Thr Tyr Thr Cys Val Val Ala His Glu Ala
    690                 695                 700

Leu Pro Asn Arg Val Thr Glu Arg Thr Val Asp Lys Ser Thr Gly Lys
705                 710                 715                 720

Pro Thr Leu Tyr Asn Val Ser Leu Val Met Ser Asp Thr Ala Gly Thr
                725                 730                 735

Cys Tyr

<210> SEQ ID NO 54
<211> LENGTH: 510
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 54

Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
                20                  25                  30

Ser Glu Pro Lys Ser Cys Asp Lys Thr His Thr Cys Pro Pro Cys Pro
            35                  40                  45

Ala Pro Glu Leu Leu Gly Gly Pro Ser Val Phe Leu Phe Pro Pro Lys
    50                  55                  60

```
Pro Lys Asp Thr Leu Met Ile Ser Arg Thr Pro Glu Val Thr Cys Val
 65                  70                  75                  80

Val Val Asp Val Ser His Glu Asp Pro Glu Val Lys Phe Asn Trp Tyr
                 85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
            115                 120                 125

Gln Asp Trp Leu Asn Gly Lys Glu Tyr Lys Cys Lys Val Ser Asn Lys
130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
            195                 200                 205

Tyr Lys Thr Thr Pro Pro Val Leu Asp Ser Asp Gly Ser Phe Phe Leu
            210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys Ser Leu Glu Gly Pro Arg Phe
            260                 265                 270

Glu Asp Gln Asp Ile Ala Ile Arg Val Phe Ala Ile Pro Pro Ser Phe
            275                 280                 285

Ala Ser Ile Phe Leu Thr Lys Ser Thr Lys Leu Thr Cys Leu Val Thr
            290                 295                 300

Asp Leu Thr Thr Tyr Asp Ser Val Thr Ile Ser Trp Thr Arg Gln Asn
305                 310                 315                 320

Gly Glu Ala Val Lys Thr His Thr Asn Ile Ser Glu Ser His Pro Asn
                325                 330                 335

Ala Thr Phe Ser Ala Val Gly Glu Ala Ser Ile Cys Glu Asp Asp Trp
            340                 345                 350

Asn Ser Gly Glu Arg Phe Thr Cys Thr Val Thr His Thr Asp Leu Pro
            355                 360                 365

Ser Pro Leu Lys Gln Thr Ile Ser Arg Pro Lys Gly Val Ala Leu His
370                 375                 380

Arg Pro Asp Val Tyr Leu Leu Pro Pro Ala Arg Glu Gln Leu Asn Leu
385                 390                 395                 400

Arg Glu Ser Ala Thr Ile Thr Cys Leu Val Thr Gly Phe Ser Pro Ala
                405                 410                 415

Asp Val Phe Val Gln Trp Met Gln Arg Gly Gln Pro Leu Ser Pro Glu
            420                 425                 430

Lys Tyr Val Thr Ser Ala Pro Met Pro Glu Pro Gln Ala Pro Gly Arg
            435                 440                 445

Tyr Phe Ala His Ser Ile Leu Thr Val Ser Glu Glu Trp Asn Thr
            450                 455                 460

Gly Glu Thr Tyr Thr Cys Val Val Ala His Glu Ala Leu Pro Asn Arg
465                 470                 475                 480

Val Thr Glu Arg Thr Val Asp Lys Ser Thr Gly Lys Pro Thr Leu Tyr
```

```
                    485                 490                 495
Asn Val Ser Leu Val Met Ser Asp Thr Ala Gly Thr Cys Tyr
            500                 505                 510

<210> SEQ ID NO 55
<211> LENGTH: 394
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 55

Met Glu Thr Asp Thr Leu Leu Leu Trp Val Leu Leu Trp Val Pro
1               5                   10                  15

Gly Ser Thr Gly Asp Ala Ala Asp Ile Val Cys Ser Arg Asp Phe Thr
                20                  25                  30

Pro Pro Thr Val Lys Ile Leu Gln Ser Ser Cys Asp Gly Gly Gly His
                35                  40                  45

Phe Pro Pro Thr Ile Gln Leu Leu Cys Leu Val Ser Gly Tyr Thr Pro
            50                  55                  60

Gly Thr Ile Asn Ile Thr Trp Leu Glu Asp Gly Gln Val Met Asp Val
65                  70                  75                  80

Asp Leu Ser Thr Ala Ser Thr Thr Gln Glu Gly Glu Leu Ala Ser Thr
                85                  90                  95

Gln Ser Glu Leu Thr Leu Ser Gln Lys His Trp Leu Ser Asp Arg Thr
            100                 105                 110

Tyr Thr Cys Gln Val Thr Tyr Gln Gly His Thr Phe Glu Asp Ser Thr
            115                 120                 125

Lys Lys Cys Gly Gly Gly Arg Ser Ser Glu Pro Lys Ser Cys Asp Lys
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Asp Glu Leu Thr Lys Asn Gln Val Ser Leu Thr
            275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
```

```
                  340                 345                 350
Ala Leu His Asn His Tyr Thr Gln Lys Ser Leu Ser Leu Ser Pro Gly
                355                 360                 365

Lys Phe Glu Gly Lys Pro Ile Pro Asn Pro Leu Leu Gly Leu Asp Ser
            370                 375                 380

Thr Arg Thr Gly His His His His His His
385                 390

<210> SEQ ID NO 56
<211> LENGTH: 362
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 56

Met Glu Thr Asp Thr Leu Leu Leu Trp Val Leu Leu Leu Trp Val Pro
1               5                   10                  15

Gly Ser Thr Gly Val Cys Ser Arg Asp Phe Thr Pro Pro Thr Val Lys
            20                  25                  30

Ile Leu Gln Ser Ser Cys Asp Gly Gly His Phe Pro Pro Thr Ile
        35                  40                  45

Gln Leu Leu Cys Leu Val Ser Gly Tyr Thr Pro Gly Thr Ile Asn Ile
    50                  55                  60

Thr Trp Leu Glu Asp Gly Gln Val Met Asp Val Asp Leu Ser Thr Ala
65                  70                  75                  80

Ser Thr Thr Gln Glu Gly Glu Leu Ala Ser Thr Gln Ser Glu Leu Thr
                85                  90                  95

Leu Ser Gln Lys His Trp Leu Ser Asp Arg Thr Tyr Thr Cys Gln Val
            100                 105                 110

Thr Tyr Gln Gly His Thr Phe Glu Asp Ser Thr Lys Lys Cys Glu Pro
        115                 120                 125

Lys Ser Cys Asp Lys Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
```

```
305                 310                 315                 320
Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly Lys Phe Glu Gly Lys
                355                 360

<210> SEQ ID NO 57
<211> LENGTH: 519
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 57

Met Glu Thr Asp Thr Leu Leu Leu Trp Val Leu Leu Leu Trp Val Pro
1               5                   10                  15

Gly Ser Thr Gly Asp Ala Ala Asp Ile Glu Arg Lys Cys Cys Val Glu
                20                  25                  30

Cys Pro Pro Cys Pro Ala Pro Pro Val Ala Gly Pro Ser Val Phe Leu
            35                  40                  45

Phe Pro Pro Lys Pro Lys Asp Thr Leu Met Ile Ser Arg Thr Pro Glu
    50                  55                  60

Val Thr Cys Val Val Val Asp Val Ser His Glu Asp Pro Glu Val Gln
65                  70                  75                  80

Phe Asn Trp Tyr Val Asp Gly Val Glu Val His Asn Ala Lys Thr Lys
                85                  90                  95

Pro Arg Glu Glu Gln Phe Asn Ser Thr Phe Arg Val Val Ser Val Leu
                100                 105                 110

Thr Val Val His Gln Asp Trp Leu Asn Gly Lys Glu Tyr Lys Cys Lys
            115                 120                 125

Val Ser Asn Lys Gly Leu Pro Ala Pro Ile Glu Lys Thr Ile Ser Lys
    130                 135                 140

Thr Lys Gly Gln Pro Arg Glu Pro Gln Val Tyr Thr Leu Pro Pro Ser
145                 150                 155                 160

Arg Glu Glu Met Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
                180                 185                 190

Pro Glu Asn Asn Tyr Lys Thr Thr Pro Pro Met Leu Asp Ser Asp Gly
            195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Lys Arg Ser Ser
                245                 250                 255

Glu Pro Lys Ser Cys Asp Lys Thr His Thr Cys Pro Pro Cys Pro Ala
                260                 265                 270

Pro Glu Leu Leu Gly Gly Pro Ser Val Phe Leu Phe Pro Pro Lys Pro
            275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
```

```
            305                 310                 315                 320
Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
                355                 360                 365

Leu Pro Ala Pro Ile Glu Lys Thr Ile Ser Lys Ala Lys Gly Gln Pro
                370                 375                 380

Arg Glu Pro Gln Val Tyr Thr Leu Pro Pro Ser Arg Glu Glu Met Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
                435                 440                 445

Ser Lys Leu Thr Val Asp Lys Ser Arg Trp Gln Gln Gly Asn Val Phe
                450                 455                 460

Ser Cys Ser Val Met His Glu Ala Leu His Asn His Tyr Thr Gln Lys
465                 470                 475                 480

Ser Leu Ser Leu Ser Pro Gly Lys Ser Leu Glu Gly Pro Arg Phe Glu
                485                 490                 495

Gly Lys Pro Ile Pro Asn Pro Leu Leu Gly Leu Asp Ser Thr Arg Thr
                500                 505                 510

Gly His His His His His His
                515

<210> SEQ ID NO 58
<211> LENGTH: 488
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 58

Met Glu Thr Asp Thr Leu Leu Leu Trp Val Leu Leu Leu Trp Val Pro
1               5                   10                  15

Gly Ser Thr Gly Asp Ala Ala Asp Ile Glu Arg Lys Cys Cys Val Glu
                20                  25                  30

Cys Pro Pro Cys Pro Ala Pro Pro Val Ala Gly Pro Ser Val Phe Leu
                35                  40                  45

Phe Pro Pro Lys Pro Lys Asp Thr Leu Met Ile Ser Arg Thr Pro Glu
                50                  55                  60

Val Thr Cys Val Val Val Asp Val Ser His Glu Asp Pro Glu Val Gln
65                  70                  75                  80

Phe Asn Trp Tyr Val Asp Gly Val Glu Val His Asn Ala Lys Thr Lys
                85                  90                  95

Pro Arg Glu Glu Gln Phe Asn Ser Thr Phe Arg Val Val Ser Val Leu
                100                 105                 110

Thr Val Val His Gln Asp Trp Leu Asn Gly Lys Glu Tyr Lys Cys Lys
                115                 120                 125

Val Ser Asn Lys Gly Leu Pro Ala Pro Ile Glu Lys Thr Ile Ser Lys
                130                 135                 140

Thr Lys Gly Gln Pro Arg Glu Pro Gln Val Tyr Thr Leu Pro Pro Ser
```

```
            145                 150                 155                 160

Arg Glu Glu Met Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Met Leu Asp Ser Asp Gly
        195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Lys Arg Ser Ser
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Glu Glu Met Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 59
<211> LENGTH: 303
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 59

Met Glu Thr Asp Thr Leu Leu Leu Trp Val Leu Leu Leu Trp Val Pro
1               5                   10                  15

Gly Ser Thr Gly Asp Ala Ala Asp Ile Glu Arg Lys Cys Cys Val Glu
```

```
                20              25              30
Cys Pro Pro Cys Pro Arg Ser Ser Glu Pro Lys Ser Cys Asp Lys Thr
             35              40              45

His Thr Cys Pro Pro Cys Pro Ala Pro Glu Leu Leu Gly Gly Pro Ser
 50              55              60

Val Phe Leu Phe Pro Pro Lys Pro Lys Asp Thr Leu Met Ile Ser Arg
 65              70              75              80

Thr Pro Glu Val Thr Cys Val Val Val Asp Val Ser His Glu Asp Pro
             85              90              95

Glu Val Lys Phe Asn Trp Tyr Val Asp Gly Val Glu Val His Asn Ala
            100             105             110

Lys Thr Lys Pro Arg Glu Glu Gln Tyr Asn Ser Thr Tyr Arg Val Val
            115             120             125

Ser Val Leu Thr Val Leu His Gln Asp Trp Leu Asn Gly Lys Glu Tyr
        130             135             140

Lys Cys Lys Val Ser Asn Lys Ala Leu Pro Ala Pro Ile Glu Lys Thr
145             150             155             160

Ile Ser Lys Ala Lys Gly Gln Pro Arg Glu Pro Gln Val Tyr Thr Leu
            165             170             175

Pro Pro Ser Arg Glu Glu Met Thr Lys Asn Gln Val Ser Leu Thr Cys
            180             185             190

Leu Val Lys Gly Phe Tyr Pro Ser Asp Ile Ala Val Glu Trp Glu Ser
            195             200             205

Asn Gly Gln Pro Glu Asn Asn Tyr Lys Thr Thr Pro Pro Val Leu Asp
            210             215             220

Ser Asp Gly Ser Phe Phe Leu Tyr Ser Lys Leu Thr Val Asp Lys Ser
225             230             235             240

Arg Trp Gln Gln Gly Asn Val Phe Ser Cys Ser Val Met His Glu Ala
            245             250             255

Leu His Asn His Tyr Thr Gln Lys Ser Leu Ser Leu Ser Pro Gly Lys
            260             265             270

Ser Leu Glu Gly Pro Arg Phe Glu Gly Lys Pro Ile Pro Asn Pro Leu
            275             280             285

Leu Gly Leu Asp Ser Thr Arg Thr Gly His His His His His
            290             295             300

<210> SEQ ID NO 60
<211> LENGTH: 272
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 60

Met Glu Thr Asp Thr Leu Leu Leu Trp Val Leu Leu Leu Trp Val Pro
 1               5              10              15

Gly Ser Thr Gly Asp Ala Ala Asp Ile Glu Arg Lys Cys Cys Val Glu
             20              25              30

Cys Pro Pro Cys Pro Arg Ser Ser Glu Pro Lys Ser Cys Asp Lys Thr
             35              40              45

His Thr Cys Pro Pro Cys Pro Ala Pro Glu Leu Leu Gly Gly Pro Ser
 50              55              60

Val Phe Leu Phe Pro Pro Lys Pro Lys Asp Thr Leu Met Ile Ser Arg
 65              70              75              80

Thr Pro Glu Val Thr Cys Val Val Val Asp Val Ser His Glu Asp Pro
```

```
            85                  90                  95
Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
            130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
            165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
            195                 200                 205

Asn Gly Gln Pro Glu Asn Asn Tyr Lys Thr Thr Pro Pro Val Leu Asp
            210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
            245                 250                 255

Leu His Asn His Tyr Thr Gln Lys Ser Leu Ser Leu Ser Pro Gly Lys
            260                 265                 270

<210> SEQ ID NO 61
<211> LENGTH: 264
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 61

Met Glu Thr Asp Thr Leu Leu Leu Trp Val Leu Leu Leu Trp Val Pro
1               5                   10                  15

Gly Ser Thr Gly Glu Arg Lys Cys Cys Val Glu Cys Pro Pro Cys Pro
            20                  25                  30

Glu Pro Lys Ser Cys Asp Lys Thr His Thr Cys Pro Pro Cys Pro Ala
            35                  40                  45

Pro Glu Leu Leu Gly Gly Pro Ser Val Phe Leu Phe Pro Pro Lys Pro
            50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
            85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
            115                 120                 125

Asp Trp Leu Asn Gly Lys Glu Tyr Lys Cys Lys Val Ser Asn Lys Ala
            130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Glu Glu Met Thr
            165                 170                 175

Lys Asn Gln Val Ser Leu Thr Cys Leu Val Lys Gly Phe Tyr Pro Ser
```

```
                180                 185                 190
Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
        210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys
            260

<210> SEQ ID NO 62
<211> LENGTH: 538
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 62

Met Glu Thr Asp Thr Leu Leu Leu Trp Val Leu Leu Leu Trp Val Pro
1               5                   10                  15

Gly Ser Thr Gly Asp Ala Ala Asp Ile Glu Arg Lys Cys Cys Val Glu
            20                  25                  30

Cys Pro Pro Cys Pro Arg Ser Ser Glu Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

Ser Leu Asp Glu Pro Lys Ser Cys Asp Lys Thr His Thr Cys Pro Pro
```

```
              275                 280                 285
Cys Pro Ala Pro Glu Leu Leu Gly Gly Pro Ser Val Phe Leu Phe Pro
    290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
            340                 345                 350

Glu Glu Gln Tyr Asn Ser Thr Tyr Arg Val Val Ser Val Leu Thr Val
        355                 360                 365

Leu His Gln Asp Trp Leu Asn Gly Lys Glu Tyr Lys Cys Lys Val Ser
    370                 375                 380

Asn Lys Ala Leu Pro Ala Pro Ile Glu Lys Thr Ile Ser Lys Ala Lys
385                 390                 395                 400

Gly Gln Pro Arg Glu Pro Gln Val Tyr Thr Leu Pro Pro Ser Arg Glu
                405                 410                 415

Glu Met Thr Lys Asn Gln Val Ser Leu Thr Cys Leu Val Lys Gly Phe
            420                 425                 430

Tyr Pro Ser Asp Ile Ala Val Glu Trp Glu Ser Asn Gly Gln Pro Glu
        435                 440                 445

Asn Asn Tyr Lys Thr Thr Pro Pro Val Leu Asp Ser Asp Gly Ser Phe
    450                 455                 460

Phe Leu Tyr Ser Lys Leu Thr Val Asp Lys Ser Arg Trp Gln Gln Gly
465                 470                 475                 480

Asn Val Phe Ser Cys Ser Val Met His Glu Ala Leu His Asn His Tyr
                485                 490                 495

Thr Gln Lys Ser Leu Ser Leu Ser Pro Gly Lys Ser Leu Glu Gly Pro
            500                 505                 510

Arg Phe Glu Gly Lys Pro Ile Pro Asn Pro Leu Leu Gly Leu Asp Ser
        515                 520                 525

Thr Arg Thr Gly His His His His His His
    530                 535

<210> SEQ ID NO 63
<211> LENGTH: 507
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 63

Met Glu Thr Asp Thr Leu Leu Leu Trp Val Leu Leu Leu Trp Val Pro
1               5                   10                  15

Gly Ser Thr Gly Asp Ala Ala Asp Ile Glu Arg Lys Cys Cys Val Glu
            20                  25                  30

Cys Pro Pro Cys Pro Arg Ser Ser Glu Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
```

```
                100             105             110
Lys Thr Lys Pro Arg Glu Glu Gln Tyr Asn Ser Thr Tyr Arg Val Val
            115                 120             125

Ser Val Leu Thr Val Leu His Gln Asp Trp Leu Asn Gly Lys Glu Tyr
            130                 135             140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
            195                 200                 205

Asn Gly Gln Pro Glu Asn Asn Tyr Lys Thr Thr Pro Pro Val Leu Asp
            210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
                260                 265                 270

Ser Leu Asp Glu Pro Lys Ser Cys Asp Lys Thr His Thr Cys Pro Pro
            275                 280                 285

Cys Pro Ala Pro Glu Leu Leu Gly Gly Pro Ser Val Phe Leu Phe Pro
            290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
                340                 345                 350

Glu Glu Gln Tyr Asn Ser Thr Tyr Arg Val Val Ser Val Leu Thr Val
            355                 360                 365

Leu His Gln Asp Trp Leu Asn Gly Lys Glu Tyr Lys Cys Lys Val Ser
            370                 375                 380

Asn Lys Ala Leu Pro Ala Pro Ile Glu Lys Thr Ile Ser Lys Ala Lys
385                 390                 395                 400

Gly Gln Pro Arg Glu Pro Gln Val Tyr Thr Leu Pro Pro Ser Arg Glu
                405                 410                 415

Glu Met Thr Lys Asn Gln Val Ser Leu Thr Cys Leu Val Lys Gly Phe
            420                 425                 430

Tyr Pro Ser Asp Ile Ala Val Glu Trp Glu Ser Asn Gly Gln Pro Glu
            435                 440                 445

Asn Asn Tyr Lys Thr Thr Pro Pro Val Leu Asp Ser Asp Gly Ser Phe
450                 455                 460

Phe Leu Tyr Ser Lys Leu Thr Val Asp Lys Ser Arg Trp Gln Gln Gly
465                 470                 475                 480

Asn Val Phe Ser Cys Ser Val Met His Glu Ala Leu His Asn His Tyr
                485                 490                 495

Thr Gln Lys Ser Leu Ser Leu Ser Pro Gly Lys
                500                 505

<210> SEQ ID NO 64
```

```
<211> LENGTH: 511
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 64

Met Glu Thr Asp Thr Leu Leu Leu Trp Val Leu Leu Leu Trp Val Pro
1               5                   10                  15

Gly Ser Thr Gly Asp Ala Ala Asp Ile Val Cys Ser Arg Asp Phe Thr
            20                  25                  30

Pro Pro Thr Val Lys Ile Leu Gln Ser Ser Cys Asp Gly Gly Gly His
        35                  40                  45

Phe Pro Pro Thr Ile Gln Leu Leu Cys Leu Val Ser Gly Tyr Thr Pro
    50                  55                  60

Gly Thr Ile Asn Ile Thr Trp Leu Glu Asp Gly Gln Val Met Asp Val
65                  70                  75                  80

Asp Leu Ser Thr Ala Ser Thr Thr Gln Glu Gly Glu Leu Ala Ser Thr
                85                  90                  95

Gln Ser Glu Leu Thr Leu Ser Gln Lys His Trp Leu Ser Asp Arg Thr
            100                 105                 110

Tyr Thr Cys Gln Val Thr Tyr Gln Gly His Thr Phe Glu Asp Ser Thr
        115                 120                 125

Lys Lys Cys Gly Gly Asp Ile Val Cys Ser Arg Asp Phe Thr Pro
    130                 135                 140

Pro Thr Val Lys Ile Leu Gln Ser Ser Cys Asp Gly Gly Gly His Phe
145                 150                 155                 160

Pro Pro Thr Ile Gln Leu Leu Cys Leu Val Ser Gly Tyr Thr Pro Gly
                165                 170                 175

Thr Ile Asn Ile Thr Trp Leu Glu Asp Gly Gln Val Met Asp Val Asp
            180                 185                 190

Leu Ser Thr Ala Ser Thr Thr Gln Glu Gly Glu Leu Ala Ser Thr Gln
        195                 200                 205

Ser Glu Leu Thr Leu Ser Gln Lys His Trp Leu Ser Asp Arg Thr Tyr
    210                 215                 220

Thr Cys Gln Val Thr Tyr Gln Gly His Thr Phe Glu Asp Ser Thr Lys
225                 230                 235                 240

Lys Cys Gly Gly Gly Arg Ser Ser Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380
```

```
Pro Pro Ser Arg Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
            450                 455                 460

Leu His Asn His Tyr Thr Gln Lys Ser Leu Ser Leu Ser Pro Gly Lys
465                 470                 475                 480

Ser Leu Glu Gly Pro Arg Phe Glu Gly Lys Pro Ile Pro Asn Pro Leu
                485                 490                 495

Leu Gly Leu Asp Ser Thr Arg Thr Gly His His His His His His
            500                 505                 510

<210> SEQ ID NO 65
<211> LENGTH: 480
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 65

Met Glu Thr Asp Thr Leu Leu Leu Trp Val Leu Leu Leu Trp Val Pro
1               5                   10                  15

Gly Ser Thr Gly Asp Ala Ala Asp Ile Val Cys Ser Arg Asp Phe Thr
            20                  25                  30

Pro Pro Thr Val Lys Ile Leu Gln Ser Ser Cys Asp Gly Gly Gly His
            35                  40                  45

Phe Pro Pro Thr Ile Gln Leu Leu Cys Leu Val Ser Gly Tyr Thr Pro
50                  55                  60

Gly Thr Ile Asn Ile Thr Trp Leu Glu Asp Gly Gln Val Met Asp Val
65                  70                  75                  80

Asp Leu Ser Thr Ala Ser Thr Thr Gln Glu Gly Glu Leu Ala Ser Thr
                85                  90                  95

Gln Ser Glu Leu Thr Leu Ser Gln Lys His Trp Leu Ser Asp Arg Thr
            100                 105                 110

Tyr Thr Cys Gln Val Thr Tyr Gln Gly His Thr Phe Glu Asp Ser Thr
            115                 120                 125

Lys Lys Cys Gly Gly Gly Asp Ile Val Cys Ser Arg Asp Phe Thr Pro
130                 135                 140

Pro Thr Val Lys Ile Leu Gln Ser Ser Cys Asp Gly Gly Gly His Phe
145                 150                 155                 160

Pro Pro Thr Ile Gln Leu Leu Cys Leu Val Ser Gly Tyr Thr Pro Gly
                165                 170                 175

Thr Ile Asn Ile Thr Trp Leu Glu Asp Gly Gln Val Met Asp Val Asp
            180                 185                 190

Leu Ser Thr Ala Ser Thr Thr Gln Glu Gly Glu Leu Ala Ser Thr Gln
        195                 200                 205

Ser Glu Leu Thr Leu Ser Gln Lys His Trp Leu Ser Asp Arg Thr Tyr
    210                 215                 220

Thr Cys Gln Val Thr Tyr Gln Gly His Thr Phe Glu Asp Ser Thr Lys
225                 230                 235                 240
```

-continued

```
Lys Cys Gly Gly Gly Arg Ser Ser Glu Pro Lys Ser Cys Asp Lys Thr
                245                 250                 255
His Thr Cys Pro Pro Cys Pro Ala Pro Glu Leu Leu Gly Gly Pro Ser
            260                 265                 270
Val Phe Leu Phe Pro Pro Lys Pro Lys Asp Thr Leu Met Ile Ser Arg
        275                 280                 285
Thr Pro Glu Val Thr Cys Val Val Val Asp Val Ser His Glu Asp Pro
    290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Tyr Thr Leu
    370                 375                 380
Pro Pro Ser Arg Glu Glu Met Thr Lys Asn Gln Val Ser Leu Thr Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Lys Leu Thr Val Asp Lys Ser
        435                 440                 445
Arg Trp Gln Gln Gly Asn Val Phe Ser Cys Ser Val Met His Glu Ala
    450                 455                 460
Leu His Asn His Tyr Thr Gln Lys Ser Leu Ser Leu Ser Pro Gly Lys
465                 470                 475                 480

<210> SEQ ID NO 66
<211> LENGTH: 332
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 66

Met Glu Thr Asp Thr Leu Leu Leu Trp Val Leu Leu Leu Trp Val Pro
1               5                   10                  15
Gly Ser Thr Gly Asp Ala Ala Asp Ile Leu Gly Gly Gly Ser Ile Lys
                20                  25                  30
Gln Ile Glu Asp Lys Ile Glu Glu Ile Leu Ser Lys Ile Tyr His Ile
            35                  40                  45
Glu Asn Glu Ile Ala Arg Ile Lys Lys Leu Ile Gly Glu Arg Gly His
        50                  55                  60
Gly Gly Gly Ser Ser Glu Pro Lys Ser Cys Asp Lys Thr His Thr Cys
65                  70                  75                  80
Pro Pro Cys Pro Ala Pro Glu Leu Leu Gly Gly Pro Ser Val Phe Leu
                85                  90                  95
Phe Pro Pro Lys Pro Lys Asp Thr Leu Met Ile Ser Arg Thr Pro Glu
            100                 105                 110
Val Thr Cys Val Val Val Asp Val Ser His Glu Asp Pro Glu Val Lys
        115                 120                 125
```

```
Phe Asn Trp Tyr Val Asp Gly Val Glu Val His Asn Ala Lys Thr Lys
            130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Glu Met Thr Lys Asn Gln Val Ser Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys Ser Leu Glu
290                 295                 300

Gly Pro Arg Phe Glu Gly Lys Pro Ile Pro Asn Pro Leu Leu Gly Leu
305                 310                 315                 320

Asp Ser Thr Arg Thr Gly His His His His His His
                325                 330

<210> SEQ ID NO 67
<211> LENGTH: 301
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 67

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Gly Ser Ile Lys
            20                  25                  30

Gln Ile Glu Asp Lys Ile Glu Glu Ile Leu Ser Lys Ile Tyr His Ile
        35                  40                  45

Glu Asn Glu Ile Ala Arg Ile Lys Lys Leu Ile Gly Glu Arg Gly His
50                  55                  60

Gly Gly Gly Ser Ser Glu Pro Lys Ser Cys Asp Lys Thr His Thr Cys
65                  70                  75                  80

Pro Pro Cys Pro Ala Pro Glu Leu Leu Gly Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Ser His Glu Asp Pro Glu Val Lys
        115                 120                 125

Phe Asn Trp Tyr Val Asp Gly Val Glu Val His Asn Ala Lys Thr Lys
            130                 135                 140

Pro Arg Glu Glu Gln Tyr Asn Ser Thr Tyr Arg Val Val Ser Val Leu
145                 150                 155                 160
```

-continued

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Glu Met Thr Lys Asn Gln Val Ser Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 68
<211> LENGTH: 444
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 68

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Ser Ile Lys
                20                  25                  30

Gln Ile Glu Asp Lys Ile Glu Glu Ile Leu Ser Lys Ile Tyr His Ile
            35                  40                  45

Glu Asn Glu Ile Ala Arg Ile Lys Lys Leu Ile Gly Glu Arg Gly His
        50                  55                  60

Gly Gly Gly Asp Ile Val Cys Ser Arg Asp Phe Thr Pro Pro Thr Val
65                  70                  75                  80

Lys Ile Leu Gln Ser Ser Cys Asp Gly Gly His Phe Pro Pro Thr
                85                  90                  95

Ile Gln Leu Leu Cys Leu Val Ser Gly Tyr Thr Pro Gly Thr Ile Asn
            100                 105                 110

Ile Thr Trp Leu Glu Asp Gly Gln Val Met Asp Val Asp Leu Ser Thr
        115                 120                 125

Ala Ser Thr Thr Gln Glu Gly Glu Leu Ala Ser Thr Gln Ser Glu Leu
    130                 135                 140

Thr Leu Ser Gln Lys His Trp Leu Ser Asp Arg Thr Tyr Thr Cys Gln
145                 150                 155                 160

Val Thr Tyr Gln Gly His Thr Phe Glu Asp Ser Thr Lys Lys Cys Gly
                165                 170                 175

Gly Gly Arg Ser Ser Glu Pro Lys Ser Cys Asp Lys Thr His Thr Cys
            180                 185                 190

Pro Pro Cys Pro Ala Pro Glu Leu Leu Gly Gly Pro Ser Val Phe Leu
        195                 200                 205

Phe Pro Pro Lys Pro Lys Asp Thr Leu Met Ile Ser Arg Thr Pro Glu
    210                 215                 220

Val Thr Cys Val Val Asp Val Ser His Glu Asp Pro Glu Val Lys
225                 230                 235                 240

Phe Asn Trp Tyr Val Asp Gly Val Glu Val His Asn Ala Lys Thr Lys
            245                 250                 255

Pro Arg Glu Glu Gln Tyr Asn Ser Thr Tyr Arg Val Val Ser Val Leu
        260                 265                 270

Thr Val Leu His Gln Asp Trp Leu Asn Gly Lys Glu Tyr Lys Cys Lys
    275                 280                 285

Val Ser Asn Lys Ala Leu Pro Ala Pro Ile Glu Lys Thr Ile Ser Lys
290                 295                 300

Ala Lys Gly Gln Pro Arg Glu Pro Gln Val Tyr Thr Leu Pro Pro Ser
305                 310                 315                 320

Arg Glu Glu Met Thr Lys Asn Gln Val Ser Leu Thr Cys Leu Val Lys
            325                 330                 335

Gly Phe Tyr Pro Ser Asp Ile Ala Val Glu Trp Glu Ser Asn Gly Gln
        340                 345                 350

Pro Glu Asn Asn Tyr Lys Thr Thr Pro Pro Val Leu Asp Ser Asp Gly
    355                 360                 365

Ser Phe Phe Leu Tyr Ser Lys Leu Thr Val Asp Lys Ser Arg Trp Gln
370                 375                 380

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Lys Ser Leu Glu
            405                 410                 415

Gly Pro Arg Phe Glu Gly Lys Pro Ile Pro Asn Pro Leu Leu Gly Leu
        420                 425                 430

Asp Ser Thr Arg Thr Gly His His His His His His
            435                 440

<210> SEQ ID NO 69
<211> LENGTH: 413
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 69

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Gly Ser Ile Lys
            20                  25                  30

Gln Ile Glu Asp Lys Ile Glu Glu Ile Leu Ser Lys Ile Tyr His Ile
        35                  40                  45

Glu Asn Glu Ile Ala Arg Ile Lys Lys Leu Ile Gly Glu Arg Gly His
    50                  55                  60

Gly Gly Gly Asp Ile Val Cys Ser Arg Asp Phe Thr Pro Pro Thr Val
65                  70                  75                  80

Lys Ile Leu Gln Ser Ser Cys Asp Gly Gly His Phe Pro Pro Thr
            85                  90                  95

Ile Gln Leu Leu Cys Leu Val Ser Gly Tyr Thr Pro Gly Thr Ile Asn
        100                 105                 110

Ile Thr Trp Leu Glu Asp Gly Gln Val Met Asp Val Asp Leu Ser Thr
    115                 120                 125

Ala Ser Thr Thr Gln Glu Gly Glu Leu Ala Ser Thr Gln Ser Glu Leu
130                 135                 140

```
Thr Leu Ser Gln Lys His Trp Leu Ser Asp Arg Thr Tyr Thr Cys Gln
145                 150                 155                 160

Val Thr Tyr Gln Gly His Thr Phe Glu Asp Ser Thr Lys Lys Cys Gly
                165                 170                 175

Gly Gly Arg Ser Ser Glu Pro Lys Ser Cys Asp Lys Thr His Thr Cys
            180                 185                 190

Pro Pro Cys Pro Ala Pro Glu Leu Leu Gly Gly Pro Ser Val Phe Leu
        195                 200                 205

Phe Pro Pro Lys Pro Lys Asp Thr Leu Met Ile Ser Arg Thr Pro Glu
    210                 215                 220

Val Thr Cys Val Val Val Asp Val Ser His Glu Asp Pro Glu Val Lys
225                 230                 235                 240

Phe Asn Trp Tyr Val Asp Gly Val Glu Val His Asn Ala Lys Thr Lys
                245                 250                 255

Pro Arg Glu Glu Gln Tyr Asn Ser Thr Tyr Arg Val Val Ser Val Leu
            260                 265                 270

Thr Val Leu His Gln Asp Trp Leu Asn Gly Lys Glu Tyr Lys Cys Lys
        275                 280                 285

Val Ser Asn Lys Ala Leu Pro Ala Pro Ile Glu Lys Thr Ile Ser Lys
    290                 295                 300

Ala Lys Gly Gln Pro Arg Glu Pro Gln Val Tyr Thr Leu Pro Pro Ser
305                 310                 315                 320

Arg Glu Glu Met Thr Lys Asn Gln Val Ser Leu Thr Cys Leu Val Lys
                325                 330                 335

Gly Phe Tyr Pro Ser Asp Ile Ala Val Glu Trp Glu Ser Asn Gly Gln
            340                 345                 350

Pro Glu Asn Asn Tyr Lys Thr Thr Pro Pro Val Leu Asp Ser Asp Gly
        355                 360                 365

Ser Phe Phe Leu Tyr Ser Lys Leu Thr Val Asp Lys Ser Arg Trp Gln
    370                 375                 380

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Lys
                405                 410

<210> SEQ ID NO 70
<211> LENGTH: 565
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 70

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Ser Ile Lys
                20                  25                  30

Gln Ile Glu Asp Lys Ile Glu Glu Ile Leu Ser Lys Ile Tyr His Ile
            35                  40                  45

Glu Asn Glu Ile Ala Arg Ile Lys Lys Leu Ile Gly Glu Arg Gly His
        50                  55                  60

Ile Leu Gly Gly Gly Asp Ile Glu Arg Lys Cys Cys Val Glu Cys Pro
65                  70                  75                  80

Pro Cys Pro Ala Pro Val Ala Gly Pro Ser Val Phe Leu Phe Pro
                85                  90                  95
```

```
Pro Lys Pro Lys Asp Thr Leu Met Ile Ser Arg Thr Pro Glu Val Thr
            100                 105                 110
Cys Val Val Asp Val Ser His Glu Asp Pro Glu Val Gln Phe Asn
        115                 120                 125
Trp Tyr Val Asp Gly Val Glu Val His Asn Ala Lys Thr Lys Pro Arg
130                 135                 140
Glu Glu Gln Phe Asn Ser Thr Phe Arg Val Val Ser Val Leu Thr Val
145                 150                 155                 160
Val His Gln Asp Trp Leu Asn Gly Lys Glu Tyr Lys Cys Lys Val Ser
                165                 170                 175
Asn Lys Gly Leu Pro Ala Pro Ile Glu Lys Thr Ile Ser Lys Thr Lys
            180                 185                 190
Gly Gln Pro Arg Glu Pro Gln Val Tyr Thr Leu Pro Pro Ser Arg Glu
        195                 200                 205
Glu Met Thr Lys Asn Gln Val Ser Leu Thr Cys Leu Val Lys Gly Phe
    210                 215                 220
Tyr Pro Ser Asp Ile Ala Val Glu Trp Glu Ser Asn Gly Gln Pro Glu
225                 230                 235                 240
Asn Asn Tyr Lys Thr Thr Pro Pro Met Leu Asp Ser Asp Gly Ser Phe
                245                 250                 255
Phe Leu Tyr Ser Lys Leu Thr Val Asp Lys Ser Arg Trp Gln Gln Gly
            260                 265                 270
Asn Val Phe Ser Cys Ser Val Met His Glu Ala Leu His Asn His Tyr
        275                 280                 285
Thr Gln Lys Ser Leu Ser Leu Ser Pro Gly Lys Arg Ser Ser Glu Pro
    290                 295                 300
Lys Ser Cys Asp Lys Thr His Thr Cys Pro Pro Cys Pro Ala Pro Glu
305                 310                 315                 320
Leu Leu Gly Gly Pro Ser Val Phe Leu Phe Pro Pro Lys Pro Lys Asp
                325                 330                 335
Thr Leu Met Ile Ser Arg Thr Pro Glu Val Thr Cys Val Val Val Asp
            340                 345                 350
Val Ser His Glu Asp Pro Glu Val Lys Phe Asn Trp Tyr Val Asp Gly
        355                 360                 365
Val Glu Val His Asn Ala Lys Thr Lys Pro Arg Glu Glu Gln Tyr Asn
    370                 375                 380
Ser Thr Tyr Arg Val Val Ser Val Leu Thr Val Leu His Gln Asp Trp
385                 390                 395                 400
Leu Asn Gly Lys Glu Tyr Lys Cys Lys Val Ser Asn Lys Ala Leu Pro
                405                 410                 415
Ala Pro Ile Glu Lys Thr Ile Ser Lys Ala Lys Gly Gln Pro Arg Glu
            420                 425                 430
Pro Gln Val Tyr Thr Leu Pro Pro Ser Arg Glu Glu Met Thr Lys Asn
        435                 440                 445
Gln Val Ser Leu Thr Cys Leu Val Lys Gly Phe Tyr Pro Ser Asp Ile
    450                 455                 460
Ala Val Glu Trp Glu Ser Asn Gly Gln Pro Glu Asn Asn Tyr Lys Thr
465                 470                 475                 480
Thr Pro Pro Val Leu Asp Ser Asp Gly Ser Phe Phe Leu Tyr Ser Lys
                485                 490                 495
Leu Thr Val Asp Lys Ser Arg Trp Gln Gln Gly Asn Val Phe Ser Cys
            500                 505                 510
```

```
Ser Val Met His Glu Ala Leu His Asn His Tyr Thr Gln Lys Ser Leu
            515                 520                 525

Ser Leu Ser Pro Gly Lys Ser Leu Glu Gly Pro Arg Phe Glu Gly Lys
        530                 535                 540

Pro Ile Pro Asn Pro Leu Leu Gly Leu Asp Ser Thr Arg Thr Gly His
545                 550                 555                 560

His His His His His
                565

<210> SEQ ID NO 71
<211> LENGTH: 534
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 71

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Ser Ile Lys
                20                  25                  30

Gln Ile Glu Asp Lys Ile Glu Glu Ile Leu Ser Lys Ile Tyr His Ile
            35                  40                  45

Glu Asn Glu Ile Ala Arg Ile Lys Lys Leu Ile Gly Glu Arg Gly His
    50                  55                  60

Ile Leu Gly Gly Gly Asp Ile Glu Arg Lys Cys Cys Val Glu Cys Pro
65                  70                  75                  80

Pro Cys Pro Ala Pro Pro Val Ala Gly Pro Ser Val Phe Leu Phe Pro
                85                  90                  95

Pro Lys Pro Lys Asp Thr Leu Met Ile Ser Arg Thr Pro Glu Val Thr
                100                 105                 110

Cys Val Val Val Asp Val Ser His Glu Asp Pro Glu Val Gln Phe Asn
            115                 120                 125

Trp Tyr Val Asp Gly Val Glu Val His Asn Ala Lys Thr Lys Pro Arg
        130                 135                 140

Glu Glu Gln Phe Asn Ser Thr Phe Arg Val Val Ser Val Leu Thr Val
145                 150                 155                 160

Val His Gln Asp Trp Leu Asn Gly Lys Glu Tyr Lys Cys Lys Val Ser
                165                 170                 175

Asn Lys Gly Leu Pro Ala Pro Ile Glu Lys Thr Ile Ser Lys Thr Lys
                180                 185                 190

Gly Gln Pro Arg Glu Pro Gln Val Tyr Thr Leu Pro Pro Ser Arg Glu
            195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Met Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys Arg Ser Ser Glu Pro
    290                 295                 300
```

-continued

Lys Ser Cys Asp Lys Thr His Thr Cys Pro Cys Pro Ala Pro Glu
305                 310                 315                 320

Leu Leu Gly Gly Pro Ser Val Phe Leu Phe Pro Pro Lys Pro Lys Asp
            325                 330                 335

Thr Leu Met Ile Ser Arg Thr Pro Glu Val Thr Cys Val Val Val Asp
            340                 345                 350

Val Ser His Glu Asp Pro Glu Val Lys Phe Asn Trp Tyr Val Asp Gly
            355                 360                 365

Val Glu Val His Asn Ala Lys Thr Lys Pro Arg Glu Glu Gln Tyr Asn
370                 375                 380

Ser Thr Tyr Arg Val Val Ser Val Leu Thr Val Leu His Gln Asp Trp
385                 390                 395                 400

Leu Asn Gly Lys Glu Tyr Lys Cys Lys Val Ser Asn Lys Ala Leu Pro
            405                 410                 415

Ala Pro Ile Glu Lys Thr Ile Ser Lys Ala Lys Gly Gln Pro Arg Glu
            420                 425                 430

Pro Gln Val Tyr Thr Leu Pro Pro Ser Arg Glu Glu Met Thr Lys Asn
            435                 440                 445

Gln Val Ser Leu Thr Cys Leu Val Lys Gly Phe Tyr Pro Ser Asp Ile
450                 455                 460

Ala Val Glu Trp Glu Ser Asn Gly Gln Pro Glu Asn Asn Tyr Lys Thr
465                 470                 475                 480

Thr Pro Pro Val Leu Asp Ser Asp Gly Ser Phe Phe Leu Tyr Ser Lys
            485                 490                 495

Leu Thr Val Asp Lys Ser Arg Trp Gln Gln Gly Asn Val Phe Ser Cys
            500                 505                 510

Ser Val Met His Glu Ala Leu His Asn His Tyr Thr Gln Lys Ser Leu
            515                 520                 525

Ser Leu Ser Pro Gly Lys
            530

<210> SEQ ID NO 72
<211> LENGTH: 344
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 72

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Ser Ile Lys
            20                  25                  30

Gln Ile Glu Asp Lys Ile Glu Glu Ile Leu Ser Lys Ile Tyr His Ile
            35                  40                  45

Glu Asn Glu Ile Ala Arg Ile Lys Lys Leu Ile Gly Glu Arg Gly His
50                  55                  60

Asp Ile Glu Arg Lys Cys Cys Val Glu Cys Pro Pro Cys Pro Arg Ser
65                  70                  75                  80

Ser Glu Pro Lys Ser Cys Asp Lys Thr His Thr Cys Pro Pro Cys Pro
            85                  90                  95

Ala Pro Glu Leu Leu Gly Gly Pro Ser Val Phe Leu Phe Pro Pro Lys
            100                 105                 110

Pro Lys Asp Thr Leu Met Ile Ser Arg Thr Pro Glu Val Thr Cys Val
            115                 120                 125

Val Val Asp Val Ser His Glu Asp Pro Glu Val Lys Phe Asn Trp Tyr
    130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ala Pro Ile Glu Lys Thr Ile Ser Lys Ala Lys Gly Gln
        195                 200                 205

Pro Arg Glu Pro Gln Val Tyr Thr Leu Pro Pro Ser Arg Glu Glu Met
210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285

Phe Ser Cys Ser Val Met His Glu Ala Leu His Asn His Tyr Thr Gln
290                 295                 300

Lys Ser Leu Ser Leu Ser Pro Gly Lys Ser Leu Glu Gly Pro Arg Phe
305                 310                 315                 320

Glu Gly Lys Pro Ile Pro Asn Pro Leu Leu Gly Leu Asp Ser Thr Arg
                325                 330                 335

Thr Gly His His His His His His
            340

<210> SEQ ID NO 73
<211> LENGTH: 313
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 73

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Gly Ser Ile Lys
                20                  25                  30

Gln Ile Glu Asp Lys Ile Glu Ile Leu Ser Lys Ile Tyr His Ile
            35                  40                  45

Glu Asn Glu Ile Ala Arg Ile Lys Lys Leu Ile Gly Glu Arg Gly His
50                  55                  60

Asp Ile Glu Arg Lys Cys Cys Val Glu Cys Pro Pro Cys Pro Arg Ser
65                  70                  75                  80

Ser Glu Pro Lys Ser Cys Asp Lys Thr His Thr Cys Pro Pro Cys Pro
                85                  90                  95

Ala Pro Glu Leu Leu Gly Gly Pro Ser Val Phe Leu Phe Pro Pro Lys
            100                 105                 110

Pro Lys Asp Thr Leu Met Ile Ser Arg Thr Pro Glu Val Thr Cys Val
        115                 120                 125

Val Val Asp Val Ser His Glu Asp Pro Glu Val Lys Phe Asn Trp Tyr
    130                 135                 140

```
Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ala Pro Ile Glu Lys Thr Ile Ser Lys Ala Lys Gly Gln
        195                 200                 205

Pro Arg Glu Pro Gln Val Tyr Thr Leu Pro Pro Ser Arg Glu Glu Met
    210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285

Phe Ser Cys Ser Val Met His Glu Ala Leu His Asn His Tyr Thr Gln
    290                 295                 300

Lys Ser Leu Ser Leu Ser Pro Gly Lys
305                 310

<210> SEQ ID NO 74
<211> LENGTH: 372
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 74

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Gly Ser Ile Lys
                20                  25                  30

Gln Ile Glu Asp Lys Ile Glu Glu Ile Leu Ser Lys Ile Tyr His Ile
            35                  40                  45

Glu Asn Glu Ile Ala Arg Ile Lys Lys Leu Ile Gly Glu Arg Gly His
        50                  55                  60

Ile Leu Gly Gly Gly Ser Ile Lys Gln Ile Glu Asp Lys Ile Glu Glu
65                  70                  75                  80

Ile Leu Ser Lys Ile Tyr His Ile Glu Asn Glu Ile Ala Arg Ile Lys
                85                  90                  95

Lys Leu Ile Gly Glu Arg Gly His Gly Gly Gly Ser Ser Glu Pro Lys
                100                 105                 110

Ser Cys Asp Lys Thr His Thr Cys Pro Pro Cys Pro Ala Pro Glu Leu
            115                 120                 125

Leu Gly Gly Pro Ser Val Phe Leu Phe Pro Pro Lys Pro Lys Asp Thr
        130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190
```

-continued

```
Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys Ser Leu Glu Gly Pro Arg Phe Glu Gly Lys Pro
            340                 345                 350

Ile Pro Asn Pro Leu Leu Gly Leu Asp Ser Thr Arg Thr Gly His His
        355                 360                 365

His His His His
    370

<210> SEQ ID NO 75
<211> LENGTH: 341
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 75

Met Glu Thr Asp Thr Leu Leu Leu Trp Val Leu Leu Leu Trp Val Pro
1               5                   10                  15

Gly Ser Thr Gly Asp Ala Ala Asp Ile Leu Gly Gly Ser Ile Lys
            20                  25                  30

Gln Ile Glu Asp Lys Ile Glu Glu Ile Leu Ser Lys Ile Tyr His Ile
        35                  40                  45

Glu Asn Glu Ile Ala Arg Ile Lys Lys Leu Ile Gly Glu Arg Gly His
    50                  55                  60

Ile Leu Gly Gly Gly Ser Ile Lys Gln Ile Glu Asp Lys Ile Glu Glu
65                  70                  75                  80

Ile Leu Ser Lys Ile Tyr His Ile Glu Asn Glu Ile Ala Arg Ile Lys
                85                  90                  95

Lys Leu Ile Gly Glu Arg Gly His Gly Gly Gly Ser Ser Glu Pro Lys
            100                 105                 110

Ser Cys Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175
```

```
Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
            195                 200                 205

Asn Gly Lys Glu Tyr Lys Cys Lys Val Ser Asn Lys Ala Leu Pro Ala
            210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
            245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
            275                 280                 285

Pro Pro Val Leu Asp Ser Asp Gly Ser Phe Phe Leu Tyr Ser Lys Leu
            290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
            325                 330                 335

Leu Ser Pro Gly Lys
            340

<210> SEQ ID NO 76
<211> LENGTH: 412
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 76

Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
            20                  25                  30

Pro Cys Pro Asp Ile Val Cys Ser Arg Asp Phe Thr Pro Pro Thr Val
            35                  40                  45

Lys Ile Leu Gln Ser Ser Cys Asp Gly Gly His Phe Pro Pro Thr
50                  55                  60

Ile Gln Leu Leu Cys Leu Val Ser Gly Tyr Thr Pro Gly Thr Ile Asn
65                  70                  75                  80

Ile Thr Trp Leu Glu Asp Gly Gln Val Met Asp Val Asp Leu Ser Thr
            85                  90                  95

Ala Ser Thr Thr Gln Glu Gly Glu Leu Ala Ser Thr Gln Ser Glu Leu
            100                 105                 110

Thr Leu Ser Gln Lys His Trp Leu Ser Asp Arg Thr Tyr Thr Cys Gln
            115                 120                 125

Val Thr Tyr Gln Gly His Thr Phe Glu Asp Ser Thr Lys Lys Cys Gly
            130                 135                 140

Gly Gly Arg Ser Ser Glu Pro Lys Ser Cys Asp Lys Thr His Thr Cys
145                 150                 155                 160

Pro Pro Cys Pro Ala Pro Glu Leu Leu Gly Gly Pro Ser Val Phe Leu
            165                 170                 175

Phe Pro Pro Lys Pro Lys Asp Thr Leu Met Ile Ser Arg Thr Pro Glu
            180                 185                 190
```

```
Val Thr Cys Val Val Asp Val Ser His Glu Asp Pro Glu Val Lys
            195                 200                 205

Phe Asn Trp Tyr Val Asp Gly Val Glu Val His Asn Ala Lys Thr Lys
210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Glu Glu Met Thr Lys Asn Gln Val Ser Leu Thr Cys Leu Val Lys
290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys Ser Leu Glu
    370                 375                 380

Gly Pro Arg Phe Glu Gly Lys Pro Ile Pro Asn Pro Leu Leu Gly Leu
385                 390                 395                 400

Asp Ser Thr Arg Thr Gly His His His His His
                405                 410

<210> SEQ ID NO 77
<211> LENGTH: 381
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 77

Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
                20                  25                  30

Pro Cys Pro Asp Ile Val Cys Ser Arg Asp Phe Thr Pro Thr Val
            35                  40                  45

Lys Ile Leu Gln Ser Ser Cys Asp Gly Gly His Phe Pro Pro Thr
    50                  55                  60

Ile Gln Leu Leu Cys Leu Val Ser Gly Tyr Thr Pro Gly Thr Ile Asn
65                  70                  75                  80

Ile Thr Trp Leu Glu Asp Gly Gln Val Met Asp Val Asp Leu Ser Thr
                85                  90                  95

Ala Ser Thr Thr Gln Glu Gly Glu Leu Ala Ser Thr Gln Ser Glu Leu
                100                 105                 110

Thr Leu Ser Gln Lys His Trp Leu Ser Asp Arg Thr Tyr Thr Cys Gln
            115                 120                 125

Val Thr Tyr Gln Gly His Thr Phe Glu Asp Ser Thr Lys Lys Cys Gly
        130                 135                 140
```

Gly Gly Arg Ser Ser Glu Pro Lys Ser Cys Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
            195                 200                 205

Phe Asn Trp Tyr Val Asp Gly Val Glu Val His Asn Ala Lys Thr Lys
        210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Glu Glu Met Thr Lys Asn Gln Val Ser Leu Thr Cys Leu Val Lys
        290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
        370                 375                 380

<210> SEQ ID NO 78
<211> LENGTH: 575
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 78

Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
                20                  25                  30

Pro Cys Pro Asp Ile Leu Gly Gly Ser Ile Lys Gln Ile Glu Asp
            35                  40                  45

Lys Ile Glu Glu Ile Leu Ser Lys Ile Tyr His Ile Glu Asn Glu Ile
    50                  55                  60

Ala Arg Ile Lys Lys Leu Ile Gly Glu Arg His Gly Gly Gly Ser
65                  70                  75                  80

Ser Glu Arg Lys Cys Cys Val Glu Cys Pro Pro Cys Pro Ala Pro Pro
                85                  90                  95

Val Ala Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

-continued

```
Ser His Glu Asp Pro Glu Val Gln Phe Asn Trp Tyr Val Asp Gly Val
130                 135                 140
Glu Val His Asn Ala Lys Thr Lys Pro Arg Glu Glu Gln Phe Asn Ser
145                 150                 155                 160
Thr Phe Arg Val Val Ser Val Leu Thr Val Val His Gln Asp Trp Leu
                165                 170                 175
Asn Gly Lys Glu Tyr Lys Cys Lys Val Ser Asn Lys Gly Leu Pro Ala
            180                 185                 190
Pro Ile Glu Lys Thr Ile Ser Lys Thr Lys Gly Gln Pro Arg Glu Pro
        195                 200                 205
Gln Val Tyr Thr Leu Pro Pro Ser Arg Glu Glu Met Thr Lys Asn Gln
210                 215                 220
Val Ser Leu Thr Cys Leu Val Lys Gly Phe Tyr Pro Ser Asp Ile Ala
225                 230                 235                 240
Val Glu Trp Glu Ser Asn Gly Gln Pro Glu Asn Asn Tyr Lys Thr Thr
                245                 250                 255
Pro Pro Met Leu Asp Ser Asp Gly Ser Phe Phe Leu Tyr Ser Lys Leu
            260                 265                 270
Thr Val Asp Lys Ser Arg Trp Gln Gln Gly Asn Val Phe Ser Cys Ser
        275                 280                 285
Val Met His Glu Ala Leu His Asn His Tyr Thr Gln Lys Ser Leu Ser
290                 295                 300
Leu Ser Pro Gly Lys Arg Ser Ser Glu Pro Lys Ser Cys Asp Lys Thr
305                 310                 315                 320
His Thr Cys Pro Pro Cys Pro Ala Pro Glu Leu Leu Gly Gly Pro Ser
                325                 330                 335
Val Phe Leu Phe Pro Pro Lys Pro Lys Asp Thr Leu Met Ile Ser Arg
            340                 345                 350
Thr Pro Glu Val Thr Cys Val Val Val Asp Val Ser His Glu Asp Pro
        355                 360                 365
Glu Val Lys Phe Asn Trp Tyr Val Asp Gly Val Glu Val His Asn Ala
370                 375                 380
Lys Thr Lys Pro Arg Glu Glu Gln Tyr Asn Ser Thr Tyr Arg Val Val
385                 390                 395                 400
Ser Val Leu Thr Val Leu His Gln Asp Trp Leu Asn Gly Lys Glu Tyr
                405                 410                 415
Lys Cys Lys Val Ser Asn Lys Ala Leu Pro Ala Pro Ile Glu Lys Thr
            420                 425                 430
Ile Ser Lys Ala Lys Gly Gln Pro Arg Glu Pro Gln Val Tyr Thr Leu
        435                 440                 445
Pro Pro Ser Arg Glu Glu Met Thr Lys Asn Gln Val Ser Leu Thr Cys
450                 455                 460
Leu Val Lys Gly Phe Tyr Pro Ser Asp Ile Ala Val Glu Trp Glu Ser
465                 470                 475                 480
Asn Gly Gln Pro Glu Asn Asn Tyr Lys Thr Thr Pro Pro Val Leu Asp
                485                 490                 495
Ser Asp Gly Ser Phe Phe Leu Tyr Ser Lys Leu Thr Val Asp Lys Ser
            500                 505                 510
Arg Trp Gln Gln Gly Asn Val Phe Ser Cys Ser Val Met His Glu Ala
        515                 520                 525
Leu His Asn His Tyr Thr Gln Lys Ser Leu Ser Leu Ser Pro Gly Lys
530                 535                 540
Ser Leu Glu Gly Pro Arg Phe Glu Gly Lys Pro Ile Pro Asn Pro Leu
```

```
                545                 550                 555                 560
Leu Gly Leu Asp Ser Thr Arg Thr Gly His His His His His
                565                 570                 575

<210> SEQ ID NO 79
<211> LENGTH: 544
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 79

Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
            20                  25                  30

Pro Cys Pro Asp Ile Leu Gly Gly Ser Ile Lys Gln Ile Glu Asp
        35                  40                  45

Lys Ile Glu Glu Ile Leu Ser Lys Ile Tyr His Ile Glu Asn Glu Ile
    50                  55                  60

Ala Arg Ile Lys Lys Leu Ile Gly Glu Arg Gly His Gly Gly Gly Ser
65                  70                  75                  80

Ser Glu Arg Lys Cys Cys Val Glu Cys Pro Pro Cys Pro Ala Pro Pro
                85                  90                  95

Val Ala Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Gln Phe Asn Trp Tyr Val Asp Gly Val
    130                 135                 140

Glu Val His Asn Ala Lys Thr Lys Pro Arg Glu Glu Gln Phe Asn Ser
145                 150                 155                 160

Thr Phe Arg Val Val Ser Val Leu Thr Val Val His Gln Asp Trp Leu
                165                 170                 175

Asn Gly Lys Glu Tyr Lys Cys Lys Val Ser Asn Lys Gly Leu Pro Ala
            180                 185                 190

Pro Ile Glu Lys Thr Ile Ser Lys Thr Lys Gly Gln Pro Arg Glu Pro
        195                 200                 205

Gln Val Tyr Thr Leu Pro Pro Ser Arg Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Met Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys Arg Ser Ser Glu Pro Lys Ser Cys Asp Lys Thr
305                 310                 315                 320

His Thr Cys Pro Pro Cys Pro Ala Pro Glu Leu Leu Gly Gly Pro Ser
                325                 330                 335

Val Phe Leu Phe Pro Pro Lys Pro Lys Asp Thr Leu Met Ile Ser Arg
```

```
                340                 345                 350
Thr Pro Glu Val Thr Cys Val Val Asp Val Ser His Glu Asp Pro
            355                 360                 365
Glu Val Lys Phe Asn Trp Tyr Val Asp Gly Val Glu Val His Asn Ala
        370                 375                 380
Lys Thr Lys Pro Arg Glu Glu Gln Tyr Asn Ser Thr Tyr Arg Val Val
385                 390                 395                 400
Ser Val Leu Thr Val Leu His Gln Asp Trp Leu Asn Gly Lys Glu Tyr
            405                 410                 415
Lys Cys Lys Val Ser Asn Lys Ala Leu Pro Ala Pro Ile Glu Lys Thr
        420                 425                 430
Ile Ser Lys Ala Lys Gly Gln Pro Arg Glu Pro Gln Val Tyr Thr Leu
        435                 440                 445
Pro Pro Ser Arg Glu Glu Met Thr Lys Asn Gln Val Ser Leu Thr Cys
        450                 455                 460
Leu Val Lys Gly Phe Tyr Pro Ser Asp Ile Ala Val Glu Trp Glu Ser
465                 470                 475                 480
Asn Gly Gln Pro Glu Asn Asn Tyr Lys Thr Thr Pro Pro Val Leu Asp
            485                 490                 495
Ser Asp Gly Ser Phe Phe Leu Tyr Ser Lys Leu Thr Val Asp Lys Ser
            500                 505                 510
Arg Trp Gln Gln Gly Asn Val Phe Ser Cys Ser Val Met His Glu Ala
        515                 520                 525
Leu His Asn His Tyr Thr Gln Lys Ser Leu Ser Leu Ser Pro Gly Lys
        530                 535                 540

<210> SEQ ID NO 80
<211> LENGTH: 315
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 80

Met Glu Thr Asp Thr Leu Leu Leu Trp Val Leu Leu Leu Trp Val Pro
1               5                   10                  15
Gly Ser Thr Gly Asp Ala Ala Glu Arg Lys Cys Cys Val Glu Cys Pro
            20                  25                  30
Pro Cys Pro Asp Ile Glu Arg Lys Cys Cys Val Glu Cys Pro Pro Cys
        35                  40                  45
Pro Arg Ser Ser Glu Pro Lys Ser Cys Asp Lys Thr His Thr Cys Pro
    50                  55                  60
Pro Cys Pro Ala Pro Glu Leu Leu Gly Gly Pro Ser Val Phe Leu Phe
65                  70                  75                  80
Pro Pro Lys Pro Lys Asp Thr Leu Met Ile Ser Arg Thr Pro Glu Val
            85                  90                  95
Thr Cys Val Val Val Asp Val Ser His Glu Asp Pro Glu Val Lys Phe
        100                 105                 110
Asn Trp Tyr Val Asp Gly Val Glu Val His Asn Ala Lys Thr Lys Pro
    115                 120                 125
Arg Glu Glu Gln Tyr Asn Ser Thr Tyr Arg Val Val Ser Val Leu Thr
    130                 135                 140
Val Leu His Gln Asp Trp Leu Asn Gly Lys Glu Tyr Lys Cys Lys Val
145                 150                 155                 160
Ser Asn Lys Ala Leu Pro Ala Pro Ile Glu Lys Thr Ile Ser Lys Ala
```

```
                    165                 170                 175
Lys Gly Gln Pro Arg Glu Pro Gln Val Tyr Thr Leu Pro Pro Ser Arg
                180                 185                 190

Glu Glu Met Thr Lys Asn Gln Val Ser Leu Thr Cys Leu Val Lys Gly
            195                 200                 205

Phe Tyr Pro Ser Asp Ile Ala Val Glu Trp Glu Ser Asn Gly Gln Pro
        210                 215                 220

Glu Asn Asn Tyr Lys Thr Thr Pro Pro Val Leu Asp Ser Asp Gly Ser
225                 230                 235                 240

Phe Phe Leu Tyr Ser Lys Leu Thr Val Asp Lys Ser Arg Trp Gln Gln
                245                 250                 255

Gly Asn Val Phe Ser Cys Ser Val Met His Glu Ala Leu His Asn His
            260                 265                 270

Tyr Thr Gln Lys Ser Leu Ser Leu Ser Pro Gly Lys Ser Leu Glu Gly
        275                 280                 285

Pro Arg Phe Glu Gly Lys Pro Ile Pro Asn Pro Leu Leu Gly Leu Asp
    290                 295                 300

Ser Thr Arg Thr Gly His His His His His His
305                 310                 315

<210> SEQ ID NO 81
<211> LENGTH: 284
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 81

Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
                20                  25                  30

Pro Cys Pro Asp Ile Glu Arg Lys Cys Cys Val Glu Cys Pro Pro Cys
            35                  40                  45

Pro Arg Ser Ser Glu Pro Lys Ser Cys Asp Lys Thr His Thr Cys Pro
        50                  55                  60

Pro Cys Pro Ala Pro Glu Leu Leu Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser His Glu Asp Pro Glu Val Lys Phe
            100                 105                 110

Asn Trp Tyr Val Asp Gly Val Glu Val His Asn Ala Lys Thr Lys Pro
        115                 120                 125

Arg Glu Glu Gln Tyr Asn Ser Thr Tyr Arg Val Val Ser Val Leu Thr
    130                 135                 140

Val Leu His Gln Asp Trp Leu Asn Gly Lys Glu Tyr Lys Cys Lys Val
145                 150                 155                 160

Ser Asn Lys Ala Leu Pro Ala Pro Ile Glu Lys Thr Ile Ser Lys Ala
                165                 170                 175

Lys Gly Gln Pro Arg Glu Pro Gln Val Tyr Thr Leu Pro Pro Ser Arg
            180                 185                 190

Glu Glu Met Thr Lys Asn Gln Val Ser Leu Thr Cys Leu Val Lys Gly
        195                 200                 205

Phe Tyr Pro Ser Asp Ile Ala Val Glu Trp Glu Ser Asn Gly Gln Pro
```

```
                    210                 215                 220
Glu Asn Asn Tyr Lys Thr Thr Pro Val Leu Asp Ser Asp Gly Ser
225                 230                 235                 240

Phe Phe Leu Tyr Ser Lys Leu Thr Val Asp Lys Ser Arg Trp Gln Gln
                245                 250                 255

Gly Asn Val Phe Ser Cys Ser Val Met His Glu Ala Leu His Asn His
                260                 265                 270

Tyr Thr Gln Lys Ser Leu Ser Leu Ser Pro Gly Lys
            275                 280

<210> SEQ ID NO 82
<211> LENGTH: 344
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 82

Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
                20                  25                  30

Pro Cys Pro Asp Ile Leu Gly Gly Ser Ile Lys Gln Ile Glu Asp
            35                  40                  45

Lys Ile Glu Glu Ile Leu Ser Lys Ile Tyr His Ile Glu Asn Glu Ile
    50                  55                  60

Ala Arg Ile Lys Lys Leu Ile Gly Glu Arg Gly His Gly Gly Gly Ser
65                  70                  75                  80

Ser Glu Pro Lys Ser Cys Asp Lys Thr His Thr Cys Pro Pro Cys Pro
                85                  90                  95

Ala Pro Glu Leu Leu Gly Gly Pro Ser Val Phe Leu Phe Pro Pro Lys
            100                 105                 110

Pro Lys Asp Thr Leu Met Ile Ser Arg Thr Pro Glu Val Thr Cys Val
            115                 120                 125

Val Val Asp Val Ser His Glu Asp Pro Glu Val Lys Phe Asn Trp Tyr
130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ala Pro Ile Glu Lys Thr Ile Ser Lys Ala Lys Gly Gln
            195                 200                 205

Pro Arg Glu Pro Gln Val Tyr Thr Leu Pro Pro Ser Arg Glu Glu Met
    210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
            275                 280                 285

Phe Ser Cys Ser Val Met His Glu Ala Leu His Asn His Tyr Thr Gln
```

```
                290                 295                 300

Lys Ser Leu Ser Leu Ser Pro Gly Lys Ser Leu Glu Gly Pro Arg Phe
305                 310                 315                 320

Glu Gly Lys Pro Ile Pro Asn Pro Leu Leu Gly Leu Asp Ser Thr Arg
                325                 330                 335

Thr Gly His His His His His His
            340

<210> SEQ ID NO 83
<211> LENGTH: 313
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 83

Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
                20                  25                  30

Pro Cys Pro Asp Ile Leu Gly Gly Gly Ser Ile Lys Gln Ile Glu Asp
            35                  40                  45

Lys Ile Glu Glu Ile Leu Ser Lys Ile Tyr His Ile Glu Asn Glu Ile
50                  55                  60

Ala Arg Ile Lys Lys Leu Ile Gly Glu Arg Gly His Gly Gly Gly Ser
65                  70                  75                  80

Ser Glu Pro Lys Ser Cys Asp Lys Thr His Thr Cys Pro Pro Cys Pro
                85                  90                  95

Ala Pro Glu Leu Leu Gly Gly Pro Ser Val Phe Leu Phe Pro Pro Lys
            100                 105                 110

Pro Lys Asp Thr Leu Met Ile Ser Arg Thr Pro Glu Val Thr Cys Val
        115                 120                 125

Val Val Asp Val Ser His Glu Asp Pro Glu Val Lys Phe Asn Trp Tyr
130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ala Pro Ile Glu Lys Thr Ile Ser Lys Ala Lys Gly Gln
        195                 200                 205

Pro Arg Glu Pro Gln Val Tyr Thr Leu Pro Pro Ser Arg Glu Glu Met
210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285

Phe Ser Cys Ser Val Met His Glu Ala Leu His Asn His Tyr Thr Gln
290                 295                 300

Lys Ser Leu Ser Leu Ser Pro Gly Lys
```

```
305              310
```

<210> SEQ ID NO 84
<211> LENGTH: 531
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 84

```
Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
            20                  25                  30

Pro Cys Pro Asp Ile Glu Arg Lys Cys Cys Val Glu Cys Pro Pro Cys
            35                  40                  45

Pro Ala Pro Pro Val Ala Gly Pro Ser Val Phe Leu Phe Pro Pro Lys
50                      55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Gln Phe Asn Trp Tyr
                    85                  90                  95

Val Asp Gly Val Glu Val His Asn Ala Lys Thr Lys Pro Arg Glu Glu
            100                 105                 110

Gln Phe Asn Ser Thr Phe Arg Val Val Ser Val Leu Thr Val Val His
            115                 120                 125

Gln Asp Trp Leu Asn Gly Lys Glu Tyr Lys Cys Lys Val Ser Asn Lys
130                 135                 140

Gly Leu Pro Ala Pro Ile Glu Lys Thr Ile Ser Lys Thr Lys Gly Gln
145                 150                 155                 160

Pro Arg Glu Pro Gln Val Tyr Thr Leu Pro Pro Ser Arg Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
            195                 200                 205

Tyr Lys Thr Thr Pro Pro Met Leu Asp Ser Asp Gly Ser Phe Phe Leu
210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys Arg Ser Ser Glu Pro Lys Ser
            260                 265                 270

Cys Asp Lys Thr His Thr Cys Pro Pro Cys Pro Ala Pro Glu Leu Leu
            275                 280                 285

Gly Gly Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
```

```
                355                 360                 365
Gly Lys Glu Tyr Lys Cys Lys Val Ser Asn Lys Ala Leu Pro Ala Pro
        370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys Ser Leu Glu Gly Pro Arg Phe Glu Gly Lys Pro Ile
            500                 505                 510

Pro Asn Pro Leu Leu Gly Leu Asp Ser Thr Arg Thr Gly His His His
        515                 520                 525

His His His
        530

<210> SEQ ID NO 85
<211> LENGTH: 500
<212> TYPE: PRT
<213> ORGANISM: ARTIFICIAL SEQUENCE
<220> FEATURE:
<223> OTHER INFORMATION: chemically-synthesized stradomer monomer

<400> SEQUENCE: 85

Met Glu Thr Asp Thr Leu Leu Leu Trp Val Leu Leu Leu Trp Val Pro
1               5                   10                  15

Gly Ser Thr Gly Asp Ala Ala Glu Arg Lys Cys Cys Val Glu Cys Pro
            20                  25                  30

Pro Cys Pro Asp Ile Glu Arg Lys Cys Cys Val Glu Cys Pro Pro Cys
        35                  40                  45

Pro Ala Pro Pro Val Ala Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Gln Phe Asn Trp Tyr
                85                  90                  95

Val Asp Gly Val Glu Val His Asn Ala Lys Thr Lys Pro Arg Glu Glu
            100                 105                 110

Gln Phe Asn Ser Thr Phe Arg Val Val Ser Val Leu Thr Val Val His
        115                 120                 125

Gln Asp Trp Leu Asn Gly Lys Glu Tyr Lys Cys Lys Val Ser Asn Lys
    130                 135                 140

Gly Leu Pro Ala Pro Ile Glu Lys Thr Ile Ser Lys Thr Lys Gly Gln
145                 150                 155                 160

Pro Arg Glu Pro Gln Val Tyr Thr Leu Pro Pro Ser Arg Glu Glu Met
                165                 170                 175

Thr Lys Asn Gln Val Ser Leu Thr Cys Leu Val Lys Gly Phe Tyr Pro
```

```
              180                 185                 190

Ser Asp Ile Ala Val Glu Trp Glu Ser Asn Gly Gln Pro Glu Asn Asn
                    195                 200                 205

Tyr Lys Thr Thr Pro Pro Met Leu Asp Ser Asp Gly Ser Phe Phe Leu
                210                 215                 220

Tyr Ser Lys Leu Thr Val Asp Lys Ser Arg Trp Gln Gln Gly Asn Val
    225                 230                 235                 240

Phe Ser Cys Ser Val Met His Glu Ala Leu His Asn His Tyr Thr Gln
                    245                 250                 255

Lys Ser Leu Ser Leu Ser Pro Gly Lys Arg Ser Ser Glu Pro Lys Ser
                260                 265                 270

Cys Asp Lys Thr His Thr Cys Pro Pro Cys Pro Ala Pro Glu Leu Leu
                275                 280                 285

Gly Gly Pro Ser Val Phe Leu Phe Pro Pro Lys Pro Lys Asp Thr Leu
                290                 295                 300

Met Ile Ser Arg Thr Pro Glu Val Thr Cys Val Val Val Asp Val Ser
    305                 310                 315                 320

His Glu Asp Pro Glu Val Lys Phe Asn Trp Tyr Val Asp Gly Val Glu
                    325                 330                 335

Val His Asn Ala Lys Thr Lys Pro Arg Glu Glu Gln Tyr Asn Ser Thr
                340                 345                 350

Tyr Arg Val Val Ser Val Leu Thr Val Leu His Gln Asp Trp Leu Asn
                355                 360                 365

Gly Lys Glu Tyr Lys Cys Lys Val Ser Asn Lys Ala Leu Pro Ala Pro
                370                 375                 380

Ile Glu Lys Thr Ile Ser Lys Ala Lys Gly Gln Pro Arg Glu Pro Gln
    385                 390                 395                 400

Val Tyr Thr Leu Pro Pro Ser Arg Glu Glu Met Thr Lys Asn Gln Val
                    405                 410                 415

Ser Leu Thr Cys Leu Val Lys Gly Phe Tyr Pro Ser Asp Ile Ala Val
                420                 425                 430

Glu Trp Glu Ser Asn Gly Gln Pro Glu Asn Asn Tyr Lys Thr Thr Pro
                435                 440                 445

Pro Val Leu Asp Ser Asp Gly Ser Phe Phe Leu Tyr Ser Lys Leu Thr
                450                 455                 460

Val Asp Lys Ser Arg Trp Gln Gln Gly Asn Val Phe Ser Cys Ser Val
    465                 470                 475                 480

Met His Glu Ala Leu His Asn His Tyr Thr Gln Lys Ser Leu Ser Leu
                    485                 490                 495

Ser Pro Gly Lys
                500

<210> SEQ ID NO 86
<211> LENGTH: 159
<212> TYPE: PRT
<213> ORGANISM: Homo sapiens

<400> SEQUENCE: 86

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45
```

```
Glu Asp Pro Asn Glu Asp Ile Val Glu Arg Asn Ile Arg Ile Ile Val
 50                  55                  60

Pro Leu Asn Asn Arg Glu Asn Ile Ser Asp Pro Thr Ser Pro Leu Arg
 65                  70                  75                  80

Thr Arg Phe Val Tyr His Leu Ser Asp Leu Cys Lys Lys Cys Asp Pro
                 85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp
145                 150                 155

<210> SEQ ID NO 87
<211> LENGTH: 15
<212> TYPE: PRT
<213> ORGANISM: Homo sapiens

<400> SEQUENCE: 87

Glu Pro Lys Ser Cys Asp Lys Thr His Thr Cys Pro Pro Cys Pro
1               5                   10                  15

<210> SEQ ID NO 88
<211> LENGTH: 110
<212> TYPE: PRT
<213> ORGANISM: Homo sapiens

<400> SEQUENCE: 88

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 89
<211> LENGTH: 107
<212> TYPE: PRT
<213> ORGANISM: Homo sapiens

<400> SEQUENCE: 89

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
```

```
                    50                  55                  60
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                     85                  90                  95

Thr Gln Lys Ser Leu Ser Leu Ser Pro Gly Lys
                100                 105

<210> SEQ ID NO 90
<211> LENGTH: 11
<212> TYPE: PRT
<213> ORGANISM: Homo sapiens

<400> SEQUENCE: 90

Arg Lys Cys Cys Val Glu Cys Pro Pro Cys Pro
 1               5                  10

<210> SEQ ID NO 91
<211> LENGTH: 109
<212> TYPE: PRT
<213> ORGANISM: Homo sapiens

<400> SEQUENCE: 91

Ala Pro Pro Val Ala Gly Pro Ser Val Phe Leu Phe Pro Pro Lys Pro
 1               5                  10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
                35                  40                  45

Asp Gly Met Glu Val His Asn Ala Lys Thr Lys Pro Arg Glu Glu Gln
 50                  55                  60

Phe Asn Ser Thr Phe Arg Val Val Ser Val Leu Thr Val Val His Gln
 65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
                100                 105

<210> SEQ ID NO 92
<211> LENGTH: 107
<212> TYPE: PRT
<213> ORGANISM: Homo sapiens

<400> SEQUENCE: 92

Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105
```

<210> SEQ ID NO 93
<211> LENGTH: 62
<212> TYPE: PRT
<213> ORGANISM: Homo sapiens

<400> SEQUENCE: 93

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Pro Cys Pro Arg Cys Pro
    50                  55                  60

<210> SEQ ID NO 94
<211> LENGTH: 110
<212> TYPE: PRT
<213> ORGANISM: Homo sapiens

<400> SEQUENCE: 94

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 95
<211> LENGTH: 107
<212> TYPE: PRT
<213> ORGANISM: Homo sapiens

<400> SEQUENCE: 95

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

```
<210> SEQ ID NO 96
<211> LENGTH: 12
<212> TYPE: PRT
<213> ORGANISM: Homo sapiens

<400> SEQUENCE: 96

Glu Ser Lys Tyr Gly Pro Pro Cys Pro Ser Cys Pro
1               5                   10

<210> SEQ ID NO 97
<211> LENGTH: 110
<212> TYPE: PRT
<213> ORGANISM: Homo sapiens

<400> SEQUENCE: 97

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 98
<211> LENGTH: 107
<212> TYPE: PRT
<213> ORGANISM: Homo sapiens

<400> SEQUENCE: 98

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

IMMUNOGLOBULIN CONSTANT REGION FC RECEPTOR BINDING AGENTS

This application is a continuation of U.S. application Ser. No. 12/602,609 filed Jun. 4, 2010, now U.S. Pat. No. 8,680,237, issued on Mar. 25, 2014, which is a National Stage tiling of PCT/US2008/065428 under 35 U.S.C. §371 which Claims priority to U.S. Provisional Appl. No. 61/015,547, filed Dec. 20, 2007, U.S. Provisional Appl. No. 61/015,127, tiled Dec. 19, 2007 and U.S. Provisional Appl. No. 60/941,044, filed Jun. 1, 2007, each of which are incorporated herein in their entirety.

BACKGROUND OF THE INVENTION

1. Field of the Invention

This invention relates generally to the fields of immunology, inflammation, and tumor immunology. More specifically, the present invention relates to biologically active biomimetic molecules comprising immunoglobulin Fc domains, compositions comprising such biomimetics, and methods of using such biomimetics.

The invention also relates to the treatment and prophylaxis of pathological conditions mediated by monocyte-derived cells, and more particularly to the use of stabilized functional portions of IgG Fc fragments for such treatment and prophylaxis.

2. Description of the Background Art

Immune globulin products from human plasma have been used since the early 1950's to treat immune deficiency disorders and more recently, and more commonly, for autoimmune and inflammatory diseases.

Initially, immune globulin products were administered by intramuscular injection. More recently, intravenous immune globulin (IVIG) has been used and was initially shown to be effective in treatment of the autoimmune disease idiopathic thrombocytopenic purpura (ITP) (Imbach P, Barandun S, d'Apuzzo V, et al: High-dose intravenous gammaglobulin for idiopathic thrombocytopenic purpura in childhood. Lancet 1981 Jun. 6; 1(8232): 1228-31). Human IVIG (referred to herein as "hIVIG") is a formulation of sterile, purified immunoglobulin G (IgG) products manufactured from pooled human plasma that typically contains more than 95% unmodified IgG, with only small and variable amounts of immunoglobulin A (IgA) or immunoglobulin M (IgM) (see, for example, Rutter A, Luger T A: High-dose intravenous immunoglobulins: an approach to treat severe immune-mediated and autoimmune diseases of the skin. J Am Acad Dermatol 2001 June; 44(6): 1010-24). Today the single most common clinical use of hIVIG is in the treatment of ITP.

While hIVIG has been an effective clinical treatment, there are several shortcomings to hIVIG formulations, including the potential for inadequate sterility, the presence of impurities, lack of availability, and lot-to-lot variation. In particular hIVIG preparations can vary greatly in their immunoglobulin A (IgA) content which can be of concern because IgA can cause allergic and anaphylactic reactions in IgA-deficient recipients.

In view of the negative aspects of hIVIG, there exists a need for an improved means of treating autoimmune and inflammatory diseases.

In addition, multiple pathological conditions of a wide variety of types are mediated by cells derived from monocytes. A simple therapeutic and/or prophylactic agent for use in many, if not all, such conditions would be invaluable.

SUMMARY OF THE INVENTION

The immuno-regulatory properties of WIG reside in the Fc domain of IgG molecules. For example, in murine models of ITP, both unmodified IVIG and the Fc fragment alone demonstrate therapeutic efficacy in restoring platelet counts, while isolated IVIG Fab fragments are not therapeutic (Samuelsson, A., Towers, T. L. & Ravetch, J. V. Anti-inflammatory Activity of IVIG Mediated Through the Inhibitory Fc Receptor. Science 291, 484-486 (2001)). Moreover Fc, but not Fab fragments of IVIG, is also therapeutically effective in the treatment of both childhood and adult idiopathic thrombocytopenic purpura (Follea, G. et al. Intravenous plasmin-treated gammaglobulin therapy in idiopathic thrombocytopenic purpura. Nouv Rev Fr Hematol 27, 5-10 (1985); Solal-Celigny, P., Bernard, J., Herrera, A. & Biovin, P. Treatment of adult autoimmune thrombocytopenic purpura with high-dose intravenous plasmin-cleaved gammaglobulins. Scand J Haematol 31, 39-44 (1983); Debre, M. & Bonnet, M.-C. Infusion of Gcgamma fragments for treatment of children with acute immune thrombocytopenic purpura. Lancet 342, 945-49 (1993); Burdach, S. E., Evers, K. & Geurson, R. Treatment of acute idiopathic thrombocytopenic purpura of childhood with intravenous immunoglobulin G: Comparative efficacy of 7S and 5S preparations. J Pediatr 109, 770-775 (1986)).

The therapeutic effect of IVIG is initially mediated through the Fc gamma receptor (FcγR) and relies on Dendritic Cell (DC)-macrophage cross-talk for its long term tolerogenic effects. FcγRIIIa plays a requisite role in the initiator phase and FcγRIIb is required for the effector phase in murine models of ITP (Samuelsson, A., Towers, T. L. & Ravetch, J. V. Anti-inflammatory Activity of IVIG Mediated Through the Inhibitory Fc Receptor. Science 291, 484-486 (2001); Siragam, V. et al. Intravenous immunoglobulin ameliorates ITP via activating Fc[gamma] receptors on dendritic cells. Nat Med 12, 688 (2006)). Similarly, human studies demonstrate that anti-Fcγ receptor antibodies are effective in the treatment of refractory ITP (Clarkson, S. et al. Treatment of refractory immune thrombocytopenic purpura with an anti-Fc gamma-receptor antibody. N Engl J Med 314, 1236-1239 (1986)). Importantly, long term tolerogenic effects are mediated by cell-cell interactions, as adoptive transfer of IVIG-treated DCs is effective in treating murine models of ITP (Siragam, V. et al. Intravenous immunoglobulin ameliorates ITP via activating Fc[gamma] receptors on dendritic cells. Nat Med 12, 688 (2006)).

The immunomodulatory effects of IVIG require aggregation of the FcγR. Aggregation of FcγR is mediated by IgG dimers present in IVIG (5-15% of the total IVIG) (Bleeker, W. K. et al. Vasoactive side effects of intravenous immunoglobulin preparations in a rat model and their treatment with recombinant platelet-activating factor acetylhydrolase. Blood 95, 1856-1861 (2000)). For example, in a murine model of ITP, treatment with IVIG with a high content of "dimers" (dimers of whole immunoglobulin molecules) enhanced platelet counts while IVIG "monomers" (whole immunoglobulin molecules) were not effective (Teeling, J. L. et al. Therapeutic efficacy of intravenous immunoglobulin preparations depends on the immunoglobulin G dimers: studies in experimental immune thrombocytopenia. Blood 98, 1095-1099 (2001)). Furthermore, despite the fact that ion exchange resin and polyethylene glycol fractionation are routinely used in the manufacture of IVIG to remove IgG aggregates, the clinical efficacy of IVIG correlates with the presence of dimers in the patient's sera (Augener, W., Friedman, B. & Brittinger, G. Are aggregates of IgG the effective part of high-dose immunoglobulin therapy in adult idiopathic thrombocytopenic purpura (ITP)? Blut 50, 249-252 (1985)). Importantly, the percentage of dimers also correlates with vasoactive side effects, which are treatable with acetylhydrolase (Bleeker, W. K. et al. Vasoactive side effects of intravenous immunoglobulin preparations in a rat model and their treatment with recombinant platelet-activating factor acetylhydrolase. Blood 95, 1856-1861 (2000)).

The present invention relates to biologically active biomimetic molecules, compositions comprising the same, and methods of using the same. These biomimetics have broad application for treating immunological and inflammatory disorders including but not limited to autoimmune diseases, and they have utility as bioimmunotherapy agents for cancer. Further, certain of these biomimetics also have utility as reagents, such as for use in immunological assays for testing immune cell function and in the diagnosis of disease. Moreover, the biomimetics and compositions of the present invention have the advantage of overcoming the above-listed limitations of hIVIG. The invention also relates to the treatment and prophylaxis of pathological conditions mediated by monocyte-derived cells, and more particularly to the use of stabilized functional portions of IgG Fc fragments for such treatment and prophylaxis.

In a first embodiment the present invention is directed to isolated serial stradomers comprising two or more associated stradomer monomers, wherein each of the stradomer monomers comprises two or more Fc domain monomers, wherein the association of the two or more stradomer monomers forms two or more Fc domains, and wherein the serial stradomer specifically binds to a first Fcγ receptor through a first of the two or more Fc domains and to a second Fcγ receptor through a second of the two or more Fc domains. In a preferred embodiment, the two or more stradomer monomers are associated through a covalent bond, a disulfide bond or chemical cross-linking.

In a preferred embodiment of the isolated serial stradomers of the present invention, the isolated serial stradomers are comprised of two associated stradomer monomers. In an equally preferred embodiment, the isolated serial stradomers are comprised of two associated stradomer monomers wherein both of the stradomer monomers comprise two Fc domain monomers, and wherein the association of the two stradomer monomers forms two Fc domains. In a first particular example of these embodiments directed to isolated serial stradomers, at least one of the two Fc domains comprises an IgG hinge and an IgG CH2 domain. In a second particular example each of the two Fc domains independently comprises an IgG hinge and an IgG CH2 domain. In a third particular example at least one of the two Fc domains comprises an IgG hinge, an IgG CH2 domain and an IgG CH3 domain. In a fourth particular example each of the two Fc domains independently comprises an IgG hinge, an IgG CH2 domain and an IgG CH3 domain. In a fifth particular example at least one of the two Fc domains comprises an IgG1 hinge or an IgG3 hinge, an IgG1 CH2 domain or an IgG3 CH2 domain, and an IgG1 CH3 domain or an IgG3 CH3 domain. In a sixth particular example at least one of the two Fc domains comprises an IgG1 hinge or an IgG3 hinge, and an IgG1 CH2 domain or an IgG3 CH2 domain. In a seventh particular example each of the two Fc domains independently comprises an IgG1 hinge or an IgG3 hinge, an IgG1 CH2 domain or an IgG3 CH2 domain, and an IgG1 CH3 domain or an IgG3 CH3 domain. In an eighth particular example each of the two Fc domains independently comprises an IgG1 hinge, an IgG1 CH2 domain, and an IgG1 CH3 domain. In a ninth particular example each of the two Fc domains independently comprises an IgG3 hinge, an IgG3 CH2 domain, and an IgG3 CH3 domain. In a tenth particular example each of the two Fc domains independently comprises an IgG1 hinge, an IgG1 CH2 domain, and an IgG3 CH3 domain.

Also in this first embodiment, the two or more Fc domains are each of a same immunoglobulin Fc class, and the immunoglobulin Fc class is selected from the group consisting of IgG1, IgG2, IgG3, and IgG4. Alternatively, the two or more Fc domains are each of a different immunoglobulin Fc class, and said immunoglobulin Fc class is selected from the group consisting of IgG1, IgG2, IgG3 and IgG4.

Further in this first embodiment, the first and second Fcγ receptors are each independently an Fcγ receptor I, an Fcγ receptor II, an Fcγ receptor III or an Fcγ receptor IV. Preferably the first and second Fcγ receptors are each Fcγ receptor IIIa.

In a second embodiment the present invention is directed to isolated serial stradomers comprising two associated stradomer monomers, wherein each of the stradomer monomers comprises two Fc domain monomers, wherein the association of the two stradomer monomers forms two Fc domains, wherein each of said two Fc domains independently comprises an IgG hinge, an IgG CH2 domain and an IgG CH3 domain, and wherein the serial stradomer specifically binds to a first Fcγ receptor through a first of the two Fc domains and to a second Fcγ receptor through a second of the two Fc domains. In a preferred embodiment, the two or more stradomer monomers are associated through a covalent bond, a disulfide bond or chemical cross-linking.

In a first particular example of this second embodiment the two Fc domains are each of a same immunoglobulin Fc class, and the immunoglobulin Fc class is selected from the group consisting of IgG1, IgG2, IgG3, and IgG4. In a second particular example the two Fc domains are each of a different immunoglobulin Fc class, and said immunoglobulin Fc class is selected from the group consisting of IgG1, IgG2, IgG3 and IgG4. In a third particular example at least one of the Fc domains comprises an IgG hinge and an IgG CH2 domain. In a fourth particular example each of the Fc domains independently comprises an IgG hinge and an IgG CH2 domain. In a fifth particular example at least one of the Fc domains comprises an IgG hinge, an IgG CH2 domain and an IgG CH3 domain. In a sixth particular example each of the Fc domains independently comprises an IgG hinge, an IgG CH2 domain and an IgG CH3 domain. In a seventh particular example at least one of the Fc domains comprises an IgG1 hinge or an IgG3 hinge, an IgG1 CH2 domain or an IgG3 CH2 domain, and an IgG1 CH3 domain or an IgG3 CH3 domain. In an eighth particular example each of the Fc domains independently comprises an IgG1 hinge or an IgG3 hinge, an IgG1 CH2 domain or an IgG3 CH2 domain, and an IgG1 CH3 domain or an IgG3 CH3 domain. In a ninth particular example each of the Fc domains independently comprises an IgG1 hinge, an IgG1 CH2 domain, and an IgG1 CH3 domain. In a tenth particular example each of the Fc domains independently comprises an IgG3 hinge, an IgG3 CH2 domain, and an IgG3 CH3 domain. In an eleventh particular example each of the Fc domains independently comprises an IgG1 hinge, an IgG1 CH2 domain, and an IgG3 CH3 domain.

In a third embodiment the present invention is directed to isolated serial stradomers further comprising a Fab domain, wherein each of the stradomer monomers comprises an Fab fragment heavy chain and two Fc domain monomers, wherein the Fab fragment heavy chain is in a position amino terminal or carboxy terminal to the two Fc domain monomers, wherein an Fab fragment light chain is independently associated with each Fab fragment heavy chain, and wherein the Fab domain has antigen-binding activity. In a preferred embodiment, each of the stradomer monomers further comprises an immunoglobulin hinge monomer, and wherein the immunoglobulin hinge monomer is in a position between the Fab fragment heavy chain and the two Fc domain monomers.

In a fourth embodiment the present invention is directed to core stradomers comprising a core moiety linked to two or more core stradomer units, wherein each of the two or more core stradomer units comprises at least one Fc domain, and wherein each of the core stradomer units is independently selected from the group consisting of:

(a) an Fc fragment, wherein said Fc fragment comprises two associated Fc fragment monomers, wherein each of said Fc fragment monomers comprises an Fc domain monomer, and wherein the association of the two Fc fragment monomers forms an Fc domain, (b) an Fc partial fragment, wherein said Fc partial fragment comprises two associated Fc partial fragment monomers, wherein each of said Fc partial fragment monomers comprises an Fc domain monomer, and wherein the association of the two Fc partial fragment monomers forms an Fc domain, (c) an Fc domain, wherein said Fc domain comprises two associated Fc domain monomers, and wherein the association of the two Fc domain monomers forms an Fc domain, (d) a serial stradomer, wherein said serial stradomer comprises two or more associated stradomer monomers, wherein each of said stradomer monomers comprises two or more Fc domain monomers, and wherein the association of the two or more stradomer monomers forms two or more Fc domains, and (e) a cluster stradomer, wherein said cluster stradomer comprises two or more multimerized cluster stradomer units, wherein each of said cluster stradomer units comprises a multimerizing region and at least one Fc domain, wherein each of said cluster stradomer units comprises two associated cluster stradomer unit monomers, wherein each of said cluster stradomer unit monomers comprises a multimerizing region monomer and at least one Fc domain monomer, wherein the association of the two cluster stradomer unit monomers forms a multimerizing region and at least one Fc domain, and wherein the multimerizing regions of the two or more cluster stradomer units multimerize to form the cluster stradomer, and wherein the core stradomer specifically binds to a first Fcγ receptor through a first of the two or more core stradomer units and to a second Fcγ receptor through a second of the two or more core stradomer units.

Preferably in this fourth embodiment, the core moiety is selected from the group consisting of an immunoglobulin J chain, albumin, liposome, bead, peptide and polyethylene glycol.

In preferred embodiments directed to core stradomers the two or more core stradomer units are each independently an Fc fragment. Alternatively, the two or more core stradomer units are each independently a serial stradomer.

In a further preferred embodiment directed to core stradomers the core stradomer comprises two core stradomer units, wherein each of the two core stradomer units is each independently a serial stradomer, wherein the serial stradomer comprises two associated stradomer monomers, wherein both of said stradomer monomers comprises two Fc domain monomers, and wherein the association of the two stradomer monomers forms two Fc domains. In a first particular example of this embodiment, at least one of the Fc domains of the two or more core stradomer units comprises an IgG1 hinge or an IgG3 hinge, an IgG1 CH2 domain or an IgG3 CH2 domain, and an IgG1 CH3 domain or an IgG3 CH3 domain. In a second particular example at least one of the Fc domains of the two or more two core stradomer units comprises an IgG1 hinge or an IgG3 hinge, and an IgG1 CH2 domain. In a third particular example each of the Fc domains of the two or more two core stradomer units independently comprises an IgG1 hinge, an IgG1 CH2 domain, and an IgG1 CH3 domain. In a fourth particular example at least one of the Fc domains of the two or more two core stradomer units comprises an IgG hinge and an IgG CH2 domain. In a fifth particular example each of the Fc domains of the two or more two core stradomer units independently comprises an IgG hinge and an IgG CH2 domain. In a sixth particular example each of the Fc domains of the two or more two core stradomer units independently comprises an IgG3 hinge, an IgG3 CH2 domain, and an IgG3 CH3 domain. In a seventh particular example each of the Fc domains of the two or more two core stradomer units independently comprises an IgG1 hinge, an IgG1 CH2 domain, and an IgG3 CH3 domain.

In this embodiment, the first and second Fcγ receptors are each independently an Fcγ receptor I, an Fcγ receptor II, an Fcγ receptor III or an Fcγ receptor IV. Preferably, the first and second Fcγ receptors are each Fcγ receptor IIIa.

In a fifth embodiment the present invention is directed to cluster stradomers comprising two or more multimerized cluster stradomer units, wherein each of the cluster stradomer units comprises a multimerizing region and at least one Fc domain, wherein each of the cluster stradomer units comprises two associated cluster stradomer unit monomers, wherein each of the cluster stradomer unit monomers comprises a multimerizing region monomer and at least one Fc domain monomer, wherein the association of the two cluster stradomer unit monomers forms a multimerizing region and at least one Fc domain, wherein the multimerizing regions of the two or more cluster stradomer units multimerize to form the cluster stradomer, and wherein the cluster stradomer specifically binds to a first Fcγ receptor through a first Fc domain and to a second Fcγ receptor through a second Fc domain.

In preferred embodiments, the multimerizing region is selected from the group consisting of an IgG2 hinge, an IgE CH2 domain, a leucine, an isoleucine zipper and a zinc finger.

In further preferred embodiment, the cluster stradomers comprising two, three, four or five multimerized cluster stradomer units.

In a first particular example of this fifth embodiment at least one of the Fc domains comprises an IgG1 hinge or an IgG3 hinge, an IgG1 CH2 domain or an IgG3 CH2 domain, and an IgG1 CH3 domain or an IgG3 CH3 domain. In a second particular example each of the Fc domains independently comprises an IgG1 hinge, an IgG1 CH2 domain, and an IgG1 CH3 domain. In a third particular example at least one of the Fc domains comprises an IgG hinge and an IgG CH2 domain. In a fourth particular example each of the Fc domains independently comprises an IgG hinge and an IgG CH2 domain. In a fifth particular example each of the Fc domains independently comprises an IgG3 hinge, an IgG3 CH2 domain, and an IgG3 CH3 domain. In a sixth particular example each of the Fc domains independently comprises an IgG1 hinge, an IgG1 CH2 domain, and an IgG3 CH3 domain. In a seventh particular example each of the Fc domains independently comprises an IgG hinge, an IgG CH2 domain and an IgG CH3 domain. In an eighth particular example at least one of the cluster stradomer units comprises two or more Fc domains. In a ninth particular example each of the cluster stradomer units comprises two or more Fc domains.

In this embodiment, the first and second Fcγ receptors are each independently an Fcγ receptor I, an Fcγ receptor II, an Fcγ receptor III or an Fcγ receptor IV. Preferably, the first and second Fcγ receptors are each Fcγ receptor IIIa.

In a sixth embodiment the present invention is directed to stradobodies comprising two or more associated stradomer monomers and an Fab domain, wherein each of the stradomer monomers comprises an Fab fragment heavy chain and two or more Fc domain monomers, wherein the Fab fragment heavy chain is in a position amino terminal or carboxy terminal to the two or more Fc domain monomers, wherein the association of the two or more stradomer monomers forms two or more Fc domains, wherein an Fab fragment light chain is independently associated with the Fab fragment heavy chain of each stradomer monomer, wherein the Fab domain has antigen-binding activity, and wherein the stradobody specifically binds to a first Fcγ receptor through a first of the two or more Fc domains and to a second Fcγ receptor through a second of the two or more Fc domains.

In preferred embodiments the two or more stradomer monomers are associated through a covalent bond, a disulfide bond or chemical cross-linking.

In a further preferred embodiment, each of said stradomer monomers of the stradobodies further comprises an immunoglobulin hinge monomer, and wherein the immunoglobulin hinge monomer is in a position between the Fab fragment heavy chain and the two Fc domain monomers.

In a particular embodiment the stradobody comprises two associated stradomer monomers, wherein each of said stradomer monomers comprises an Fab fragment heavy chain and two Fc domain monomers, and wherein the association of the two stradomer monomers forms two Fc domains. In a first particular example of this embodiment, at least one of the two Fc domains comprises an IgG hinge, an IgG CH2 domain and an IgG CH3 domain. In a second particular example each of the two Fc domains independently comprises an IgG hinge, an IgG CH2 domain and an IgG CH3 domain. In a third particular example at least one of the two Fc domains comprises an IgG hinge and an IgG CH3 domain. In a fourth particular example each of the Fc two domains independently comprises an IgG hinge and an IgG CH3 domain. In a fifth particular example at least one of the two Fc domains comprises an IgG1 hinge or an IgG3 hinge, an IgG1 CH2 domain or an IgG3 CH2 domain, and an IgG1 CH3 domain or an IgG3 CH3 domain. In a sixth particular example each of the two Fc domains independently comprises an IgG1 hinge or an IgG3 hinge, an IgG1 CH2 domain or an IgG3 CH2 domain, and an IgG1 CH3 domain or an IgG3 CH3 domain. In a seventh particular example each of the two Fc domains independently comprises an IgG1 hinge, an IgG1 CH2 domain, and an IgG1 CH3 domain. In an eighth particular example each of the two Fc domains independently comprises an IgG3 hinge, an IgG3 CH2 domain, and an IgG3 CH3 domain. In a ninth particular example each of the two Fc domains independently comprises an IgG1 hinge, an IgG1 CH2 domain, and an IgG3 CH3 domain. In a tenth particular example at least one of the two Fc domains comprises an IgG1 hinge or an IgG3 hinge, and an IgG1 CH2 domain or an IgG3 CH2 domain. In an eleventh particular example at least one of the two Fc domains comprises an IgG1 hinge or an IgG3 hinge, and an IgG1 CH2 domain.

In this embodiment, the first and second Fcγ receptors are each independently an Fcγ receptor I, an Fcγ receptor II, an Fcγ receptor III or an Fcγ receptor IV. Preferably, the first and second Fcγ receptors are each Fcγ receptor IIIa.

In a seventh embodiment the present invention is directed to methods of altering an immune response in a subject comprising administering to a subject in need thereof a pharmaceutical composition comprising a therapeutically effective amount of a serial stradomer and a carrier or diluent. In a preferred embodiment, the pharmaceutical composition comprises a therapeutically effective amount of a heterogeneous mixture of serial stradomers and a carrier or diluent.

In an eighth embodiment the present invention is directed to methods of altering an immune response in a subject comprising administering to a subject in need thereof a pharmaceutical composition comprising a therapeutically effective amount of a core stradomer and a carrier or diluent. In a preferred embodiment, the pharmaceutical composition comprises a therapeutically effective amount of a heterogeneous mixture of core stradomers and a carrier or diluent.

In a ninth embodiment the present invention is directed to methods of altering an immune response in a subject comprising administering to a subject in need thereof a pharmaceutical composition comprising a therapeutically effective amount of a cluster stradomer and a carrier or diluent. In a preferred embodiment, the pharmaceutical composition comprises a therapeutically effective amount of a heterogeneous mixture of cluster stradomers and a carrier or diluent.

In a tenth embodiment the present invention is directed to methods of altering an immune response in a subject comprising administering to a subject in need thereof a pharmaceutical composition comprising a therapeutically effective amount of a stradobody and a carrier or diluent. In a preferred embodiment, the pharmaceutical composition comprises a therapeutically effective amount of a heterogeneous mixture of stradobodies and a carrier or diluent.

In an eleventh embodiment the present invention is directed to methods of screening an antibody for a specific activity on a cell of the immune system, comprising: (a) contacting a homogenous population of cells of the immune system with a candidate antibody, (b) measuring an activity of the population of cells of (a), (c) contacting a homogenous population of cells of the same cell type as in (a) with a serial stradomer of claim 1, (d) measuring an activity of the population of cells of (c), and (e) comparing the activity measured in (b) with the activity measured in (d), thereby screening an antibody for a specific activity on a cell of the immune system. In a preferred embodiment, the candidate antibody and the serial stradomer are species-matched and isotype-matched. In a further preferred embodiment, the comparison in (e) is a ratio of activity measured in (d) versus the activity measured in (b).

In a twelfth embodiment the present invention is directed methods of inhibiting the activity of a monocyte-derived cell (MDC). The method involves contacting the cell with a composition containing a substrate with an Fc reagent bound to it. The contacting can be in vitro, in vivo, or ex vivo. The cell can be in an animal, e.g., an animal that has or is at risk of developing a monocyte derived cell mediated condition (MDCMC). The cell can be, for example, a dendritic cell, a macrophage, a monocyte, or an osteoclast.

In a thirteenth embodiment the present invention is directed methods of treatment that includes administering to an animal a composition comprising a substrate having an Fc reagent bound thereto, the animal having or being at risk of developing a monocyte-derived cell mediated condition (MDCMC).

The following are embodiments common to both these two methods (the twelfth and thirteenth embodiments).

The animal can be, for example, a human.

The Fc reagent can contain or be a functional portion of a human Fc fragment, e.g., a human IgG1 Fc fragment, a human IgG3 Fc fragment, a human IgG2, or a human IgG4 Fc fragment. Moreover it can include or be an IgG molecule. The Fc reagent can also be or include a functional portion of a non-human Fc fragment.

The substrate can be or include a synthetic polymer, e.g., nylon, teflon, dacron, polyvinyl chloride, PEU (poly(ester urethane)), PTFE (polytetrafluoroethylene), or PMMA (methyl methacrylate). The substrate can include or be a metal or a metal alloy, e.g., stainless steel, platinum, iridium, titanium, tantalum, a nickel-titanium alloy, or a cobalt-chromium alloy. The substrate can contain or be animal tissue or an animal tissue product, e.g., a tissue or organ graft, bone (e.g., osteogenic bone), or cartilage. The substrate can contain or be a protein, e.g., collagen or keratin. The substrate can also be or contain a polysaccharide, e.g., agarose. Moreover, the substrate can contain or be a tissue matrix, e.g., an acellular tissue matrix. The substrate can contain or be an animal cell (e.g., a tissue repair cell such as a fibroblasts or a mesenchymal stem cell). The substrate can contain or be a salt, e.g., calcium sulfate. Furthermore the substrate can be or contain a gel or cream. It can also contain or be silicon or silastic. It can also contain be a natural fiber, e.g., silk, cotton, or wool.

The substrate can be a hair transplant plug or an implantable medical device such as a stent (e.g., a vascular stent such as a coronary artery stent; an airway stent such as an endotracheal or nasal stent; a gastrointestinal stent such a biliary or pancreatic stent; or a urinary stent such as a ureteral stent). It can also be a surgical suture (e.g., a braid silk, chromic gut, nylon, plastic, or metal suture or a surgical clip (e.g., an aneurism clip)). In addition, the substrate the can be an artificial hip, an artificial hip joint, an artificial knee, an artificial knee joint, an artificial shoulder, an artificial shoulder joint, an artificial finger or toe joint, a bone plate, a bone dowel, a bone non-union implant, an intervertebral disk implant, bone cement, or a bone cement spacer. It can be an arterial-venous shunt, an implantable wire, a pacemaker, an artificial heart, a heart assist device, a cochlear implant, an implantable defibrillator, a spinal cord stimulator, a central nervous system stimulator, a peripheral nerve implant, a dental prosthesis, or a dental crown. Furthermore, the substrate can be a large vessel embolic filtering device or cage, a percutaneous device, a dermal or sub-mucosal patch, or an implantable drug delivery device.

The substrate can also be a large blood vessel graft, wherein the blood vessel is, for example, a carotid artery, a femoral artery, or an aorta. It can also be a sub-dermal implant, a corneal implant, an intraocular lens, or a contact lens.

The substrate can be in the form of, e.g., a sheet, a bead, a mesh, a powder particle, a thread, a bead, or a fiber. The substrate can contain or be a solid, a semi-solid, or a gelatinous substance. Thus, a substrate includes substances that are substantially insoluble in aqueous solvents, e.g., a fat-soluble lipid such as a liposome.

The MDCMC can be an inflammatory condition, an autoimmune disease, a cancer, a disorder of bone density, an acute infection, or a chronic infection.

It can be a hematoimmunological process, e.g., Idiopathic Thrombocytopenic Purpura, alloimmune/autoimmune thrombocytopenia, Acquired immune thrombocytopenia, Autoimmune neutropenia, Autoimmune hemolytic anemia, Parvovirus B19-associated red cell aplasia, Acquired antifactor VIII autoimmunity, acquired von Willebrand disease, Multiple Myeloma and Monoclonal Gammopathy of Unknown Significance, Sepsis, Aplastic anemia, pure red cell aplasia, Diamond-Blackfan anemia, hemolytic disease of the newborn, Immune-mediated neutropenia, refractoriness to platelet transfusion, neonatal post-transfusion purpura, hemolytic uremic syndrome, systemic Vasculitis, Thrombotic thrombocytopenic purpura, or Evan's syndrome.

Alternatively, the MDCMC can be a neuroimmunological process, e.g., Guillain-Barré syndrome, Chronic Inflammatory Demyelinating Polyradiculoneuropathy, Paraproteinemic IgM demyelinating Polyneuropathy, Lambert-Eaton myasthenic syndrome, Myasthenia gravis, Multifocal Motor Neuropathy, Lower Motor Neuron Syndrome associated with anti-GM1 antibodies, Demyelination, Multiple Sclerosis and optic neuritis, Stiff Man Syndrome, Paraneoplastic cerebellar degeneration with anti-Yo antibodies, paraneoplastic encephalomyelitis, sensory neuropathy with anti-Hu antibodies, epilepsy, Encephalitis, Myelitis, Myelopathy especially associated with Human T-cell lymphotropic virus-1, Autoimmune Diabetic Neuropathy, or Acute Idiopathic Dysautonomic Neuropathy.

The MDCMC can be a Rheumatic disease process, e.g., Kawasaki's disease, Rheumatoid arthritis, Felty's syndrome, ANCA-positive Vasculitis, Spontaneous Polymyositis, Dermatomyositis, Antiphospholipid syndromes, Recurrent spontaneous abortions, Systemic Lupus Erythematosus, Juvenile idiopathic arthritis, Raynaud's, CREST syndrome, or Uveitis.

Moreover, the MDCMC can be a dermatoimmunological disease process, e.g., Epidermal Necrolysis, Gangrene, Granuloma, Autoimmune skin blistering diseases including *Pemphigus vulgaris*, Bullous Pemphigoid, and *Pemphigus foliaccus*, Vitiligo, Streptococcal toxic shock syndrome, *Scleroderma*, systemic sclerosis including diffuse and limited cutaneous systemic sclerosis, Atopic dermatitis, or steroid dependent Atopic dermatitis.

In addition, the MDCMC can be a musculoskeletal immunological disease, e.g., Inclusion Body Myositis, Necrotizing fasciitis, Inflammatory Myopathies, Myositis, Anti-Decorin (BJ antigen) Myopathy, Paraneoplastic Necrotic Myopathy, X-linked Vacuolated Myopathy, Penacillamine-induced Polymyositis, Atherosclerosis, Coronary Artery Disease, or Cardiomyopathy.

The MDCMC can also be a gastrointestinal immunological disease process, e.g., pernicious anemia, autoimmune chronic active hepatitis, primary biliary cirrhosis, Celiac disease, dermatitis herpetiformis, cryptogenic cirrhosis, Reactive arthritis, Crohn's disease, Whipple's disease, ulcerative colitis, or sclerosing cholangitis.

The MDCMC can be, for example, Graft Versus Host Disease, Antibody-mediated rejection of the graft, Post-bone marrow transplant rejection, Post-infectious disease inflammation, Lymphoma, Leukemia, Neoplasia, Asthma, Type 1 Diabetes mellitus with anti-beta cell antibodies, Sjogren's syndrome, Mixed Connective Tissue Disease, Addison's disease, Vogt-Koyanagi-Harada Syndrome, Membranoproliferative glomerulonephritis, Goodpasture's syndrome, Graves' disease, Hashimoto's thyroiditis, Wegener's granulomatosis, micropolyarterits, Churg-Strauss syndrome, Polyarteritis nodosa or Multisystem organ failure.

Where the MDCMC is a cancer, it can be fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, or Schwanoma.

Where the MDCMC is a disorder of bone density, it can be osteoporosis, osteopenia, osteopetrosis, idiopathic hypogonadotropic hypogonadism, anorexia nervosa, non-healing fracture, post-menopausal osteoporosis, Vitamin D deficiency or excess, primary or secondary hyperparathyroidism, thyroid disease, or bisphosphonate toxicity.

Where the MDCMC is an acute infection, it can be: a fungal disorder including Candidiasis, Candidemia, or Aspergillosis; a bacterial disorder, including *staphylococcus* including Methicillin Resistant *Staph aureus*, streptococcal skin and oropharyngeal conditions, or gram negative sepsis; a mycobacterial infection including tuberculosis; a viral infection including mononucleosis, Respiratory Syntitial virus infection, or Herpes zoster infection; a parasitic infection including malaria, schistosomiasis, or trypanosomiasis.

Where the MDCMC is a chronic infection, it can be onchyomycosis; a bacterial disorder including *Helicobacter pylori*; a mycobacterial infection including tuberculosis; a viral infection including Epstein Barr virus infection, Human Papilloma Virus infection, or Herpes Simplex Virus infection; or a parasitic infection including malaria or schistosomiasis.

In a fourteenth embodiment the present invention is directed a composition that contains or is an implantable or attachable medical device and an Fc reagent bound thereto.

In a fifteenth embodiment the present invention is directed a kit that contains an implantable or attachable medical device and an Fc reagent. In both these embodiments, the implantable or attachable medical device and the Fc reagent can be any of those recited herein. The kit can further contain a suitable container.

Additional advantages and features of the present invention will be apparent from the following detailed description, drawings and examples, which illustrate preferred embodiments of the invention.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIGS. 2A and 2B show higher order aggregates of the native Fc fragment structure shown in FIG. 1B. Fc fragments may naturally multimerize into dimers of dimer (i.e. tetramers) or even higher order multimer aggregates.

FIG. 11A shows an IgG1 Fc-IgG1 (hinge-CH2) stradomer monomer. FIG. 11B demonstrates how the stradomer monomer in FIG. 11A can auto-dimerize to form a serial stradomer. FIG. 11C demonstrates how the same stradomer monomer in FIG. 11A can have monomer Fc domains align with the same or similar Fc domain monomers on another stradomer monomer but not as an autodimer, thereby forming a stradomer composed of the same stradomer monomer as the autodimer but with a zipper effect structure.

FIG. 13A shows an IgE CH2-IgG1 Fc-IgG1 (hinge-CH2)-IgE CH4 stradomer monomer. FIG. 13B shows the autodimer of the FIG. 13A monomer and highlights two FcγR binding sites formed.

FIG. 14A shows a stradomer composed of two IgG1 Fc domains joined by a linker. FIG. 14B shows a stradomer composed of two serial stradomers (specifically in each case a 2(IgG1 Fc) stradomer) joined by a linker.

FIG. 15A shows the nucleic acid (SEQ ID NO:1) and amino acid (SEQ ID NO:2) sequences of the human IgG1 Fc fragment. FIG. 15B shows the nucleic acid (SEQ ID NO:3) and amino acid (SEQ ID NO:4) sequences of the human IgG2 Fc fragment. FIG. 15C shows the nucleic acid (SEQ ID NO:5) and amino acid (SEQ ID NO:6) sequences of the human IgG3 Fc fragment. FIG. 15D shows the nucleic acid (SEQ ID NO:7) and amino acid (SEQ ID NO:8) sequences of the human IgG4 Fc fragment.

FIG. 16 shows the nucleic acid (SEQ ID NO:17) and amino acid (SEQ ID NO:18) sequences of a construct comprising {IgK signal sequence-IgG1 Fc fragment-IgG1 Fc fragment}. The amino acid sequence of the IgK signal is in bold. The amino acid sequence of the first IgG1 Fc fragment is single underlined. The amino acid sequence of the second IgG1 Fc fragment is double underlined. The serine and lysine marked with an asterisk are those amino acids that may be mutated to alter Fcγ receptor binding.

FIG. 17 shows the nucleic acid (SEQ ID NO:19) and amino acid (SEQ ID NO:20) sequences of a construct comprising {Restriction Enzyme Sites-IgK signal sequence-Restriction Enzyme Sites-IgG1(Hinge-CH2-CH3)-Restriction Enzyme Sites-epitope tags(V5 and His)-STOP}. The amino acid sequence of the IgK signal is in bold. The amino acid sequence of the IgG1 Fc fragment is single underlined. The amino acid sequence of the V5 tag is underlined with a dashed line. The amino acid sequence of the His tag is underlined in bold.

FIG. 18 shows the nucleic acid (SEQ ID NO:21) and amino acid (SEQ ID NO:22) sequences of a construct comprising {Restriction Enzyme Sites-IgK signal-Restriction Enzyme Sites-IgG1(Hinge-CH2-CH3)-XbaI site-IgG1 (Hinge-CH2-CH3)-STOP}. The amino acid sequence of the IgK signal is in bold. The amino acid sequence of the first IgG1 Fc fragment is single underlined. The amino acid sequence of the second IgG1 Fc fragment is double underlined.

FIG. 19 shows the nucleic acid (SEQ ID NO:23) and amino acid (SEQ ID NO:24) sequences of a construct comprising {Restriction Enzyme Sites-IgK signal-Restriction Enzyme Sites-IgG1(Hinge-CH2-CH3)-XbaI site-IgG1 (Hinge-CH2-CH3)-Restriction Enzyme Sites-epitope tags (V5 and His)-STOP}. The amino acid sequence of the IgK signal is in bold. The amino acid sequence of the first IgG1 Fc fragment is single underlined. The amino acid sequence of the second IgG1 Fc fragment is double underlined. The amino acid sequence of the V5 tag is underlined with a dashed line. The amino acid sequence of the His tag is underlined in bold.

FIG. 20A shows the nucleic acid (SEQ ID NO:31) and amino acid (SEQ ID NO:32) sequences of the N-terminal signal sequence of FcRgammaIIIa with the phenylalanine (F) polymorphism shown in bold and underlined. The variable nucleic acid is also in bold and underlined. FIG. 20B shows the nucleic acid (SEQ ID NO:33) and amino acid (SEQ ID NO:34) sequences of the N-terminal signal sequence of FcRgammaIIIa with valine (V) polymorphism shown in bold and underlined. The variable nucleic acid is also in bold and underlined. Both constructs contain a C-terminal hexaHis tag for purification.

FIG. 21 shows the nucleic acid (SEQ ID NO:25) and amino acid (SEQ ID NO:26) sequences of a construct comprising {Restriction Enzyme Sites-IgK signal-EcoRV Site-IgG3(Hinge-CH2-CH3)-IgG1(Hinge-CH2-CH3)-Restriction Enzyme Sites-epitope tags(V5 and His)-STOP}. The amino acid sequence of the IgK signal is in bold. The amino acid sequence of the IgG3 Fc fragment is single underlined. The amino acid sequence of the IgG1 Fc fragment is double underlined. The amino acid sequence of the V5 tag is underlined with a dashed line. The amino acid sequence of the His tag is underlined in bold.

FIG. 22 shows the nucleic acid (SEQ ID NO:27) and amino acid (SEQ ID NO:28) sequences of a construct comprising {Restriction Enzyme Sites-IgK signal-EcoRV Site-IgE (CH2)-IgG1(Hinge-CH2-CH3)-IgG1(Hinge-CH2)-IgE(CH4)-STOP}. The amino acid sequence of the IgK signal is in bold. The amino acid sequence of the IgE(CH2) domain is single underlined. The amino acid sequence of the IgG1(Hinge-CH2-CH3) domain is double underlined. The amino acid sequence of the IgG1(Hinge-CH2) domain is underlined with a dashed line. The amino acid sequence of the IgE (CH4) domain is underlined with a wavy line.

FIG. 23C shows the composition of a core stradomer comprising a core moiety to which are bound core stradomer units that contain at least one Fc domain each. The core stradomer units may be an Fc fragment, a serial stradomer or a cluster stradomer unit. FIG. 23D shows the composition of a cluster stradomer comprising multimerized cluster stradomer units, each of which has a multimerizing region and a region containing at least one Fc domain. The cluster stradomer unit may be an Fc fragment or a serial stradomer. The multimerizing region, once multimerized, forms the head of a cluster stradomer. The legs of the cluster stradomer are formed by the Fc domain regions of the cluster stradomer units that are spatially less constrained than the multimerized head of the cluster stradomer.

FIG. 24 shows the amino acid sequences of the stradomer set forth in Table 3.

FIG. 25 shows the amino acid sequences for the Fc partial domains monomers (hinge, CH2 and CH3) of human IgG1, IgG2, IgG3 and IgG4 (Kabat, E A, Wu, T T, Perry, H M, Gottesman, K S, and Foeller, C. 1991. Sequences of proteins of immunological interest 5th Ed. US Public Health Services, NIH, Bethesda).

DETAILED DESCRIPTION OF THE INVENTION

Figure 1A:
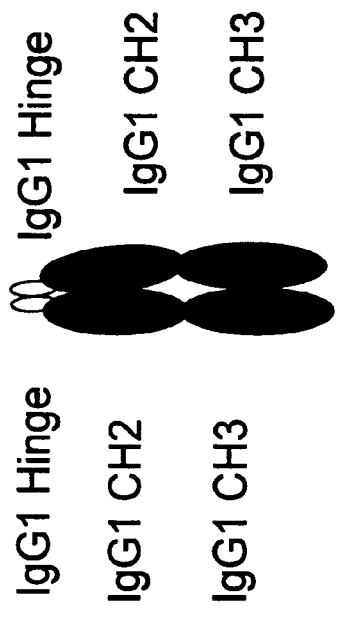
FIG. 1A shows in schematic form a native Fc fragment monomer structure from IgG1 having a Hinge domain linked to a CH2 domain linked to a CH3 domain.

The approach to rational molecular design for hIVIG replacement compounds described herein includes recombinant and/or biochemical creation of immunologically active biomimetic(s). In preferred methods, these replacement compounds are screened in vitro to assess each replacement compound's efficiency at binding to Fcγ receptor and modulating immune function. Particular replacement compounds are selected for further in vivo validation and dosage/administration optimization. The replacement compounds have utility for treating, for example, autoimmune diseases, inflammatory diseases, osteoporosis, and cancer. Each phase is described in detail below along with specific exemplary embodiments.

As used herein, the use of the word "a" or "an" when used in conjunction with the term "comprising" in the claims and/or the specification may mean "one," but it is also consistent with the meaning of "one or more," "at least one," and "one or more than one."

As used herein, the terms "biomimetic", "biomimetic molecule", "biomimetic compound", and related terms, refer to a human made compound that imitates the function of another compound, such as pooled hIVIG, a monoclonal antibody or the Fc fragment of an antibody. "Biologically active" biomimetics are compounds which possess biological activities that are the same as or substantially similar to their naturally occurring counterparts. "Immunologically active" biomimetics are biomimetics which exhibit immunological activity the same as or substantially similar to naturally occurring immunologically active molecules, such as antibodies, cytokines, interleukins and other immunological molecules known in the art. In preferred embodiments, the biomimetics of the present invention are stradomers and stradobodies, as defined herein.

The immunologically active biomimetics of the present invention are designed to possess one or more immune modulating activities of the IgG Fc domain and have at least (i) a first Fc domain capable of binding an FcγR, including FcγRI, FcγRII, FcγRIII and FcγRIV, and (ii) a second Fc domain capable of binding an FcγR, including FcγRI, FcγRII, FcγRIII and FcγRIV.

The following paragraphs define the building blocks of the biomimetics of the present invention, both structurally and functionally, and then define biomimetics themselves. However, it is first helpful to note that, as indicated above, each of the biomimetics of the present invention has at least two Fc domains. At a minimum, an Fc domain is a dimeric polypeptide (or a dimeric region of a larger polypeptide) that comprises two peptide chains or arms (monomers) that associate to form a functional Fcγ receptor binding site. Therefore, the functional form of the individual fragments and domains discussed herein generally exist in a dimeric (or multimeric) form. The monomers of the individual fragments and domains discussed herein are the single chains or arms that must associate with a second chain or arm to form a functional dimeric structure.

Fc Fragment

Figure 1B:
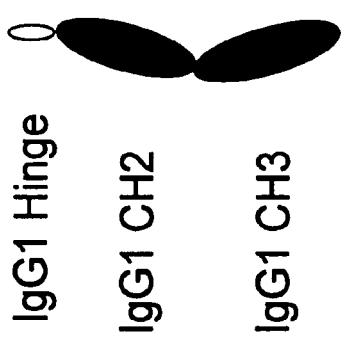
FIG. 1B shows a self-aggregated, native IgG1 Fc fragment formed from two associated Fc fragment monomers.
Figures 1C, 1D:
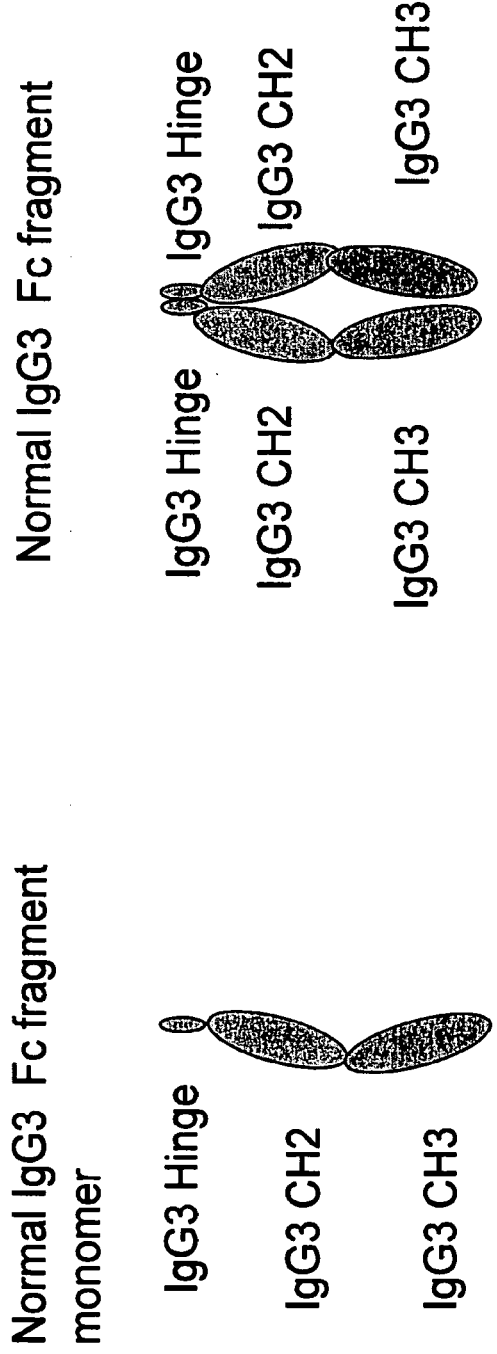
FIG. 1C shows in schematic form a native Fc fragment monomer structure from IgG3 having a Hinge domain linked to a CH2 domain linked to a CH3 domain.
FIG. 1D shows a self-aggregated, native IgG3 Fc fragment formed from two associated Fc fragment monomers.
Figures 3A, 3B:
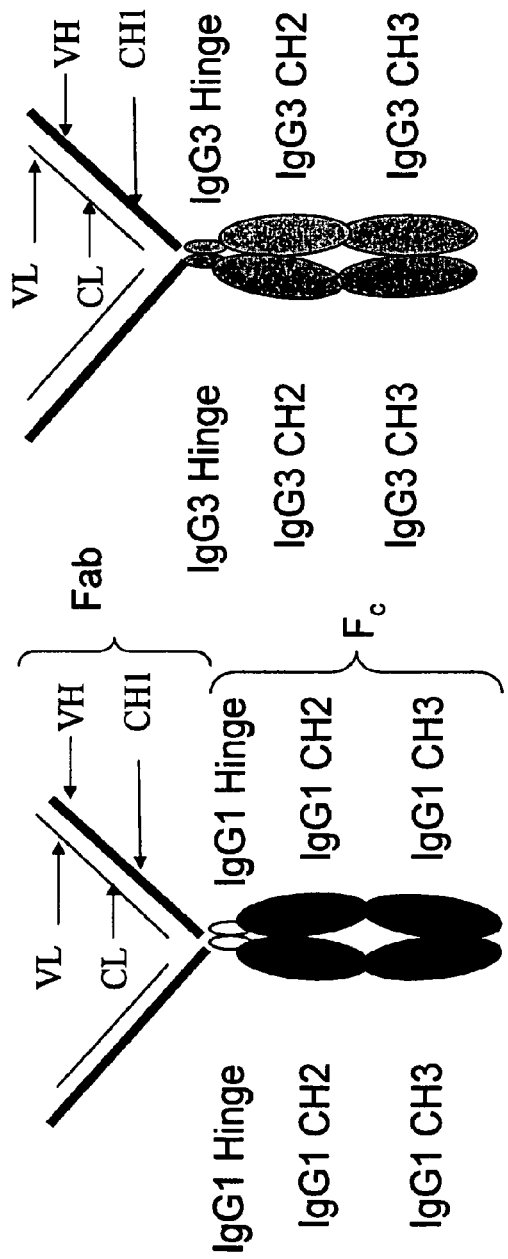
FIG. 3A shows a schematic of a native IgG1 antibody having a native Fab fragment linked to the Fc fragment at the hinge of the Fc fragment.
FIG. 3B shows the analogous IgG3 structure.

"Fc fragment" is a term of art that is used to describe the protein region or protein folded structure that is routinely found at the carboxy terminus of immunoglobulins (see FIG. 3A-3B). The Fc fragment can be isolated from the Fab fragment of a monoclonal antibody through the use of papain digestion, which is an incomplete and imperfect process (see Mihaesco C and Seligmann M. Papain Digestion Fragments Of Human IgM Globulins. Journal of Experimental Medicine, Vol 127, 431-453 (1968)). In conjunction with the Fab fragment (containing the antibody binding domain) the Fc fragment constitutes the holoantibody, meaning here the complete antibody. The Fc fragment consists of the carboxy terminal portions of the antibody heavy chains. Each of the chains in an Fc fragment is between about 220-265 amino acids in length and the chains are often linked via a disulfide bond. The Fc fragment often contains one or more independent structural folds or functional subdomains. In particular, the Fc fragment encompasses an Fc domain, defined herein as the minimum structure that binds an Fcγ receptor (see, e.g., FIGS. 1B and 1D). An isolated Fc fragment is comprised of two Fc fragment monomers (e.g., the two carboxy terminal portions of the antibody heavy chains; further defined herein) that are dimerized. When two Fc fragment monomers associate, the resulting Fc fragment has Fcγ receptor binding activity.

Fc Partial Fragment

An "Fc partial fragment" is a domain comprising less than the entire Fc fragment of an antibody, yet which retains sufficient structure to have the same activity as the Fc fragment, including Fcγ receptor binding activity. An Fc partial fragment may therefore lack part or all of a hinge region, part or all of a CH2 domain, part or all of a CH3 domain, and/or part or all of a CH4 domain, depending on the isotype of the antibody from which the Fc partial domain is derived. An example of a Fc partial fragment includes a molecule comprising the upper, core and lower hinge regions plus the CH2 domain of IgG3 (Tan, L K, Shopes, R J, Oi, V T and Morrison, S L, Influence of the hinge region on complement activation, C1q binding, and segmental flexibility in chimeric human immunoglobulins, *Proc Natl Acad Sci USA*. 1990 January; 87(1): 162-166). Thus, in this example the Fc partial fragment lacks the CH3 domain present in the Fc fragment of IgG3. Fc partial fragments are comprised of two Fc partial fragment monomers. As further defined herein, when two such Fc partial fragment monomers associate, the resulting Fc partial fragment has Fcγ receptor binding activity.

Fc Domain

As used herein, "Fc domain" describes the minimum region (in the context of a larger polypeptide) or smallest protein folded structure (in the context of an isolated protein) that can bind to or be bound by an Fcγ receptor. In both an Fc fragment and an Fc partial fragment, the Fc domain is the minimum binding region that allows binding of the molecule to an Fcγ receptor. While an Fc domain can be limited to a discrete polypeptide that is bound by an Fcγ receptor, it will also be clear that an Fc domain can be a part or all of an Fc fragment, as well as part or all of an Fc partial fragment. When the term "Fc domains" is used in this invention it will be recognized by a skilled artisan as meaning more than one Fc domain. An Fc domain is comprised of two Fc domain monomers. As further defined herein, when two such Fc domain monomers associate, the resulting Fc domain has Fcγ receptor binding activity. Thus an Fc domain is a dimeric structure that functionally can bind an Fcγ receptor.

Fc Partial Domain

As used herein, "Fc partial domain" describes a portion of an Fc domain. Fc partial domains include the individual heavy chain constant region domains (e.g., CH1, CH2, CH3 and CH4 domains) and hinge regions of the different immunoglobulin classes and subclasses. Thus, Fc partial domains of the present invention include the CH1 domains of IgG1, IgG2, IgG3, IgG4, IgM, IgA1, IgA2, IgD and IgE, the CH2 domains of IgG1, IgG2, IgG3, IgG4, IgM, IgA1, IgA2, IgD and IgE, the CH3 domains of IgG1, IgG2, IgG3, IgG4, IgM, IgA1, IgA2, IgD and IgE, the CH4 domains of IgM and IgE, and the hinge regions of IgG1, IgG2, IgG3, IgG4, IgM, IgA1, IgA2, IgD and IgE. The Fc partial domain of the present invention may further comprise a combination of more than one more of these domains and hinges. However, the individual Fc partial domains of the present invention and combinations thereof lack the ability to bind an FcγR. Therefore, the Fc partial domains and combinations thereof comprise less than an Fc domain. Fc partial domains may be linked together to form a peptide that has Fcγ receptor binding activity, thus forming an Fc domain. In the present invention, Fc partial domains are used with Fc domains as the building blocks to create the biomimetics of the present invention, as defined herein. Each Fc partial domain is comprised of two Fc partial domain monomers. When two such Fc partial domain monomers associate, an Fc partial domain is formed.

As indicated above, each of Fc fragments, Fc partial fragments, Fc domains and Fc partial domains are dimeric proteins or domains. Thus, each of these molecules is comprised of two monomers that associate to form the dimeric protein or domain. While the characteristics and activity of the dimeric forms was discussed above the monomeric peptides are discussed as follows.

Fc Fragment Monomer

As used herein, an "Fc fragment monomer" is a single chain protein that, when associated with another Fc fragment monomer, comprises an Fc fragment. The Fc fragment monomer is thus the carboxy terminal portion of one of the antibody heavy chains that make up the Fc fragment of a holo-antibody (e.g., the contiguous portion of the heavy chain that includes the hinge region, CH2 domain and CH3 domain of IgG) (see FIG. 1A and FIG. 1C)). In one embodiment, the Fc fragment monomer comprises, at a minimum, one chain of a hinge region (a hinge monomer), one chain of a CH2 domain (a CH2 domain monomer) and one chain of a CH3 domain (a CH3 domain monomer), contiguously linked to form a peptide. In another embodiment, the Fc fragment monomer comprises at least one chain of a hinge region, one chain of a CH2 domain, one chain of a CH3 domain, and one chain of a CH4 domain (a CH4 domain monomer) contiguously linked to form a peptide.

Fc Domain Monomer

As used herein, "Fc domain monomer" describes the single chain protein that, when associated with another Fc domain monomer, comprises an Fc domain that can bind to an Fcγ receptor. The association of two Fc domain monomers creates one Fc domain. An Fc domain monomer alone, comprising only one side of an Fc domain, cannot bind an Fcγ receptor.

Fc Partial Domain Monomer

As used herein, "Fc partial domain monomer" describes the single chain protein that, when associated with another Fc partial domain monomer, comprises an Fc partial domain. The amino acid sequences of the Fc partial domain hinge, CH2 and CH3 monomers for IgG1, IgG2, IgG3 and IgG4 are shown in FIG. 25. The association of two Fc partial domain monomers creates one Fc partial domain.

Stradomers

In particular embodiments, the biomimetics of the present invention include stradomers. Stradomers are biomimetic compounds capable of binding two or more Fcγ receptors (see, e.g., FIG. 13B). In a preferred embodiment, the stradomers of the present invention are used to bind Fcγ receptors on effector cells such as NK cells and immature dendritic cells and other monocyte-derived cells. In one embodiment, the Fcγ receptors are low affinity Fcγ receptors. A stradomer can have four different physical conformations: serial, cluster, core or Fc fragment, each of which is discussed in the following paragraphs. As will be evident, the Fc fragments, Fc partial fragments, Fc domains and Fc partial domains discussed above are used in the construction of the various stradomer conformations. Further, it is the individual Fc domain monomers and Fc partial domain monomers, also discussed above, that are first produced, and that then self-associate to form the dimeric structures that are the stradomers of the present invention.

Serial Stradomer

A "serial stradomer" is dimeric polypeptide comprised of two linear stradomer monomers that, when associated, form two or more Fc domains. The Fc domains of the stradomer are only functional when the two peptide chains (stradomer monomers) are associated (i.e., non-functional in the monomeric state). Thus a serial stradomer is a biomimetic compound capable of binding two or more Fcγ receptors. In different embodiments, serial stradomer may have two, three, four, five, six, seven, eight, nine, ten, eleven, twelve, thirteen, fourteen or more Fc domains, as well as Fc partial domains. The Fc domains, and Fc partial domains, within a serial stradomer may be linked by domain linkages, as further defined herein.

As used herein, a "stradomer dimer" is a specific form of a stradomer, composed of only two stradomers. In one embodiment, the stradomer dimers are molecules formed by self-aggregation of relevant stradomer monomers. In another embodiment, stradomer monomers in the stradomer dimers are physically linked through an inter-stradomer monomer linkage, as defined herein. A "multimeric stradomer" is comprised of three or more stradomers, formed by self-aggregation of stradomer monomers, or through an inter-stradomer monomer linkage, as defined herein in.

Stradomer Monomer

Figure 5B:
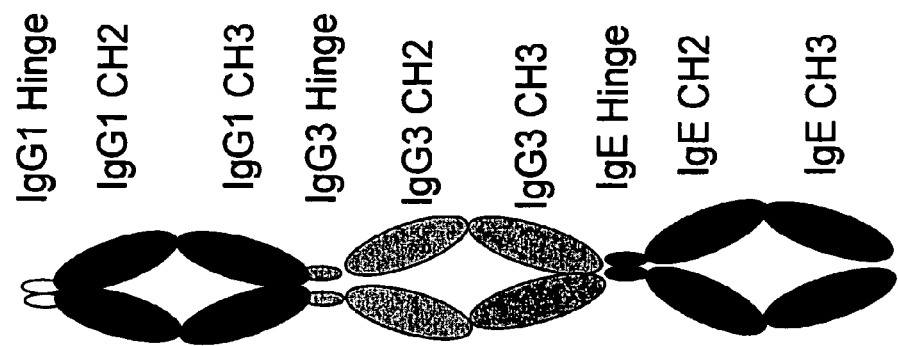
FIGS. 5A & B show the stradomer monomers of FIGS. 4A & B autodimerizing into a serial stradomer due to the intrinsic capacity of the component Fc domain monomers.
Figure 5A:
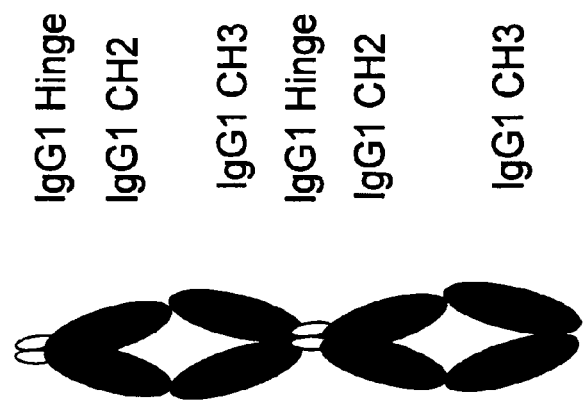
Figures 6A, 6B:
FIG. 6A shows a stradomer monomer containing IgG1 Fc-IgG1 (hinge-CH2)
FIG. 6B shows a stradomer containing IgG1 (hinge-CH2)-IgG3 (hinge-CH2)-IgE (hinge-CH2) derived sequences.
Figure 7B:
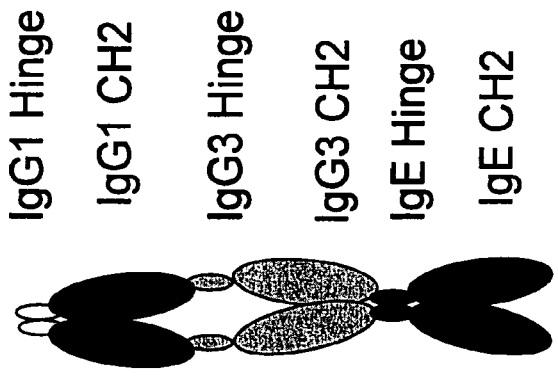
FIGS. 7A & B show the stradomer monomers of 6A & B autodimerizing into a serial stradomer due to the intrinsic capacity of the component Fc domains.
FIG. 7C shows a serial stradomer containing IgE(hinge)-IgG1 Fc-IgG1 (hinge-CH2)-IgE (CH3).
FIG. 7D shows a serial stradomer containing an IgG3Fc-IgG1Fc.
Figure 7A:
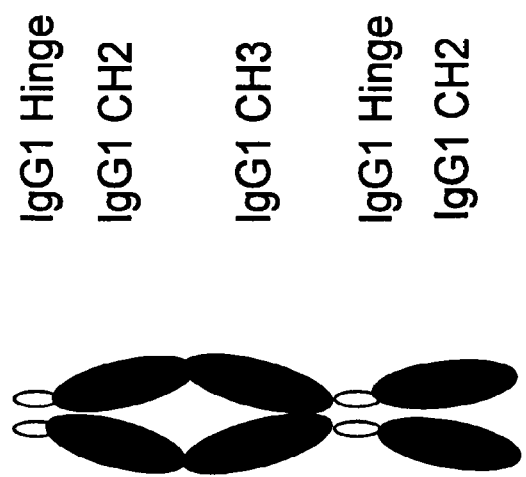
Figure 7D:
Figure 7C:
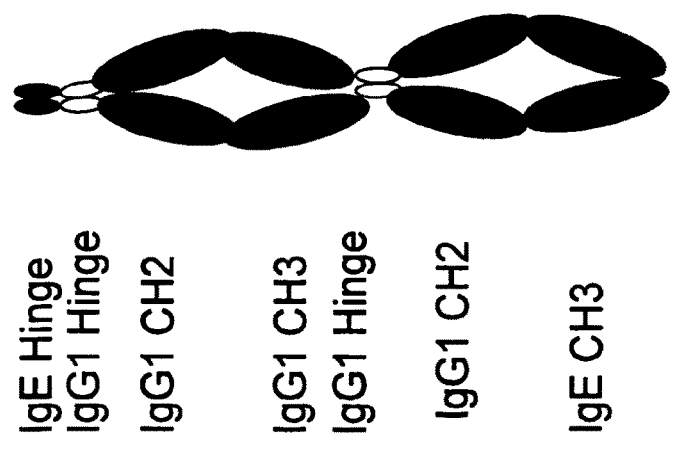
Figure 12A:
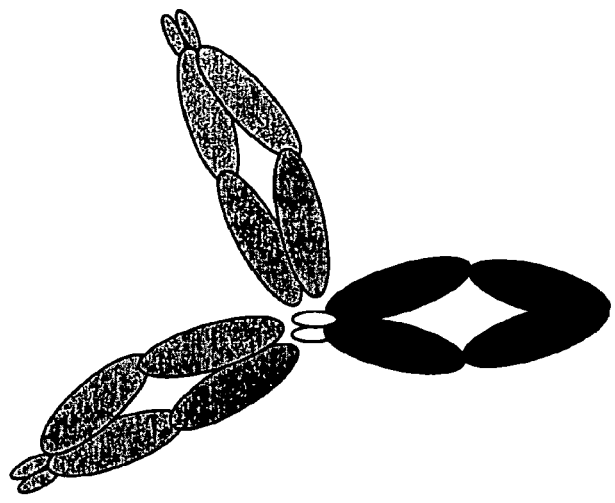
FIG. 12A shows an IgG3 Fc-IgG1 Fc stradomer monomer.

As used herein, the term "stradomer monomer" refers to a single, contiguous peptide molecule that, when associated with at least a second stradomer monomer, forms a polypeptide comprising at least two Fc domains (see, e.g., FIGS. 6A-6B, FIG. 12A). While in preferred embodiments serial stradomer are comprised of two associated stradomer monomers (see, for example, FIGS. 5A, 5B, 7A, 7B, 7C, 7D), a serial stradomer may also contain three (see FIG. 11C) or more stradomer monomers. Stradomer monomers may be associated to form stradomers by inter-stradomer monomer linkages or they may form stradomers through self-aggregation.

A stradomer monomer may have an amino acid sequence that will form one, two, three, four, five, six, seven, eight, nine, ten, eleven, twelve, thirteen, fourteen or more Fc domains when associated with another stradomer monomer to form a stradomer. A stradomer monomer may further have an amino acid sequence that will form one, two, three, four, five, six, seven, eight, nine, ten, eleven, twelve, thirteen, fourteen or more Fc partial domains when associated with another stradomer monomer to form a stradomer.

Figure 4B:
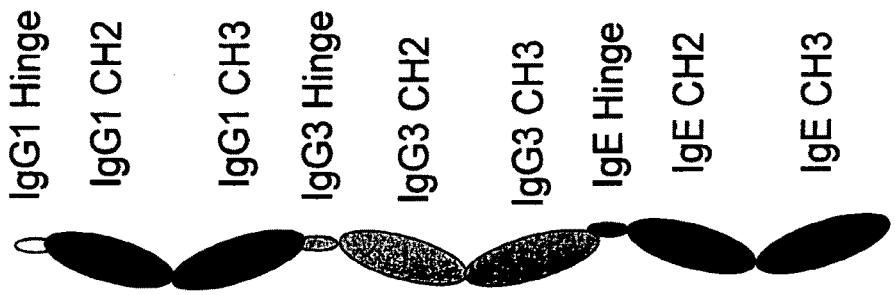
FIG. 4B shows an alternative stradomer monomer structure having linked in series IgG1 Fc-IgG3 Fc-IgE Fc.
Figure 4A:
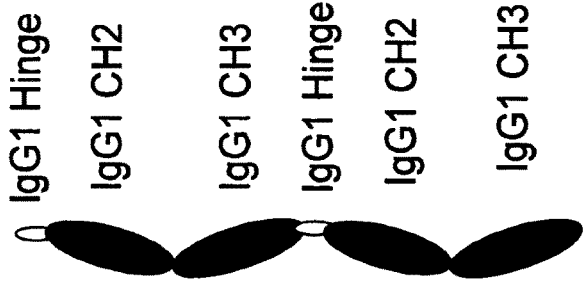
FIG. 4A shows a stradomer monomer composed of two IgG1 Fc domain monomers in series.

The regions of stradomer monomers that will form Fc domains and Fc partial domains in the context of a stradomer may simply be arranged from carboxy terminal to amino terminal of successive regions of the stradomer monomer molecule (see, e.g., FIG. 4A-4B). Alternatively, the successive regions of the stradomer monomers may be linked through a peptide sequence termed a "domain linkage" herein. The arrangement of the particular Fc domain monomers and Fc partial domain monomers comprising a stradomer monomer is not critical. However, the arrangement must permit formation of two functional Fc domains upon association of two stradomer monomers.

In one embodiment of the stradomers of the present invention, stradomer monomers are produced that contain at the N-terminus of the peptide an Fc domain monomer or Fc partial domain monomer that binds strongly to itself, such as a single or two terminal IgE CH2 domain monomers or a partial IgG3 hinge domain monomer, to create an Fc domain or an Fc partial domain, respectively. Each of these stradomer monomers has the requisite complement of Fc domain monomers and/or partial Fc domain monomers to bind to two Fc gamma receptors upon formation of a stradomer. Stradomers that result from association of such stradomer monomers are biomimetics capable of binding two or more Fc gamma receptors. In a preferred embodiment the N-terminal Fc domain or Fc partial domain contains an additional glycosylation site such as that which exists on the IgE CH2 domain.

As a clarifying example, the skilled artisan will understand that the stradomer molecules of the present invention may be constructed by preparing a polynucleotide molecule that encodes various combinations of Fc domain monomers and Fc partial domain monomers, but with a combination that will form a minimum of two Fc domain monomers. Such a polynucleotide molecule may be inserted into an expression vector, which can be used to transform a population of bacteria. Stradomer monomers can then produced by culturing the transformed bacteria under appropriate culture conditions. Stradomer monomers can then form functional stradomers upon either self-aggregation of the stradomer monomers or association of stradomer monomers using inter-stradomer monomer linkages. The present invention encompasses both stradomers formed through the association of stradomer monomers having identical amino acid sequences, stradomer monomers having substantially similar amino acid sequences, or stradomer monomers having dissimilar sequences. In the latter embodiment the amino acid sequence of the stradomer monomers comprising a stradomer need only be of such similarity that two or more functional Fcγ receptor binding sites are formed.

As indicated above, an Fc domain can be functionally defined by its ability to bind an Fcγ receptor. As a result, the particular amino acid sequence of an Fc domain will vary based on the Fc partial domains that comprise the Fc domain. However, in one embodiment of the present invention the Fc domain comprises the hinge region and a CH2 domain of an immunoglobulin molecule. In a further embodiment the Fc domain comprises the hinge region, a CH2 domain and CH3 domain of an immunoglobulin molecule. In a further embodiment, the Fc domain comprises the hinge region, a CH2 domain, CH3 domain and CH4 domain of an immunoglobulin molecule. In yet another embodiment, the Fc domain comprises the hinge region, a CH2 domain and CH4 domain of an immunoglobulin molecule.

Domain Linkage

As indicated above, a "domain linkage" is a peptide linkage between Fc domain monomers and/or Fc partial domain monomers that comprise each of the individual stradomer monomers of the serial stradomers or stradobodies of the present invention. The domain linkage may be 1, 2, 3, 4, 5, 6, 7, 8, 9, 10, 11, 12, 13, 14, 15, 16, 17, 18, 19, 20 or more amino acids. A domain linkage does not occur between Fc partial domain monomers that are in their natural sequence. That is, where linked naturally contiguous portions of Fc domain monomers are used, such as the hinge region, CH2 domain and CH3 domain of IgG, these Fc partial domain monomers comprise a contiguous sequence and no domain linkage between these elements is required. In contrast, for example, when two or more Fc domain monomers or partial Fc domain monomers are linked in a manner that is not naturally occurring to form an individual stradomer monomer, domain linkages may be used. An example would be the linkage between two hinge/CH2/CH3 peptides, creating an individual stradomer monomer of a stradomer comprising: hinge/CH2/CH3/L/hinge/CH2/CH3, where "L" is the domain linkage (see, e.g., FIG. 4A where the domain linkage (not shown) occurs between the IgG1 CH3 domain and the IgG1 hinge). In the various cases described, the domain linkage may be one of the naturally occurring portions of the heavy chain that joins the hinge and CH domains in the Fc domain monomer of an antibody. Alternatively, the domain linkage may be any other amino acid sequence that provides needed spacing and flexibility between the Fc domain monomers and partial Fc domain monomers of an individual stradomer monomer and that allows the individual stradomer monomers to pair with other each other to form the stradomers of the present invention.

The skilled artisan will understand that the identity of the domain linkage is not particularly important as long as it permits two or more individual stradomer monomers to form the biomimetic compounds of the present invention, and that the resulting compounds have the ability to cross-link more than one FcγR. It is envisioned that each immunologically active biomimetic compound will preferably contain at least one domain linkage in each stradomer monomer of the serial stradomer or stradobody which will function to maintain the Fc domains of the immunologically active biomimetic within a restricted spatial region and which will facilitate FcγR activation activity, for example, by aggregating FcγRs through co-binding to the Fc domains within the immunologically active biomimetic. Preferably, the domain linkages will allow the same or a greater degree of conformational variability as is provided by the hinge domain of IgG molecules. All the above linkages are well-known in the art.

Inter-Stradomer Monomer Linkage

A separate linkage found in the biomimetic compounds of the present invention is the "inter-stradomer monomer linkage" that occurs between two or more individual stradomer monomers that comprise the stradomers and stradobodies of the present invention. While the domain linkages are short amino acid sequences that serve to link the Fc domain monomers and partial Fc domain monomers that comprise individual stradomer monomers of the biomimetic compounds to each other, the inter-stradomer monomer linkages serve to join two or more individual stradomer monomers that comprise the biomimetic compounds. The inter-stradomer monomer linkage may be any linkage capable of stably associating the individual stradomer monomers. In some embodiments, the inter-stradomer monomer linkage may be a covalent link between the stradomer monomers. Alternatively, the inter-stradomer monomer linkage between stradomer monomers may be by direct chemical crosslinking. In preferred embodiments, the stradomer monomer structures take advantage of the natural self-aggregation properties between Fc domain monomers to create self-aggregating stradomers. In such embodiments, disulfide bonds form between the individual stradomer monomers to form the stradomers (see, e.g., FIG. 5A, where inter-stradomer monomer linkages (not shown) serve to join the two individual stradomer monomers of the stradomer). The disulfide bonds form between cysteine residues of the Fc domain monomers that comprise the biomimetic molecules, using either cysteine residues occurring in the natural Fc domain monomer sequence or cysteine residues incorporated into an Fc domain monomer by site-directed mutagenesis. Such natural self-aggregation properties can also be used to form the inter-stradomer monomer linkages between individual stradomer monomers in stradomer multimers. Alternative embodiments include inter-stradomer monomer linkages where disulfide bonds form between cysteine residues introduced through site-directed mutagenesis into the amino acid sequence comprising the individual stradomer monomers.

As discussed above, in a preferred embodiment, the inter-stradomer monomer linkage that forms a stradomer is a linkage that results from self-aggregation of stradomer monomers. In one embodiment, the two stradomer monomers that comprise the stradomer are identical peptides, such that the two individual stradomer monomers that comprise the stradomer are identical in sequence. However, the skilled artisan will understand that other embodiments include stradomers where the stradomer monomers differ from each other in amino acid sequence.

Two stradomer monomers can form a stradomer by, for example, aligning in parallel such that pairing takes place between identical Fc partial domain monomers in the stradomer monomers (see, e.g., FIGS. 5A-B). However, the present invention also includes embodiments where pairing occurs between non-identical Fc partial domain monomers, and embodiments (see FIG. 11C) where pairing occurs between identical Fc partial domain monomers in the stradomer monomers but where the alignment of the two stradomer monomers is offset.

Figure 12B:
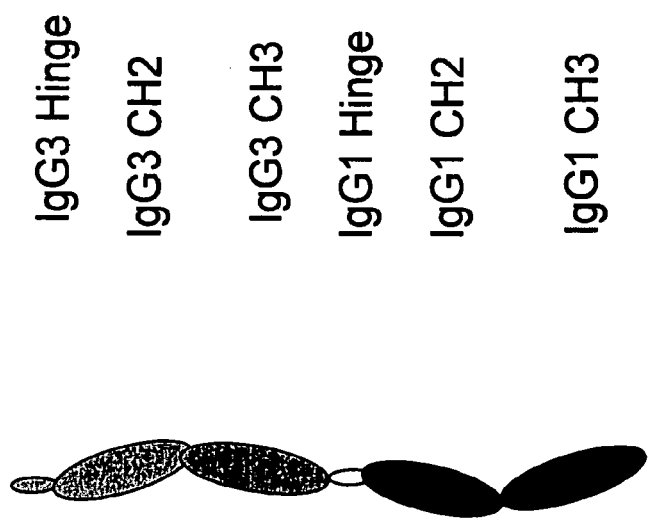
FIG. 12B shows that the addition of a second IgG3 Fc followed by autodimerization can form a branched structured IgG3 Fc-IgG1 Fc-IgG3 Fc stradomer.
Figure 23A:
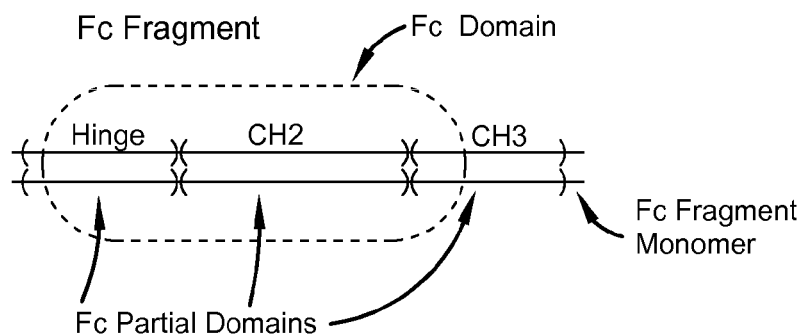
FIG. 23A shows an Fc fragment and demonstrates that such Fc fragment is composed of two Fc fragment monomers, and further comprises an Fc domain (dashed circle) and Fc partial domains (hinge, CH2 and CH3 as indicated).
Figure 23B:
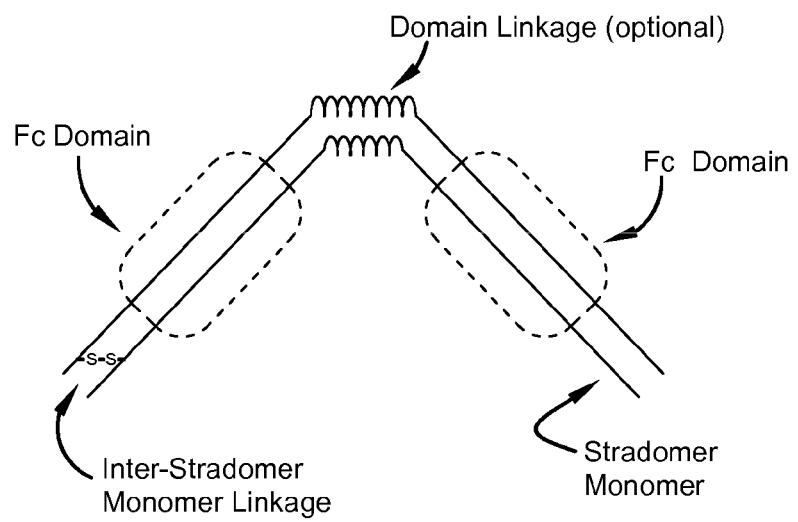
FIG. 23B shows the composition of a serial stradomer, composed of two stradomer monomers which are connected by an inter-stradomer monomer linkage. The serial stradomer comprises at least two Fc domains (indicated as dashed circles) and may optionally comprise a domain linkage region.

In order to control the production and self-dimerization of a stradomer monomer, "capping regions" may be used. For example, a stradomer monomer sequence may comprise the following Fc partial domains: IgE CH2/IgG1 hinge/IgG1 CH2/IgG1 CH3/IgG1 hinge/IgG1 CH2/IgE CH4, (see FIG. 13A) where the IgE domains serve as a cap to prevent a "zippering effect." A zippering effect can occur when a stradomer monomer (see FIG. 11A) can auto-dimerize (see FIG. 11B) or can align itself not as an auto-dimer but as alternating monomers in parallel (see FIG. 11C). One of ordinary skill in the art will understand that a variety of Fc partial domains, such as the hinge of any immunoglobulin or the CH4 domain of IgM or IgE, may be used alone or in combination to direct the stradomer to auto-dimerize and to prohibit the zippering effect when desired. Other non-series structures may contain branched molecules (see FIG. 12B), two or more stradomers lined up in parallel joined by linkers such as a simple covalent bond, peptide linkers, or non-peptide linkers (see FIGS. 14A and 14B).

Core Stradomer

A "core stradomer" is comprised of a core moiety to which are bound two or more core stradomer units, wherein each core stradomer unit comprises at least one Fc domain, thereby creating a biomimetic compound capable of binding two or more Fcγ receptors. An Fc fragment, Fc partial fragment, serial stradomer or cluster stradomer unit can each independently serve as one or both (if they comprise two Fc domains) of the core stradomer units in a core stradomer because each of these molecules contains at least one Fc domain. Thus, a core stradomer may comprise a core moiety to which is bound at least one serial stradomer.

As used herein, the core moiety of a core stradomer is any physical structure to which the core stradomer units may be linked or covalently bound. Preferred polypeptides that may serve as the core moiety include keyhole limpet hemocyanin, bovine serum albumin and ovalbumin. Chemical cross-linking between such core moieties and core stradomer units (e.g., Fc fragment, Fc partial fragment, Fc domain, serial stradomer and cluster stradomer unit) may be achieved by means of numerous chemicals using well known techniques. Exemplary chemicals generally suitable for use in the cross-linking include glutaraldehyde, carbodiimide, succinimide esters (e.g. MBS, SMCC), benzidine, periodate, isothiocyanate; PEO (polyethylene)/PEG (polyethylene glycol) spacers such as Bis(NHS)PEO$_5$, DFDNB (1,5-Difluoro-2,4-dinitrobenzene); and Amine Reactive homobifunctional cross-linking reagents including Aldehyde-Activated Dextran, Bis(Sulfosuccinimidyl)suberate, Bis[2-(succinimidooxycarbonyloxy)ethyl]sulfone, Dimethyl adipimidate.2 HCl, Dimethyl pimelimidate.2 HCl, Dimethyl Suberimidate.2 HCl, Disuccinimidyl glutarate, Dithiobis(succinimidyl) propionate, Disuccinimidyl suberate, Disuccinimidyl tartrate, Dimethyl 3,3'-dithiobispropionimidate.2 HCl, 3,3'-Dithiobis(sulfosuccinimidylpropionate), Ethylene glycol bis [succinimidylsuccinate], Ethylene glycol bis[sulfosuccinimidylsuccinate], β-[Tris(hydroxymethyl)phosphino]propionic acid and Tris-succinimidyl aminotriacetate. One of skill in the art will be able to select the appropriate crosslinking chemical and conditions based upon the particular core moiety selected and the sequence of the Fc domain-containing polypeptides being combined to form an immunologically active biomimetic. See, e.g., Wong, Shan S. Chemistry of protein conjugation and cross-linking Boca Raton: CRC Press, c1991 (ISBN 0849358868).

In another preferred embodiment, a joining (J) chain polypeptide may be used as the core moiety. When a J chain is used as the core moiety, cysteine bridges may be used to connect individual core stradomer units to form a core stradomer (See FIG. 10A-10D). In an embodiment of a core stradomer, serial stradomers (serving as the core stradomer units) containing a terminal IgM CH4 domain are associated with a J chain to form a core stradomer. The inclusion of the IgM CH4 domain results in the self-aggregation of stradomers comprising this Fc partial domain with a J chain to form a biomimetic capable of binding multiple Fc gamma receptors. Another exemplary core stradomer is one comprising Fc domains (serving as the core stradomer units) where the Fc domains have the structure IgG3 hinge/IgG3 CH2/IgG3 CH3/IgM CH4. The component Fc domains of this molecule cannot individually bind more than one Fc gamma receptor, but the entire structure can bind five Fc gamma receptors when the component Fc domains associate with a J chain.

In another embodiment, the core moiety may be a non-polypeptide entity. A variety of suitable compositions may be physically associated with the core stradomer units to produce an immunologically active biomimetic. Non-toxic beads, hyperbranched polymers and dendrimers, nanoparticles, and various compounds that are classified by the FDA as Generally Regarded As Safe (e.g. propylene glycol, sorbitol, liposomes and silicate calcium) may be used. See, e.g., Nanoparticulates as Drug Carriers by Vladimir P. Torchilin (Editor), Imperial College Press (September 2006) ISBN: 1860946305/ISBN-13: 9781860946301.

Preferred core moieties of the present invention include a bead, albumin, a liposome, a peptide and polyethylene glycol.

Cluster Stradomer

A "cluster stradomer" is a biomimetic that has an octopus-like form with a central moiety "head" and two or more "legs", wherein each leg comprises one or more Fc domain that is capable of binding at least one Fc gamma receptor, thus creating a biomimetic capable of binding two or more Fc gamma receptors. Each cluster stradomer is comprised of more than one dimeric protein, each called a "cluster stradomer unit." Each cluster stradomer unit is comprised of a region that multimerizes and a "leg" region that comprises at least one functional Fc domain. The multimerizing region creates a cluster stradomer "head" once multimerized with the multimerizing region of another cluster stradomer unit. The leg region is capable of binding as many Fcγ receptors as there are Fc domains in each leg region. Thus a cluster stradomer is a biomimetic compound capable of binding two or more Fcγ receptors.

The multimerizing region may be a peptide sequence that causes dimeric proteins to further multimerize or alternatively the multimerizing region may be a glycosylation that enhances the multimerization of dimeric proteins. Examples of peptide multimerizing regions include IgG2 hinge, IgE CH2 domain, isoleucine zipper, and zinc fingers. The influence of glycosylation on peptide multimerization is well described in the art (e.g., Role of Carbohydrate in Multimeric Structure of Factor VIII/V on Willebrand Factor Protein. Harvey R. Gralnick, Sybil B. Williams and Margaret E. Rick. Proceedings of the National Academy of Sciences of the United States of America, Vol. 80, No. 9, [Part 1: Biological Sciences] (May 1, 1983), pp. 2771-2774; Multimerization and collagen binding of vitronectin is modulated by its glycosylation. Kimie Asanuma, Fumio Arisaka and Haruko Ogawa. International Congress Series Volume 1223, December 2001, Pages 97-101).

A trained artisan will recognize that a cluster stradomer unit may itself comprise a serial stradomer (containing two or more Fc domains) along with a multimerizing region. Thus the "legs" of a cluster stradomer may be comprised of any of the types of serial stradomers discussed herein and/or one or more of an IgG1 Fc fragment and/or an IgG3 Fc fragment and/or a single Fc domain. One trained in the art will recognize that each of the IgG1 Fc fragments and IgG3 Fc fragment in such biomimetics may be modified to comprise partial Fc fragments from any immunoglobulin. The monomers that comprise the cluster stradomer unit (which, as indicated above, exists as a dimeric association of two peptides) are "cluster stradomer unit monomers." An exemplary cluster stradomer that has been made whose cluster stradomer unit would not bind more than one low affinity Fc gamma receptor prior to multimerization is: IgE CH2/IgG1 hinge/IgG1 CH2/IgG1 CH3.

One trained in the art will recognize that when a serial stradomer is used as the "leg" of a cluster stradomer, each "leg" will be capable of binding more than one Fc gamma receptor (as at least two Fc domains are present in a serial stradomer), thus creating a biomimetic capable of binding more than one Fc gamma receptor. Fc partial domains, other immunoglobulin sequences, and non-immunoglobulin sequences may be placed at the termini of individual cluster stradomer unit monomers comprising the legs to create a cluster stradomer wherein each leg has preferred spatial proximity to increase their availability to bind one or more than one Fc gamma receptor.

The multimerizing region may be a peptide sequence that causes peptides to dimerize or multimerize and includes the IgG2 hinge, the IgE CH2 domain, an isoleucine zipper and a zinc finger. As is known in the art, the hinge region of human IgG2 can form covalent dimers (Yoo, E. M. et al. J. Immunol. 170, 3134-3138 (2003); Salfeld Nature Biotech. 25, 1369-1372 (2007)). The dimer formation of IgG2 is potentially mediated through the IgG2 hinge structure by C—C bonds (Yoo et al 2003), suggesting that the hinge structure alone can mediate dimer formation. Thus, serial stradomers having an IgG2 hinge (and thus serving as cluster stradomer units) will form a cluster stradomer that may comprise two serial stradomers or even three serial stradomers.

The amino acid sequence of the human IgG2 hinge monomer is as follows: ERKCCVECPPCP (SEQ ID NO: 36). The core structure of the hinge is the C-X-X-C portion of the hinge monomer. Thus, stradomer monomers of the present invention may comprise either the complete 12 amino acid sequence of the IgG2 hinge monomer, or the four amino acid core, along with Fc domain monomers. While the X-X of the core structure can be any amino acid, in a preferred embodiment the X-X sequence is V-E or P-P. The skilled artisan will understand that the IgG2 hinge monomer may be comprised of any portion of the hinge sequence in addition to the core four amino acid structure, including all of the IgG2 hinge sequence and some or all of the IgG2 CH2 and CH3 domain monomer sequences. Specific examples of possible IgG2 hinge-IgG1 Fc domain serial stradomer constructs are as follows:

TABLE 1

| N-term | H | CH2 | CH3 | H | CH2 | CH3 | H | CH2 | CH3 | C-term |
|---|---|---|---|---|---|---|---|---|---|---|
|  | CXXC |  |  | 1 | 1 | 1 |  |  |  |  |
|  | CXXC |  |  | 1 | 1 | 1 | 1 | 1 | 1 |  |
|  | 2 | 2 | 2 | 1 | 1 | 1 |  |  |  |  |
|  | 2 | 2 | 2 | 1 | 1 | 1 | 1 | 1 | 1 |  |
|  | 2 |  |  | 1 | 1 | 1 |  |  |  |  |
|  | 2 |  |  | 1 | 1 | 1 | 1 | 1 | 1 |  |
|  | 2x | 2 | 2 | 1 | 1 | 1 |  |  |  |  |
|  | 2x | 2 | 2 | 1 | 1 | 1 | 1 | 1 | 1 |  |
|  | 2x | 2 | 2 | 1 | 1 | 1 | 1 | 1 | 1 | IgE hinge |
|  | 2x |  |  | 1 | 1 | 1 |  |  |  |  |

Nomenclature:

H = hinge,

CH2 = constant heavy domain 2,

CH3 = constant heavy domain 3,

1 = IgG1,

2 = IgG2,

X = any amino acid;

2x = two hinges in consecutive order

These are only a few of many examples. Any of the IgG1 Fc domains can, for example, be replaced with an IgG3 Fc domain. Additional proteins with IgG2 dimerization domains includes IgG2-IgG1 chimeric proteins with the addition of N and/or C terminal sequences comprising IgM or IgE domain monomer sequences. These N and C terminal sequences can be hinge regions, constant domains, or both.

As indicated above, leucine and isoleucine zippers may also be used as the multimerizing region. Leucine and isoleucine zippers (coiled-coil domains) are known to facilitate formation of protein dimers, trimers and tetramers (Harbury et al. Science 262:1401-1407 (1993); O'Shea et al. Science 243:538 (1989)). By taking advantage of the natural tendency of an isoleucine zipper to form a trimer, cluster stradomers may be produced using serial stradomers comprising an isoleucine zipper. Association of three or more serial stradomers (as cluster stradomer units) having isoleucine zippers results in the formation of cluster stradomers having at least six Fc gamma receptor binding regions.

While the skilled artisan will understand that different types of leucine and isoleucine zippers may be used, in a preferred embodiment the isoleucine zipper from the GCN4 transcriptional regulator modified as described (Morris et al., Mol. Immunol. 44:3112-3121 (2007); Harbury et al. Science 262:1401-1407 (1993)) is used: YTQKSLSLSPGKELLG GGSIKQIEDKIEEILSKIYHIENEIARIKKLIGERGHGG GSNSQVSHRYPRFQSIKVQFTEYKKEKGFILTS (SEQ ID NO:37) This isoleucine zipper sequence is only one of several possible sequences that can be used for multimerization of Fc domain monomers. While the entire sequence shown in SEQ ID NO:37 may be used, the underlined portion of the sequence represents the core sequence of the isoleucine zipper that may be used in the cluster stradomers of the present invention. Thus, stradomer monomers of the present invention may comprise either the complete 88 amino acid sequence of the isoleucine zipper (ILZ), or the 28 amino acid core, along with one or more Fc domain monomers. The skilled artisan will also understand that the isoleucine zipper may be comprised of any portion of the zipper in addition to the core 28 amino acid structure, and thus may be comprised of more than 28 amino acids, but less than 88 amino acids of the isoleucine zipper. Specific examples of possible ILZ-IgG1 Fc domain constructs are shown as follows.

TABLE 2

|  | H | CH2 | CH3 | H | CH2 | CH3 |
|---|---|---|---|---|---|---|
| ILZ | 1 | 1 | 1 |  |  |  |
| ILZ | 1 | 1 | 1 | 1 | 1 |  |
| ILZ | 1 | 1 | 1 | 1 | 1 | 1 |
| ILZ | 1 | 1 | 1 | 3 | 3 | 3 |

Nomenclature:
H = hinge,
CH2 = constant heavy domain 2,
CH3 = constant heavy domain 3,
1 = IgG1,
3 = IgG3,
ILZ = isoleucine zipper domain These are only a few of many examples. Any of the IgG1 domains can, for example, be replaced with IgG3 domains. Additional proteins with ILZ domains include IgG1 chimeric proteins with the addition of N and/or C terminal sequences from other Ig molecules like IgM or IgE. These N and C terminal sequences can be hinge regions, constant domains or both.

Fc Fragment Stradomer

An "Fc fragment stradomer" is comprised of more than one Fc fragment. Under certain circumstances attributable to post-translational modification of the Fc fragment, the Fc fragment binds with sufficient strength to another Fc fragment to permit the formation of a molecule that binds to more than one Fcγ receptor. The post-translational modification that permits such binding includes glycosylation and methylation. The identity of the cell line in which the recombinant Fc fragments are produced, and conditions under which they are produced, govern whether Fc fragments will form Fc fragment stradomers. For example, a recombinant Fc fragment produced in a FreestyleMax CHO transient transfection cell forms multimers that are visible on western blots, binds according to a bivalent fit on plasmon resonance binding assay, and demonstrates biological activity in a dendritic cell assay comparable to IVIG. In contrast, the same recombinant Fc fragment produced in a stable CHO cell line does not form multimers of the Fc fragment on western blots, binds according to a univalent fit on Plasmon resonance binding assay, and does not demonstrate comparable biological activity. Thus an Fc fragment stradomer is a biomimetic compound capable of binding two or more Fcγ receptors.

As also used herein, the term "Fc dimer" is a dimer of Fc fragments (see FIG. 2A), the term "Fc trimer" is a trimer of Fc fragments, and the term "Fc multimer" is a multimer of Fc fragments (see FIG. 2B).

Stradobody

The present invention also encompasses stradobodies. As used herein, "stradobody" refers to a molecule comprising two or more Fc domains, preferably in the context of a stradomer (including serial stradomers, core stradomers, cluster stradomers and Fc fragment stradomers), to which one or more Fab domains is attached (see, e.g., FIGS. 8A-B and 9A-B). Thus, by virtue of such Fab domains, stradobodies have both antigen binding capacity, as well as stradomer Fcγ receptor binding activity. In some embodiments, the Fcγ receptor binding activity may be due to an ability to bind and cross-link FcγR equal to or greater than the Fc portion of a native structure holo-antibody. Preferably the Fab portion of the stradobody comprises both a heavy and a light chain. The variable heavy chain and the light chain may be independently from any compatible immunoglobulin such as IgA1, IgA2, IgM, IgD, IgE, IgG1, IgG2, IgG3, or IgG4, and may be from the same or different Ig isotype, but preferably are from the same Ig isotype. The light chains kappa or lambda may also be from different Ig isotypes. Stradobodies, like stradomers, can bind two or more FCγRs and modulate immune function.

Figure 8B:
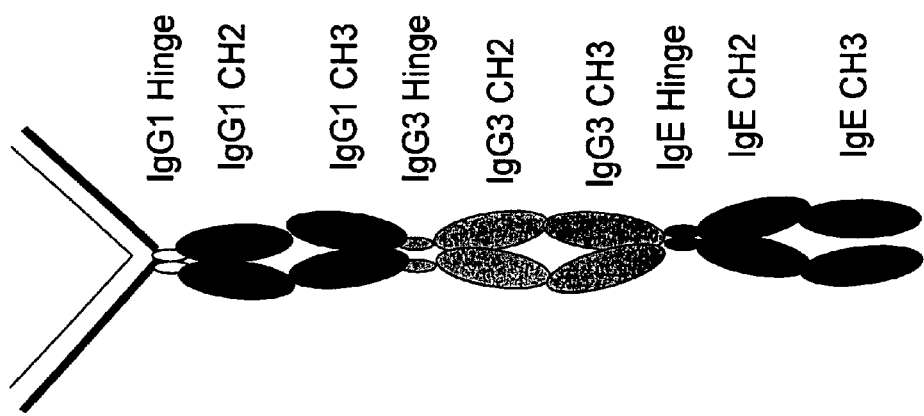
FIG. 8B shows a stradobody construct as in 8A but with a stradomer structure containing an IgG1 Fc linked to an IgG3 Fc linked to an IgE Fc.
Figure 8A:
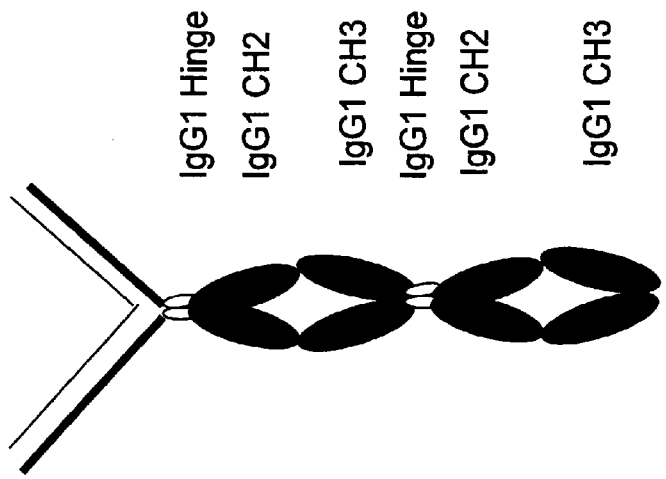
FIG. 8A shows a stradobody construct containing a Fab with a serial stradomer structure with each stradomer monomer containing two IgG1 CH2-CH3 derived Fc domain monomers.
Figures 9A, 9B:
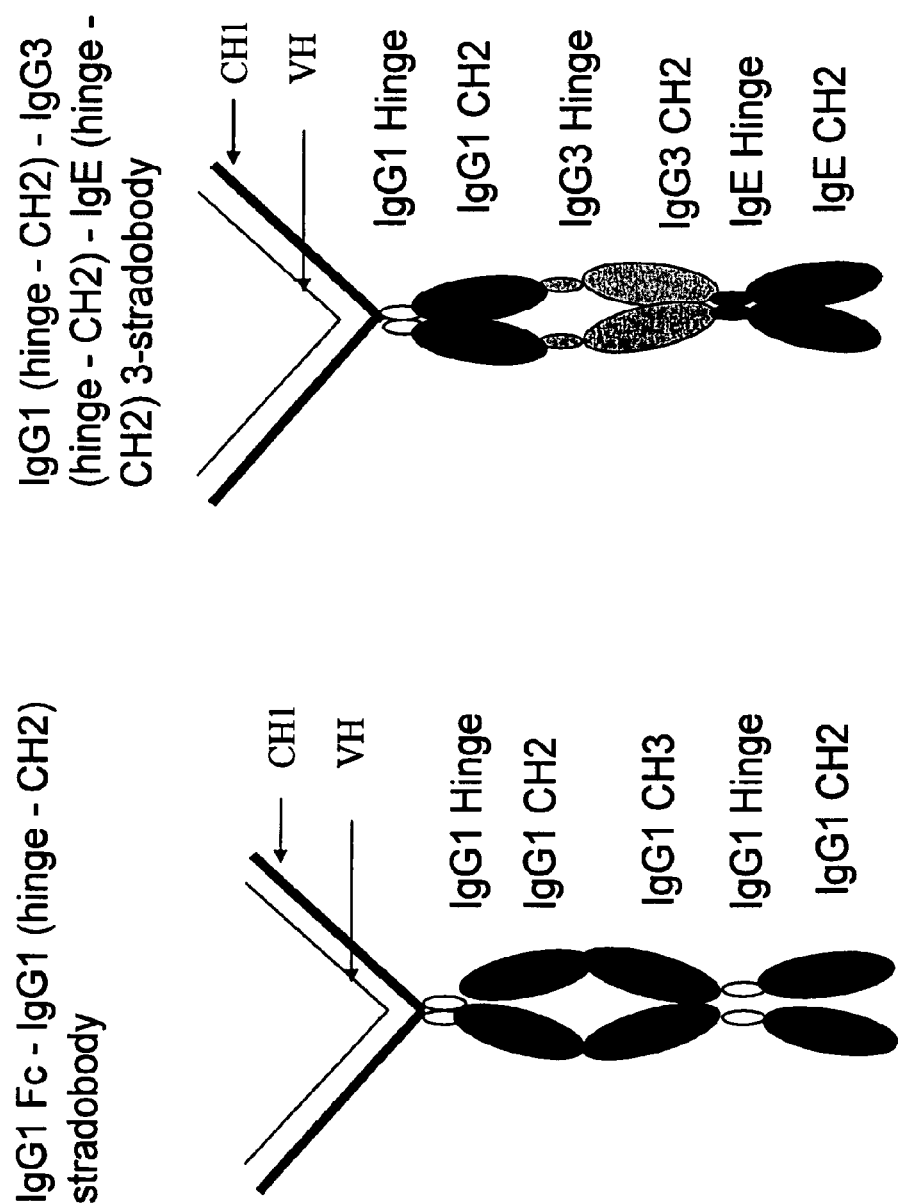
FIG. 9A shows an IgG1 Fc-IgG1 (hinge-CH2) stradobody.
FIG. 9B shows IgG1 (hinge-CH2)-IgG3 (hinge-CH2)-IgE (hinge-CH2) 3-stradobody.
Figure 10A:
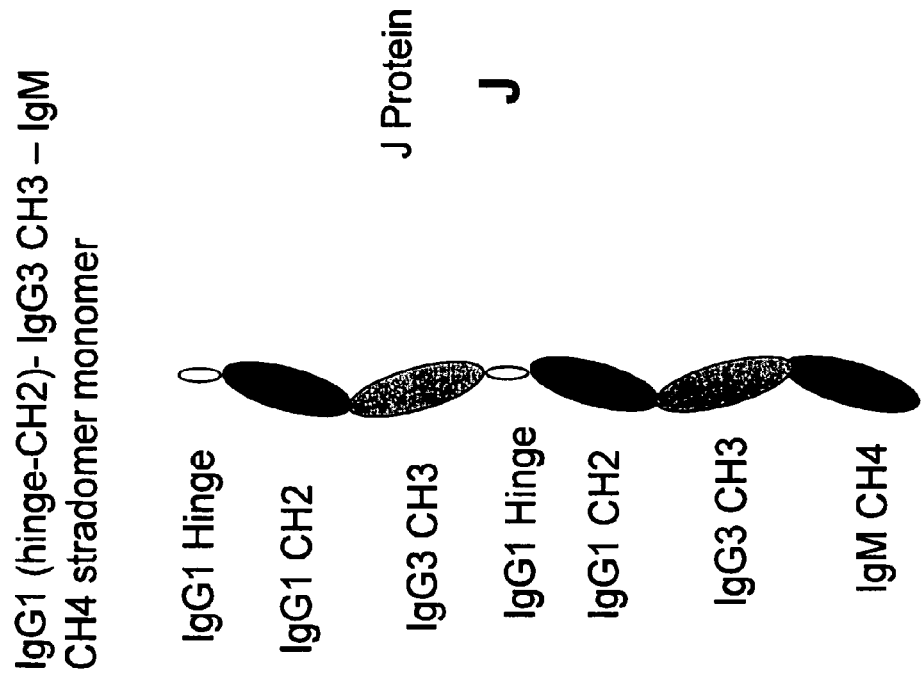
FIG. 10A shows an IgG1 (hinge-CH2)-IgG3 CH3-IgM CH4 stradomer monomer and a J chain protein.
Figure 10B:
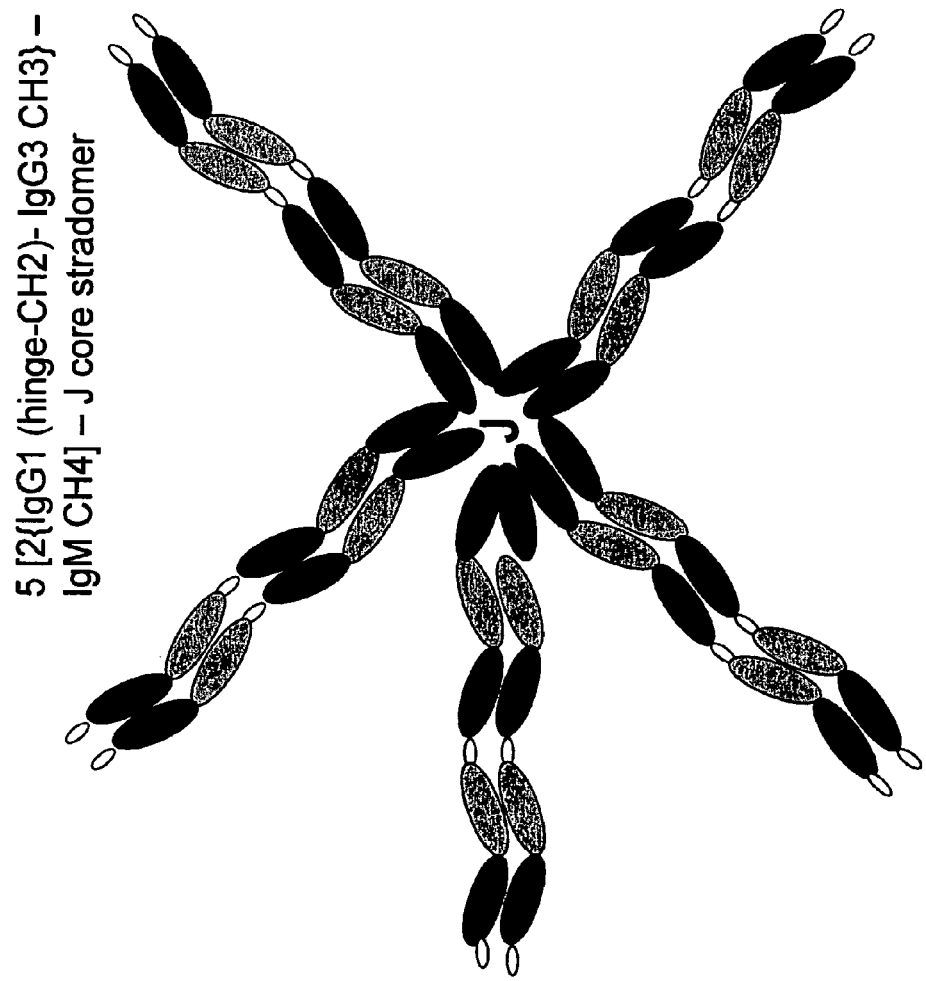
FIG. 10B shows a core stradomer based on a fivemer of the stradomer of FIG. 10A formed by association through the IgM CH4 domain to a J chain.
Figure 10C:
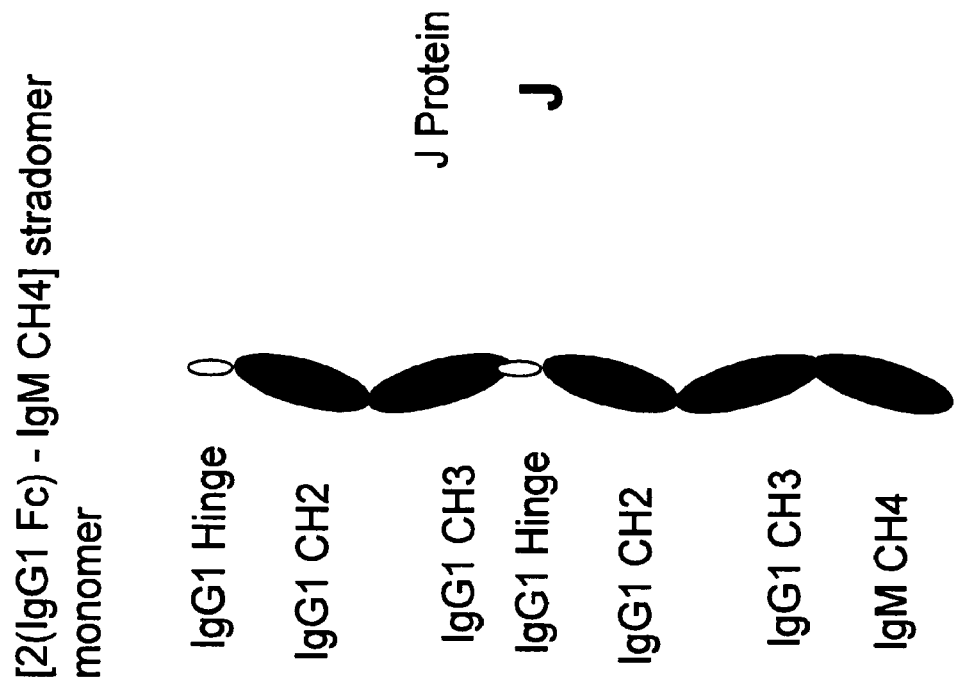
FIG. 10C shows an IgG1 Fc-IgG1 Fc-IgM CH4 stradomer monomer and a J chain protein.
Figure 10D:
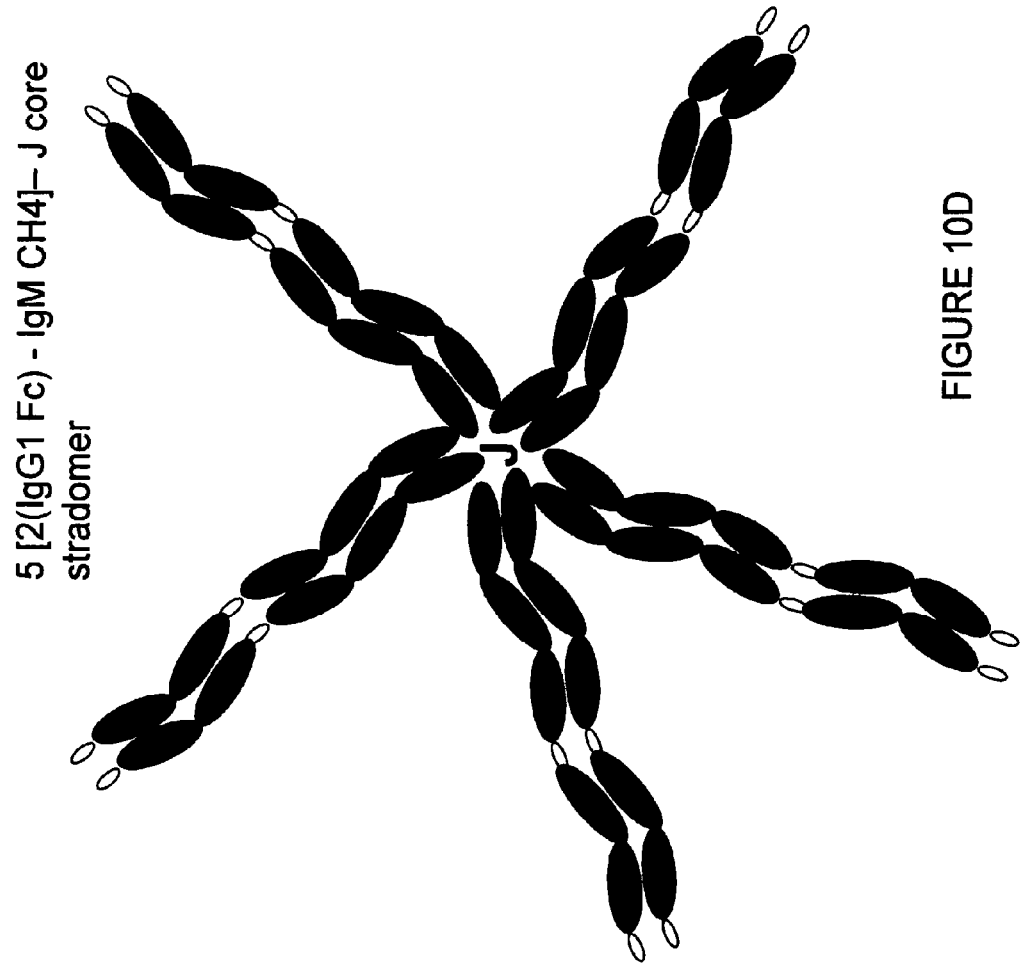
FIG. 10D shows a core stradomer based on a fivemer of the stradomer of FIG. 10C formed by association through the IgM CH4 domain to a J chain.

In one embodiment, the stradomers may have a Fab of an immunoglobulin linked to an Fc hinge (H) domain of a stradomer to generate a stradobody (e.g. FIGS. 8A & B). In another embodiment, the stradobody may be comprised of IgG1 Fc-IgG1 (hinge-CH2) (e.g., FIG. 9A). In other embodiments, the stradobody may be comprised of an IgG1 domain and hinge, an IgG3 domain and hinge and an IgGE domain and hinge (e.g., FIG. 9B). The Fab comprises both a heavy and a light chain as found in native immunoglobulin structures (FIG. 3A-B).

Stradobodies will possess the antigen binding properties of the Fab portion and the above described stradomer properties. Such a combination will serve to bind, cross-link, and activate Fcγ receptors on effector cells at a higher rate than can be accomplished by an Fc backbone of a holo-antibody, particularly in the environment of low epitope expression (e.g. the 90% of breast cancer patients whose tumors are not classified as her/2-neu high expressors), inducing ADCC in a higher percentage of patients. As indicated above, one or more antigen-binding Fab fragments can be added to the stradomers to form stradobodies. Preferably, polypeptides (other than the linkages described herein) added to stradomers are not all or parts of non-immunoglobulin polypeptides.

The Fab may be a chimeric structure comprised of human constant regions and non-human variable regions such as the variable region from a mouse, rat, rabbit, monkey, or goat antibody. One of ordinary skill in the art would be able to make a variety of Fab chimeric structures for incorporation into stradobodies using methodologies currently available and described in the scientific literature for such constructions. Thus, "humanized" stradobodies may be designed analogous to "humanized monoclonal antibodies.

Variants and Homologs

The skilled artisan will understand that the stradomers and other biomimetics of the present invention can be designed to include specific immunoglobulin Fc domains, such as two Fc domains from IgG1 (i.e., IgG1 hinge/IgG1 CH2/IgG1 CH3/IgG1 hinge/IgG1 CH2/IgG1 CH3). Such a stradomer could be constructed by first preparing a polynucleotide encoding two IgG1 Fc domain monomers (i.e., IgG1 hinge monomer/IgG1 CH2 monomer/IgG1 CH3 monomer/IgG1 hinge monomer/IgG1 CH2 monomer/IgG1 CH3 monomer), and then expressing stradomer monomers there from. Upon association of two such stradomer monomers a serial stradomer having two IgG1 Fc domains would be produced.

The stradomers and other biomimetics of the present invention can also be designed based on the identity of specific immunoglobulin Fc partial domains that comprise the Fc domains. For example, a serial stradomer could be produced having two Fc domains, where the first Fc domain comprises IgG1 hinge/IgG3 CH2/IgG1 CH3 and the second Fc domain comprises IgG3 hinge/IgG1 CH2/IgG3 CH3.

It is understood that the stradomers and other biomimetic molecules disclosed herein can be derived from any of a variety of species. Indeed, Fc domains, or Fc partial domains, in any one biomimetic molecules of the present invention can be derived from immunoglobulin from more than one (e.g., from two, three, four, five, or more) species. However, they will more commonly be derived from a single species. In addition, it will be appreciated that any of the methods disclosed herein (e.g., methods of treatment) can be applied to any species. Generally, the components of a biomimetic applied to a species of interest will all be derived from that species. However, biomimetics in which all the components are of a different species or are from more than one species (including or not including the species to which the relevant method is applied) can also be used.

The specific CH1, CH2, CH3 and CH4 domains and hinge regions that comprise the Fc domains and Fc partial domains of the stradomers and other biomimetics of the present invention may be independently selected, both in terms of the immunoglobulin subclass, as well as in the organism, from which they are derived. Accordingly, the stradomers and other biomimetics disclosed herein may comprise Fc domains and partial Fc domains that independently come from various immunoglobulin types such as IgG1, IgG2, IgG3, IgG4, IgA1, IgA2, IgD, IgE, and IgM. Similarly each Fc domain and partial Fc domain may be derived from various species, preferably a mammalian species, including non-human primates (e.g., monkeys, baboons, and chimpanzees), humans, murine, rattus, bovine, equine, feline, canine, porcine, rabbits, goats, deer, sheep, ferrets, gerbils, guinea pigs, hamsters, bats, birds (e.g., chickens, turkeys, and ducks), fish and reptiles to produce species-specific or chimeric stradomer molecules.

The individual Fc domains and partial Fc domains may also be humanized. One of skill in the art will realize that different Fc domains and partial Fc domains will provide different types of functionalities. For example, FcγRs bind specifically to IgG immunoglobulins and not other classes of immunoglobulins. Thus, one of skill in the art, intending to design a stradomer with multiple Fcγ receptor binding capacity, would design stradomer Fc domains that at least incorporate the well characterized Fcγ receptor binding sequences of IgG, including those in the IgG hinge region and the IgG CH2 & CH3 domains. One of ordinary skill in the art will also understand various deleterious consequences can be associated with the use of particular Ig domains, such as the anaphylaxis associated with IgA infusions. The biomimetics disclosed herein should generally be designed to avoid such effects, although in particular circumstances such effects may be desirable.

The present invention also encompasses stradomers comprising Fc domains and Fc partial domains having amino acids that differ from the naturally-occurring amino acid sequence of the Fc domain or Fc partial domain. Preferred Fc domains for inclusion in the biomimetic compounds of the present invention have a measurable specific binding affinity to either a holo-Fcγ receptor or a soluble extracellular domain portion of an FcγR. Primary amino acid sequences and X-ray crystallography structures of numerous Fc domains and Fc domain monomers are available in the art. See, e.g., Woof J M, Burton D R. Human antibody-Fc receptor interactions illuminated by crystal structures. Nat Rev Immunol. 2004 February; 4(2):89-99. Representative Fc domains with Fcγ receptor binding capacity include the Fc domains from human immunoglobulin G isotypes 1-4 ($hIgG_{1-4}$) (SEQ ID NOS: 1, 3, 5 and 7 respectively; see also FIG. 15A-D). (See FIG. 2 of Robert L. Shields, et al. High Resolution Mapping of the Binding Site on Human IgG1 for FcγRI, FcγRII, FcγRIII, and FcRn and Design of IgG1 Variants with Improved Binding to the FcγR. J. Biol. Chem., February 2001; 276: 6591-6604). These native sequences have been subjected to extensive structure-function analysis including site directed mutagenesis mapping of functional sequences[14]. Based on these prior structure-function studies and the available crystallography data, one of skill in the art may design functional Fc domain sequence variants (e.g., of SEQ ID NOS: 1, 3, 5 and 7) while preserving the Fc domain's Fcγ receptor binding capacity.

The amino acid changes may be found throughout the sequence of the Fc domain, or be isolated to particular Fc partial domains that comprise the Fc domain. The functional variants of the Fc domain used in the stradomers and other biomimetics of the present invention will have at least about 50%, 60%, 70%, 80%, 90%, 95%, 96%, 97%, 98% or 99% sequence identity to a native Fc domain. Similarly, the functional variants of the Fc partial domains used in the stradomers and other biomimetics of the present invention will have at least about 50%, 60%, 70%, 80%, 90%, 95%, 96%, 97%, 98% or 99% sequence identity to a native Fc partial domain.

The skilled artisan will appreciate that the present invention further encompasses the use of functional variants of Fc domain monomers in the construction of Fc fragment monomers, Fc partial fragment monomers, stradomer monomers and the other monomers of the present invention. The functional variants of the Fc domain monomers will have at least about 50%, 60%, 70%, 80%, 90%, 95%, 96%, 97%, 98% or 99% sequence identity to a native Fc domain monomer sequence.

Similarly, the present invention also encompasses the use of functional variants of Fc partial domain monomers in the construction of Fc fragment monomers, Fc partial fragment monomers, Fc domains monomers, stradomer monomers and the other monomers of the present invention. The functional variants of the Fc partial domain monomers will have at least about 50%, 60%, 70%, 80%, 90%, 95%, 96%, 97%, 98% or 99% sequence identity to a native Fc partial domain monomer sequence.

The amino acid changes may decrease, increase, or leave unaltered the binding affinity of the stradomer to the Fcγ receptor. Preferably such amino acid changes will be conservative amino acid substitutions, however, such changes include deletions, additions and other substitutions. Conservative amino acid substitutions typically include changes within the following groups: glycine and alanine; valine, isoleucine, and leucine; aspartic acid and glutamic acid; asparagine, glutamine, serine and threonine; lysine, histidine and arginine; and phenylalanine and tyrosine.

The term "functional variant" as used herein refers to a sequence related by homology to a reference sequence which is capable of mediating the same biological effects as the reference sequence (when a polypeptide), or which encodes a polypeptide that is capable of mediating the same biological effects as a polypeptide encoded by the reference sequence (when a polynucleotide). For example, a functional variant of any of the biomimetics herein described would have a specified homology or identity and would be capable of immune modulation of DCs. Functional sequence variants include both polynucleotides and polypeptides. Sequence identity is assessed generally using BLAST 2.0 (Basic Local Alignment Search Tool), operating with the default parameters: Filter-On, Scoring Matrix—BLOSUM62, Word Size—3, E value—10, Gap Costs—11,1 and Alignments—50.

From the above, it will be appreciated that stradomers of the present invention include stradomers having: (a) only naturally occurring Fc domains; (b) a mixture of naturally occurring Fc domains and Fc domains with altered amino acid sequences; and (c) only Fc domains with altered amino acid sequences. All that is required is that stradomers containing altered amino acid sequences have at least 25%; 30%; 40%; 50%; 60%; 70%; 80%; 90%; 95%; 96%; 97%; 98%; 99%; 99.5%; or 100% or even more of the ability of a corresponding stradomer comprising Fc domains with naturally-occurring sequences to bind to two or more Fcγ receptors.

The aforementioned Fcγ receptor binding sites occurring in the stradomers and stradobodies of the present invention may be altered in sequence through genetic engineering to predictably derive binding sites with altered binding capabilities and affinities relative to a native sequence. For example, specific residues may be altered that reduce Fc domain binding of the biomimetic compounds to FcγRII while increasing binding to FcγRIIIa. An example of an extensive mutagenesis based structure-function analysis for hIgG Fcγ receptor binding sequences is Robert L. Shields, et al. High Resolution Mapping of the Binding Site on Human IgG1 for FcγRI, FcγRII, FcγRIII, and FcRn and Design of IgG1 Variants with Improved Binding to the FcγR. J. Biol. Chem., February 2001; 276: 6591-6604. Similar studies have been performed on murine IgG Fc (mIgG Fc). Based on the structural and primary sequence homologies of native IgG Fc domains across species, one of skill in the art may translate the extensive structure-function knowledge of hIgG Fc and mIgG Fc to rational mutagenesis of all native Fcγ receptor binding site sequences in the biomimetic compounds of the present invention to design binding sites with particular Fcγ receptor specificities and binding affinities.

In addition to the amino acid sequence composition of native Fc domains, the carbohydrate content of the Fc domain is known to play an important role on Fc domain structure and binding interactions with FcγR. See, e.g., Robert L. Shields, et al. Lack of Fucose on Human IgG1 N-Linked Oligosaccharide Improves Binding to Human Fc RIII and Antibody-dependent Cellular Toxicity. J. Biol. Chem., July 2002; 277: 26733-26740 (doi:10.1074/jbc.M202069200); Ann Wright and Sherie L. Morrison. Effect of C2-Associated Carbohydrate Structure on Ig Effector Function: Studies with Chimeric Mouse-Human IgG1 Antibodies in Glycosylation Mutants of Chinese Hamster Ovary Cells. J. Immunol., April 1998; 160: 3393-3402. Carbohydrate content may be controlled using, for example, particular protein expression systems including particular cell lines or in vitro enzymatic modification. Thus, the present invention includes stradomers and stradobodies comprising Fc domains with the native carbohydrate content of holo-antibody from which the domains were obtained, as well as those biomimetic compounds have an altered carbohydrate content.

The addition to the polypeptide chain of an Fc partial domain, a multimerization region, or glycosylation changes may create a conformational change in the Fc domain permitting enhanced binding of the Fc domain to an Fcγ receptor. Thus, seemingly minor changes to the polypeptide may also create a stradomer capable of binding multiple Fcγ receptors.

Partial Domains and Partial Fragments

The skilled artisan will further recognize that the Fc domains and Fc partial domains used in the embodiments of the present invention need not be full-length versions. That is, the present invention encompasses the use of Fc domain monomers and Fc partial domain monomers lacking amino acids from the amino terminus, carboxy terminus or middle of the particular Fc domain monomers and Fc partial domain monomers that comprise the stradomers and other biomimetics of the present invention.

For example, the binding site on human IgG immunoglobulins for Fcγ receptors has been described (e.g. Radaev, S., Sun, P., 2001. Recognition of Immunoglobulins by Fcγ Receptors. Molecular Immunology 38, 1073-1083; Shields, R. L. et. al., 2001. High Resolution Mapping of the Binding Site on Human IgG1 for FcγRI, FcγRII, FcγRIII, and FcRn and Design of IgG1 Variants with Improved Binding to the FcγR. J. Biol. Chem. 276 (9), 6591-6604). Based on that knowledge, one may remove amino acids from the Fc domain of these immunoglobulins and determine the effects on the binding interaction between the Fc domain and the receptor. Thus, the present invention encompasses IgG Fc domains having at least about 90% of the amino acids encompasses positions 233 through 338 of the lower hinge and CH2 as defined in Radaev, S., Sun, P., 2001

Fc partial domains of IgG immunoglobulins of the present invention include all or part of the hinge region, all or part of the CH2 domain, and all or part of the CH3 domain.

The IgG Fc partial domains having only a part of the hinge region, part of the CH2 domain or part of the CH3 domain are constructed from Fc partial domain monomers. Thus, the present invention includes IgG hinge region monomers derived from the N-terminus of the hinge region or the C-terminus of the hinge region. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 (up to 15 for IgG1, up to 12 for IgG2, up to 62 for IgG3, up to 12 for IgG4) amino acids of the hinge region.

The present invention also includes IgG CH2 domain monomers derived from the N-terminus of the CH2 domain or the C-terminus of the CH2 domain. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 (up to 110 for IgG1 and IgG3, up to 109 for IgG2 and IgG4) amino acids of the CH2 domain.

The present invention further includes IgG CH3 domain monomers derived from the N-terminus of the CH3 domain or the C-terminus of the CH3 domain. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, or 107 (up to 106 for IgG1 and IgG3, up to 107 for IgG2 and IgG4) amino acids of the CH3 domain.

Fc partial domains of IgA1, IgA2 and IgD immunoglobulins of the present invention include all or part of the hinge region, all or part of the CH2 domain, and all or part of the CH3 domain. Moreover all or part of the CH1 domain of the IgA1, IgA2, or IgD immunoglobulin can be used as Fc partial domains.

The IgA1, IgA2 and IgD partial domains having only a part of the hinge region, part of the CH1 domain, part of the CH2 domain or part of the CH3 domain are constructed from Fc partial domain monomers. Thus, the present invention includes hinge region monomers derived from the N-terminus of the hinge region or the C-terminus of the hinge region of IgA1, IgA2 or IgD. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64 (up to 26 for IgA1, up to 13 for IgA2, up to 64 for IgD) amino acids of the hinge region.

The present invention includes CH2 domain monomers derived from the N-terminus of the CH2 domain or the C-terminus of the CH2 domains of IgA1, IgA2 or IgD. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, or 107 (up to 102 for IgA1, up to 96 for IgA2, up to 107 for IgD) amino acids of the CH2 domain.

The present invention includes CH3 domains derived from the N-terminus of the CH3 domain or the C-terminus of the CH3 domains of IgA1, IgA2 or IgD. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, or 131 (up to 113 for IgA1, up to 131 for IgA2, up to 110 for IgD) amino acids of the CH3 domain.

Fc partial domains of IgM and IgE immunoglobulins of the present invention include all or part of the hinge/CH2 domain, all or part of the CH3 domain, and all or part of the CH4 domain of these molecules. Moreover all or part of the CH1 domain of the IgM and IgE immunoglobulins can be used as Fc partial domains.

The IgM and IgE partial domains having only a part of the hinge/CH2 domain, part of the CH3 domain, or part of the CH4 domain are constructed from Fc partial domain monomers. Thus, the present invention includes hinge/CH2 domain monomers derived from the N-terminus of the hinge/CH2 domain or the C-terminus of the hinge/CH2 domain of IgM or IgE. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, or 112 (up to 112 for IgM, up to 109 for IgE) amino acids of the hinge/CH2 domain.

The present invention includes IgM and IgE CH3 domain monomers derived from the N-terminus of the CH3 domain or the C-terminus of the CH3 domain of IgM or IgE. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, or 106 (up to 106 for IgM, up to 105 for IgE) amino acids of the CH3 domain.

The present invention includes IgM and IgE CH4 domain monomers derived from the N-terminus of the CH4 domain or the C-terminus of the CH4 domain of IgM or IgE. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 (up to 130 for IgM, up to 105 for IgE) amino acids of the CH4 domain. However, parts of the CH4 domain of IgM or IgE that include the C-terminal end of the CH4 domain will preferably be more than 18 amino acids in length, and more preferably will be more than 30 amino acids in length, and most preferably will be more than 50 amino acids in length.

From the above, it will be appreciated that different embodiments of the present invention include stradomers containing: (a) full-length Fc domains; (b) a mixture of full-length Fc domains and Fc partial domains; and (c) Fc partial domains. In each of these embodiments, the stradomers may further comprise CH1 domains. As discussed herein, in each embodiment of the stradomers of the present invention, the stradomers have the ability to bind two or more Fcγ receptors.

Preferred Embodiments of Stradomers and Stradomer Monomers

The following are examples of stradomer monomers of the present invention:

1. IgG1 hinge-IgG1 CH2-IgG1 CH3-IgG1 hinge-IgG1 CH2-IgG1 CH3
2. IgG1 hinge-IgG3 CH2-IgG1 CH3-IgG1 hinge-IgG1 CH2-IgG1 CH3
3. IgG1 hinge-IgG1 CH2-IgG3 CH3-IgG1 hinge-IgG1 CH2-IgG1 CH3
4. IgG1 hinge-IgG1 CH2-IgG1 CH3-IgG3 hinge-IgG1 CH2-IgG1 CH3
5. IgG1 hinge-IgG1 CH2-IgG1 CH3-IgG1 hinge-IgG3 CH2-IgG1 CH3
6. IgG1 hinge-IgG1 CH2-IgG1 CH3-IgG1 hinge-IgG1 CH2-IgG3 CH3
7. IgG1 hinge-IgG3 CH2-IgG1 CH3-IgG3 hinge-IgG1 CH2-IgG1 CH3
8. IgG3 hinge-IgG1 CH2-IgG1 CH3-IgG1 hinge-IgG1 CH2-IgG1 CH3
9. IgG3 hinge-IgG1 CH2-IgG1 CH3-IgG3 hinge-IgG1 CH2-IgG1 CH3
10. IgG3 hinge-IgG1 CH2-IgG1 CH3-IgG1 hinge-IgG1 CH2-IgG3 CH3-IgG1 hinge-IgG3 CH2-IgG3 CH3
11. IgG1 hinge-IgG1 CH2-IgG1 CH3-IgG3 hinge-IgG3 CH2-IgG3 CH3-IgG1 hinge-IgG1 CH2-IgG1 CH3
12. IgG1 hinge-IgG1 CH2-IgG1 CH3-IgG3 hinge-IgG1 hinge-IgG3 CH2-IgG3 CH3-IgG1 hinge-IgG1 CH2-IgG1 CH3
13. IgG1 hinge-IgG1 CH2-IgG1 CH3-IgG3 hinge-IgG3 CH2-IgG3 CH3-IgG1 hinge-IgG2 CH2-IgG3 CH3.
14. IgG1 hinge-IgG1 CH2-IgG1 CH3-IgG4 hinge-IgG4 CH2-IgG4 CH3-IgG1 hinge-IgG1 CH2-IgG1 CH3

In each of these embodiments, and the other embodiments presented herein, it will be understood that domain linkages may be used to link the individual Fc partial domain monomers that make up the stradomer monomers. In one embodiment, the Fc partial domain monomers shown for each of the stradomer monomers set forth above are human Fc partial domain monomers.

The present invention includes stradomers comprising two or more of the stradomer monomers listed above. In preferred embodiments, the present invention includes serial stradomers comprising two identical stradomer monomers provided above.

As indicated above, the stradomer functionality of binding more than one Fcγ receptor can also be achieved by incorporating a J chain as a core moiety in a core stradomer, similar to a natural IgM or IgA molecule. In native IgA and IgM immunoglobulins the joining (J) chain is a 15 kDa peptide that joins the heavy and light chains of IgA and IgM antibodies through disulfide bridges with an 18 amino acid "secretory tailpiece" of the Fc portions of the antibodies. Braathen, R., et al., The Carboxyl-terminal Domains of IgA and IgM Direct Isotype-specific Polymerization and Interaction with the Polymeric Immunoglobulin Receptor, *J. Bio. Chem.* 277(45), 42755-42762 (2002).

Such core stradomers may be comprised of stradomer monomers containing a naturally occurring CH4 Fc domain, preferably from IgM immunoglobulins, thereby permitting association of the stradomers comprising such stradomer monomers to a J chain (see FIGS. 10A-10D). The following are examples of stradomer monomers which can self-dimerize to form a stradomer and then be associated with a J chain to form a core stradomer composed of a plurality (e.g., two, three, four, five, six, seven, eight, nine, ten, eleven, twelve, fifteen, eighteen, twenty, or more) of stradomers:

1. IgG1 hinge-IgG1 CH2-IgG1 CH3-IgG1 hinge-IgG1 CH2-IgG1 CH3-IgM CH4 (see FIGS. 10C-10D)
2. IgG1 hinge-IgG3 CH2-IgG1 CH3-IgG1 hinge-IgG1 CH2-IgG1 CH3-IgM CH4
3. IgG1 hinge-IgG1 CH2-IgG3 CH3-IgG1 hinge-IgG1 CH2-IgG1 CH3-IgM CH4 (see FIGS. 10A-10B)
4. IgG1 hinge-IgG1 CH2-IgG1 CH3-IgG3 hinge-IgG1 CH2-IgG1 CH3-IgM CH4
5. IgG1 hinge-IgG1 CH2-IgG1 CH3-IgG1 hinge-IgG3 CH2-IgG1 CH3-IgM CH4
6. IgG1 hinge-IgG1 CH2-IgG1 CH3-IgG1 hinge-IgG1 CH2-IgG1 CH3-IgM CH4
7. IgG1 hinge-IgG1 CH2-IgG1 CH3-IgG1 hinge-IgG1 CH2-IgG3 CH3-IgM CH4
8. IgG1 hinge-IgG3 CH2-IgG1 CH3-IgG3 hinge-IgG1 CH2-IgG1 CH3-IgM CH4
9. IgG3 hinge-IgG1 CH2-IgG1 CH3-IgG1 hinge-IgG1 CH2-IgG1 CH3-IgM CH4
10. IgG3 hinge-IgG1 CH2-IgG1 CH3-IgG3 hinge-IgG1 CH2-IgG1 CH3-IgM CH4
11. IgG3 hinge-IgG1 CH2-IgG1 CH3-IgG1 hinge-IgG1 CH2-IgG1 hinge IgG3 CH2-IgG3 CH3-IgM CH4

In each of these embodiments, and the other embodiments presented herein, it will be understood that domain linkages may be used to link the individual Fc partial domain monomers that make up the stradomer monomers. In one embodiment, the Fc partial domain monomers shown for each of the stradomer monomers set forth above are human Fc partial domain monomers.

Core stradomers based on a J chain may be also be comprised of Fc fragments, Fc partial fragments and/or Fc domains that have a CH4 Fc domain. In this example, each of the Fc fragments, Fc partial fragments and Fc domains having a CH4 Fc domain linked to the core moiety may contain only one Fcγ receptor binding site but in the context of such a core stradomer, forms a biologically active biomimetic containing more than one Fcγ receptor binding site. A skilled artisan will recognize that the Fc partial domains from different native immunoglobulins can be used to generate the functional Fc fragments, Fc partial fragments and Fc domains of such a core stradomer. The following are examples of monomers of Fc fragments, Fc partial fragments and Fc domains which can self-dimerize and then be associated with a J chain to form a core stradomer:

1. IgG1 hinge-IgG1 CH2-IgG1 CH3-IgM CH4
2. IgG3 hinge-IgG1 CH2-IgG1 CH3-IgM CH4
3. IgG1 hinge-IgG3 CH2-IgG1 CH3-IgM CH4
4. IgG1 hinge-IgG1 CH2-IgG3 CH3-IgM CH4
5. IgG1 hinge-IgG3 CH2-IgG3 CH3-IgM CH4
6. IgG3 hinge-IgG3 CH2-IgG1 CH3-IgM CH4
7. IgG3 hinge-IgG3 CH2-IgG1 CH3-IgM CH4
8. IgG1 hinge-IgG3 CH2-IgG2 CH3-IgM CH4
9. IgG1 hinge-IgG3 hinge-IgG3 CH2-IgG2 CH3-IgM CH4
10. IgG1 hinge-IgG1 CH2-IgG1 CH3-IgE CH4-IgM CH4

In each of these embodiments, and the other embodiments presented herein, it will be understood that domain linkages may be used to link the individual Fc partial domain monomers that make up the stradomer monomers. In one embodiment, the Fc partial domain monomers shown for each of the stradomer monomers set forth above are human Fc partial domain monomers.

It is clear from the above examples that stradomer monomers can be of differing lengths and compositions to accomplish the goal, when associated through self-aggregation or inter-stradomer monomer linkages to a second stradomer monomer and associated with a J chain, producing a core stradomer containing more than one Fcγ receptor binding site. The examples are in no way limiting and one skilled in the art will appreciate that multiple other stradomer configurations in stradomers are possible.

Fcγ Receptors

The terms "FcγR" and "Fcγ receptor" as used herein includes each member of the Fc gamma receptor family of proteins expressed on immune cell surfaces as described in Nimmerjahn F and Ravetch J V. Fcgamma receptors: old friends and new family members. Immunity. 2006 January; 24(1):19-28, or as may later be defined. It is intended that the term "FcγR" herein described encompasses all members of the Fc gamma RI, RII, and RIII families. Fcγ receptor includes low affinity and high affinity Fcγ receptors, including but not limited to FcγRI (CD64); FcγRII (CD32) and its isotypes and allotypes FcγRIIa LR, FcγRIIa HR, FcγRIIb, and FcγRIIc; FcγRIII (CD16) and its isotypes FcγRIIIa and FcγRIIIb. A skilled artisan will recognize that the present invention, which includes compounds that bind to FcγR, will apply to future FcγRs and associated isotypes and allotypes that may not yet have been discovered.

It has been described that IVIG binds to and fully saturates the neonatal Fc receptor ("FcRn") and that such competitive inhibition of FcRn may play an important role in the biological activity of IVIG (e.g. Mechanisms of Intravenous Immunoglobulin Action in Immune Thrombocytopenic Purpura. F. Jin, J. Balthasar. Human Immunology, 2005, Volume 66, Issue 4, Pages 403-410.) Since immunoglobulins that bind strongly to Fcγ receptors also bind at least to some degree to FcRn, a skilled artisan will recognize that stradomers which are capable of binding to more than one Fcγ receptor will also bind to and may fully saturate the FcRn.

"Immunological activity of aggregated native IgG" refers to the properties of multimerized IgG which impact the functioning of an immune system upon exposure of the immune system to the IgG aggregates. Specific properties of native multimerized IgG includes altered specific binding to FcγRs, cross-linking of FcγRs on the surfaces of immune cells, or an effector functionality of multimerized IgG such as antibody dependent cell-mediated cytotoxicity (ADCC), phagocytosis (ADCP), or complement fixation (See, e.g., Nimmerjahn F, Ravetch J V. The anti-inflammatory activity of IgG: the intravenous IgG paradox. J Exp Med. 2007; 204:11-15; Augener W, Friedman B, Brittinger G. Are aggregates of IgG the effective part of high-dose immunoglobulin therapy in adult idiopathic thrombocytopenic purpura (ITP)? Blut. 1985; 50:249-252; Arase N, Arase H, Park S Y, Ohno H, Ra C, Saito T. Association with FcRgamma is essential for activation signal through NKR-P1 (CD161) in natural killer (NK) cells and NK1.1+ T cells. J Exp Med. 1997; 186:1957-1963; Teeling J L, Jansen-Hendriks T, Kuijpers T W, et al. Therapeutic efficacy of intravenous immunoglobulin preparations depends on the immunoglobulin G dimers: studies in experimental immune thrombocytopenia. Blood. 2001; 98:1095-1099; Anderson C F, Mosser D M. Cutting edge: biasing immune responses by directing antigen to macrophage Fc gamma receptors. J Immunol. 2002; 168:3697-3701; Jefferis R, Lund J. Interaction sites on human IgG-Fc for Fc[gamma]R: current models. Immunology Letters. 2002; 82:57; Banki Z, Kacani L, Mullauer B, et al. Cross-Linking of CD32 Induces Maturation of Human Monocyte-Derived Dendritic Cells Via NF-{kappa}B Signaling Pathway. J Immunol. 2003; 170:3963-3970; Siragam V, Brinc D, Crow A R, Song S, Freedman J, Lazarus A H. Can antibodies with specificity for soluble antigens mimic the therapeutic effects of intravenous IgG in the treatment of autoimmune disease? J Clin Invest. 2005; 115:155-160). These properties are generally evaluated by comparison to the properties of monomeric IgG.

"Comparable to or superior to an Fcγ receptor cross-linking or an effector functionality of a plurality of naturally-occurring, aggregated IgG immunoglobulins" as used herein means the stradomer generates an assay value of about 70% or more of the value achieved using 1V1G. In some embodiments, the assay value is at least within the standard error range of the assay values achieved using 1V1G. In other embodiments, the assay value is 110% or higher than that of IVIG. Assays for FcγR cross-linking are well known to those of ordinary skill in the art (see e.g., Falk Nimmerjahn and Jeffrey Ravetch. Fcγ receptors as regulators of immune responses. *Nature Reviews Immunology*, advanced published on line Dec. 7, 2007).

"Immune modulating activities," "modulating immune response," "modulating the immune system," and "immune modulation" mean altering immune systems by changing the activities, capacities, and relative numbers of one or more immune cells, including maturation of a cell type within its cell type or into other cell types. For example, immune modulation of immature monocytes may lead to greater populations of more mature monocytes, dendritic cells, macrophages, or osteoclasts, all of which are derived from immature monocytes. For example, immune cell receptors may be bound by immunologically active biomimetics and activate intracellular signaling to induce various immune cell changes, referred to separately as "activating immune modulation." Blockading immune cell receptors to prevent receptor activation is also encompassed within "immune modulation" and may be separately referred to as "inhibitory immune modulation."

Modulation of maturation of a monocyte refers to the differentiation of a monocyte into a mature DC, a macrophage, or an osteoclast. Differentiation may be modulated to accelerate the rate of maturation and/or to increase the number of monocytes undergoing differentiation. Alternatively, differentiation may be reduced in terms of rate of differentiation and/or number of cells undergoing differentiation.

The term "isolated" polypeptide or peptide as used herein refers to a polypeptide or a peptide which either has no naturally-occurring counterpart or has been separated or purified from components which naturally accompany it, e.g., in tissues such as pancreas, liver, spleen, ovary, testis, muscle, joint tissue, neural tissue, gastrointestinal tissue, or breast tissue or tumor tissue (e.g., breast cancer tissue), or body fluids such as blood, serum, or urine. Typically, the polypeptide or peptide is considered "isolated" when it is at least 70%, by dry weight, free from the proteins and other naturally-occurring organic molecules with which it is naturally associated. Preferably, a preparation of a polypeptide (or peptide) of the invention is at least 80%, more preferably at least 90%, and most preferably at least 99%, by dry weight, the polypeptide (peptide), respectively, of the invention. Since a polypeptide or peptide that is chemically synthesized is, by its nature, separated from the components that naturally accompany it, the synthetic polypeptide or peptide is "isolated."

An isolated polypeptide (or peptide) of the invention can be obtained, for example, by extraction from a natural source (e.g., from tissues or bodily fluids); by expression of a recombinant nucleic acid encoding the polypeptide or peptide; or by chemical synthesis. A polypeptide or peptide that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Pharmaceutical Compositions

Administration of the immunologically active biomimetic compositions described herein will be via any common route, orally, parenterally, or topically. Exemplary routes include, but are not limited to oral, nasal, buccal, rectal, vaginal, ophthalmic, subcutaneous, intramuscular, intraperitoneal, intravenous, intraarterial, intratumoral, spinal, intrathecal, intra-articular, intra-arterial, sub-arachnoid, sublingual, oral mucosal, bronchial, lymphatic, intra-uterine, subcutaneous, intratumor, integrated on an implantable device, intradural, intracortical, or dermal. Such compositions would normally be administered as pharmaceutically acceptable compositions as described herein. In a preferred embodiment the isolated immunologically active biomimetic is administered intravenously.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The immunologically active biomimetic compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the immunologically active biomimetic in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further, one embodiment is an immunologically active biomimetic composition suitable for oral administration is provided in a pharmaceutically acceptable carrier with or without an inert diluent. The carrier should be assimulable or edible and includes liquid, semi-solid, i.e., pastes, or solid carriers. Except insofar as any conventional media, agent, diluent or carrier is detrimental to the recipient or to the therapeutic effectiveness of an immunologically active biomimetic preparation contained therein, its use in an orally administrable an immunologically active biomimetic composition for use in practicing the methods of the present invention is appropriate. Examples of carriers or diluents include fats, oils, water, saline solutions, lipids, liposomes, resins, binders, fillers and the like, or combinations thereof. The term "oral administration" as used herein includes oral, buccal, enteral or intragastric administration.

In one embodiment, the composition is combined with the carrier in any convenient and practical manner, i.e., by solution, suspension, emulsification, admixture, encapsulation, microencapsulation, absorption and the like. Such procedures are routine for those skilled in the art.

In a specific embodiment, the immunologically active biomimetic composition in powder form is combined or mixed thoroughly with a semi-solid or solid carrier. The mixing can be carried out in any convenient manner such as grinding. Stabilizing agents can be also added in the mixing process in order to protect the composition from loss of therapeutic activity through, i.e., denaturation in the stomach. Examples of stabilizers for use in an orally administrable composition include buffers, antagonists to the secretion of stomach acids, amino acids such as glycine and lysine, carbohydrates such as dextrose, mannose, galactose, fructose, lactose, sucrose, maltose, sorbitol, mannitol, etc., proteolytic enzyme inhibitors, and the like. More preferably, for an orally administered composition, the stabilizer can also include antagonists to the secretion of stomach acids.

Further, the immunologically active biomimetic composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, i.e., U.S. Pat. No. 5,629,001. Upon reaching the small intestines, the basic pH therein dissolves the coating and permits the composition to be released to interact with intestinal cells, e.g., Peyer's patch M cells.

In another embodiment, the immunologically active biomimetic composition in powder form is combined or mixed thoroughly with materials that create a nanoparticle encapsulating the immunologically active biomimetic or to which the immunologically active biomimetic is attached. Each nanoparticle will have a size of less than or equal to 100 microns. The nanoparticle may have mucoadhesive properties that allow for gastrointestinal absorption of an immunologically active biomimetic that would otherwise not be orally bioavailable.

In another embodiment, a powdered composition is combined with a liquid carrier such as, i.e., water or a saline solution, with or without a stabilizing agent.

A specific immunologically active biomimetic formulation that may be used is a solution of immunologically active biomimetic protein in a hypotonic phosphate based buffer that is free of potassium where the composition of the buffer is as follows: 6 mM sodium phosphate monobasic monohydrate, 9 mM sodium phosphate dibasic heptahydrate, 50 mM sodium chloride, pH 7.0.+/−0.1. The concentration of immunologically active biomimetic protein in a hypotonic buffer may range from 10 microgram/ml to 100 milligram/ml. This formulation may be administered via any route of administration, for example, but not limited to intravenous administration.

Further, an immunologically active biomimetic composition for topical administration which is combined with a semi-solid carrier can be further formulated into a cream or gel ointment. A preferred carrier for the formation of a gel ointment is a gel polymer. Preferred polymers that are used to manufacture a gel composition of the present invention include, but are not limited to carbopol, carboxymethylcellulose, and pluronic polymers. Specifically, a powdered Fc multimer composition is combined with an aqueous gel containing an polymerization agent such as Carbopol 980 at strengths between 0.5% and 5% wt/volume for application to the skin for treatment of disease on or beneath the skin. The term "topical administration" as used herein includes application to a dermal, epidermal, subcutaneous or mucosal surface.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Office of Biologics standards.

The route of administration will vary, naturally, with the location and nature of the disease being treated, and may include, for example intradermal, transdermal, parenteral, intravenous, intramuscular, intranasal, subcutaneous, percutaneous, intratracheal, intraperitoneal, intratumoral, perfusion, lavage, direct injection, and oral administration.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intratumoral, intraocular, or intraarticular administration.

Below are specific examples of various pharmaceutical formulation categories and preferred routes of administration, as indicated, for specific exemplary diseases:

Buccal or sub-lingual dissolvable tablet: angina, polyarteritis nodosa.

Intravenous: Idiopathic Thrombocytopenic Purpura, Inclusion Body Myositis, Paraproteinemic IgM demyelinating Polyneuropathy, Necrotizing fasciitis, Pemphigus, Gangrene, Dermatomyositis, Granuloma, Lymphoma, Sepsis, Aplastic anemia, Multisystem organ failure, Multiple Myeloma and Monoclonal Gammopathy of Unknown Significance, Chronic Inflammatory Demyelinating Polyradiculoneuropathy, Inflammatory Myopathies, Thrombotic thrombocytopenic purpura, Myositis, Anemia, Neoplasia, Hemolytic anemia, Encephalitis, Myelitis, Myelopathy especially associated with Human T-cell lymphotropic virus-1, Leukemia, Multiple sclerosis and optic neuritis, Asthma, Epidermal necrolysis, Lambert-Eaton myasthenic syndrome, Myasthenia gravis, Ncuropathy, Uveitis, Guillain-Barre syndrome, Graft Versus Host Disease, Stiff Man Syndrome, Paraneoplastic cerebellar degeneration with anti-Yo antibodies, paraneoplastic encephalomyelitis and sensory neuropathy with anti-Hu antibodies, systemic vasculitis, Systemic Lupus Erythematosus, autoimmune diabetic neuropathy, acute idiopathic dysautonomic neuropathy, Vogt-Koyanagi-Harada Syndrome, Multifocal Motor Neuropathy, Lower Motor Neuron Syndrome associated with anti-/GM1, Demyelination, Membranoproliferative glomerulonephritis, Cardiomyopathy, Kawasaki's disease, Rheumatoid arthritis, and Evan's syndrome IM—ITP, CIDP, MS, dermatomyositis, mysasthenia gravis, muscular dystrophy. The term "intravenous administration" as used herein includes all techniques to deliver a compound or composition of the present invention to the systemic circulation via an intravenous injection or infusion.

Dermal gel, lotion, cream or patch: vitiligo, Herpes zoster, acne, chelitis.

Rectal suppository, gel, or infusion: ulcerative colitis, hemorrhoidal inflammation.

Oral as pill, troche, encapsulated, or with enteric coating: Crohn's disease, celiac sprue, irritable bowel syndrome, inflammatory liver disease, Barrett's esophagus.

Intra-cortical: epilepsy, Alzheimer's, multiple sclerosis, Parkinson's Disease, Huntingdon's Disease.

Intra-abdominal infusion or implant: endometriosis.

Intra-vaginal gel or suppository: bacterial, trichomonal, or fungal vaginitis.

Medical devices: coated on coronary artery stent, prosthetic joints.

The immunologically active biomimetics described herein may be administered in dosages from about 0.01 mg per kg to about 300 mg per kg body weight, and especially from 0.01 mg per kg body weight to about 300 mg per kg body weight, and may be administered at least once daily, weekly, biweekly or monthly. A biphasic dosage regimen may be used wherein the first dosage phase comprises about 0.1% to about 10% of the second dosage phase.

Therapeutic Applications of Stradomers and Stradobodies

Based on rational design and in vitro and in vivo validations, the immunologically active biomimetics of the present invention will serve as important biopharmaceuticals for treating autoimmune diseases and for modulating immune function in a variety of other contexts such as bioimmunotherapy for cancer and inflammatory diseases. Medical conditions suitable for treatment with the immunologically active biomimetics described herein include those currently routinely treated with hIVIG or in which hIVIG has been found to be clinically useful such as autoimmune cytopenias, Guillain-Barre' syndrome, myasthenia gravis, anti-Factor VIII autoimmune disease, dermatomyositis, vasculitis, and uveitis (See, F. G. van der Meche, P. I. Schmitz, N. Engl. J. Med. 326, 1123 (1992); P. Gajdos et al., Lancet i, 406 (1984); Y. Sultan, M. D. Kazatchkine, P. Maisonneuve, U. E. Nydegger, Lancet ii, 765 (1984); M. C. Dalakas et al., N. Engl. J. Med. 329, 1993 (1993); D. R. Jayne, M. J. Davies, C. J. Fox, C. M. Black, C. M. Lockwood, Lancet 337, 1137 (1991); P. LeHoang, N. Cassoux, F. George, N. Kullmann, M. D. Kazatchkine, Ocul. Immunol. Inflamm. 8, 49 (2000)) and those cancers or inflammatory disease conditions in which a monoclonal antibody may be used or is already in clinical use. Conditions included among those that may be effectively treated by the compounds that are the subject of this invention include an inflammatory disease with an imbalance in cytokine networks, an autoimmune disorder mediated by pathogenic autoantibodies or autoaggressive T cells, or an acute or chronic phase of a chronic relapsing autoimmune, inflammatory, or infectious disease or process.

In addition, other medical conditions having an inflammatory component will benefit from treatment with immunologically active biomimetics such as Amyotrophic Lateral Sclerosis, Huntington's Disease, Alzheimer's Disease, Parkinson's Disease, Myocardial Infarction, Stroke, Hepatitis B, Hepatitis C, Human Immunodeficiency Virus associated inflammation, adrenoleukodystrophy, and epileptic disorders especially those believed to be associated with postviral encephalitis including Rasmussen Syndrome, West Syndrome, and Lennox-Gastaut Syndrome.

The general approach to therapy using the isolated immunologically active biomimetics described herein is to administer to a subject having a disease or condition, a therapeutically effective amount of the isolated immunologically active biomimetic to effect a treatment. In some embodiments, diseases or conditions may be broadly categorized as inflammatory diseases with an imbalance in cytokine networks, an autoimmune disorder mediated by pathogenic autoantibodies or autoaggressive T cells, or an acute or chronic phase of a chronic relapsing disease or process.

The term "treating" and "treatment" as used herein refers to administering to a subject a therapeutically effective amount of a biomimetic of the present invention so that the subject has an improvement in a disease or condition, or a symptom of the disease or condition. The improvement is any improvement or remediation of the disease or condition, or symptom of the disease or condition. The improvement is an observable or measurable improvement, or may be an improvement in the general feeling of well-being of the subject. Thus, one of skill in the art realizes that a treatment may improve the disease condition, but may not be a complete cure for the disease. Specifically, improvements in subjects may include one or more of: decreased inflammation; decreased inflammatory laboratory markers such as C-reactive protein; decreased autoimmunity as evidenced by one or more of: improvements in autoimmune markers such as autoantibodies or in platelet count, white cell count, or red cell count, decreased rash or purpura, decrease in weakness, numbness, or tingling, increased glucose levels in patients with hyperglycemia, decreased joint pain, inflammation, swelling, or degradation, decrease in cramping and diarrhea frequency and volume, decreased angina, decreased tissue inflammation, or decrease in seizure frequency; decreases in cancer tumor burden, increased time to tumor progression, decreased cancer pain, increased survival or improvements in the quality of life; or delay of progression or improvement of osteoporosis.

The term "therapeutically effective amount" as used herein refers to an amount that results in an improvement or remediation of the symptoms of the disease or condition.

As used herein, "prophylaxis" can mean complete prevention of the symptoms of a disease, a delay in onset of the symptoms of a disease, or a lessening in the severity of subsequently developed disease symptoms.

The term "subject" as used herein, is taken to mean any mammalian subject to which biomimetics of the present invention are administered according to the methods described herein. In a specific embodiment, the methods of the present disclosure are employed to treat a human subject. The methods of the present disclosure may also be employed to treat non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish and reptiles to produce species-specific or chimeric stradomer molecules.

In particular, the biomimetics of the present invention may be used to treat conditions including but not limited to congestive heart failure (CHF), vasculitis, rosecea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; multiple myeloma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasissas and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, tumors of the vascular system (angiosarcoma and hemagiopericytoma)) or other cancer.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, lymphangiosarcoma, lymphangioendotheliosarcoma, leiomyosarcoma, rhabdomyosarcoma, fibrosarcoma, myxosarcoma, chondrosarcoma), neuroendocrine tumors, mesothelioma, chordoma, synovioma, schwanoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwanoma, and other carcinomas, as well as head and neck cancer.

The biomimetics of the present invention may be used to treat autoimmune diseases. The term "autoimmune disease" as used herein refers to a varied group of more than 80 diseases and conditions. In all of these diseases and conditions, the underlying problem is that the body's immune system attacks the body itself. Autoimmune diseases affect all major body systems including connective tissue, nerves, muscles, the endocrine system, skin, blood, and the respiratory and gastrointestinal systems. Autoimmune diseases include, for example, systemic lupus erythematosus, rheumatoid arthritis, multiple sclerosis, myasthenia gravis, and type 1 diabetes.

The disease or condition treatable using the compositions and methods of the present invention may be a hematoimmunological process, including but not limited to Idiopathic Thrombocytopenic Purpura, alloimmune/autoimmune thrombocytopenia, Acquired immune thrombocytopenia, Autoimmune neutropenia, Autoimmune hemolytic anemia, Parvovirus B19-associated red cell aplasia, Acquired antifactor VIII autoimmunity, acquired von Willebrand disease, Multiple Myeloma and Monoclonal Gammopathy of Unknown Significance, Sepsis, Aplastic anemia, pure red cell aplasia, Diamond-Blackfan anemia, hemolytic disease of the newborn, Immune-mediated neutropenia, refractoriness to platelet transfusion, neonatal, post-transfusion purpura, hemolytic uremic syndrome, systemic Vasculitis, Thrombotic thrombocytopenic purpura, or Evan's syndrome.

The disease or condition may also be a neuroimmunological process, including but not limited to Guillain-Barré syndrome, Chronic Inflammatory Demyelinating Polyradiculoneuropathy, Paraproteinemic IgM demyelinating Polyneuropathy, Lambert-Eaton myasthenic syndrome, Myasthenia gravis, Multifocal Motor Neuropathy, Lower Motor Neuron Syndrome associated with anti-/GM1, Demyelination, Multiple Sclerosis and optic neuritis, Stiff Man Syndrome, Paraneoplastic cerebellar degeneration with anti-Yo antibodies, paraneoplastic encephalomyelitis, sensory neuropathy with anti-Hu antibodies, epilepsy, Encephalitis, Myelitis, Myelopathy especially associated with Human T-cell lymphotropic virus-1, Autoimmune Diabetic Neuropathy, or Acute Idiopathic Dysautonomic Neuropathy.

The disease or condition may also be a Rheumatic disease process, including but not limited to Kawasaki's disease, Rheumatoid arthritis, Felty's syndrome, ANCA-positive Vasculitis, Spontaneous Polymyositis, Dermatomyositis, Antiphospholipid syndromes, Recurrent spontaneous abortions, Systemic Lupus Erythematosus, Juvenile idiopathic arthritis, Raynaud's, CREST syndrome, or Uveitis.

The disease or condition may also be a dermatoimmunological disease process, including but not limited to Toxic Epidermal Necrolysis, Gangrene, Granuloma, Autoimmune skin blistering diseases including *Pemphigus vulgaris*, Bullous Pemphigoid, and *Pemphigus foliaccus*, Vitiligo, Streptococcal toxic shock syndrome, *Scleroderma*, systemic sclerosis including diffuse and limited cutaneous systemic sclerosis, or Atopic dermatitis (especially steroid dependent).

The disease or condition may also be a musculoskeletal immunological disease process, including but not limited to Inclusion Body Myositis, Necrotizing fasciitis, Inflammatory Myopathies, Myositis, Anti-Decorin (BJ antigen) Myopathy, Paraneoplastic Necrotic Myopathy, X-linked Vacuolated Myopathy, Penacillamine-induced Polymyositis, Atherosclerosis, Coronary Artery Disease, or Cardiomyopathy.

The disease or condition may also be a gastrointestinal immunological disease process, including but not limited to pernicious anemia, autoimmune chronic active hepatitis, primary biliary cirrhosis, Celiac disease, dermatitis herpetiformis, cryptogenic cirrhosis, Reactive arthritis, Crohn's disease, Whipple's disease, ulcerative colitis, or sclerosing cholangitis.

The disease or condition may also be Graft Versus Host Disease, Antibody-mediated rejection of the graft, Post-bone marrow transplant rejection, Post-infectious disease inflammation, Lymphoma, Leukemia, Neoplasia, Asthma, Type 1 Diabetes mellitus with anti-beta cell antibodies, Sjogren's syndrome, Mixed Connective Tissue Disease, Addison's disease, Vogt-Koyanagi-Harada Syndrome, Membranoproliferative glomerulonephritis, Goodpasture's syndrome, Graves' disease, Hashimoto's thyroiditis, Wegener's granulomatosis, micropolyarterits, Churg-Strauss syndrome, Polyarteritis nodosa or Multisystem organ failure.

In another embodiment, the stradomers herein described could be utilized in a priming system wherein blood is drawn from a patient and transiently contacted with the stradomer(s) for a period of time from about one half hour to about three hours prior to being introduced back into the patient. In this form of cell therapy, the patient's own effector cells are exposed to stradomer that is fixed on a matrix ex vivo in order to modulate the effector cells through exposure of the effector cells to stradomer. The blood including the modulated effector cells are then infused back into the patient. Such a priming system could have numerous clinical and therapeutic applications.

Therapeutic Stradobody Applications in Oncology

In addition to having clinical utility for treating immunological disorders, stradobodies have therapeutic use in cancer and inflammatory disease treatment. The stradobodies may be used essentially following known protocols for any corresponding therapeutic antibody. The stradobodies will generally be designed to enhance the effect demonstrated on an effector cell by a monoclonal antibody, such as ADCC in cancer or decreased monocyte and DC maturation with decreased cytokine release in autoimmune disease, and thereby potentiate the immune response against the cancer relative to that which would occur using, for example, a source monoclonal antibody for the Fab portion of the stradobody.

Exemplary monoclonal antibody Fab domains from which a stradobody may be designed includes cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, 1-131 tositumomab, efalizumab, bevacizumab, panitumumab, pertuzumab, natalizumab, etanercept, IGN101, volociximab, Anti-CD80 mAb, Anti-CD23 mAb, CAT-3888, CDP-791, eraptuzumab, MDX-010, MDX-060, MDX-070, matuzumab, CP-675, 206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab pegol, eculizumab, pexelizumab, abciximab, ranibizimumab, mepolizumab, and TNX-355, MYO-029.

The stradomers and stradobodies, collectively immunologically active biomimetics, disclosed herein have a number of further applications and uses.

Altering Immune Responses

The immunologically active biomimetics disclosed herein may also be readily applied to alter immune system responses in a variety of contexts to affect specific changes in immune response profiles. Altering or modulating an immune response in a subject refers to increasing, decreasing or changing the ratio or components of an immune response. For example, cytokine production or secretion levels may be increased or decreased as desired by targeting the appropriate combination of FcRs with a stradomer designed to interact with those receptors. Antibody production may also be increased or decreased; the ratio of two or more cytokines or immune cell receptors may be changed; or additional types of cytokines or antibodies may be caused to be produced. The immune response may also be an effector function of an immune cell expressing a FcγR, including increased or decreased phagocytic potential of monocyte macrophage derived cells, increased or decreased osteoclast function, increased or decreased antigen presentation by antigen-presenting cells (e.g. DCs), increased or decreased NK cell function, increased or decreased B-cell function, as compared to an immune response which is not modulated by an immunologically active biomimetic disclosed herein.

In a preferred embodiment, a subject with cancer or an autoimmune or inflammatory disease has their immune response altered comprising the step of administering a therapeutically effective amount of an immunologically active biomimetic described herein to a subject, wherein the therapeutically effective amount of the immunologically active biomimetic alters the immune response in the subject. Ideally this intervention treats the disease or condition in the subject. The altered immune response may be an increased or a decreased response and may involve altered cytokine levels including the levels of any of IL-6, IL-10, IL-8, IL-23, IL-7, IL-4, IL-12, IL-13, IL-17, TNF-alpha and IFN-alpha. The invention is however not limited by any particular mechanism of action of the described biomimetics. The altered immune response may be an altered autoantibody level in the subject. The altered immune response may be an altered autoaggressive T-cell level in the subject.

For example, reducing the amount of TNF-alpha production in autoimmune diseases can have therapeutic effects. A practical application of this is anti-TNF-alpha antibody therapy (e.g. REMICADE®) which is clinically proven to treat Plaque Psoriasis, Rheumatoid Arthritis, Psoriatic Arthritis, Crohn's Disease, Ulcerative Colitis and Ankylosing Spondylitis. These autoimmune diseases have distinct etiologies but share key immunological components of the disease processes related to inflammation and immune cell activity. A stradomer designed to reduce TNF-alpha production will likewise be effective in these and may other autoimmune diseases. The altered immune response profile may also be direct or indirect modulation to effect a reduction in antibody production, for example autoantibodies targeting a subjects own tissues, or altered autoaggressive T-cell levels in the subject. For example, Multiple Sclerosis is an autoimmune disorder involving autoreactive T-cells which may be treated by interferon beta therapy. See, e.g., Zafranskaya M, et al., Interferon-beta therapy reduces CD4+ and CD8+ T-cell reactivity in multiple sclerosis, *Immunology* 2007 May; 121(1):29-39-Epub 2006 Dec. 18. A stradomer design to reduce autoreactive T-cell levels will likewise be effective in Multiple Sclerosis and may other autoimmune diseases involving autoreactive T-cells.

Applications in Immunological Assays

The immunologically active biomimetics disclosed herein may be used to perform immunological assays for testing the immune cell functions for which the immunologically active biomimetics were designed to modulate.

Signaling through low affinity Fcγ receptor pathways requires receptor aggregation and cross linking on the cell surface. These aggregation and cross linking parameters are postulated to be met through Fab binding to an antigen specific target with subsequent interaction between the Fc region and low affinity FcγRs on the surface of responding cells. In this context, antibodies have the potential to evoke cellular responses through two distinct pathways: 1. Fab interaction/blocking with/of an epitope specific target and 2. Fc interactions with FcRs. Despite this knowledge, current controls for the majority of therapeutic studies using monoclonal antibodies employed in vivo do not adequately address the potential of Fc: Fcγ receptor interactions as contributors to observed functional effects. Multiple strategies are currently employed to eliminate Fc:FcR interactions as confounding variables. For example, some studies employ Scv (single chain variable regions) or Fab fragments, which retain epitope specificity but lack the Fc region. These approaches are limited by the short half life of these reagents and their limited potential to induce signaling. Other studies employ fusion proteins composed of a receptor or ligand fused to an Fc fragment. While these types of approaches help to differentiate Fab specific effects from those observed with receptor ligand interactions, they do not effectively control for Fc mediated effects. Evaluations of antibody based therapeutics in animal models may also employ isotype control antibodies with an irrelevant Fab binding site. The rationale for this choice is based on presumed functional similarity between antibodies of the same isotype regardless of their Fab binding specificity or affinity. However, this use of irrelevant isotype controls has several fundamental flaws:

1. If the Fab fragments of these antibodies cannot bind a ligand or antigenic epitope, it is likely that the Fc fragments will not stimulate signaling through low affinity FcR interactions because of the absence of Fcγ receptor cross-linking. Therefore, observed functional differences between experimental and control antibodies cannot be correctly attributed to Fab interaction with an epitope specific target lacking a means to cross-link the FcγR.
2. If these isotypes are produced in cells which yield different glycoforms or different relative percentages of individual glycoforms than the parent antibody, binding to both low and high affinity FcRs will be altered, even if Fab affinity is identical.

While there is no perfect control to overcome this problem, one option is the use of isotype specific stradomers produced in the same cells as the parent antibodies and given at a dose proportional to the expression levels of the epitope targeted by the experimental antibody. For example, the appropriate control for an epitope-specific antibody produced in rat would be a rat isotype-specific stradomer capable of aggregating Fcγ receptor on the surface of effector cells.

Generally, an immune cell is exposed to an effective amount of an immunologically active biomimetic to modulate an activity of an immune cell in a known way and this immune modulation is compared to a test compound or molecule to determine if the test compound has similar immune modulating activity.

In another embodiment, heat aggregated stradomers, and aggregated immunoglobulins may be used as reagents for laboratory controls in various immunological assays herein described and known to those of ordinary skill in the art.

Immunological assays may be in vitro assays or in vivo assays and may involve human or non-human immune cells using a species-matched or species-unmatched immunologically active biomimetic. In one embodiment an immunological assay is performed by using an effective amount of the immunologically active biomimetic to modulate an activity of an immune cell and comparing the modulation with a modulation of an immune cell by a test compound. The stradomer or stradobody may serve the function of a positive control reagent in assays involving the testing of other compounds for immunological effect. The assay may compare the effect of the subject monoclonal antibody in comparison to the stradomer for effector cell Fcγ receptor binding and functional response as measured by changes in receptor expression level, cytokine release, and function such as by using a Mixed Lymphocyte Reaction. In this manner, if a stradomer (which lacks the Fab) generates a response which is in part similar to the monoclonal antibody then the monoclonal antibody's effect is, in some part, not due to specificity of its Fab but to the general effect of binding and cross-linking more than one Fcγ receptor on the effector cell. The stradobody which contains both this same stradomer and the Fab from this same monoclonal antibody can further help distinguish the specificity of the monoclonal antibody Fab from the general effect of binding and cross-linking more than one Fcγ receptor on the effector cell.

If the biological activity of a species-specific and isotype-specific antibody is replicated in part or in whole by a species-specific and isotype-specific stradomer then it is clear that Fc-Fcγ receptor activity accounts for the portion of observed biological activity attributable to the species-specific and isotype-specific stradomer. Thus species-specific and isotype-specific stradomers are useful in assessing potential therapeutic antibodies to determine whether and to what degree the observed biological activity is attributable either to the Fab portion of the test antibody or to a non-specific effect of the Fc portion of the molecule binding to and cross-linking more than one Fcγ receptor.

In one embodiment an isolated immunologically active biomimetic of the present invention comprises at least one stradomer which comprises at least two Fc domains, or partial domains thereof, from the same immunoglobulin Fc class, where the immunoglobulin Fc class is selected from the group consisting of IgG1, IgG2, IgG3, IgG4 and combinations thereof. Such biomimetics are further capable of specifically binding to a first FcγRx$_1$, wherein x$_1$ is I, II, III, or IV and to a second FcγRx$_2$, wherein x$_2$ is I, II, III, or IV. These biomimetics can be further characterized as having an immunological activity comprising an Fcγ receptor cross-linking or effector functionality comparable to or superior to an Fcγ receptor cross-linking or an effector functionality of a plurality of naturally-occurring, aggregated IgG immunoglobulins.

In another embodiment the present invention includes an isolated immunologically active biomimetic that comprises at least one stradomer comprising at least two Fc domains from different immunoglobulin classes, or partial domains thereof, wherein the biomimetic binds specifically to a first FcγRx$_1$, wherein x$_1$ is 1, 11, III, or IV and to a second FcγRx$_2$, wherein x$_2$ is I, II, III, or IV. This biomimetic can be further characterized as having an immunological activity comprising an Fcγ receptor cross-linking or effector functionality comparable to or superior to an Fcγ receptor cross-linking or an effector functionality of a plurality of naturally-occurring, aggregated IgG immunoglobulins to FcγRs.

In a further embodiment the present invention includes an isolated immunologically active biomimetic that comprises one or more stradomers that each independently comprises three or more Fc domains, wherein the three or more Fc domains comprise: a) a first Fc domain, wherein the first Fc domain comprises a Fc hinge (H) of a first immunoglobulin, b) a second Fc domain, wherein the second Fc domain comprises a constant region 2 (CH2) of a second immunoglobulin, wherein the second Fc domain is capable of binding specifically to a FcγRx$_1$, wherein x$_1$ is I, II, III, or IV; c) a third Fc domain, wherein the third Fc domain comprises a constant region 3 (CH3) of a third immunoglobulin, wherein the third Fc domain is capable of binding specifically to an FcγRx$_2$, wherein x$_2$ is I, II, III, or IV. These biomimetics may optionally comprise a fourth Fc domain, wherein the fourth Fc domain comprises of a constant region 4 (CH4) of a fourth immunoglobulin IgM. With this molecule the Fc hinge may contain at least one cysteine.

In yet another embodiment the present invention includes an isolated immunologically active biomimetic that comprises: a) a first Fc domain or Fc partial domain thereof, wherein the first Fc domain comprises a Fc hinge (H) domain from a first immunoglobulin, wherein the Fc hinge domain comprises at least one cysteine, wherein the first Fc domain contributes to binding specificity to a FcγRx, wherein x is I, II, III, or IV; and at least one of: i) a second Fc domain or partial domain thereof, wherein the second Fc domain comprises a constant region 2 (CH2) from a second immunoglobulin which may or may not be the same as the first immunoglobulin, wherein the second Fc domain contributes to binding specificity to a FcγRx, wherein x is I, II, or III, IV; and, optionally, and ii) a third Fc domain or partial domain thereof, wherein the third Fc domain comprises a constant region 3 (CH3) from a third immunoglobulin, wherein the third Fc domain contributes to binding specificity to an FcγRx, wherein x is I, II, III, or IV; and b), optionally, a fourth Fc domain or partial domain thereof, wherein the fourth Fc domain specificity a constant region 4 (CH4) from an IgM immunoglobulin.

In another embodiment, the isolated immunologically active biomimetic is a stradomer wherein the immunoglobulin source of the Fc domains are the same or different and include IgA isotypes, IgG isotypes, IgD, IgE, and IgM. Another stradomer embodiment is an isolated immunologically active biomimetic comprising a secretory signal sequence.

In one preferred embodiment the therapeutically effective amount of the isolated immunologically active biomimetics of the present invention is an amount sufficient to permit binding of the biomimetics to two or more FcγRx, wherein x is I, II, III, or IV, on the surface of an immune cell, thereby causing the FcγRx to aggregate. The immune cell may be any immune effector cell such as a monocyte, a dendritic cell, a macrophage, an osteoclast, or an NK cell. The immune effector cell's maturation may be modulated by the immunologically active biomimetic. The ratio of FcγR IIa to FcγRIIb may also become altered on the immune cell. The immune cell may be located in the plasma, bone marrow, gut, bone, lymphoid tissue, thymus, brain, a site of infection or a tumor. The functional activity of a macrophage, dendritic cell, osteoclast, or NK cell may be modulated.

The therapeutically effective amount of the isolated immunologically active biomimetic described herein above may be administered ex vivo to an immune cell to generate a treated immune cell followed by the step of infusing the treated immune cell into the subject. The treated immune cell may be a dendritic cell, macrophage, osteoclast or a monocyte.

Additional immunotherapy may be given together with any of the isolated immunologically active biomimetics described herein in a therapeutically effective amount to the subject. The additional immunotherapy may include, for example, one or more of a co-stimulatory molecule, a monoclonal antibody, a polyclonal antibody, a fusion protein, a biospecific antibody, a cytokine, an immunologically recognized antigen, a small molecule anti-cancer agent or anti-proliferative agent. The additional immunotherapy may be administered concurrently with or separately from the administration of the immunologically active biomimetic.

Cytokine (including those listed above) levels can be altered by for, example, administering one or more cytokines of interest, one or more other cytokines that modulate the level of the one or more cytokines of interest, and/or antibodies (of any of the types and classes recited herein) specific for one or more of any of the above two categories of cytokines.

The immunologically active biomimetics described herein may be used to modulate expression of co-stimulatory molecules from an immune cell, including a dendritic cell, a macrophage, an osteoclast, a monocyte, or an NK cell or to inhibit in these same immune cells differentiation, maturation, or cytokine secretion, including interleukin-12 (IL-12), or of increasing cytokine secretion, including interleukin-10 (IL-10), or interleukin-6 (IL-6). A skilled artisan may also validate the efficacy of an immunologically active biomimetic by exposing an immune cell to the immunologically active biomimetic and measuring modulation of the immune cell function, wherein the immune cell is a dendritic cell, a macrophage, an osteoclast, or a monocyte. In one embodiment the immune cell is exposed to the immunologically active biomimetic in vitro and further comprising the step of determining an amount of a cell surface receptor or of a cytokine production, wherein a change in the amount of the cell surface receptor or the cytokine production indicates a modulation of the immune cell function. In another embodiment the immune cell is exposed to the immunologically active biomimetic in vivo in a model animal for an autoimmune disease further comprising a step of assessing a degree of improvement in the autoimmune disease.

"Capable of specifically binding to a FcγRx" as used herein refers to binding to an FcγR, such as FcγRIII. Specific binding is generally defined as the amount of labeled ligand which is displaceable by a subsequent excess of unlabeled ligand in a binding assay. However, this does not exclude other means of assessing specific binding which are well established in the art (e.g., Mendel C M, Mendel D B, 'Non-specific' binding. The problem, and a solution. Biochem J. 1985 May 15; 228(1):269-72). Specific binding may be measured in a variety of ways well known in the art such as surface plasmon resonance (SPR) technology (commercially available through BIACORE®) to characterize both association and dissociation constants of the immunologically active biomimetics (Aslan K, Lakowicz J R, Geddes C. Plasmon light scattering in biology and medicine: new sensing approaches, visions and perspectives. Current Opinion in Chemical Biology 2005, 9:538-544).

Methods Employing Fixed Fc

In order to understand the role of Fc: Fc gamma receptor (FcγR, the Fc receptor for IgG Fc) interactions and the importance to IVIG function of its Fc being biologically immobilized within an immunoglobulin, we compared the effects of IVIG with both a fixed form of a recombinant IgG1 Fc fragment (rFCF) and a soluble form of a recombinant IgG1 Fc fragment (sFc) containing the hinge-CH2-CH3 domains on the function of monocytes during the process of differentiation from monocytes to immature dendritic cells (iDC).

Exposure of monocytes cultured in granulocyte-macrophage colony stimulating factor (GM-CSF) and interleukin-4 (IL-4), to immobilized rFCF and to immobilized IVIG, but not low dose soluble IVIG, enhanced CD86 expression, delayed the expression of CD11c, and suppressed the expression of CD1a on the cells. Furthermore, these changes are likely not secondary to non-specific protein immobilization of the rFCF on plastic, as soluble heat aggregated (sHA) IVIG, sHA rFCF or high dose IVIG (recognized to contain multimeric Fcs), induced changes similar to those observed with immobilized rFCF.

Taken in concert, our data indicate that exposure of iDC to IVIG immobilized on the surface of a solid, semi-solid, or gelatinous substrate results in a unique population of DC's (high CD86, low CD1a), capable of orchestrating immune tolerance, and that immobilized molecules that include the functional portion of immunoglobulin G (IgG) Fc fragments can be useful as mimetics of IVIG for the treatment of local and systemic inflammation, as well as a wide variety of other pathological conditions that are, directly or indirectly, mediated by monocyte derived cells (MDC) such as iDC. Moreover, immobilizing the functional portion of IgG Fc on devices, described herein as "coating devices", that are implanted into the bodies or attached to the bodies of animals (e.g., human patients) with molecules containing the functional portion of IgG Fc fragment can lessen, if not prevent, inflammatory responses to such devices.

The invention provides a method of inhibiting the activity of a monocyte-derived cell (MDC). The method includes contacting the cell with a composition comprising a substrate with an Fc reagent bound thereto. The contacting can be in vitro, in vivo, or ex vivo. Alternatively, the cell can be in an animal. The animal can be one that has, or is at risk of developing, a monocyte derived cell mediated condition (MDCMC). The MDC can be, for example, a dendritic cell, a macrophage, a monocyte, or an osteoclast.

The invention also provides a method of treatment or prophylaxis. The method that includes administering to an animal a composition containing a substrate having an Fc reagent bound to it, the animal being one that has or is at risk of developing a MDCMC.

As used herein, the term "monocyte-derived cell mediated condition (MDCMC)" refers to a pathologic condition that is directly or indirectly, partially or wholly, due to the activity of, or factors produced by, monocyte-derived cells. Monocyte-derived cells include, but are not limited to, monocytes, macrophages, interdigitating dendritic cells (generally referred to herein as "dendritic cells" comprising dendritic-like cells and follicular dendritic-like cells) (mature and immature), osteoclasts, microglia-like cells, monocyte derived insulin-producing islet-like cells, monocyte-derived immature mast cells and monocyte-derived microparticles.

With respect to methods using fixed Fc, the term "Fc reagent" refers to any molecule, or molecular complex, that includes one or more (e.g., 2, 3, 4, 5, 6, 7, 8, 9, 10, 12, 15, 18, 20, or more) functional portions of an immunoglobulin Ig (IgG) Fc fragment. The Fc fragment of IgG consists of the C-terminal portions of the two IgG heavy chains of an IgG molecule linked together and consists of the hinge regions, the CH2 domains, and the CH3 domains of both heavy chains linked together. The "functional portion of the IgG Fc fragment" consists of the hinge regions, the CH2 domains, and optionally, all or some (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49) of the first 50 (from the N-terminus) amino acids of the CH3 domains, of both heavy chains linked together. In humans, (a) the IgG1 hinge region contains 15 amino acids, the CH2 domain contains 110 amino acids, and the CH3 domain contains 106 amino acids; (b) the IgG2 hinge region contains 12 amino acids, the CH2 domain contains 109 amino acids, and the CH3 domain contains 107 amino acids; (c) the IgG3 hinge region contains 62 amino acids, the CH2 domain contains 104 amino acids, and the CH3 domain contains 106 amino acids; and (d) the IgG4 hinge region contains 12 amino acids, the CH2 domain contains 109 amino acids, and the CH3 domain contains 107 amino acids.

As in wild-type IgG molecules, in the above-described Fc reagents the two polypeptide chains derived from IgG heavy chains are generally, but not necessarily, identical. Thus, an Fc reagent can be, without limitation, a whole IgG molecule, a whole IgG molecule linked to a non-immunoglobulin derived polypeptide, an IgG Fc fragment, an IgG Fc fragment linked to a non-immunoglobulin derived polypeptide, a functional portion of an IgG Fc fragment, a functional portion of an IgG Fc fragment linked to a non-immunoglobulin derived polypeptide or multimers (e.g., dimers, trimers, tetramers, pentamers, hexamers, heptamers, octamers, nonamers, or decamers) of any of these. Fc reagents can also be the above-described stradomers and stradobodies provided that they fall within the definition of a Fc reagent above.

In the fixed Fc, immunoglobulin heavy chain components of the Fc reagents can have wild-type amino acid sequences or they can be wild-type amino acid sequences but with not more than 20 (e.g., not more than: 19, 18, 17, 16, 15, 14, 13, 12, 11, 10, 9, 8, 7, 6, 5, 4, 3, 2, or 1) amino acid substitutions. Such substitutions are preferably, but not necessarily, conservative substitutions. Conservative changes typically include changes within the following groups: glycine and alanine; valine, isoleucine, and leucine; aspartic acid and glutamic acid; asparagine, glutamine, serine and threonine; lysine, histidine and arginine; and phenylalanine and tyrosine.

An "Fc reagent" of the invention has least 25% (e.g., at least: 30%; 40%; 50%; 60%; 70%; 80%; 90%; 95%; 98%; 99%; 99.5%; or 100% or even more) of the ability of the IgG molecule from which the IgG heavy chain components of the Fc reagent were derived (the reference IgG molecule) to bind to an Fc receptor of interest. Where an "Fc reagent" has heavy chain components derived from more than one type of IgG molecule, the reference IgG molecule is the one that binds with the greatest avidity to the relevant Fc receptor of interest.

As used herein "fixed Fc" refers to an Fc reagent that is bound to a "substrate" as defined below. The terms "fixed Fc," "bound Fc" and "stabilized Fc" are synonymous terms. Fixed Fc is comprised of the functional portion of Fc (including but not limited to any polypeptide that includes the functional portion of Fc) attached to a substrate. Fixed Fc includes, for example, direct binding as well as indirect binding through polymers of Fc to substrate; incorporation of the full IgG Fc in isolation; incorporation of only the functional domains of IgG Fc; or incorporation of the full IgG Fc or functional domains of IgG Fc as part of a larger polypeptide such as an antibody, a stradomer, or a stradobody.

As applied to fixed Fc, the term "substrate" refers to a solid, semi-solid, or gelatinous object. The substrate can be implanted in, or attached (or adhered) to the surface of, the body of an animal. The substrates can include, for example, liquid or gaseous components but at least a portion of the substrate is solid, semi-solid, or gelatinous. Thus, a substrate can be a substance that is substantially insoluble in an aqueous solvent but soluble in a non-aqueous solvent. Such substances include lipids (e.g., phospholipids), fatty acids, and other fat-soluble, aqueous solvent-insoluble compounds. From this, it will be clear that substrates include liposomes. The substrate may be porous or non-porous. In certain embodiments, the substrate is inert to the surface and/or body to which it is implanted, attached, or adhered.

The substrate can contain or be made of a synthetic polymer, e.g., nylon, teflon, dacron, polyvinyl chloride, PEU (poly(ester urethane)), PTFE (polytetrafluoroethylene), PMMA (methyl methacrylate) PEEK, thermoplastic elastomers, radiopaque polymers, polyethersulfone, silicons, polycarbonates, polyurethanes, polyisobutylene and its copolymers, polyesters, polyolefins, polyisobutylene, ethylene-alphaolefin copolymers, acrylic polymers and copolymers, vinyl halide polymers and copolymers such as polyvinyl chloride, polyvinyl ethers, polyvinyl methyl ether, polyvinylidene halides, polyvinylidene fluoride, polyvinylidene chloride, polyacrylonitrile, polyvinyl ketones, polyvinyl aromatics, polystyrene, polyvinyl esters, polyvinyl acetate, copolymers of vinyl monomers, copolymers of vinyl monomers and olefins, ethylene-methyl methacrylate copolymers, acrylonitrile-styrene copolymers, ABS resins, ethylene-vinyl acetate copolymers, polyamides, Nylon 66, polycaprolactone, alkyd resins, polyoxyethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, polysiloxanes, substituted polysiloxanes, ethylene vinyl acetate copolymers, polyolefin elastomers, and EPDM rubbers, and combinations thereof.

The substrate can also contain or be made of a metal or a metal alloy, e.g., stainless steel, platinum, iridium, titanium, tantalum, nickel-titanium alloy, or cobalt-chromium alloy. Moreover, the substrate can include or be an animal tissue or an animal tissue product, e.g., a tissue or organ graft. The animal tissue can be, for example, bone (e.g., osteogenic bone) or cartilage. Furthermore, the substrate can contain a protein, e.g., collagen or keratin. The substrate can also be or contain a tissue matrix, e.g., an acellular tissue matrix. Particulate and non-particulate acellular matrices are described in detail in, for example, U.S. Pat. Nos. 5,336,616 and 6,933,326, the disclosures of which are incorporated herein by reference in their entirety. The substrate can also be or include an animal cell (e.g., tissue repair cells such as fibroblasts; mesenchymal stem cells) and it can be, for example, a hair transplant plug. The substrate can contain or be a polysaccharide, e.g., agarose. It can also contain or be a salt, preferably a relatively insoluble salt, e.g., calcium sulfate. The substrate can be a gel or cream. Moreover, it can contain silicon or silastic. Substrates can also contain a natural fiber, e.g., silk, cotton, or wool.

In addition, the substrate can be an implantable medical device. It can be, for example, a stent (e.g., a vascular stent such as a coronary artery stent; an airway stent such as an endotracheal or nasal stent; a gastrointestinal stent such a biliary or pancreatic stent; or a urinary stent such as a ureteral stent) or a surgical suture (e.g., a braid silk, chromic gut, nylon, plastic, or metal suture) or a surgical clip (e.g., an aneurism clip). The substrate can be, for example, an artificial hip, an artificial hip joint, an artificial knee, an artificial knee joint, an artificial shoulder, an artificial shoulder joint, an artificial finger or toe joint, a bone plate, a bone dowel, a bone non-union implant, an intervertebral disk implant, bone cement, or a bone cement spacer. It can also be an arterial-venous shunt, an implantable wire, a pacemaker, an artificial heart, a heart assist device, a cochlear implant, an implantable defibrillator, a spinal cord stimulator, a central nervous system stimulator, or a peripheral nerve implant. Other substrates are dental prostheses or dental crowns.

In other embodiments, the substrate can be a large vessel embolic filtering device or cage, a percutaneous device, a dermal or sub-mucosal patch, or an implantable drug delivery device. The substrate can also be a large blood vessel graft, wherein the blood vessel is, for example, a carotid artery, a femoral artery, or an aorta. Moreover, the substrate can be a sub-dermal implant, a corneal implant, an intraocular lens, or a contact lens.

The substrate can be in the form of a sheet, a bead, a mesh, a powder particle, a thread, a bead, or a fiber. It can also include or be a solid, a semi-solid or a gelatinous substance.

Polymers useful in the invention are preferably those that are biostable, biocompatible, particularly during insertion or implantation of the device into the body, and avoid irritation to body tissue.

Fc reagents can be coated (i.e., fixed or stabilized) onto substrates in any of a variety of manners. For example, they can be coated directly on the surface of substrates where they remain attached by, for example, hydrophobic interactions. Below are described a few other methodologies ((a)-(e)) involving the use of polymers:

(a) The Fc reagent is mixed with a miscible polymer blend which is then layered on to the surface of the implantable synthetic material, thereby stabilizing the Fc reagent. Monomers routinely used in the art to make polymer blends include PLMA [poly(lauryl methacrylate)]; PEG [polyethylene glycol], PEO [polyethylene oxide]; the alkyl functionalized methacrylate polymers PMMA, PEMA, PPMA, and PBMA; itaconates; fumarates; and styrenics.

(b) A polymeric undercoat layer or a nanometer dimension film is adhered to the substrate surface and then the Fc reagent is adhered to the polymeric undercoat layer or nanometer dimension film, thereby stabilizing the F reagent.

(c) A thin film of a polymer monomer is applied to the implantable substrate surface and the monomer is then caused to polymerize Such monomers include, for example, Methane, Tetrafluorethylene, Benzene, Methanol, Ethylene oxide, Tetraglyme, Acrylic acid, Allylamine, Hydroxyethyl methacrylate, N-vinyl pyrrolidone, and mercaptoethanol. The Fc reagent is then attached to the resulting monomer.

(d) The substrate is coated with a protein such as protein A or albumin which attaches to the Fc reagent, thereby stabilizing Fc to the surface of the substrate.

(e) The Fc reagent can be tagged with a chain of hydrophobic amino acids that bind to implantable synthetic materials and cause the stabilized Fc to orient uniformly.

The methods of the invention can be applied to any animal species and the IgG molecules from which the IgG-derived portions of Fc reagents are made can be from any animal species. Naturally, relevant animal species are those in which IgG or IgG-like molecules occur. Generally the species to which the methods are applied and the species from which the IgG-derived portions of the Fc reagents used in the methods are the same. However, they are not necessarily the same. Relevant animal species are preferably mammals and these include, without limitation, humans, non-human primates (e.g., monkeys, baboons, and chimpanzees), horses, bovine animals (e.g., bulls, cows, or oxen), pigs, goats, sheep, dogs, cats, rabbits, gerbils, hamsters, rats, and mice. Non-mammalian species include, for example, birds (e.g., chickens, turkeys, and ducks) and fish.

The terms "treating", "treatment", and "prophylaxis" have the same meaning using fixed Fc as described above for stradomers and stradobodies.

Where the fixed Fc are implantable devices coated with Fc reagents, they can be implanted in, attached to, or adhered to relevant internal organs or tissue or body surfaces of relevant subjects using methods well known in the art. Where they are formulated as, for example, suspensions, powders, they can be formulated and administered as described above for stradomers and stradobodies.

The fixed Fc reagents of the present invention may be used to treat or prevent conditions including but not limited to cancer, congestive heart failure (CHF), vasculitis, rosecea, acne, eczema, myocarditis and other conditions of the myocardium, systemic lupus erythematosus, diabetes, spondylopathies, synovial fibroblasts, and bone marrow stroma; bone loss; Paget's disease, hypertrophic bone formation; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures, bone pain management, and humoral malignant hypercalcemia, ankylosing spondylitis and other spondyloarthropathies; transplantation rejection, and viral infections.

All autoimmune diseases may be in part or in whole an MDCMD. The term "autoimmune disease" as used herein refers to a varied group of more than 80 chronic illnesses. In all of these diseases, the underlying problem is that the body's immune system attacks the body itself. Autoimmune diseases affect all major body systems including connective tissue, nerves, muscles, the endocrine system, skin, blood, and the respiratory and gastrointestinal systems.

The autoimmune disease or condition may be a hematoimmunological process, including but not limited to Idiopathic Thrombocytopenic Purpura, alloimmune/autoimmune thrombocytopenia, Acquired immune thrombocytopenia, Autoimmune neutropenia, Autoimmune hemolytic anemia, Parvovirus B19-associated red cell aplasia, Acquired antifactor VIII autoimmunity, acquired von Willebrand disease, Multiple Myeloma and Monoclonal Gammopathy of Unknown Significance, Sepsis, Aplastic anemia, pure red cell aplasia, Diamond-Blackfan anemia, hemolytic disease of the newborn, Immune-mediated neutropenia, refractoriness to platelet transfusion, neonatal, post-transfusion purpura, hemolytic uremic syndrome, systemic Vasculitis, Thrombotic thrombocytopenic purpura, or Evan's syndrome.

The autoimmune disease or condition may be a neuroimmunological process, including but not limited to Guillain-Barré syndrome, Chronic Inflammatory Demyelinating Polyradiculoneuropathy, Paraproteinemic IgM demyelinating Polyneuropathy, Lambert-Eaton myasthenic syndrome, Myasthenia gravis, Multifocal Motor Neuropathy, Lower Motor Neuron Syndrome associated with anti-/GM1, Demyelination, Multiple Sclerosis and optic neuritis, Stiff Man Syndrome, Paraneoplastic cerebellar degeneration with anti-Yo antibodies, paraneoplastic encephalomyelitis, sensory neuropathy with anti-Hu antibodies, epilepsy, Encephalitis, Myelitis, Myelopathy especially associated with Human T-cell lymphotropic virus-1, Autoimmune Diabetic Neuropathy, or Acute Idiopathic Dysautonomic Neuropathy.

The autoimmune disease or condition may be a Rheumatic disease process, including but not limited to Kawasaki's disease, Rheumatoid arthritis, Felty's syndrome, ANCA-positive Vasculitis, Spontaneous Polymyositis, Dermatomyositis, Antiphospholipid syndromes, Recurrent spontaneous abortions, Systemic Lupus Erythematosus, Juvenile idiopathic arthritis, Raynaud's, CREST syndrome, or Uveitis.

The autoimmune disease or condition may be a dermatoimmunological disease process, including but not limited to Toxic Epidermal Necrolysis, Gangrene, Granuloma, Autoimmune skin blistering diseases including *Pemphigus vulgaris*, Bullous Pemphigoid, and *Pemphigus foliaceus*, Vitiligo, Streptococcal toxic shock syndrome, *Scleroderma*, systemic sclerosis including diffuse and limited cutaneous systemic sclerosis, or Atopic dermatitis (especially steroid dependent).

The autoimmune disease or condition may be a musculoskeletal immunological disease process, including but not limited to Inclusion Body Myositis, Necrotizing fasciitis, Inflammatory Myopathies, Myositis, Anti-Decorin (BJ antigen) Myopathy, Paraneoplastic Necrotic Myopathy, X-linked Vacuolated Myopathy, Penacillamine-induced Polymyositis, Atherosclerosis, Coronary Artery Disease, or Cardiomyopathy.

The autoimmune disease or condition may be a gastrointestinal immunological disease process, including but not limited to pernicious anemia, autoimmune chronic active hepatitis, primary biliary cirrhosis, Celiac disease, dermatitis herpetiformis, cryptogenic cirrhosis, Reactive arthritis, Crohn's disease, Whipple's disease, ulcerative colitis, or sclerosing cholangitis.

The autoimmune disease or condition may be Graft Versus Host Disease, Antibody-mediated rejection of the graft, Post-bone marrow transplant rejection, Post-infectious disease inflammation, Lymphoma, Leukemia, Neoplasia, Asthma, Type 1 Diabetes mellitus with anti-beta cell antibodies, Sjogren's syndrome, Mixed Connective Tissue Disease, Addison's disease, Vogt-Koyanagi-Harada Syndrome, Membranoproliferative glomerulonephritis, Goodpasture's syndrome, Graves' disease, Hashimoto's thyroiditis, Wegener's granulomatosis, micropolyarterits, Churg-Strauss syndrome, Polyarteritis nodosa or Multisystem organ failure.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, lymphangiosarcoma, lymphangioendotheliosarcoma, leiomyosarcoma, rhabdomyosarcoma, fibrosarcoma, myxosarcoma, chondrosarcoma), osteoclastoma, neuroendocrine tumors, mesothelioma, chordoma, synovioma, schwanoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwanoma, and other carcinomas, head and neck cancer, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, tumors of the vascular system (angiosarcoma and hemagiopericytoma), hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, ostcolytic bone cancers, and bone metastasis.

As used herein, a subject "at risk of developing a monocyte-derived cell mediated disease (MDCMD)" is a subject that has a predisposition to develop the MDCMD, i.e., a genetic predisposition to develop the MDCMD or has been exposed to conditions that can result in MDCMD. A subject "suspected of having a MDCMD" is one having one or more symptoms of a MDCMD. From the above it will be clear that neither subjects "at risk of developing a MDCMD" nor subjects "suspected of having a MDCMD" are all individuals within a species of interest.

In any of the above methods, the MDCMC can be one caused by the substrate and the Fc reagent serves to prevent or ameliorate the MDCMC.

Example 1

Construct Design of Immunologically Active Biomimetics

A sequence encoding a Fc fragment monomer from human IgG$_1$ (SEQ ID NO: 1) has been cloned into an expression vector (pCDNA 3.1D/V5 His TOPO Invitrogen)

comprising selected restriction enzyme cleavage sites, an IgK signal (further defined below) and epitope tags to create the IgG1 monomer sequence {RestEnzSites-IgK signal-RestEnzSites-IgG1 (Hinge-CH2-CH3)-RestEnzSites-epitope tags (V5 and His)-STOP}, shown in FIG. 17 (SEQ ID NO:19). The construct was transfected into CHO cells (CHO-002) for protein production. Additionally, we have designed several stradomer constructs with the general structures:

a) {RestEnzSites-IgK signal-RestEnzSites-IgG1(Hinge-CH2-CH3)-XbaI site-IgG1(Hinge-CH2-CH3)-STOP} (SEQ ID NO: 21) (see also FIG. 4A and FIG. 18);

b) {RestEnzSites-IgK signal-RestEnzSites-IgG1(Hinge-CH2-CH3)-XbaI site-IgG1(Hinge-CH2-CH3)-RestEnzSites-epitope tags (V5 and His)-STOP} (SEQ ID NO: 23) (see also FIG. 19);

c) {RestEnzSites-IgK signal-EcoRV Site-IgG3(Hinge-CH2-CH3)-IgG1(Hinge-CH2-CH3)-RestEnzSites-epitope tags(V5 and His)-STOP} (SEQ ID NO.: 25) (see also FIG. 21); and d) {RestEnzSites-IgK signal-EcoRV Site-IgE(CH2)-IgG1(Hinge-CH2-CH3)-IgG1(Hinge-CH2)-IgE(CH4)-STOP} (SEQ ID NO.: 27) (see also FIG. 22).

The IgG$_1$ stradomer construct a) (SEQ ID NO: 21; FIG. 18) was engineered using PCR. Primers complementary to the hinge sequence (at the 5' end) of IgG$_1$ (SEQ ID NO: 29) and to the C terminus of the IgG$_1$ (at the 3' end) (SEQ ID NO: 30) were used to amplify the IgG$_1$ Hinge-Fc region. Restriction sites were added to the primers to permit in-frame cloning of the second Fc domain in series with the first, which was cloned into a pcDNA cloning vector (pCDNA 3.1 D/V5 His TOPO, Invitrogen). A stop codon was added before the restriction site of the C terminal primer to prevent read through of flanking sequences for this construct.

The stradomer construct b) (SEQ ID NO: 23; FIG. 19), was similarly made and contained the IgG$_1$ Fc-IgG$_1$ Fc as described above but also contained two epitope tags added to the C terminus of the construct. These epitope tags are used for identification or purification of the protein. In this second construct the two epitope tags, V5 and His tag, are present in frame prior to the stop codon.

Proteins that are normally secreted routinely contain a hydrophobic signal sequence at the N terminus of the protein. For the stradomer constructs, we used the IgK signal sequence METDTLLLWVLLLWVPGSTG (SEQ ID NO:35) which is removed from the protein as it is secreted by mammalian cells such as Chinese Hamster Ovary cells. The predicted cleavage site was based on algorithms for signal site cleavage prediction (SignalP 3.0).

Additional stradomer constructs, similar to a) and b) above were made that contained the IgG$_1$ Fc-IgG$_1$ Fc structure as described above (with and without the epitope tag) but using the IgG$_3$ Hinge domain in the construct: IgG$_1$ Fc-IgG$_3$ hinge-IgG$_1$ (CH2-CH3).

Example 2

Design and Testing of Immunologically Active Biomimetics

Coated IVIG and Coated Fc Stimulate Similar Phenotypic Changes

IVIG and Fc when coated onto the walls and floor of the wells of a sterile plate stimulate nearly identical changes in CD1a and CD86 levels on immature DC and delay the up regulation of CD11c. Because of the recognized critical role of DC in ITP, these data provide a rational model for evaluating the function of IVIG mimetics such as stradomers. We also conclude that the fact that the phenotypic changes induced by IVIG are completely recapitulated by recombinant Fc suggest that the effects of IVIG on DC are highly likely to be Fc mediated.

Stradomer Generation

We have constructed stradomers of four different classes to mimic the effects of IVIG on immature DC. The serial stradomers, cluster stradomer units comprising cluster stradomers, core stradomer units comprising core stradomers, and Fc fragment stradomers shown below in Table 3 were each produced except where noted. To obtain the appropriate sequences for each of the human constructs shown below, cDNA was synthesized from total RNA extracted from human PBMC. To obtain those sequences from other species RNA was purified from tissue of those species. Random priming was used to produce the cDNA. The cDNA was used to amplify the desired fragments using PCR to synthesize, clone and subsequently characterize by sequence analysis the DNA fragments. The final constructs were produced by either sewing by overlap extension with PCR (Horton R M, Hunt H D, Ho S N, Pullen, J K and Pease L R. Engineering hybrid genes without the use of restriction enzymes: gene splicing by overlap extension. Gene 77:61-68, 1989) or utilized existing compatible restriction sites to fuse the appropriate fragments.

For example, in the cloning of G-007, the IgECH4 domain was directly fused to the CH2 domain of IgG1 at the 3' end of the protein. This was accomplished by making primers that contain the overlapping sequences for IgG1CH2 (C terminus) with the N terminal amino acids for IgECH4. In one case, a hybrid primer was used to amplify 5' with IgG1 sequences and the complementary primer was used to amplify with a 3' primer from the C terminus of the IgECH4. Products from these two reactions were mixed and the flanking primers were used to amplify the fusion protein. Sequence analysis confirmed the construct.

In many cases, restriction sites were utilized that were conveniently present at the ends of the molecules to be joined. When restriction sites are in fusion there are detectable remnant restriction sequences at the ends of the linked sequences. This approach was used for most of the constructs shown below in Table 3. The amino acid sequences of the stradomers shown in Table 3 are provided in FIG. 24. Some of the sequence are shown with His-tags, known in the art to be useful in purifying proteins.

TABLE 3

| | N-term | CH2 | CH3 | | CH2 | CH3 | H | CH2 | CH3 |
|---|---|---|---|---|---|---|---|---|---|
| | | | | Serial Stradomers | | | | | |
| | | Hin | | | Hin | | | | |
| G-003 | | IgG1 | IgG1 | IgG1 | IgG1 | IgG1 | IgG1 | | |
| G-004 | | IgG1 | IgG1 | IgG1 | IgG1 | IgG1 | IgG1 | | |
| G-007 | IgECh2 | IgG1 | IgG1 | IgG1 | IgG1 | IgG1 | | IgCh4 | |
| G-011 | IgECh2 | IgG1 | IgG1 | IgG1 | IgG1 | IgG1 | IgG1 | | |
| G-012 | IgECh2 | IgG1 | IgG1 | IgG1 | IgG1 | IgG1 | IgG1 | IgCh4 | |

TABLE 3-continued

| | N-term | CH2 | CH3 | | CH2 | CH3 | H | CH2 | CH3 |
|---|---|---|---|---|---|---|---|---|---|
| G-012 | IgECh2 | IgG1 | IgG1 | IgG1 | IgG1 | IgG1 | IgG1 | IgCh4 | | |
| G-014 | | IgG1 | IgG1 | IgG1 | IgG1 | IgG1 | IgG1 | IgG1 | IgG1 | IgG1 |
| G-016 | | IgG3 | IgG3 | IgG3 | IgG1 | IgG1 | IgG1 | | | |
| G-017 | (x-b) RestEnz linker | IgG1 | IgG | IgG1x-b | IgG1 | IgG1 | IgG1 | | | |
| G-023 | | IgG1 | IgG1 | IgG1 | IgG1 | IgG1 | IgG1 | Ig3H 32/62 | | |
| G-024 | | IgG3 | IgG3 | IgG3 | IgG1 | IgG1 | IgG1 | IgG1 | IgG1 | IgG1 |
| G-025 | 107aa | IgG1 | IgG1 | IgG1 | | | | | | |
| G-026 | 107aa | IgG1 | IgG1 | IgG1 | IgG1 | IgG1 | IgG1 | | | |

Fc Fragment Stradomer and Core Stradomer Components

| | N-term | CH2 | CH3 | | CH2 | CH3 | H | CH2 | CH3 |
|---|---|---|---|---|---|---|---|---|---|
| G-002 | | IgG1 | IgG1 | IgG1 | | | | | | |
| G-022 | | IgG1 | IgG1 | IgG1 | IgG3Hing | | | | | |

Cluster Stradomer Units

| | N-term | CH2 | CH3 | | CH2 | CH3 | H | CH2 | CH3 |
|---|---|---|---|---|---|---|---|---|---|
| G-008 | | IgG1 | IgG1 | IgG1 | IgG1 | IgG1 | IgG1 | IgM CH3-CH4-TP | | |
| G-009 | | IgG1 | IgG1 | IgG1 | IgMCH3-CH4-TP | | | | | |
| G-010 | IgECh2 | IgG1 | IgG1 | IgG1 | | | | | | |
| G-018 | | IgG2 | IgG2 | IgG2 | IgG1 | IgG1 | IgG1 | | | |
| G-019 | IgG2Hing | IgG1 | IgG1 | IgG | | | | | | |
| G-020 | IgG2Hing | IgG1 | IgG1 | IgG1 | IgG1 | IgG1 | IgG1 | | | |
| G-021 | IgG2Hing | IgG1 | IgG1 | IgG1 | | | | | | |
| G-027 | IgECh2-IgECh2 | IgG1 | IgG1 | IgG1 | | | | | | |
| G-028 | ILZ | IgG1 | IgG1 | IgG1 | | | | | | |
| G-029 | ILZ-IgECh2 | IgG1 | IgG1 | IgG1 | | | | | | |
| G-030 | ILZ | IgG2 | IgG2 | IgG2 | IgG1 | IgG1 | IgG1 | | | |
| G-031 | ILZ-IgG2hing | IgG1 | IgG1 | IgG1 | | | | | | |
| G-032 | ILZ-ILZ | IgG1 | IgG1 | IgG1 | | | | | | |
| G-033 | IgG2Hing-IgECh2 | | IgG1 | IgG1 | IgG | | | | | |
| G-034 | IgG2hing-ILZ | IgG2 | IgG2 | IgG2 | IgG1 | IgG1 | IgG1 | | | |
| G-035 | IgG2hing -IgG2hing | IgG1 | IgG1 | IgG1 | | | | | | |
| G-036 | IgG2hing-ILZ | IgG1 | IgG1 | IgG1 | | | | | | |

To Be Made

| | H | | | H | | | | | |
|---|---|---|---|---|---|---|---|---|---|
| 401 | IgG1 | IgG1 | IgG1 | IgG3 | IgG3 | IgG3 | | | |
| 402 | IgG3 | IgG1 | IgG1 | IgG3 | IgG1 | IgG1 | | | |
| 403 | IgG1 | IgG3 | IgG1 | IgG1 | IgG3 | IgG1 | | | |
| 404 | IgG1 | IgG1 | IgG3 | IgG1 | IgG1 | IgG3 | | | |
| 405 | IgG3 | IgG3 | IgG1 | IgG3 | IgG3 | IgG1 | | | |
| 406 | IgG1 | IgG1 | none | IgG3 | IgG3 | none | | | |
| 407 | IgG3 | IgG3 | IgG3 | IgG3 | IgG3 | IgG3 | IgG3 | IgG3 | IgG3 |
| 408 | IgG1 | IgG1 | IgG1 | IgG3 | IgG3 | IgG3 | IgG1 | IgG1 | IgG1 |
| 409 | IgG3 | IgG3 | IgG3 | IgG1 | IgG1 | IgG1 | IgG3 | IgG3 | IgG3 |
| 410 | IgG3 | IgG1 | IgG1 | IgG3 | IgG1 | IgG1 | IgG3 | IgG1 | IgG1 |
| 411 | IgG3 | IgG3 | IgG1 | IgG3 | IgG3 | IgG1 | IgG3 | IgG3 | IgG1 |
| 412 | IgG1 | IgG1 | IgG4CH4 | IgG3 | IgG3 | IgG4CH4 | IgG1 | IgG1 | IgGCH4 |
| 413 | IgG1 | IgG1 | | IgG3 | IgG3 | | IgG1 | IgG1 | |
| 414 | IgG1 | IgG1 | IgG1 | IgG1 | IgG1 | IgG1 | IgG1 | IgG1 | IgG1 |
| 415 | IgG3 | IgG3 | IgG3 | IgG3 | IgG3 | IgG3 | IgG3 | IgG3 | IgG3 |

Stradomer Protein Expression

For protein expression of the stradomers, plasmid DNA encoding the stradomers described above were transfected into CHO suspension cells (Freestyleim MAX CHO expression system, Invitrogen CA). Following protein expression the expressed stradomers were purified from the culture media by affinity column chromatography using protein A or protein G affinity columns. Purified stradomers were analyzed by SDS-PAGE (sodium dodecyl sulfate polyacrylamide gel electrophoresis) under reducing conditions followed by Coomasie Blue staining to confirm the presence of monomeric protein bands of expected size as exemplified: G-002: approximately 35 KD band, G-004 approximately 70 KD band, G-010: approximately 45 KD band, G-011: approximately 80 KD band, G-012: approximately 85 KD band, G-018 approximately 70 KD band, G-019: approximately 35 KD, G-028 approximately 37 KD band. Plasmid DNA encoding the stradomers described can also be transfected into other mammalian cells such as HEK 293, BHK cells, murine NSO, and murine SP2/0 cells.

Multimer Formation

We observed that these constructs, when transfected, cultured, and purified may create proteins of the expected size in non-denatured and denatured protein analysis. In addition, we observed that certain compounds also exhibited larger bands which by size criteria are multimers of the expected dimeric protein.

Formation of higher order compounds by selected stradomers was analyzed by SDS-PAGE followed by Western blot under non-reducing conditions (A) and reducing conditions (B). SDS-PAGE analysis shows formation of high molecular weight compounds of stradomers G-002, G-010, and G-019 under non-reducing conditions as compared to reducing conditions:

G-002: an approximately 35 KD band under reducing condition—bands at approximately 70 KD (dimer) and 135 KD (tetramer) under non-reducing conditions.
G-010: an approximately 45 KD band under reducing condition—bands at approximately 90 KD (dimer) and 180 KD (tetramer) under non-reducing conditions.

G-019: an approximately 35 KD band under reducing conditions—bands at approximately 70 KD (dimer), 140 KD (tetramer) under non-reducing conditions.

We anticipate that the tetrameric and other higher order multimers of the dimerized protein will contribute significantly to the biological activity of the compound as measured by the immature Dendritic Cell assay (see below).
Stradomer Monomers, Stradomers, and Higher Order Multimers of Stradomers Maintain Recognition Sites.

Each of the proteins in Table 3 are recognized by a rabbit anti-human IgG (Fc) [Thermo Scientific 31789]. We conclude from this that each of these proteins maintains the recognition sites for this antibody.
Plasmon Resonance Imaging The ability of the stradomers in Table 3 to bind FcγRIIIa was assessed using surface plasmon resonance (SPR) technology (commercially available through Biacore®). Human FcγRIIIa was directly immobilized via amine coupling to a CM5 Biacore chip by diluting the ligand in Acetate pH5.0 to a concentration of 5 ug/ml. Ligands were perfused over specified flow cell at a rate of 5 ul/min until an RU of 250 was reached. The flow cells were then blocked with ethanolamine. Stradomers and IVIG were diluted to 1000 nM in HBS-EP (0.01M HEPES pH 7.4; 0.15M NaCl; 3 mM EDTA; 0.005% Surfactant P20) and serially diluted 500 nM, 250 nM, 125 nM and finally 62.5 nM. A baseline sample containing only buffer (HBS-EP) was also included. A flow rate of 20 ul/min was used for all samples. A total of 60 uL of sample was injected, for an injection time of 3 minutes. Regeneration was achieved by perfusing running buffer over flow cells for an extended period of time of approximately 10 minutes.

At 500 nM, the measured Req (equilibrium), relative to baseline for the stradomer G-010 construct was 24.9 RU when perfused over human FcγRIIIa, and the KD was 1.95e-7 using a 1:1 binding model. IVIG at 500 nM on human FcγRIIIa gave a Req of 63.6 RU and a KD of 1.89e-7 using a 1:1 binding model. G-010 was therefore determined to bind to FcγRIIIa. Similar binding ability has been assessed on other biomimetic compounds. Here are some further examples:

|  | 1:1 w Mass Transfer | | | | Bivalent Fit | |
| --- | --- | --- | --- | --- | --- | --- |
|  | Rmax | Chi2 | $KD_{(M)}$ | $KA_{(1/M)}$ | Rmax | Chi2 |
| Controls: | | | | | | |
| Neg. (mouse IgG2a) | 2.05 | 0.451 | 4.7e-9 | 2.1e8 | 5.21 | 0.39 |
| Pos. (IVIG) | 87.7 | 6.8 | 1.9e-7 | 5.3e6 | | |
| Biomimetics: | | | | | | |
| 002 | 6.46 | 1.12 | 2.2e-8 | 4.9e7 | 16.7 | 0.82 |
| 004 | 30.2 | 1.74 | 4.8e-8 | 2.5e7 | 88.2 | 2.47 |
| 011 | 25.9 | 0.361 | 5.5e-6 | 1.8e7 | 57.4 | 0.15 |

We conclude that these proteins have varied ability to bind to recombinant FcγRIIIa by plasmon resonance analysis and that certain compounds such as G-010 have a bivalent curve fit, consistent with that seen by bivalent antibodies and indicating that the stradomer may have multi-valent binding to FcγRIIIa.
Stradomers Mimic the Biological Effect of IVIG The biological function of these stradomers was assessed. In order to determine the ability of each of the stradomers in Table 3 to mimic the functional utility of IVIG in individuals with ITP, we developed an in vitro assay using immature dendritic cells (iDC). The rationale for choosing iDC as target cells was based on published data demonstrating that adoptive transfer of DC from mice treated with IVIG, conferred protection against the development of ITP to naïve animals. (Siragam, V. et al. Intravenous immunoglobulin ameliorates ITP via activating Fc[gamma] receptors on dendritic cells. Nat Med 12, 688 (2006)). In our initial studies, we evaluated the impact of coated, meaning fixed to the plate, recombinant Fc (rFc) and IVIG on the expression of a variety of activation, maturation and costimulatory markers on human CD14+ cells, cultured in the presence of IL-4 and GM-CSF. When compared to cells cultured in cytokines alone, cells exposed to coated IVIG or coated rFc demonstrated striking enhancement of CD86 expression and down regulation of CD1a expression as well as a delay in CD11c upregulation.

Next, we determined whether the stradomers in Table 3 mimicked the described effect of coated IVIG or coated Fc on iDC. These compounds when coated to the plate well walls and floors did mimic the effect: G-002, G-004, G-005, G-014, G-018, and G-019. These compounds when coated to the plate well walls and floors did not mimic the effect: G-010, G-011, and G-012

These compounds when soluble did mimic the effect of coated IVIG or coated Fc on iDC: G-002, G-010, G-014, G-018, and G-019. These compounds when soluble did not mimic the effect: G-004, G-005, G-011, and G-012.

Whether exposure of iDC to coated IVIG would influence subsequent responses to pro-inflammatory stimuli can be tested.

We draw the following conclusions from these data:
i. that select stradomers, when coated on a tissue culture plate, mimic the functional ability of coated IVIG to upregulate CD86 and suppress CD1a expression on immature DC,
ii. that select stradomers administered at a low dose in a soluble form mimic the functional ability of coated IVIG to up regulate CD86 and suppress CD1a expression on iDC,
iii. that certain stradomers can induce phenotypic change in both a soluble and coated form and that other stradomers, such as G-010, can induce phenotypic change in a soluble but not a coated form,
iv. that stradomers of differing structures can be biologically active as evidenced by the Fc fragment stradomer formed from G-002 and the cluster stradomer formed from G-010,
v. that structures larger than expected by dimerization of stradomer monomers are seen on protein analysis and that these multimeric structures may correspond with biological activity in comparison to IVIG, and
vi. that stradomers formed from dimerized stradomer monomers can demonstrate a bivalent fit on plasmon resonance consistent with binding of multiple Fcγ receptors and suggesting the presence of multimeric tertiary structures of the stradomers.

Example 3

Heat Aggregated Biomimetics are More Potent than IVIG

A stradomer is a biologically active mimetic of aggregated immunoglobulin and especially of the aggregated Fc fragments of those immunoglobulin. In some instances, heat aggregation of the biomimetics described herein can increase biological activity. We conclude that heat-aggregated biomimetics as herein described can be as potent as IVIG.

Example 4

Fc Fragment Exhibits Several Activities

The Fc fragment has been used as a positive control in experiments described above in which the protein is coated and thereby fixed to plastic thereby exhibiting biological behavior that mimics coated IVIG. The Fc fragment also can be used as a core stradomer unit such as when it is attached to core moieties such as a liposome, a bead, or albumin. Further, we have demonstrated that the Fc fragment when cultured in certain expression systems and certain cell types, such as the Invitrogen FreestyleMax transient transfection system using CHO—S cells, can form higher order multimers on protein analysis, exhibit bivalent binding pattern on plasmon resonance imaging, and exhibit profound biological activity in soluble form comparable to coated IVIG in the immature DC assay. We conclude therefore that under certain carefully controlled conditions, the Fc fragment forms a Fc fragment stradomer. This effect may be due to post-translational modifications such as glycosylation changes.

Example 5

A Core Stradomer which is an Fc-Coated Bead May Alter Phagocytic Potential Relative to Uncoated Beads PBMCs are isolated from the buffy coat of healthy donors using Ficoll-Hypaque density gradient centrifugation. After isolation, PBMCs are washed twice with PBS. CD14+ cells are then purified using MACS separation column (Miltenyi). The purified cells are counted and resuspended to 2×10^5/ml RPM' complete media containing 800 ug/ml GM-CSF and 5 ng/ml IL-4. The cells are then seeded in the wells of non-tissue culture but sterile 6-well plates. After seeding the CD14+ cells in the non-tissue culture, polystyrene FITC microspheres (0.52 um) coated with or without saturating amounts of Fc or IVIG are added to the cells at a 1:1 ratio and incubated for 6 days at 37° C., 5.0% CO2 and then analyzed for phagocytosis of microspheres by FACS.

Both IVIG-coated beads and Fc-coated beads act as core stradomers and may thereby alter phagocytotic potential relative to uncoated beads.

Example 6

Design of Immunologically Active Biomimetics with Altered FcγRIII Binding Affinities It has been shown that a shared set of residues of IgG1 are involved in binding to all FcγRs. It has also been demonstrated that additional residues in IgG1 molecules are involved in the binding to both FcγRII and FcγRIII. Some residues when altered inhibited binding of one or more receptors. Interestingly, the specific double mutation of S298A/K334A enhanced binding of FcγIIIa and reduced binding to FcγIIb. Those residues have been noted on the stradomer construct shown in FIG. 16 (using an asterisk at both amino acids). We therefore can use site directed mutagenesis to generate a stradomer molecule having the structure encoded by SEQ ID NO: 17 but with the corresponding S298A/K334A mutations.

Example 7

Expression of Recombinant Proteins

Numerous expression systems exist that are suitable for use in producing the compositions discussed above. Eukaryote-based systems in particular can be employed to produce nucleic acid sequences, or their cognate polypeptides, proteins and peptides. Many such systems are commercially and widely available.

In a preferred embodiment, the stradomers described herein are produced using Chinese Hamster Ovary (CHO) cells which are well established for the recombinant production of immunoglobulin proteins following standardized protocols. Alternatively, for example, transgenic animals may be utilized to produce the human stradomers described herein, generally by expression into the milk of the animal using well established transgenic animal techniques. Lonberg N. Human antibodies from transgenic animals. Nat Biotechnol. 2005 September; 23(9):1117-25; Kipriyanov S M, Le Gall F. Generation and production of engineered antibodies. Mol Biotechnol. 2004 January; 26(1):39-60; See also Ko K, Koprowski H. Plant biopharming of monoclonal antibodies. Virus Res. 2005 July; 111(1):93-100.

The insect cell/baculovirus system can produce a high level of protein expression of a heterologous nucleic acid segment, such as described in U.S. Pat. Nos. 5,871,986, 4,879,236, both incorporated herein by reference in their entirety, and which can be bought, for example, under the name MAXBAC® 2.0 from INVITROGEN® and BAC-PACK™ BACULOVIRUS EXPRESSION SYSTEM FROM CLONTECH®.

Other examples of expression systems include STRATAGENE®'s COMPLETE CONTROL™ Inducible Mammalian Expression System, which utilizes a synthetic ecdysone-inducible receptor. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express vectors such as an expression construct described herein, to produce its encoded nucleic acid sequence or its cognate polypeptide, protein, or peptide. See, generally, Recombinant Gene Expression Protocols By Rocky S. Tuan, Humana Press (1997), ISBN 0896033333; Advanced Technologies for Biopharmaceutical Processing By Roshni L. Dutton, Jeno M. Scharer, Blackwell Publishing (2007), ISBN 0813805171; Recombinant Protein Production With Prokaryotic and Eukaryotic Cells By Otto-Wilhelm Merten, Contributor European Federation of Biotechnology, Section on Microbial Physiology Staff, Springer (2001), ISBN 0792371372.

Example 8

Expression and Purification of Immunologically Active Biomimetics

Nucleic acid constructs described in Examples 1 and 2 are transfected into cell lines that do not naturally express Ig.

The encoded polypeptides are expressed as secreted proteins due to their secretory leader sequences, which generally are removed by endogenous proteases during transport out of the cells or may be subsequently cleaved and removed by techniques well known in the art. These secreted immunologically active biomimetics are purified using Protein A or His tag chromatographic approaches well known in the art and size is verified by reducing and/or non-reducing SDS PAGE (sodium dodecyl sulfate polyacrylamide gel electrophoresis).

Example 9

Expression and Purification of Immunologically Active Biomimetics for Large Scale Production While various systems can be used to produce large amounts of a specific protein including bacteria, insect cells or yeast, expression in mammalian cells can minimize problems due to altered glycosylation of the proteins. Mammalian cells like CHO cells have been used to overproduce various proteins fused to an Ig backbone. The Fc domain in the construct becomes a tag that permits subsequent purification from the cell supernatant using protein affinity column purification (Harris, C L, D M Lublin and B P Morgan Efficient generation of monoclonal antibodies for specific protein domains using recombinant immunoglobulin fusion proteins: pitfalls and solutions., J. Immunol. Methods 268: 245-258, 2002). Many fusion proteins are directly cloned in frame with the constant region of Ig, specifically the CH2 and CH3 partial Fc domain monomers. A specific example of expression of interferon gamma receptor extracellular domain being expressed with Ig has been used to produce large amounts of the protein with functional activity (Fountoulakis, M, C. Mesa, G. Schmid, R. Gentz, M. Manneberg, M. Zulauf, Z. Dembic and G. Garotta, Interferon gamma receptor extracellular domain expressed as IgG fusion protein in Chinese hamster ovary cells: Purification, biochemical, characterization and stoichiometry of binding, J. Biol. Chem. 270:3958-3964, 1995).

Example 10

Design of Immunologically Active Biomimetics with Altered Fc Glycosylation

By a method essentially the same as that described by Shields et al. with regard to homo-antibodies, de-fucosylated Fc domains can be made in mutant CHO cells lacking enzymatic activity for adding fucose to protein carbohydrates. These are used to express stradomers with stronger FcγRIII binding affinities relative to a fucosylated form of the same molecule. (Robert L. Shields, et al. Lack of Fucose on Human IgG1 N-Linked Oligosaccharide Improves Binding to Human Fc RIII and Antibody-dependent Cellular Toxicity. J. Biol. Chem., July 2002; 277: 26733-26740 (doi:10.1074/jbc.M202069200)).

It has been shown that changes in sialylation in the Fc N-glycan can increase biological activity. Kaneko Y, Nimmerjahn F, Ravetch J V. Science. 2006 Aug. 4; 313(5787): 627-8. Thus stradomer molecule having altered sialylation can be produced using similar methods.

Alternative means to altering glycosylation of stradomer Fc domains include chemoenzymatic techniques for producing polypeptides with a specific glycosylation structure. See, Li, B., Song, H., Hauser, S., and Wang, L. X. 2006. A Highly Efficient Chemoenzymatic Approach Toward Glycoprotein Synthesis. Org. Lett. 8:3081-3084; See, also, International Pat. App. No. PCT/US07/70818.

Example 11

Fusion Constructs of FcγRIIIa (176 V/F) Polymorphism

As discussed previously, the anti-inflammatory activity of IVIG is dependent on primary interactions between the Fc domain and FcγRIIIa. These interactions can be effectively quantitated using (SPR) technology to characterize both association and dissociation constants of the immunologically active biomimetics with the two recognized polymorphic variants of FcγRIIIa (176 V/F). In order to define the binding affinity and dissociation of our Fc domain monomeric control and stradomer constructs, FcγRIIIa HIS tag fusion proteins will be produced in CHO cells with both V (SEQ ID NO:33) and F (SEQ ID NO:31) polymorphic variants at position 176 (FIG. 20). These sequences can be put into pCDNA 3.1 and transfected into CHO cells. These FcγRIIIa fusion proteins are purified from the supernatants from transfected cells using affinity $Ni^{2+}$ columns to purify the proteins. All FcγRIIIa fusion proteins are characterized by both cDNA sequencing and SDS PAGE.

Various other protocols in the art can be utilized to express FcγRIIIa and characterize interactions with immunologically active biomimetic. See, e.g., the materials and methods section of Robert L. Shields, et al. High Resolution Mapping of the Binding Site on Human IgG1 for FcγRI, FcγRII, FcγRIII, and FcRn and Design of IgG1 Variants with Improved Binding to the FcγR. J. Biol. Chem., February 2001; 276: 6591-6604 (doi:10.1074/jbc.M009483200).

Example 12

Screening Immunologically Active Biomimetic Function In Vitro

To test the function of immunologically active biomimetics such as those presented in Example 1, an in vitro assay is designed to recapitulate the mechanism by which it appears that native Fc domains reduce inflammation in vivo. It has recently been demonstrated that hIVIG inhibits the maturation of DCs and alters the secretion of IL-10, IL-12 and TNF-alpha (Bayry, J, et al., Inhibition of maturation and function of dendritic cells by intravenous immunoglobulin, *Blood* 101(2):758-765(2003)). Our stradomers mediate effects on DCs similar to hIVIG. The inhibition of DC maturation and alterations in cytokine secretion in vitro can serve as an effective means to define some of the biological activities of many stradomer constructs. The stradomer constructs described above may be further validated using the following experimental parameters:

TABLE 4

| Group | Experimental condition | Outcome measure 1 (FACS) | Outcome measure 2 ELISA/Elispot |
|---|---|---|---|
| 1 | None | CD1a, 14, 40, 80, 83, 86, HLADR | IL-10, IL-12, TNFa, IL-23 |
| 2 | Soluble IVIG | CD1a, 14, 40, 80, 83, 86, HLADR | IL-10, IL-12, TNFa, IL-23 |
| 3 | Fixed IVIG | CD1a, 14, 40, 80, 83, 86, HLADR | IL-10, IL-12, TNFa, IL-23 |
| 4 | Soluble Fc | CD1a, 14, 40, 80, 83, 86, HLADR | IL-10, IL-12, TNFa, IL-23 |

TABLE 4-continued

| Group | Experimental condition | Outcome measure 1 (FACS) | Outcome measure 2 ELISA/Elispot |
|---|---|---|---|
| 5 | Fixed Fc | CD1a, 14, 40, 80, 83, 86, HLADR | IL-10, IL-12, TNFa, IL-23 |
| 6 | Soluble Stradomer | CD1a, 14, 40, 80, 83, 86, HLADR | IL-10, IL-12, TNFa, IL-23 |
| 7 | Fixed Stradomer | CD1a, 14, 40, 80, 83, 86, HLADR | IL-10, IL-12, TNFa, IL-23 |

In one preferred in vitro assay shown in Table 4, the impact on human DC phenotype of soluble, immunologically active biomimetics, having appropriate binding affinities, is measured. Soluble non-cross-linked natural sequence Fc domain constructs can serve as controls. Specific DC markers on the DC surface are evaluated including markers of activation (CD80, CD83 and CD86) as well as the FcγRs. See Prechtel A T, Turza N M, Theodoridis A A, Steinkasserer A. CD83 knockdown in monocyte-derived DCs by small interfering RNA leads to a diminished T cell stimulation. J Immunol. 2007 May 1; 178(9):5454-64. In addition, multiplex analysis can be employed to evaluate the impact of our immunologically active biomimetics on DC cytokine production. Jongbloed, Sarah L., et al. Enumeration and phenotypic analysis of distinct dendritic cell subsets in psoriatic arthritis and rheumatoid arthritis. Arthritis Res Ther. 2006; 8(1): R15 (Published online 2005 Dec. 16. doi: 10.1186/ar1864). Finally, to confirm DCs interact with monocytes as expected, control DCs and DCs exposed to immunologically active biomimetics are cultured with purified monocytes and evaluated by flow cytometry for changes in the levels of activating FcγRIIa receptors and other cell surface determinants related to the activation state of the monocytes.

In particular embodiments, stradomers can decrease the FcγRIIa receptors present on an immune cell thereby increasing the ratio of inhibitory FcγRIIb receptors to the FcγRIIa receptors which results in inhibition of immune cell functions.

Example 13

Screening Immunologically Active Biomimetic Function In Vivo

Numerous autoimmune diseases such as idiopathic thrombocytopenic purpura, multiple sclerosis, asthma, and inflammatory bowel diseases have established, art recognized animal models for in vivo testing. Wu G F, Laufer T M. The role of dendritic cells in multiple sclerosis. Curr Neurol Neurosci Rep. 2007 May; 7(3):245-52; Targan S R, Karp L C. Defects in mucosal immunity leading to ulcerative colitis. Immunol Rev. 2005 August; 206:296-305. For example, multiple models of ITP are currently available. See, e.g., Crow A R, et al. IVIG inhibits reticuloendothelial system function and ameliorates murine passive immune thrombocytopenia independent of anti-idiotype reactivity. Br J Haematol. 2001; 115:679-686. Immunologically active biomimetics designed to modulate the immune system, as appropriate for each specific autoimmune disease, can be validated in such in vivo models. Importantly, in many of these models, administration of hIVIG likely results in a foreign species (e.g. mouse) anti-human antibody response which has the potential to obscure or create false positive product related anti-inflammatory effects.

We established a mouse model of Idiopathic Thrombocytopenic Purpura according to the following methodology: Platelet counts were measured in C57BL6 mice by serial tail vein nicking. 10 ul. of blood was diluted in 15 ul citrate buffer. Samples were then analyzed for absolute platelet count on a HemaVet 950 cytometer. For mice in an ITP control group, starting day 2, every afternoon platelets were depleted by giving intra peritoneal injection of 2 ug Rat Anti-Mouse CD41 (MWReg30), an anti-platelet antibody from BD Biosciences pharmingen. Mice in the IVIG pretreatment control group received 2 g/kg (40 mg/mice) human IVIG by i.p. injection every morning and the same dose MWReg30 as the ITP control group. We determined that IVIG is highly protective of platelet count in this model of induced ITP and conclude that this model is useful for testing stradomers against IVIG for relative degree of protection from platelet count decreases. A stradomer can be assessed in this model at various concentrations to assess protection relative to IVIG as follows:

Groups in an Experiment

1) Control—No ITP, No IVIG

2) ITP control group—2 ug MWReg30 every evening starting day 2

3) IVIG pretreatment group—40 mg IVIG every morning and 2 ug MWReg30 every evening starting day 2

4) Stradomer equivalent to $10^{12}$ Fc domains IV every morning

5) Stradomer equivalent to $10^{11}$ Fc domains IV every morning

6) Stradomer equivalent to $10^{10}$ Fc domains IV every morning

7) Stradomer equivalent to $10^{9}$ Fc domains IV every morning

8) Stradomer equivalent to $10^{8}$ Fc domains IV every morning

9) Stradomer equivalent to $10^{7}$ Fc domains IV every morning

10) Stradomer equivalent to $10^{6}$ Fc domains IV every morning

Example 14

Validating Immunologically Active Biomimetic Efficacy In Vivo for Treating ITP

In another murine model of ITP, mice deficient in normal B cell function can be used. Deficiency in normal B cell function serves to eliminate the idiotype-antiidiotype effects of murine anti-human Fc fragment antibodies that would be generated by the administration of human Fc fragment or Fc partial fragment to a mouse and consequent false positive results. The deficiency in B cell function can be generated, for example, through the administration of anti-B cell antibodies or occurs in genetically engineered mice such as the m chain-knock out mouse (Jackson Labs strain B6.129S2-Igh-6$^{tm1Cgn}$/J) that are deficient in mature B-cells.

The immune system of immunodeficient mice is reconstituted with either unmodified or B cell depleted PBMCs from immunocompetent animals. These animals are subsequently treated with anti-platelet antibodies to mimic ITP using well defined techniques in the art. Animals are then treated with immunologically active biomimetics according to the following scheme:

TABLE 5

In vivo efficacy of [hIgG₁ Fc domain - hIgG₁ Fc domain] (SEQ ID NO.: 22) immunologically active biomimetics for the treatment of ITP.

| Group | Animal # | PBMC's used to reconstitute mice | Treatment | Outcome Measure |
|---|---|---|---|---|
| 1 | 5 | None | IgG1 Fc | Platelet Count |
| 2 | 5 | None | IgG1 Fc - IgG1 Fc Stradomer | Platelet Count |
| 3 | 5 | Unmodified | IgG1 Fc | Platelet Count |
| 4 | 5 | Unmodified | IgG1 Fc - IgG1 Fc Stradomer | Platelet Count |
| 5 | 5 | B cell depleted | IgG1 Fc | Platelet Count |
| 6 | 5 | B cell depleted | IgG1 Fc - IgG1 Fc Stradomer | Platelet Count |
| 7 | 5 | Unmodified | hIVIG | Platelet Count |

It is anticipated that groups 1 and 2 will not develop ITP upon antibody infusion as they do not have the B cells to produce anti-platelet antibodies necessary for platelet destruction. In groups 3 and 4, it is expected that both the {hIgG₁ Fc-hIgG₁ Fc} stradomer polypeptide and the hIgG₁ Fc monomer polypeptide effectively ameliorate ITP because endogenous murine antibodies react with hIgG₁ Fc domain epitopes to crosslink the hIgG₁ Fc monomer polypeptides. In contrast, in the absence of endogenous murine antibodies, the {hIgG₁ Fc-hIgG₁ Fc} stradomer polypeptide (group 6) is more effective than the uncross-linked IgG₁ Fc monomer polypeptide (group 5) in ameliorating ITP. Group 7 serves as a positive control for treatment effect.

Example 15

Treating Patients with ITP Using Intravenous Formulations of Stradomer Proteins (SEQ ID NOs: 18 & 22)

Treatment protocols for ITP with the exemplary stradomer proteins encoded by SEQ. ID. NO: 17 & 21 are utilized in a manner tracking standard guidelines for ITP hIVIG therapy such as the Executive Committee of the American Society of Hematology practice guideline for the diagnosis and management of primary immune thrombocytopenic purpura. See George, J N, et al. Idiopathic thrombocytopenic purpura: a practice guideline developed by explicit methods for the American Society of Hematology. Blood. 1996 Jul. 1; 88(1):3-40; See also, the 2000 guidelines by Italian pediatric hematologists, the 2003 British hematologists guidelines and the 2006 Japanese pediatric hematologists guidelines. Alternatively, the stradomer IV protocols for ITP may include an initial administration phase with dosages of about 0.1 to about 0.001 times the above treatment protocol dosages. The initial low dose phase is designed to minimize any short term pro-inflammatory effects of the stradomer administration while still being sufficient to induce a long term anti-inflammatory effect, which is subsequently enhanced and maintained by the second phase standard dosing described above. The rationale for this alternative approach is that some embodiments of a stradomer may have both a short term inflammatory effect as well as a long term anti-inflammatory effect through decreasing the expression of FcγRIIa. An initial low dose (or initial low doses) can be used to stimulate the long term anti-inflammatory effect while minimizing the short term inflammatory effect.

The effective stradomer dose is generally from about 0.01% to about 15% of the effective hIVIG dose, more preferably, about 0.1% to about 3% of the effective hIVIG dose. The effective hIVIG dose in ITP is generally in the range of about 100 mg/Kg to about 2 grams/Kg administered every 10-21 days.

The stradomer intravenous formulation will be substantially the same as FDA approved hIVIG formulations but may exclude the stabilizers present in some hIVIG formulations. See, e.g., the product insert for Gammagard S/D, distributed by Baxter Healthcare Corporation and approved for ITP therapy by the FDA.

Example 16

Treating Patients with ITP Using Intraperitoneal Administration of a Core Stradomer Treatment protocols for ITP with exemplary stradomer proteins representing Fc fragments fixed to a core moiety such as a liposome are utilized by intraperitoneal administration with dosages of about 1% to about 0.001% of standard intravenous IVIG protocol dosages. The rationale for this alternative approach is that core stradomers comprised of fixed Fc fragments delivered in a stable formulation to the intraperitoneal cavity will make available the multiple Fc domains to affect monocyte-derived effector cells similarly to IVIG but at substantially lower doses.

Example 17

Design of Immunologically Active Biomimetics (Stradobodies)

Two stradobodies have been constructed and transfected. For each stradobody, encoding cDNA was synthesized from total RNA made from hybridoma cell lines expressing the antibody of interest. Establishing hybridoma cell lines is well known in the art. Amplification of cDNA of interest encoding the antibody heavy and light variable regions was done by BD SMART™ RACE amplification kit (Clontech CA). Numerous other methods are available to generate cDNA encoding the heavy and light chains for variable regions of antibodies (Sassano, M. et. al., 1994. Nucleic Acids Res. May 11; 22(9):1768-9; Jones, S. T., Bendig, M. M., 1991. Biotechnology (NY) January: 9(1):88-9.) To generate the stradobodies the heavy chain variable regions are fused to the stradomer constructs by either sewing by overlap extension with PCR (Hutton and Pease) or utilize existing compatible restriction sites to fuse the appropriate fragments. Stradobody proteins are expressed in CHO—S cells and isolated from cell supernatants by protein A column affinity purification. Binding of the purified stradobodies to the antigen of interest is confirmed by flow cytometry binding studies utilizing cell lines expressing the antigen.

A standard ADCC assay employing NK cells as effectors and antigen expressing tumor cells as targets at various effector-to-target ratios is employed to compare the potential of the stradobody and the monoclonal antibody (Mab) that shares the same Fab region to induce ADCC against high and low antigen expressing tumor cell lines. Stradobodies are selected for development that demonstrate similar results to the paired Mab in the NK assay against the high epitope expressing cell line but superior results to the paired Mab in the NK assay against the low epitope expressing cell line.

Example 18

Treating Patients with Breast Cancer Using Intravenous Formulations of Stradobody Containing the Antigen-Binding Domain of Trastuzumab Treatment protocols for breast cancer with the exemplary stradobody containing a Fab that is or is similar to the Fab from the marketed product trastuzumab having activity against the her2/neu epitope are utilized in a manner tracking standard guidelines for breast cancer therapy. See Romond, E H et. al. Trastuzumab plus Adjuvant Chemotherapy for Operable HER2-Positive Breast Cancer. NEJM. 2005 Oct. 20; 353:1673-1684; Seidman, A D et. al. Weekly Trastuzumab and Paclitaxel Therapy for Metastatic Breast Cancer With Analysis of Efficacy by HER2 Immunophenotype and Gene Amplification. Journal of Clinical Oncology. Vol 19, Issue 10 (May), 2001: 2587-2595; Vogel, C L et. al. Journal of Clinical Oncology. Vol 20, Issue 3 (February), 2002:719-726

It is anticipated that the effective stradobody dose will generally range from about 1% to about 500% of the effective monoclonal antibody whose Fab is the same as the stradobody, more preferably, about 50% to about 100% of the effective monoclonal antibody dose. The effective monoclonal antibody dose in clinical cancer treatment varies. For the Her-2 neu monoclonal antibody the dose is generally in the range of about 2 mg/Kg to about 4 mg/Kg administered every 7-21 days.

Example 19

Treating Patients with Head and Neck or Colon Cancer Using Intravenous Formulations of Stradobody Containing the Antigen-Binding Domain of Cetuximab It is anticipated that treatment protocols for breast cancer with the exemplary stradobody containing a Fab that is or is similar to the Fab from the marketed product cetuximab having activity against the EGFR epitope can be utilized in a manner tracking standard guidelines for head and neck and colon cancer therapies. See Robert, F et. al. Phase I Study of Anti-Epidermal Growth Factor Receptor Antibody Cetuximab in Combination With Radiation Therapy in Patients With Advanced Head and Neck Cancer. Journal of Clinical Oncology, Vol 19, Issue 13 (July), 2001: 3234-3243; Bonner, J A et. al. Cetuximab prolongs survival in patients with locoregionally advanced squamous cell carcinoma of head and neck: A phase III study of high dose radiation therapy with or without cetuximab. Journal of Clinical Oncology, 2004 ASCO Annual Meeting Proceedings (Post-Meeting Edition). Vol 22, No 14S (July 15 Supplement), 2004: 5507; Shin, D M et. al. Epidermal Growth Factor Receptor-targeted Therapy with C225 and Cisplatin in Patients with Head and Neck Cancer. Clinical Cancer Research Vol. 7, 1204-1213, May 2001; Cunningham, D et al. Cetuximab Monotherapy and Cetuximab plus Irinotecan in Irinotecan-Refractory Metastatic Colorectal Cancer. NEJM. Volume 351:337-345, 2004.

It is anticipated that the effective EGFR/HER1 stradobody dose will generally range from about 1% to about 500% of the effective monoclonal antibody whose Fab is the same as the stradobody, more preferably, about 50% to about 100% of the effective monoclonal antibody dose. The effective monoclonal antibody dose in clinical cancer treatment varies. For the EGFR monoclonal antibody the dose is generally in the range of about 250-400 mg/square meter which is about 5 mg/Kg-25 mg/Kg administered every 7-21 days.

Example 20

Increased Multimerization by Altered Glycosylation May Increase Immunologically Active Biomimetic Activity The glycosylation patterns of expressed proteins are dependent on the cell line in which the protein is expressed. The Chinese Hamster Ovarian cell (CHO cell) commonly used for protein expression and purification results in a glycosylation pattern that is different from, for example, the HEK 293 cells which are of human origin and also is commonly used for protein expression of endogeneous proteins. As the binding properties of Fc fragments and cluster stradomer units can be affected by the glycosylation pattern, increased multimerization and therefore increased biological activity of the expressed peptides can be achieved by expression in cell lines other than CHO or in cell lines including CHO that are genetically altered to change the glycosylation pattern to an N-glycan that promotes increased aggregation between Fc fragments or Fc domain-containing peptides. Increased multimerization of Fc fragment or selected cluster stradomer units by altering glycosylation patterns may increase the ability of immunologically active biomimetics to mimic the effects of hIVIG.

Example 21

Does Exposure of Mature DC (mDC) to IVIG or rFcF (Recombinant Fc Fragments) Alter their Phenotype?

The rFCF fragments from human IgG1 to be used in this experiment were produced by standard recombinant protein technology. The two chains of the human rFCF each consisted of the hinge region (15 amino acids), the CH2 domain (110 amino acids), and the CH3 domain (106 amino acids) of human IgG1 heavy chain.

CD14+ cells can be isolated from peripheral blood mononuclear cells (PBMC) obtained from the blood of a healthy human donor using a Miltenyi MACS separation column. The cells are cultured at a final concentration of $2 \times 10^5$/mL in GM-CSF (800 IU/mL) and IL-4 (5 ng/mL) for 5 days at 37° C. The media in all cultures is refreshed on day 3 of culture. At day 5, lipopolysaccharide (LPS; 10 µg/ml) is added to appropriate cultures to induce maturation to a mature DC. Mature DCs are known in the art not to express substantive levels of the CD16, CD32 or CD64. The cells are then cultured for an additional two days and aliquots are analyzed for CD11c, CD80, CD83, CD86, CD1a, and CD14 expression by two dimensional fluorescence flow cytometry (FFC). The remaining cells cultured with LPS are then placed in wells with soluble or coated IVIG or human rFcF (all at 10 µg/mL) for 24 hours at 37° C., harvested and analyzed for expression of the markers listed above by two-dimensional FFC.

Experimental groups are as follows:
(1) CD14+ cells; GM-CSF; IL-4; no LPS ("7d-LPS")
(2) CD14+ cells: GM-CSF; IL-4; LPS ("7d+LPS")
(3) CD14+ cells; GM-CSF; IL-4; LPS; coated IVIG ("cIVIG")
(4) CD14+ cells; GM-CSF; IL-4; LPS; soluble IVIG ("sIVIG")

(5) CD14+ cells; GM-CSF; IL-4; LPS; coated rFcF ("cFc")
(6) CD14+ cells; GM-CSF; IL-4; LPS; soluble rFcF ("sFc")
(7) CD14+ cells; GM-CSF; IL-4; LPS ("Control")

Example 22

Does Exposure of iDC to Coated IVIG Inhibit Phagocytosis of Opsonized Red Blood Cells CD14+ cells are purified from human PBMC of a healthy human donor as described in Example 21 and cultured at 37° C. for 6 days with GM-CSF and IL-4 at the concentrations indicated in the previous examples and in the presence or absence of coated or soluble IVIG. The cells are harvested and then incubated at either 37° C. or 4° C. for two hours with Rho-positive human red blood cells that are uncoated or coated with fluorescein isothiocyanate (FITC) conjugated anti-D antibody. After incubation with red blood cells, CD14+ cells are stained for APC-conjugated CD1a. Phagocytosis is then evaluated by two dimensional FFC measuring side light scatter (SSC-A), forward light scatter (FSC-A), FITC fluorescence (FITC-A), and APC fluorescence (CD1a).

Example 23

Does Exposure to Coated IVIG Decrease the Ability of iDC to Stimulate an Allogeneic Mixed Lymphocyte Reaction CD14+ cells are isolated from the blood of a healthy human donor as described in the previous examples. They are then cultured at 37° C. for 6 days with GM-CSF and IL-4 in the presence or absence of soluble and coated IVIG. The concentrations of all these reagents are as described in above. The cells are then harvested and plated into the wells of 96 well microtiter tissue culture plates at various numbers (with the highest dose being $2.5 \times 10^4$ per well). CD3+ T cells are purified from the PBMC of a second human donor that was HLA incompatible with the donor from which the CD14+ cells are isolated. The T cells are added to each of the wells of the 96 well tissue culture plates ($10^5$ T cells per well). After five days of co-culture, 1 μCi of $^3$H-thymidine is added to each of the culture wells. The cultures are then incubated for a further 6 hours and incorporation of the $^3$H-thymidine ("cpm") is measured as an indication of the degree of cell proliferation in the cultures. Three different iDC stimulator populations are tested: one generated by culture with GM-CSF and IL-4 only, one generated by culture with GM-CSF, IL-4, and coated IVIG, and one generated by culture with GM-CSF, IL-4, and soluble IVIG.

Example 24

Effect of Exposure of iDC to Coated and Soluble rFcF and IVIG on Cytokine Expression by the iDC and mDC Cultures containing CD14+ cells, GM-CSF, and IL-4 and either rFcF (coated or soluble) or IVIG (coated or soluble) are set up under the conditions described in the previous examples. Instead of testing the cells for expression of cell surface markers, phagocytic ability, or the ability to stimulate allogeneic MLRs, the cytokines the cells produce are measured. It is expected that coated rFcF will modulate cytokine production by the cells in a manner similar to IVIG but not similar to soluble rFcF. Thus, it is expected that the level of cytokines that inhibit inflammatory responses (e.g., interleukin-4, interleukin-6, and interleukin-12) will be enhanced by exposure of the cells to coated rFcF. Moreover, it is expected that exposure of the cells to coated rFcF will result in a decrease in the level of production by the cells of cytokines that enhance inflammatory responses (e.g., interferon, interleukin-23, and tumor necrosis factor-I).

Example 25

Recombinant Mouse Fc Fragments

Recombinant Fc fragments (rFcF) from mouse IgG2a were produced using standard cloning and recombinant protein expression techniques. The two chains of the mouse rFcF each consisted of the hinge region (21 amino acids), the CH2 domain (110 amino acids), and the CH3 domain (107 amino acids) of mouse IgG2a heavy chain. The mouse IgG2a was active in the human iDC assay when coated to the walls and floors of plate wells.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. All U.S. and foreign patents, patent application publications, and non-patent literature (including, but not limited to, abstracts, scientific journal articles, books, product literature and manuals) referred to or cited herein are hereby incorporated by reference in their entireties.

LIST OF REFERENCES

The following references are incorporated by reference in their entirety.
1. Smiley, D. & MG, T. Southwestern internal medicine conference: High dose intravenous gamma globulin therapy: How does it work? *Am J Med Sci* 309, 295-303 (1995).
2. Nimmerjahn, F. & Ravetch, J. V. The antiinflammatory activity of IgG: the intravenous IgG paradox. *J. Exp. Med.* 204, 11-15 (2007).
3. Samuelsson, A., Towers, T. L. & Ravetch, J. V. Antiinflammatory Activity of IVIG Mediated Through the Inhibitory Fc Receptor. *Science* 291, 484-486 (2001).
4. Follea, G. et al. Intravenous plasmin-treated gammaglobulin therapy in idiopathic thrombocytopenic purpura. *Nouv Rev Fr Hematol* 27, 5-10 (1985).
5. Solal-Celigny, P., Bernard, J., Herrera, A. & Biovin, P. Treatment of adult autoimmune thrombocytopenic pur- 5. pura with high-dose intravenous plasmin-cleaved gammaglobulins. *Scand J Haematol* 31, 39-44 (1983).
6. Debre, M. & Bonnet, M.-C. Infusion of Gcgamma fragments for treatment of children with acute immune thrombocytopenic purpura. *Lancet* 342, 945-49 (1993).
7. Burdach, S. E., Evers, K. & Geurson, R. Treatment of acute idiopathic thrombocytopenic purpura of childhood with intravenous immunoglobulin G: Comparative efficacy of 7S and 5S preparations. *J Pediatr* 109, 770-775 (1986).
8. Siragam, V. et al. Intravenous immunoglobulin ameliorates ITP via activating Fc[gamma] receptors on dendritic cells. *Nat Med* 12, 688 (2006).
9. Clarkson, S. et al. Treatment of refractory immune thrombocytopenic purpura with an anti-Fc gamma-receptor antibody. *N Engl J Med* 314, 1236-1239 (1986).
10. Bleeker, W. K. et al. Vasoactive side effects of intravenous immunoglobulin preparations in a rat model and their treatment with recombinant platelet-activating factor acetylhydrolase. *Blood* 95, 1856-1861 (2000).
11. Teeling, J. L. et al. Therapeutic efficacy of intravenous immunoglobulin preparations depends on the immunoglobulin G dimers: studies in experimental immune thrombocytopenia. *Blood* 98, 1095-1099 (2001).
12. Augener, W., Friedman, B. & Brittinger, G. Are aggregates of IgG the effective part of high-dose immunoglobulin therapy in adult idiopathic thrombocytopenic purpura (ITP)? *Blut* 50, 249-252 (1985).
13. Tankersley, D. L., Preston, M. S. & Finlayson, J. S. Immunoglobulin G dimer: An idiotype-anti-idiotype complex. *Molecular Immunology* 25, 41 (1988).
14. Robert L. Shields, Angela K. Namenuk, Kyu Hong, Y. Gloria Meng, Julie Rae, John Briggs, Dong Xie, Jadine Lai, Andrew Stadlen, Betty Li, Judith A. Fox, and Leonard G. Presta. High Resolution Mapping of the Binding Site on Human IgG1 for FcγRI, FcγRII, FcγRIII, and FcRn and Design of IgG1 Variants with Improved Binding to the FcγR J. Biol. Chem., February 2001; 276: 6591-6604; doi:10.1074/jbc.M009483200
15. Sondermann, P., Huber, R., Oosthuizen, V., and Jacob, U. (2000) *Nature* 406, 267-273
16. Robert L. Shields, Jadine Lai, Rodney Keck, Lori Y. O'Connell, Kyu Hong, Y. Gloria Meng, Stefanie H. A. Weikert, and Leonard G. Presta Lack of Fucose on Human IgG1 N-Linked Oligosaccharide Improves Binding to Human FcγRIII and Antibody-dependent Cellular Toxicity. J. Biol. Chem., July 2002; 277: 26733-26740; doi: 10.1074/jbc.M202069200
17. Ann Wright and Sherie L. Morrison. Effect of C2-Associated Carbohydrate Structure on Ig Effector Function: Studies with Chimeric Mouse-Human IgG1 Antibodies in Glycosylation Mutants of Chinese Hamster Ovary Cells. J. Immunol., April 1998; 160: 3393-3402.
18. Crow A R, et al. IVIg inhibits reticuloendothelial system function and ameliorates murine passive immune thrombocytopenia independent of antiidiotype reactivity. Br J Haematol. 2001; 115:679-686.
19. Inhibition of maturation and function of dendritic cells by intravenous immunoglobulin Jagadeesh Bayry, Sébastien Lacroix-Desmazes, Cedric Carbonneil, Namita Misra, Vladimira Donkova, Anastas Pashov, Alain Chevailler, Luc Mouthon, Bernard Weill, Patrick Bruneval, Michel D. Kazatchkine, and Srini V. Kaveri Blood 2003 101: 758-765. Prepublished online Aug. 29, 2002; DOI 10.1182/blood-2002-05-1447
20. R. Deng and J. P. Balthasar. Comparison of the effects of antibody-coated liposomes, IVIG, and anti-RBC immunotherapy in a murine model of passive chronic immune thrombocytopenia. Blood, Mar. 15, 2007; 109(6): 2470-2476. Prepublished online as a Blood First Edition Paper on Nov. 28, 2006; DOI 10.1182/blood-2006-04-018093.
21. Kabat, E. A., Wu, T. T., Perry, H. M., Gottesman, K. S., and Foeller, C. (1991) *Sequences of Proteins of Immunological Interest*, 5th Ed., United States Public Health Service, National Institutes of Health, Bethesda
22. U.S. Published Patent Application 20060074225.

What is claimed is:

1. A cluster stradomer comprising two or more multimerized cluster stradomer units, wherein each of said cluster stradomer units comprises from amino terminus to carboxy terminus,
   (a) at least one multimerization region which multimerizes the cluster stradomer units to form the cluster stradomer wherein the multimerizing region is an IgG2 hinge and
   (b) at least one Fc domain comprising a hinge, CH2 and CH3 domain from IgG1 wherein the cluster stradomer is capable of specifically binding to at least two Fc receptors.

2. The cluster stradomer of claim 1 wherein said cluster stradomer does not contain an antigen-binding Fab domain.

3. The cluster stradomer of claim 1, comprising two multimerized cluster stradomer units.

4. The cluster stradomer of claim 1, comprising three multimerized cluster stradomer units.

5. The cluster stradomer of claim 1, comprising four multimerized cluster stradomer units.

6. The cluster stradomer of claim 1, comprising five or more multimerized cluster stradomer units.

7. The cluster stradomer of claim 1 wherein each of the cluster stradomer units is capable of specifically binding to at least one FcR.

8. The cluster stradomer of claim 1 wherein the at least one FcR is human Fcγ receptor I, human Fcγ receptor II, human Fcγ receptor III, or FcRN.

9. The cluster stradomer of claim 8 wherein the human Fcγ receptor III is human FcγRIIIa.

10. The cluster stradomer of claim 1 comprising cluster stradomer units each of which comprise a homodimer of the protein of SEQ ID NO: 61.

11. A homodimeric cluster stradomer unit wherein each monomer of the homodimer comprises from amino terminus to carboxy terminus:
   (a) a multimerizing domain monomer comprising an IgG2 hinge that when homodimerized is capable of multimerizing the cluster stradomer unit; and
   (b) an Fc domain monomer comprising an IgG1 hinge monomer, an IgG1 CH2 monomer, and a IgG1 CH3 monomer
   wherein the homodimer is capable of specifically binding to at least one Fc receptor and multimerizes to form a compound capable of binding to two or more Fc receptors.

12. The homodimeric cluster stradomer unit of claim 11 wherein each monomer of the homodimer comprises the protein of SEQ ID NO: 61.

* * * * *